(12) United States Patent
Hennequin et al.

(10) Patent No.: US 7,625,908 B2
(45) Date of Patent: Dec. 1, 2009

(54) QUINAZOLINE DERIVATIVES

(75) Inventors: Laurent Francois Andre Hennequin, Reims (FR); Robert Hugh Bradbury, Macclesfield (GB); Jason Grant Kettle, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 200 days.

(21) Appl. No.: 10/578,663

(22) PCT Filed: Nov. 11, 2004

(86) PCT No.: PCT/GB2004/004761

§ 371 (c)(1),
(2), (4) Date: Jan. 17, 2007

(87) PCT Pub. No.: WO2005/051923

PCT Pub. Date: Jun. 9, 2005

(65) Prior Publication Data

US 2007/0244136 A1   Oct. 18, 2007

(30) Foreign Application Priority Data

Nov. 13, 2003   (GB) .................................. 0326459.5

(51) Int. Cl.
  *A61K 31/517* (2006.01)
  *A61P 35/02* (2006.01)
  *C07D 239/84* (2006.01)
  *A61K 31/4965* (2006.01)

(52) U.S. Cl. .............................. 514/266.2; 514/266.21; 514/266.23; 514/266.3; 514/255.05; 544/284; 544/293

(58) Field of Classification Search ............... 514/266.2, 514/266.21, 266.23, 266.3, 255.05; 544/284, 544/293

See application file for complete search history.

(56) References Cited

U.S. PATENT DOCUMENTS

| | | | |
|---|---|---|---|
| 4,322,420 A | 3/1982 | Kobayashi et al. | 514/266.4 |
| 4,335,127 A | 6/1982 | Vandenberk et al. | |
| 4,640,920 A | 2/1987 | Boyle et al. | 514/248 |
| 4,921,863 A | 5/1990 | Sugimoto et al. | |
| 5,405,843 A | 4/1995 | Fukazawa et al. | 514/183 |
| 5,721,237 A | 2/1998 | Myers et al. | 514/266.1 |
| 5,747,498 A | 5/1998 | Schnur et al. | 514/266.4 |
| 5,929,080 A | 7/1999 | Frost | 514/266.4 |
| 5,962,458 A | 10/1999 | Lohmann et al. | 514/266.21 |
| 6,004,967 A | 12/1999 | McMahon et al. | 514/266.4 |
| 6,046,206 A | 4/2000 | Pamukcu et al. | 514/266.21 |
| 6,117,433 A | 9/2000 | Edens et al. | 424/400 |
| 6,297,258 B1 | 10/2001 | Wissner et al. | |
| 6,313,130 B1 | 11/2001 | Uckun et al. | 514/266.24 |
| 6,326,373 B1 | 12/2001 | Uckun et al. | 514/266.1 |
| 6,384,223 B1 | 5/2002 | Gletsos | 544/293 |
| 6,562,319 B2 | 5/2003 | Mishani et al. | |
| 6,972,288 B1 | 12/2005 | Himmelsbach et al. | |
| 7,148,230 B2 | 12/2006 | Bradbury et al. | |
| 2002/0082270 A1 | 6/2002 | Himmelsbach et al. | |
| 2002/0128553 A1 | 9/2002 | Mishani et al. | |
| 2003/0186995 A1 | 10/2003 | Kath et al. | |
| 2004/0048880 A1 | 3/2004 | Himmelsbach et al. | |
| 2004/0176361 A1 | 9/2004 | Fujio et al. | |
| 2005/0043336 A1 | 2/2005 | Hennequin et al. | |
| 2005/0054662 A1 | 3/2005 | Hennequin et al. | |
| 2005/0215574 A1 | 9/2005 | Bradbury et al. | |
| 2006/0211714 A1 | 9/2006 | Hennequin et al. | |
| 2006/0287295 A1 | 12/2006 | Barlaam et al. | |
| 2007/0015743 A1 | 1/2007 | Bradbury et al. | |
| 2007/0032508 A1 | 2/2007 | Bradbury et al. | |
| 2007/0032513 A1 | 2/2007 | Hennequin et al. | |
| 2007/0037837 A1 | 2/2007 | Hennequin et al. | |
| 2007/0043009 A1 | 2/2007 | Hennequin et al. | |
| 2007/0043010 A1 | 2/2007 | Bradbury et al. | |
| 2007/0082921 A1 | 4/2007 | Hennequin et al. | |
| 2007/0088044 A1 | 4/2007 | Hennequin et al. | |
| 2007/0099943 A1 | 5/2007 | Bradbury et al. | |
| 2007/0149546 A1 | 6/2007 | Bradbury et al. | |
| 2007/0232607 A1 | 10/2007 | Bradbury et al. | |
| 2007/0293490 A1 | 12/2007 | Delouvrie et al. | |

FOREIGN PATENT DOCUMENTS

| | | |
|---|---|---|
| CA | 2476008 | 10/2003 |
| CA | 2543649 | 5/2005 |

(Continued)

OTHER PUBLICATIONS

Grunwald, V. et. al., "Developing Inhibitors . . . for Cancer Treatment", Review, J. Nat. Can. Inst., (Jun. 18, 2003) vol. 95, No. 12, pp. 851-867.*

(Continued)

*Primary Examiner*—James O Wilson
*Assistant Examiner*—Tamthom N Truong
(74) *Attorney, Agent, or Firm*—Morgan, Lewis & Bockius LLP

(57) ABSTRACT

A quinazoline derivative of the Formula (I): wherein the substituents are as defined in the text for use in the production of an anti proliferative effect which effect is produced alone or in part by inhibiting erbB2 receptor tyrosine kinase in a warm-blooded animal such as man.

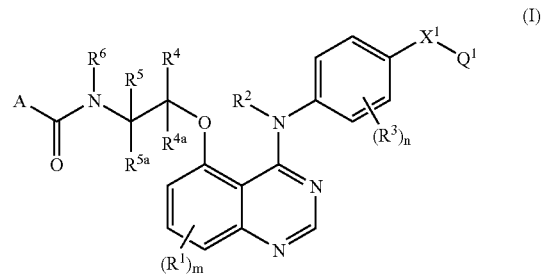

21 Claims, No Drawings

FOREIGN PATENT DOCUMENTS

| | | |
|---|---|---|
| EP | 0288563 | 11/1988 |
| EP | 0 566 226 | 11/1995 |
| EP | 0 602 851 | 10/1996 |
| EP | 0 520 722 | 12/1996 |
| EP | 0 787 722 | 8/1997 |
| EP | 0 837 063 | 4/1998 |
| EP | 0 326 330 | 7/2002 |
| EP | 1230919 | 8/2002 |
| EP | 1369418 | 12/2003 |
| GB | 2295387 | 5/1966 |
| JP | 08-003144 | 1/1996 |
| JP | 11-189586 | 7/1999 |
| WO | WO 88/02365 | 4/1988 |
| WO | WO 92/20642 | 11/1992 |
| WO | WO 93/08170 | 4/1993 |
| WO | WO 93/17682 | 9/1993 |
| WO | WO 95/15758 | 6/1995 |
| WO | WO 96/09294 | 3/1996 |
| WO | WO 96/15118 | 5/1996 |
| WO | WO 96/16960 | 6/1996 |
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/11692 | 4/1997 |
| WO | WO 97/13771 | 4/1997 |
| WO | WO 97/22596 | 6/1997 |
| WO | WO 97/30034 | 8/1997 |
| WO | WO 97/30035 | 8/1997 |
| WO | WO 97/30044 | 8/1997 |
| WO | WO 97/38983 | 10/1997 |
| WO | WO 97/38994 | 10/1997 |
| WO | WO 98/02434 | 1/1998 |
| WO | WO 98/02437 | 1/1998 |
| WO | WO 98/02438 | 1/1998 |
| WO | WO 98/13354 | 4/1998 |
| WO | WO 98/38984 | 9/1998 |
| WO | WO 98/50038 | 11/1998 |
| WO | WO 98/50370 | 11/1998 |
| WO | WO 99/06378 | 2/1999 |
| WO | WO 99/09016 | 2/1999 |
| WO | WO 99/24037 | 5/1999 |
| WO | WO 99/35132 | 7/1999 |
| WO | WO 99/35146 | 7/1999 |
| WO | WO 99/61428 | 12/1999 |
| WO | WO 00/00202 | 1/2000 |
| WO | WO 00/06555 | 2/2000 |
| WO | WO 00/09481 | 2/2000 |
| WO | WO 00/10981 | 3/2000 |
| WO | WO 00/18740 | 4/2000 |
| WO | WO 00/20402 | 4/2000 |
| WO | WO 00/24718 | 5/2000 |
| WO | WO 00/44728 | 8/2000 |
| WO | WO 00/47212 | 8/2000 |
| WO | WO 00/51587 | 9/2000 |
| WO | WO 00/51991 | 9/2000 |
| WO | WO 00/55141 | 9/2000 |
| WO | WO 00/73260 | 12/2000 |
| WO | WO 01/07432 | 2/2001 |
| WO | WO 01/12227 | 2/2001 |
| WO | WO 01/21594 | 3/2001 |
| WO | WO 01/21595 | 3/2001 |
| WO | WO 01/21596 | 3/2001 |
| WO | WO 01/21596 A | 3/2001 |
| WO | WO 01/21597 | 3/2001 |
| WO | WO 01/32632 | 5/2001 |
| WO | WO 01/45641 | 6/2001 |
| WO | WO 01/77085 | 10/2001 |
| WO | WO 01/94341 | 12/2001 |
| WO | WO 01/98277 | 12/2001 |
| WO | WO 02/18372 | 3/2002 |
| WO | WO 02/24684 | 3/2002 |
| WO | WO 02/30924 | 4/2002 |
| WO | WO 02/34744 | 5/2002 |
| WO | WO 02/41882 | 5/2002 |
| WO | WO 02/44166 | 6/2002 |
| WO | WO 02/48117 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |
| WO | WO 02/092577 | 11/2002 |
| WO | WO 02/092578 | 11/2002 |
| WO | WO 02/094790 | 11/2002 |
| WO | WO 03/040108 A | 5/2003 |
| WO | WO 03/040109 A | 5/2003 |
| WO | WO 03/049740 | 6/2003 |
| WO | WO 03/082290 | 10/2003 |
| WO | WO 03/082831 | 10/2003 |
| WO | WO 2004/006846 | 1/2004 |
| WO | WO 2004/046101 | 6/2004 |
| WO | WO 2004/064718 | 8/2004 |
| WO | WO 2004/093880 | 11/2004 |
| WO | WO 2004/096226 | 11/2004 |
| WO | WO 2005/012290 | 11/2004 |
| WO | WO 2005/013998 | 2/2005 |
| WO | WO 2005/026150 | 3/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | WO 2005/030757 | 4/2005 |
| WO | WO 2005/030765 | 4/2005 |
| WO | WO 2005/041973 | 5/2005 |
| WO | WO 2005/075439 | 8/2005 |
| WO | WO 2005/097134 | 10/2005 |
| WO | WO 2005/118572 | 12/2005 |
| WO | WO 2006/008526 | 1/2006 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |
| WO | WO 2006/117521 | 11/2006 |
| WO | WO 2006/117523 | 11/2006 |
| WO | WO 2007/034143 | 3/2007 |
| WO | WO 2007/034144 | 3/2007 |
| WO | WO 2007/063291 | 6/2007 |
| WO | WO 2007/063293 | 6/2007 |

OTHER PUBLICATIONS

Ballard et al. "5-Substituted 4-anilinoquinazolines as potent, selective and orally active inhibitors of erbB2 receptor tyrosine kinase" Bioorg Med Chem Lett. 15(19):4226-4229 (2005).

Ballard et al. "Inhibitors of epidermal growth factor receptor tyrosine kinase: Novel C-5 substituted anilinoquinazolines designed to target the ribose pocket" Bioorg Med Chem Lett. 16(6):1633-1637 (2006).

Barker et al. "Studies leading to the identification of ZD1839 (Iressa™): an orally active, selective epidermal growth factor receptor tyrosine kinase inhibitor targeted to the treatment of cancer" *Bioorganic and Medicinal Chemistry Letters* 11(14):1911-1914 (2001).

Bridges et al. "Tyrosine kinase inhibitors. 8. An unusually steep structure-activity relationship for analogues of 4-(3-bromoanilino)-

6,7-dimethoxyquinazoline (PD 153035), a potent inhibitor of the epidermal growth factor receptor" J. Med. Chem. 39(1):267-276 (1996).

Denny et al. "Structure-activity relationships for 4-anilinoquinazolines as potent inhibitors at the ATP binding site for the epidermal growth factor receptor in vitro" Clinical and Experimental Pharmacology and Physiology 23:424-427 (1996).

Hennequin et al. "Novel 4-Anilinoquinazolines with C-7 Basic Side Chains: Design and Structure Activity Relationship of a Series of Potent, Orally Active, VEGF Receptor Tyrosine Kinase Inhibitors" J. Med. Chem. 45 (6):1300-1312 (2002).

Rewcastle et al. "Tyrosine kinase inhibitors. 5. Synthesis and structure-activity relationships for 4-[(phenylmethyl)amino]- and 4-(phenylamino)quinazolines as potent adenoisine 5'-triphosphate binding site inhibitors of the tyrosine kinase domain of the epidermal growth factor receptor" J. Med. Chem. 38:3482-3487 (1995).

Ballard et al. "Inhibitors of epidermal growth factor receptor tyrosine kinase: optimisation of potency and in vivo pharmacokinetics" Bioorg Med Chem Lett. 16(18):4908-4912 (2006).

Harris et al. "Facile synthesis of 7-amino anilinoquinazolines via direct amination of the quinazoline core" Tetrahedron letters 46(43):7381-7384 (2005).

Harris et al. "Selective alkylation of a 6,7-dihydroxyquinazoline" Tetrahedron letters 46(45):7715-7719 (2005).

Hennequin et al. "Novel 4-anilinoquinazolines with C-6 carbon-linked side chains: synthesis and structure-activity relationship of a series of potent, orally active, EGF receptor tyrosine kinase inhibitors" Bioorg Med Chem Lett. 16(10):2672-2676 (2006).

Stamos et al. "Structure of the Epidermal Growth Factor Receptor Kinase Domain Alone and in Complex with a 4-Anilinoquinazoline Inhibitor" J. Biol. Chem. 277(48):46265-46272 (2002).

Traxler et al. "Protein tyrosine kinase inhibitors in cancer treatment" Exp. Opin. Ther. Patents 7(6):571-588 (1997).

Traxler et al. "Tyrosine kinase inhibitors in cancer treatment (Part II)" Exp. Opin. Ther. Patents 8(12):1599-1625 (1998).

Tsou et al. "6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity" J. Med. Chem. 44:2719-2734 (2001).

Vema et al. "Design of EGFR kinase inhibitors: a ligand-based approach and its confirmation with structure-based studies" Bioorg Med Chem. 11(21):4643-4653 (2003).

Ballard et al. "Developing a small molecule erbB2 inhibitor:challenges with optimising DMPK properties" Poster—Presented at DMDG Cambridge (Feb. 6, 2008).

Ballard et al. "Neutral 5-substituted 4-anilinoquinazolines as potent, orally active inhibitors of erbB2 receptor tyrosine kinase" Bioorg Med Chem Lett. 17(22):6326-6329 (2007).

Barlaam et al. "A new series of neutral 5-substituted 4-anilinoquinazolines as potent, orally active inhibitors of erbB2 receptor tyrosine kinase" Bioorganic & Medicinal Chemistry Letters 18(2):674-678 (2008).

Barlaam et al. "Indazolylamino/Anilinoquinazolines Bearing a C-5 substitution as erbB2 kinase inhibitors: Structure-activity relationships and identification of a candidate drug" at AACR in 2007.

Barlaam et al. "Neutral 5-substituted 4-indazolylaminoquinazolines as potent, orally active inhibitors of erbB2 receptor tyrosine kinase" Bioorganic & Medicinal Chemistry Letters 18(6):1799-1803 (2008).

Barlaam et al. "Indazolylamino/Anilinoquinazolines Bearing a C-5 Substitution As erbB2 Kinase Inhibitors: Structure-Activity Relationships and Identification of a Candidate Drug" Poster No. P044, presented at XXth International Symposium on Medicinal Chemistry (EFMC-ISMC 2008),Vienna, Austria, Aug. 31-Sep. 4, 2008.

Cockerill et al "Indazolylamino quinazolines and pyridopyrimidines as inhibitors of the EGFr and c-erbB-2" Bioorganic & Medicinal Chemistry Letters 11(11):1401-1405 (2001).

Ducray et al. "Novel 3-alkoxy-1H-pyrazolo[3,4-d]pyrimidines as EGFR and erbB2 receptor tyrosine kinase inhibitors" Bioorganic & Medicinal Chemistry Letters 18(3):959-962 (2008).

Gaul et al. "Discovery and Biological Evaluation of Potent Dual ErbB-2/EGFR Tyrosine Kinase Inhibitors: 6-Thiazolylquinazolines" Bioorganic & Medicinal Chemistry Letters 13(4):637-640 (2003).

Harris et al. "Systematic variation of a key quinazoline core" Presented at the XXII European Colloquium on Heterocyclic Chemistry (XXII ECHC-2006) Bari, Italy, Sep. 2-6, 2006.

Hennequin et al. "N-(5-chloro-1,3-benzodioxol-4-y1)-7-[2-(4-methylpiperazin-1-yl)ethoxy]-5- (tetrahydro-2H-pyran-4-yloxy)quinazolin-4-amine a novel, highly selective, orally available, dual-specific c-Src/Abl kinase inhibitor" J Med Chem. 49(22):6465-6488 (2006).

Jani et al. "Discovery and pharmacologic characterization of CP-724,714, a selective ErbB2 tyrosine kinase inhibitor" Cancer Research 67(20):9887-9893 (2007).

Klutchko et al. "Tyrosine Kinase inhibitors. 19. 6-Alkynamides of 4-anilinoquinazolines and 4-anilinopyrido[3,4-d]pyrimidines as irreversible inhibitors of the erbB family of tyrosine kinase receptors" J Med Chem. 49(4):1475-1485 (2006).

Petrov et al. "Optimization and SAR for dual ErbB-1/ErbB-2 tyrosine kinase inhibition in the 6-furanylquinazoline series" Bioorg Med Chem Lett. 16(17):4686-4691 (2006).

* cited by examiner

QUINAZOLINE DERIVATIVES

The invention concerns certain novel quinazoline derivatives, or pharmaceutically acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol*, 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al, Biochimica et Biophysica Acta, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases e.g. EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to 20 receptor tyrosine kinase and 10 non-receptor tyrosine kinase subfamilies (Robinson et al, *Oncogene*, 2000, 19, 5548-5557).

The receptor tyrosine kinases are of particular importance in the transmission of mitogenic signals that initiate cellular replication. These large glycoproteins, which span the plasma membrane of the cell possess an extracellular binding domain for their specific ligands (such as Epidermal Growth Factor (EGF) for the EGF Receptor). Binding of ligand results in the activation of the receptor's kinase enzymatic activity that is encoded by the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.*, 2000, 19, 3159). One mechanism in which this can be accomplished is by overexpression of the receptor at the protein level, generally as a result of gene amplification. This has been observed in many common human cancers (reviewed in Klapper et al., *Adv. Cancer Res.*, 2000, 77, 25) such as breast cancer (Sainsbury et al., *Brit. J. Cancer*, 1988, 58, 458; Guerin et al., *Oncogene Res.*, 1988, 3, 21; Slamon et al., *Science*, 1989, 244, 707; Klijn et al., *Breast Cancer Res. Treat.*, 1994, 29, 73 and reviewed in Salomon et al., *Crit. Rev. Oncol. Hematol.*, 1995, 19, 183), non-small cell lung cancers (NSCLCs) including adenocarcinomas (Cerny et al., *Brit. J. Cancer*, 1986, 54, 265; Reubi et al. *Int. J. Cancer*, 1990, 45, 269; Rusch et al., *Cancer Research*, 1993, 53, 2379; Brabender et al, *Clin. Cancer Res.*, 2001, 7, 1850) as well as other cancers of the lung (Hendler et al., *Cancer Cells*, 1989, 7, 347; Ohsaki et al., *Oncol. Rep.*, 2000, 7, 603), bladder cancer (Neal et al., *Lancet*, 1985, 366; Chow et al, *Clin. Cancer Res.*, 2001, 7, 1957, Zhau et al., *Mol Carcinog.*, 3, 254), oesophageal cancer (Mukaida et al., *Cancer*, 1991, 68, 142), gastrointestinal cancer such as colon, rectal or stomach cancer (Bolen et al., *Oncogene Res.*, 1987, 1, 149; Kapitanovic et al., *Gastroenterology*, 2000, 112, 1103; Ross et al., *Cancer Invest.*, 2001, 19, 554), cancer of the prostate (Visakorpi et al., *Histochem. J.*, 1992, 24, 481; Kumar et al., 2000, 32, 73; Scher et al., *J. Natl. Cancer Inst.*, 2000, 92, 1866), leukaemia (Konaka et al., *Cell*, 1984, 37, 1035, Martin-Subero et al., *Cancer Genet Cytogenet.*, 2001, 127, 174), ovarian (Hellstrom et al., *Cancer Res.*, 2001, 61, 2420), head and neck (Shiga et al., *Head Neck*, 2000, 22, 599) or pancreatic cancer (Ovotny et al., *Neoplasma*, 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors (in particular erbB2), it is widely believed that many tumours become clinically more aggressive and so correlate with a poorer prognosis for the patient (Brabender et al, *Clin. Cancer Res.*, 2001, 7, 1850; Ross et al, *Cancer Investigation*, 2001, 19, 554, Yu et al. *Bioessays*, 2000, 22.7, 673). In addition to these clinical findings, a wealth of preclinical information suggests that the erbB family of receptor tyrosine kinases are involved in cellular transformation. This includes the observations that many tumour cell lines overexpress one or more of the erbB receptors and that EGFR or erbB2 when transfected into non-tumour cells have the ability to transform these cells. This tumourigenic potential has been further verified as transgenic mice that overexpress erbB2 spontaneously develop tumours in the mammary gland. In addition to this, a number of pre-clinical studies have demonstrated that anti-proliferative effects can be induced by knocking out one or more erbB activities by small molecule inhibitors, dominant negatives or inhibitory antibodies (reviewed in Mendelsohn et al., *Oncogene*, 2000, 19, 6550). Thus it has been recognised that inhibitors of these receptor tyrosine kinases should be of value as a selective inhibitor of the proliferation of mammalian cancer cells (Yaish et al. *Science*, 1988, 242, 933, Kolibaba et al, *Biochimica et Biophysica Acta*, 1997, 133, F217-F248; Al-Obeidi et al, 2000, *Oncogene*, 19, 5690-5701; Mendelsohn et al, 2000, *Oncogene*, 19, 6550-6565). In addition to this pre-clinical data, findings using inhibitory antibodies against EGFR and erbB2 (c-225 and trastuzumab respectively) have proven to be beneficial in the clinic for the treatment of selected solid tumours (reviewed in Mendelsohn et al, 2000, *Oncogene*, 19, 6550-6565).

Amplification and/or activity of members of the ErbB type receptor tyrosine kinases have been detected and so have been implicated to play a role in a number of non-malignant proliferative disorders such as psoriasis (Ben-Bassat, *Curr. Pharm. Des.*, 2000, 6, 933; Elder et al., *Science*, 1989, 243, 811), benign prostatic hyperplasia (BPH) (Kumar et al., *Int. Urol. Nephrol.*, 2000, 32, 73), atherosclerosis and restenosis (Bokemeyer et al., *Kidney Int.*, 2000, 58, 549). It is therefore expected that inhibitors of erbB type receptor tyrosine kinases will be useful in the treatment of these and other non-malignant disorders of excessive cellular proliferation.

International Patent Applications WO 96/09294, WO 96/15118, WO 96/16960, WO 96/30347, WO 96/33977, WO 96/33978, WO 96/33979, WO 96/33980, WO 96/33981, WO 97/03069, WO 97/13771, WO 97/30034, WO 97/30035, WO 97/38983, WO 98/02437, WO 98/02434, WO 98/02438, WO 98/13354, WO 99/35132, WO 99/35146, WO 01/21596, WO 01/55141 and WO 02/18372 disclose that certain quinazoline derivatives which bear an anilino substituent at the 4-position possess receptor tyrosine kinase inhibitory activity.

International Patent Applications WO 97/22596 and WO 98/13354 disclose that certain 4-anilinoquinazoline derivatives that are substituted at the 7-position are inhibitors VEGF or mixed VEGF/EGF receptor tyrosine kinase inhibitors. The anilino group in these applications is substituted with small groups such as halogeno or (1-3C)alkyl.

International Patent Application WO 01/94341 discloses that certain quinazoline derivatives which are substituted at the 5-position are inhibitors of the Src family of non-receptor tyrosine kinases, such as c-Src, c-Yes and c-Fyn. There are no disclosures in WO 01/94341 of 4-anilinoquinazolines wherein the aniline group is substituted in the para position by a substituent containing an aryl or a heteroaryl group.

International Patent applications WO 03/040108 and WO 03/040109 disclose that certain 5-substitued quinazoline derivatives are inhibitors of the erbB family of tyrosine kinase inhibitors, particularly EGFR and erb-B2 receptor tyrosine kinases. All the compounds in these applications carry a ring containing substituent at the 5-position on the quinazoline ring.

None of the prior art discloses 4-anilinoquinazolines that are substituted at the 5-position by an acylaminoethoxy group and which carry an aryl or heteroaryl containing substituent at the para-position on the aniline ring.

We have now found that surprisingly certain quinazoline derivatives substituted at the 5-position with a substituent containing an acylaminoethoxy group possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of inhibition of EGFR and/or erbB2 receptor tyrosine kinases.

Generally the compounds of the present invention possess potent inhibitory activity against the erbB receptor tyrosine kinase family, for example by inhibition of EGFR and/or erbB2 and/or erbB4 receptor tyrosine kinases, whilst possessing less potent inhibitory activity against other kinases. Furthermore, generally the compounds of the present invention possess substantially better potency against the erbB2 over that of the EGFR tyrosine kinase, thus potentially providing effective treatment for erbB2 driven tumours. Accordingly, it may be possible to administer a compound according to the present invention at a dose that is sufficient to inhibit erbB2 tyrosine kinase whilst having no significant effect upon EGFR (or other) tyrosine kinases. The selective inhibition provided by the compounds according to the present invention may provide treatments for conditions mediated by erbB2 tyrosine kinase, whilst reducing undesirable side effects that may be associated with the inhibition of other tyrosine kinases. Generally the compounds according to the invention also exhibit favourable DMPK properties, for example high bioavailability, and favourable physical properties such as solubility.

Furthermore, many of the compounds according to the present invention are inactive or only weakly active in a hERG assay.

According to a first aspect of the invention there is provided a quinazoline derivative of the formula I:

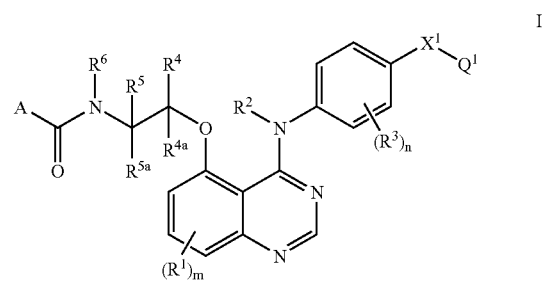

wherein:
  m is 0, 1 or 2;
  each $R^1$, which may be the same or different, is selected from hydroxy, (1-6C)alkoxy, (3-7C)cycloalkyl-oxy and (3-7C)cycloalkyl-(1-6C)alkoxy,
  and wherein any $CH_2$ or $CH_3$ group within a $R^1$ substituent optionally bears on each said $CH_2$ or $CH_3$ group one or more halogeno or (1-6C)alkyl substituents, or a substituent selected from hydroxy and (1-6C)alkoxy,
  $R^2$ is hydrogen or (1-4C)alkyl;
  n is 0, 1, 2, 3 or 4;
  each $R^3$, which may be the same or different, is selected from cyano, halogeno, (1-4C)alkyl, trifluoromethyl, (1-4C)alkoxy, (2-4C)alkenyl and (2-4C)alkynyl;
  $X^1$ is selected from O, S, SO, $SO_2$, $N(R^7)$, $CH(OR^7)$, $CON(R^7)$, $N(R^7)CO$, $SO_2N(R^7)$, $N(R^7)SO_2$, $OC(R^7)_2$, $C(R^7)_2O$, $SC(R^7)_2$, $C(R^7)_2S$, CO, $C(R^7)_2N(R^7)$ and $N(R^7)C(R^7)_2$, wherein each $R^7$, which may be the same or different, is hydrogen or (1-6C)alkyl;

$Q^1$ is aryl, or heteroaryl, and wherein $Q^1$ optionally bears one or more substituents (for example 1, 2 or 3), which may be the same or different, selected from halogeno, cyano, nitro, hydroxy, amino, carboxy, carbamoyl, sulfamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (3-6C)alkenoyl, (3-6C)alkynoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, and a group of the formula:

—$X^2$—$R^8$ wherein $X^2$ is a direct bond or is selected from O, CO and N($R^9$), wherein $R^9$ is hydrogen or (1-6C)alkyl, and $R^8$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkylthio-(1-6C)alkyl, (1-6C)alkylsulfinyl-(1-6C)alkyl, (1-6C)alkylsulfonyl-(1-6C)alkyl sulfamoyl(1-6C)alkyl, N-(1-6C)alkylsulfamoyl(1-6C)alkyl, N,N-di-(1-6C)alkylsulfamoyl(1-6C)alkyl, (2-6C)alkanoyl-(1-6C)alkyl, (2-6C)alkanoyloxy-(1-6C)alkyl or (1-6C)alkoxycarbonyl-(1-6C)alkyl, and wherein any $CH_2$ or $CH_3$ group within —$X^1$-$Q^1$ optionally bears on each said $CH_2$ or $CH_3$ group one or more (for example 1, 2, or 3) halogeno or (1-6C)alkyl substituents or a substituent selected from hydroxy, cyano, amino, (1-4C)alkoxy, (1-4C)alkylamino and di-[(1-4C)alkylamino];

$R^4$, $R^{4a}$, $R^5$ and $R^{5a}$, which may be the same or different, are selected from hydrogen and (1-6C)alkyl, or $R^4$ and $R^{4a}$ together with the carbon atom to which they are attached form a (3-7C)cycloalkyl ring, or $R^5$ and $R^{5a}$ together with the carbon atom to which they are attached form a (3-7C)cycloalkyl ring, and wherein any $CH_2$ or $CH_3$ group within any of $R^4$, $R^{4a}$, $R^5$ and $R^{5a}$ optionally bears on each said $CH_2$ or $CH_3$ group one or more (for example 1, 2 or 3) halogeno substituents or a substituent selected from hydroxy, cyano, (1-6C)alkoxy, amino, (2-6C)alkanoyl, (1-6C)alkylamino and di-[(1-6C)alkylamino];

$R^6$ is selected from hydrogen, (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, and wherein any heterocyclyl group within an $R^6$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^3$—$R^{10}$ wherein $X^3$ is a direct bond or is selected from O, CO, $SO_2$ and N($R^{11}$), wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo or thioxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

A is selected from hydrogen, a group of the formula Z-($CR^{12}R^{13}$)$_p$— and $R^{14}$, wherein p is 1, 2, 3, or 4, each $R^{12}$ and $R^{13}$, which may be the same or different, is selected from hydrogen, (1-6C)alkyl, (2-6C)alkenyl and (2-6C)alkynyl, or an $R^{12}$ and an $R^{13}$ group attached to the same carbon atom form a (3-7C)cycloalkyl or (3-7C)cycloalkenyl ring, and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkyl]amino, Z is selected from hydrogen, $OR^{15}$, $NR^{16}R^{17}$, (1-6C)alkylsulfonyl, (1-6C)alkanesulfonylamino and N-(1-6C)alkyl-(1-6C)alkanesulfonylamino, wherein each of $R^{15}$, $R^{16}$ and $R^{17}$, which may be the same or different, is selected from hydrogen, (1-6C)alkyl, 2-6C)alkenyl, (2-6C)alkynyl and (1-6C)alkoxycarbonyl, or Z is a group of the formula:

$Q^2$-$X^4$— wherein $X^4$ is selected from O, N($R^{18}$), $SO_2$ and $SO_2$N ($R^{18}$), wherein $R^{18}$ is hydrogen or (1-6C)alkyl, and $Q^2$ is (3-7C)cycloalkyl, (3-7C)cycloalkenyl or heterocyclyl, $R^{14}$ is selected from hydrogen, $OR^{19}$ and $NR^{16}R^{17}$, wherein $R^{19}$ is selected from (1-6C)alkyl, (2-6C)alkenyl and (2-6C)alkynyl, and wherein $R^{16}$ and $R^{17}$ are as defined above, or $R^{14}$ is a group of the formula:

$Q^3$-$X^5$— wherein $X^5$ is selected from O and N($R^{20}$), wherein $R^{20}$ is hydrogen or (1-6C)alkyl, and $Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, or $R^{14}$ is $Q^4$ wherein $Q^4$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein adjacent carbon atoms in any (2-6C)alkylene chain within a Z or $R^{14}$ substituent are optionally separated by the insertion into the chain of a group selected from O, S, SO, $SO_2$, $N(R^{21})$, CO, —C═C— and —C≡C—, wherein $R^{21}$ is hydrogen or (1-6C)alkyl, and wherein any heterocyclyl group within a Z or $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$ wherein $X^6$ is a direct bond or is selected from O, CO, $SO_2$ and $N(R^{23})$, wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within a Z or $R^{14}$ substituent optionally bears 1 or 2 oxo or thioxo substituents, and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

or a pharmaceutically acceptable salt thereof.

According to a second aspect of the invention there is provided a quinazoline derivative of the formula I, wherein:
m is 0, 1 or 2;
each $R^1$, which may be the same or different, is selected from hydroxy, (1-6C)alkoxy, (3-7C)cycloalkyl-oxy and (3-7C)cycloalkyl-(1-6C)alkoxy,
and wherein any $CH_2$ or $CH_3$ group within a $R^1$ substituent optionally bears on each said $CH_2$ or $CH_3$ group one or more halogeno or (1-6C)alkyl substituents, or a substituent selected from hydroxy and (1-6C)alkoxy,
$R^2$ is hydrogen or (1-4C)alkyl;
n is 0, 1, 2, 3 or 4;
each $R^3$, which may be the same or different, is selected from halogeno, (1-4C)alkyl, trifluoromethyl, (1-4C)alkoxy, (2-4C)alkenyl and (2-4C)alkynyl;
$X^1$ is selected from O, S, SO, $SO_2$, $N(R^7)$, $CH(OR^7)$, $CON(R^7)$, $N(R^7)CO$, $SO_2N(R^7)$, $N(R^7)SO_2$, $OC(R^7)_2$, $C(R^7)_2O$, $SC(R^7)_2$, $C(R^7)_2S$, CO, $C(R^7)_2N(R^7)$ and $N(R^7)C(R^7)_2$, wherein each $R^7$, which may be the same or different, is hydrogen or (1-6C)alkyl;

$Q^1$ is aryl, or heteroaryl,
and wherein $Q^1$ optionally bears one or more substituents (for example 1, 2 or 3), which may be the same or different, selected from halogeno, cyano, nitro, hydroxy, amino, carboxy, carbamoyl, sulfamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (3-6C)alkenoyl, (3-6C)alkynoyl, (2-6C)alkanoyloxy, (2-6C)alkanoylamino, N-(1-6C)alkyl-(2-6C)alkanoylamino, (3-6C)alkenoylamino,
N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, and a group of the formula:

—$X^2$—$R^8$ wherein $X^2$ is a direct bond or is selected from O, CO and $N(R^9)$, wherein $R^9$ is hydrogen or (1-6C)alkyl, and $R^8$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl,
N-(1-6C)alkyl-(2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkylthio-(1-6C)alkyl, (1-6C)alkylsulfinyl-(1-6C)alkyl, (1-6C)alkylsulfonyl-(1-6C)alkyl sulfamoyl(1-6C)alkyl, N-(1-6C)alkylsulfamoyl(1-6C)alkyl, N,N-di-(1-6C)alkylsulfamoyl(1-6C)alkyl, (2-6C)alkanoyl-(1-6C)alkyl, (2-6C)alkanoyloxy-(1-6C)alkyl or (1-6C)alkoxycarbonyl-(1-6C)alkyl,
and wherein any $CH_2$ or $CH_3$ group within —$X^1$-$Q^1$ optionally bears on each said $CH_2$ or $CH_3$ group one or more (for example 1, 2, or 3) halogeno or (1-6C)alkyl substituents or a substituent selected from hydroxy, cyano, amino, (1-4C)alkoxy, (1-4C)alkylamino and di-[(1-4C)alkylamino];
$R^4$, $R^{4a}$, $R^5$ and $R^{5a}$, which may be the same or different, are selected from hydrogen and (1-6C)alkyl, or
$R^4$ and $R^{4a}$ together with the carbon atom to which they are attached form a (3-7C)cycloalkyl ring, or
$R^5$ and $R^{5a}$ together with the carbon atom to which they are attached form a (3-7C)cycloalkyl ring,
and wherein any $CH_2$ or $CH_3$ group within any of $R^4$, $R^{4a}$, $R^5$ and $R^{5a}$ optionally bears on each said $CH_2$ or $CH_3$ group one or more (for example 1, 2 or 3) halogeno substituents or a substituent selected from hydroxy, cyano, (1-6C)alkoxy, amino, (2-6C)alkanoyl, (1-6C)alkylamino and di-[(1-6C)alkylamino];
$R^6$ is selected from hydrogen, (1-6C)alkenyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl,
and wherein any heterocyclyl group within an $R^6$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^3$—$R^{10}$ wherein $X^3$ is a direct bond or is selected from O, CO, $SO_2$ and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo or thioxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

A is selected from hydrogen, a group of the formula Z-$(CR^{12}R^{13})_p$— and $R^{14}$, wherein p is 1, 2, 3, or 4, each $R^{12}$ and $R^{13}$, which may be the same or different, is selected from hydrogen, (1-6C)alkyl, (2-6C)alkenyl and (2-6C)alkynyl, or an $R^{12}$ and an $R^{13}$ group attached to the same carbon atom form a (3-7C)cycloalkyl or (3-7C)cycloalkenyl ring, and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkyl]amino, Z is selected from hydrogen, $OR^{15}$, $NR^{16}R^{17}$, (1-6C)alkylsulfonyl, (1-6C)alkanesulfonylamino and N-(1-6C)alkyl-(1-6C)alkanesulfonylamino, wherein each of $R^{15}$, $R^{16}$ and $R^{17}$, which may be the same or different, is selected from hydrogen, (1-6C)alkyl, (2-6C)alkenyl and (2-6C)alkynyl, or Z is a group of the formula:

$Q^2$-$X^4$— wherein $X^4$ is selected from O, $N(R^{18})$, $SO_2$ and $SO_2N(R^{18})$, wherein $R^{18}$ is hydrogen or (1-6C)alkyl, and $Q^2$ is (3-7C)cycloalkyl, (3-7C)cycloalkenyl or heterocyclyl, $R^{14}$ is selected from hydrogen, $OR^{19}$ and $NR^{16}R^{17}$, wherein $R^{19}$ is selected from (1-6C)alkyl, (2-6C)alkenyl and (2-6C)alkynyl, and wherein $R^{16}$ and $R^{17}$ are as defined above, or $R^{14}$ is a group of the formula:

$Q^3$-$X^5$— wherein $X^5$ is selected from O and $N(R^{20})$, wherein $R^{20}$ is hydrogen or (1-6C)alkyl, and $Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, or $R^{14}$ is $Q^4$ wherein $Q^4$ is (3-7C)cycloalkyl, (3-7C)cycloalkenyl or heterocyclyl, and wherein adjacent carbon atoms in any (2-6C)alkylene chain within a Z or $R^{14}$ substituent are optionally separated by the insertion into the chain of a group selected from O, S, SO, $SO_2$, $N(R^{21})$, CO, —C=C— and —C≡C—, wherein $R^{21}$ is hydrogen or (1-6C)alkyl, and wherein any heterocyclyl group within a Z or $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$ wherein $X^6$ is a direct bond or is selected from O, CO, $SO_2$ and $N(R^{23})$, wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within a Z or $R^{14}$ substituent optionally bears 1 or 2 oxo or thioxo substituents, and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

or a pharmaceutically acceptable salt thereof.

According to a third aspect of the invention there is provided a quinazoline derivative of the formula I, wherein:

m is 0, 1 or 2;

each $R^1$, which may be the same or different, is selected from hydroxy, (1-6C)alkoxy, (3-7C)cycloalkyl-oxy and (3-7C)cycloalkyl-(1-6C)alkoxy, and wherein any $CH_2$ or $CH_3$ group within a $R^1$ substituent optionally bears on each said $CH_2$ or $CH_3$ group one or more halogeno or (1-6C)alkyl substituents, or a substituent selected from hydroxy and (1-6C)alkoxy, $R^2$ is hydrogen or (1-4C)alkyl;

n is 0, 1, 2, 3 or 4;

each $R^3$, which may be the same or different, is selected from cyano, halogeno, (1-4C)alkyl, trifluoromethyl, (1-4C)alkoxy, (2-4C)alkenyl and (2-4C)alkynyl;

$X^1$ is selected from O, S, SO, $SO_2$, $N(R^7)$, $CH(OR^7)$, $CON(R^7)$, $N(R^7)CO$, $SO_2N(R^7)$, $N(R^7)SO_2$, $OC(R^7)_2$, $C(R^7)_2O$, $SC(R^7)_2$, $C(R^7)_2S$, CO, $C(R^7)_2N(R^7)$ and $N(R^7)C(R^7)_2$, wherein each $R^7$, which may be the same or different, is hydrogen or (1-6C)alkyl;

$Q^1$ is aryl, or heteroaryl, and wherein $Q^1$ optionally bears one or more substituents (for example 1, 2 or 3), which may be the same or different, selected from halogeno, cyano, nitro, hydroxy, amino, carboxy, carbamoyl, sulfamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (3-6C)alkenoyl, (3-6C)alkynoyl, (2-6C)alkanoyloxy, (2-6C)alkanoylamino, N-(1-6C)alkyl-(2-6C)alkanoylamino, (3-6C)alkenoylamino,
N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, and a group of the formula:

$$—X^2—R^8$$

wherein $X^2$ is a direct bond or is selected from O, CO and $N(R^9)$, wherein $R^9$ is hydrogen or (1-6C)alkyl, and $R^8$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl,
N-(1-6C)alkyl-(2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkylthio-(1-6C)alkyl, (1-6C)alkylsulfinyl-(1-6C)alkyl, (1-6C)alkylsulfonyl-(1-6C)alkyl sulfamoyl(1-6C)alkyl, N-(1-6C)alkylsulfamoyl(1-6C)alkyl, N,N-di-(1-6C)alkylsulfamoyl(1-6C)alkyl, (2-6C)alkanoyl-(1-6C)alkyl, (2-6C)alkanoyloxy-(1-6C)alkyl or (1-6C)alkoxycarbonyl-(1-6C)alkyl, and wherein any $CH_2$ or $CH_3$ group within $—X^1$-$Q^1$ optionally bears on each said $CH_2$ or $CH_3$ group one or more (for example 1, 2, or 3) halogeno or (1-6C)alkyl substituents or a substituent selected from hydroxy, cyano, amino, (1-4C)alkoxy, (1-4C)alkylamino and di-[(1-4C)alkylamino];

$R^4$, $R^{4a}$, $R^5$ and $R^{5a}$, which may be the same or different, are selected from hydrogen and (1-6C)alkyl, and wherein any $CH_2$ or $CH_3$ group within any of $R^4$, $R^{4a}$, $R^5$ and $R^{5a}$ optionally bears on each said $CH_2$ or $CH_3$ group one or more (for example 1, 2 or 3) halogeno substituents or a substituent selected from hydroxy, cyano, (1-6C)alkoxy, amino, (2-6C)alkanoyl, (1-6C)alkylamino and di-[(1-6C)alkylamino];

$R^6$ is selected from hydrogen, (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, and wherein any heterocyclyl group within an $R^6$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$—X^3—R^{10}$$

wherein $X^3$ is a direct bond or is selected from O, CO, $SO_2$ and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo or thioxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

A is selected from hydrogen, a group of the formula $Z$-$(CR^{12}R^{13})_p—$ and $R^{14}$, wherein p is 1, 2, 3, or 4, each $R^{12}$ and $R^{13}$, which may be the same or different, is selected from hydrogen, (1-6C)alkyl, (2-6C)alkenyl and (2-6C)alkynyl, or an $R^{12}$ and an $R^{13}$ group attached to the same carbon atom form a (3-7C)cycloalkyl or (3-7C)cycloalkenyl ring, and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkyl]amino, Z is selected from hydrogen, $OR^{15}$, $NR^{16}R^{17}$, (1-6C)alkylsulfonyl, (1-6C)alkanesulfonylamino and N-(1-6C)alkyl-(1-6C)alkanesulfonylamino, wherein each of $R^{15}$, $R^{16}$ and $R^{17}$, which may be the same or different, is selected from hydrogen, (1-6C)alkyl, (2-6C)alkenyl, (2-6C)alkynyl and (1-6C)alkoxycarbonyl, or Z is a group of the formula:

$$Q^2\text{-}X^4—$$

wherein $X^4$ is selected from O, $N(R^{18})$, $SO_2$ and $SO_2N(R^{18})$, wherein $R^{18}$ is hydrogen or (1-6C)alkyl, and $Q^2$ is (3-7C)cycloalkyl, (3-7C)cycloalkenyl or heterocyclyl, $R^{14}$ is selected from hydrogen, $OR^{19}$ and $NR^{16}R^{17}$, wherein $R^{19}$ is selected from (1-6C)alkyl, (2-6C)alkenyl and (2-6C)alkynyl, and wherein $R^{16}$ and $R^{17}$ are as defined above, or $R^{14}$ is a group of the formula:

$$Q^3\text{-}X^5—$$

wherein $X^5$ is selected from O and $N(R^{20})$, wherein $R^{20}$ is hydrogen or (1-6C)alkyl, and $Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, or R$^{14}$ is Q$^4$ wherein Q$^4$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein adjacent carbon atoms in any (2-6C)alkylene chain within a Z or R$^{14}$ substituent are optionally separated by the insertion into the chain of a group selected from O, S, SO, SO$_2$, N(R$^{21}$), CO, —C=C— and —C≡C—, wherein R$^{21}$ is hydrogen or (1-6C)alkyl, and wherein any heterocyclyl group within a Z or R$^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

wherein X$^6$ is a direct bond or is selected from O, CO, SO$_2$ and N(R$^{23}$), wherein R$^{23}$ is hydrogen or (1-4C)alkyl, and R$^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within a Z or R$^{14}$ substituent optionally bears 1 or 2 oxo or thioxo substituents, and wherein any CH$_2$ or CH$_3$ group within a Z or R$^{14}$ group, other than a CH$_2$ group within a heterocyclyl ring, optionally bears on each said CH$_2$ or CH$_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

or a pharmaceutically acceptable salt thereof.

In this specification the generic term "alkyl" includes both straight-chain and branched-chain alkyl groups such as propyl, isopropyl and tert-butyl. However references to individual alkyl groups such as "propyl" are specific for the straight-chain version only and references to individual branched-chain alkyl groups such as "isopropyl" are specific for the branched-chain version only. An analogous convention applies to other generic terms, for example (1-6C)alkoxy includes methoxy, ethoxy and isopropoxy, (1-6C)alkylamino includes methylamino, ethylamino and isopropylamino and di-[(1-6C)alkyl]amino includes dimethylamino, diethylamino and N-isopropyl-N-methylamino.

It is to be understood that, insofar as certain of the compounds of formula I defined above may exist in optically active or racemic forms by virtue of one or more asymmetric carbon atoms, the invention includes in its definition any such optically active or racemic form which possesses the above-mentioned activity. It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ratio 50:50. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the substituents herein (for example Q$^1$) when it is aryl or for the aryl group within a 'Q' group is, for example, phenyl or naphthyl, preferably phenyl.

A suitable value for any one of the substituents herein when it is (3-7C)cycloalkyl or for a (3-7C)cycloalkyl group defined herein within, for example a 'Q' group or R$^1$ substituent is, for example, cyclopropyl, cyclobutyl, cyclopentyl, cyclohexyl, cycloheptyl or bicyclo[2.2.1]heptyl. A suitable value for any one of the substituents herein, when it is (3-7C)cycloalkenyl or for the (3-7C)cycloalkenyl group within a substituent is, for example, cyclobutenyl, cyclopentenyl, cyclohexenyl or cycloheptenyl.

A suitable value for any one of the substituents herein when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulfur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyridinyl, pyrazinyl, 1,3,5-triazenyl, 1,3-benzodioxolyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

Particular heteroaryl groups include, for example, pyridyl, pyrimidyl, pyrazinyl, thiazolyl, isothiazolyl, oxazolyl and isoxazolyl (more particularly pyridyl, pyrazinyl, thiazolyl and isoxazolyl).

A suitable value for any one of the substituents when it is heterocyclyl or for the heterocyclyl group within a substituent is a non-aromatic saturated (i.e. ring systems with the maximum degree of saturation) or partially saturated (i.e. ring systems retaining some, but not the full, degree of unsaturation) 3 to 10 membered monocyclic or bicyclic ring with up to five heteroatoms selected from oxygen, nitrogen and sulfur, which, unless specified otherwise, may be carbon or nitrogen linked, for example oxiranyl, oxetanyl, azetidinyl, dihydrofuranyl, tetrahydrofuranyl, 1,3-dioxolanyl, tetrahydropyranyl, 1,4-dioxanyl, oxepanyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl, decahydroisoquinolinyl or decahydroquinolinyl, particularly tetrahydrofuranyl, tetrahydropyranyl, pyrrolidinyl, morpholinyl, 1,4-oxazepanyl, thiamorpholinyl, 1,1-dioxotetrahydro-4H-1,4-thiazinyl, piperidinyl or piperazinyl, more particularly tetrahydrofuran-2-yl, tetrahydrofuran-3-yl, tetrahydropyran-4-yl, tetrahydrothien-3-yl, tetrahydrothiopyran-4-yl, pyrrolidin-1-yl, pyrrolidin-2-yl, pyrrolidin-3-yl, morpholino, morpholin-2-yl, piperidino, piperidin-4-yl, piperidin-3-yl, piperidin-2-yl or piperazin-1-yl. A nitrogen or sulfur atom within a heterocyclyl group may be oxidized to give the corresponding N or S oxide, for example 1,1-dioxotetrahydrothienyl, 1-oxotetrahydrothienyl, 1,1-dioxotetrahydrothiopyranyl or 1-oxotetrahydrothiopyranyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

Particular heterocyclyl groups include, for example, non-aromatic saturated or partially saturated 3 to 7 membered monocyclic heterocyclyl rings with 1 ring nitrogen or sulfur heteroatom and optionally 1 or 2 heteroatoms selected from nitrogen, oxygen and sulfur. Examples of such rings include azetidinyl, oxazepanyl, pyrrolinyl, pyrrolidinyl, morpholinyl, tetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl or thiomorpholinyl.

Other particular heterocyclyl groups include, for example, 4, 5, 6 or 7 membered monocyclic saturated or partially saturated heterocyclyl rings containing 1 or 2 heteroatoms selected from oxygen, nitrogen and sulfur such as oxetanyl, azetidinyl, dihydrofuranyl, tetrahydrofuranyl, 1,3-dioxolanyl, tetrahydropyranyl, 1,4-dioxanyl, oxepanyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl or tetrahydrothiopyranyl, Further particular heterocyclyl groups include, for example 4, 5, 6 or 7 membered saturated or partially saturated monocyclic heterocyclyl rings containing 1 nitrogen atom and optionally 1 heteroatom selected from nitrogen, oxygen and sulfur such as piperazinyl, pyrrolidinyl, piperidinyl, particularly pyrrolidin-1-yl, pyrrolidin-2-yl, piperazin-1-yl, piperidino or morpholino.

Other heterocyclyl groups include, for example, non-aromatic saturated or partially saturated 4, 5, 6 or 7 membered monocyclic heterocyclyl rings containing 1 or 2 oxygen atoms such as tetrahydrofuranyl, 1,3-dioxolanyl and tetrahydropyranyl (for example tetrahydrofuran-2-yl and tetrahydropyran-4-yl).

A suitable value for a substituent herein when it is heterocyclyl-(1-6C)alkyl is, for example, heterocyclylmethyl, 2-heterocyclylethyl and 3-heterocyclylpropyl. The invention comprises corresponding suitable values for other substituents when, for example, rather than a heterocyclyl-(1-6C)alkyl group, an (3-7C)cycloalkyl-(1-6C)alkyl or (3-7C)cycloalkenyl-(1-6C)alkyl is present.

Suitable values for any of the substituents herein, for example the 'R' groups ($R^1$ to $R^{23}$) or for various groups within a $Q^1$, $X^1$ or A group include:—

| | |
|---|---|
| for halogeno | fluoro, chloro, bromo and iodo; |
| for (1-6C)alkyl: | methyl, ethyl, propyl, isopropyl and tert-butyl; |
| for (2-8C)alkenyl: | vinyl, isopropenyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulfinyl: | methylsulfinyl and ethylsulfinyl; |
| for (1-6C)alkylsulfonyl: | methylsulfonyl and ethylsulfonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl, propionyl, butyryl and isobutyryl; |
| for (3-6C)alkenyl | acryloyl and but-2-enoyl; |
| for (3-6C)alkynoyl: | prop-2-ynoyl; |
| for (2-6C)alkanoyloxy: | acetoxy and propionyloxy; |
| for (2-6C)alkanoylamino: | acetamido and propionamido; |
| for N-(1-6C)alkyl-(2-6C)alkanoylamino: | N-methylacetamido and N-methylpropionamido; |
| for N-(1-6C)alkylsulfamoyl: | N-methylsulfamoyl and N-ethylsulfamoyl; |
| for N,N-di-[(1-6C)alkyl]sulfamoyl: | N,N-dimethylsulfamoyl; |
| for (1-6C)alkanesulfonylamino: | methanesulfonylamino and ethanesulfonylamino; |
| for N-(1-6C)alkyl-(1-6C)alkanesulfonylamino: | N-methylmethanesulfonylamino and N-methylethanesulfonylamino; |
| for (3-6C)alkenoylamino: | acrylamido, methacrylamido and crotonamido; |
| for N-(1-6C)alkyl-(3-6C)alkenoylamino: | N-methylacrylamido and N-methylcrotonamido; |
| for (3-6C)alkynoylamino: | propiolamido; |
| for N-(1-6C)alkyl-(3-6C)alkynoylamino: | N-methylpropiolamido; |
| for amino-(1-6C)alkyl: | aminomethyl, 2-aminoethyl, 1-aminoethyl and 3-aminopropyl; |
| for N-(1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for N,N-di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl; |
| for halogeno-(1-6C)alkyl: | chloromethyl, 2-chloroethyl, 1-chloroethyl and 3-chloropropyl; |
| for hydroxy-(1-6C)alkyl: | hydroxymethyl, 2-hydroxyethyl, 1-hydroxyethyl and 3-hydroxypropyl; |

| | -continued |
|---|---|
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for carboxy-(1-6C)alkyl: | carboxymethyl and 2-carboxyethyl; |
| for cyano-(1-6C)alkyl: | cyanomethyl, 2-cyanoethyl, 1-cyanoethyl and 3-cyanopropyl; |
| for (1-6C)alkylthio-(1-6C)alkyl: | methylthiomethyl, ethylthiomethyl, 2-methylthioethyl, 1-methylthioethyl and 3-methylthiopropyl; |
| for (1-6C)alkylsulfinyl-(1-6C)alkyl: | methylsulfinylmethyl, ethylsulfinylmethyl, 2-methylsulfinylethyl, 1-methylsulfinylethyl and 3-methylsulfinylpropyl; |
| for (1-6C)alkylsulfonyl-(1-6C)alkyl: | methylsulfonylmethyl, ethylsulfonylmethyl, 2-methylsulfonylethyl, 1-methylsulfonylethyl and 3-methylsulfonylpropyl; |
| for (2-6C)alkanoylamino-(1-6C)alkyl: | acetamidomethyl, propionamidomethyl and 2-acetamidoethyl; |
| for N-(1-6C)alkyl-(2-6C)alkanoylamino-(1-6C)alkyl: | N-methylacetamidomethyl, 2-(N-methylacetamido)ethyl and 2-(N-methylpropionamido)ethyl; |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl; |
| for (2-6C)alkanoyl-(1-6C)alkyl: | acetylmethyl and 2-acetylethyl; |
| (2-6C)alkanoyloxy-(1-6C)alkyl: | acetoxymethyl, 2-acetoxyethyl and 2-propionyloxyethyl; |
| for carbamoyl-(1-6C)alkyl: | carbamoylmethyl, 1-carbamoylethyl, 2-carbamoylethyl and 3-carbamoylpropyl; |
| for N-(1-6C)alkylcarbamoyl-(1-6C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for N,N-di[(1-6C)alkyl]carbamoyl-(1-6C)alkyl: | N,N-dimethylcarbamoylmethyl, N,N-diethylcarbamoylmethyl, 2-(N,N-dimethylcarbamoyl)ethyl, and 3-(N,N-dimethylcarbamoyl)propyl; |
| for sulfamoyl(1-6C)alkyl: | sulfamoylmethyl, 1-sulfamoylethyl, 2-sulfamoylethyl and 3-sulfamoylpropyl; |
| for N-(1-6C)alkylsulfamoyl(1-6C)alkyl: | N-methylsulfamoylmethyl, N-ethylsulfamoylmethyl, N-propylsulfamoylmethyl, 1-(N-methylsulfamoyl)ethyl, 2-(N-methylsulfamoyl)ethyl and 3-(N-methylsulfamoyl)propyl; and |
| for N,N di-(1-6C)alkylsulfamoyl(1-6C)alkyl: | N,N-dimethylsulfamoylmethyl, N,N-diethylsulfamoylmethyl, N methyl, N-ethylsulfamoylmethyl, 1-(N,N-dimethylsulfamoyl)ethyl, 1-(N,N-diethylsulfamoyl)ethyl, 2-(N,N-dimethylsulfamoyl)ethyl, 2-(N,N-diethylsulfamoyl)ethyl and 3-(N,N-dimethylsulfamoyl)propyl. |

When in this specification reference is made to a (1-4C) alkyl group it is to be understood that such groups refer to alkyl groups containing up to 4 carbon atoms. A skilled person will realise that representative examples of such groups are those listed above under (1-6C)alkyl that contain up to 4 carbon atoms, such as methyl, ethyl, propyl, isopropyl, butyl and tert-butyl. Similarly, reference to a (1-3C)alkyl group refers to alkyl groups containing up to 3 carbon atoms such as methyl, ethyl, propyl and isopropyl. A similar convention is adopted for the other groups listed above such as (1-4C) alkoxy, (2-4C)alkenyl, (2-4C)alkynyl and (2-4C)alkanoyl.

When, as defined hereinbefore, in the group of the formula —$X^1$-$Q^1$, and $X^1$ is, for example, a OC($R^7$)$_2$ linking group, it is the oxygen atom, not the carbon atom, of the OC($R^7$)$_2$ linking group which is attached to the phenyl ring in the formula I and the carbon atom is attached to the $Q^1$ group. Similarly when $X^1$ is a N($R^7$)C($R^7$)$_2$ linking group the nitrogen atom of the N($R^7$)C($R^7$)$_2$ group is attached to the phenyl ring in formula I and the carbon atom is attached to the $Q^1$ group. A similar convention is applied to other linking groups used herein, for example when A is a group of the formula Z-(C$R^{12}R^{13}$)$_p$— and Z is $Q^2$-$X^4$— and $X^4$ is SO$_2$N($R^{18}$), the SO$_2$ group is attached to $Q^2$ and the nitrogen atom is attached to $X^4$ in formula I.

It is to be understood that references herein to adjacent carbon atoms in any (2-6C)alkylene chain within a group may be optionally separated by the insertion into the chain of a group such as O or C≡C refer to insertion of the specified group between two carbon atoms in an alkylene chain. For example, when A is $R^{14}$ and $R^{14}$ is a 2-pyrrolidin-1-ylethoxy group insertion of a C≡C group into the ethylene chain gives rise to a 4-pyrrolidin-1-ylbut-2-ynyloxy group.

When reference is made herein to a CH$_2$ or CH$_3$ group optionally bearing on each said CH$_2$ or CH$_3$ group one or more halogeno or (1-6C)alkyl substituents, there are suitably 1 or 2 halogeno or (1-6C)alkyl substituents present on each said $CH_2$ group and there are suitably 1, 2 or 3 such substituents present on each said $CH_3$ group.

Where reference is made herein to any $CH_2$ or $CH_3$ group optionally bearing on each said $CH_2$ or $CH_3$ group a substituent as defined herein, suitable substituents so formed include, for example, hydroxy-substituted heterocyclyl-(1-6C)alkoxy groups such as 2-hydroxy-3-piperidinopropoxy and 2-hydroxy-3-morpholinopropoxy, hydroxy-substituted heterocyclyl-(1-6C)alkylamino groups such as 2-hydroxy-3-piperidinopropylamino and 2-hydroxy-3-morpholinopropylamino, and hydroxy-substituted (2-6)alkanoyl groups such as hydroxyacetyl, 2-hydroxypropionyl and 2-hydroxybutyryl.

Where reference is made herein to, for example, $R^4$ and $R^{4a}$ together with the carbon atom to which they are attached forming a (3-7C)cycloalkyl ring herein, the ring so formed is a (3-7C)cycloalkylidene group, for example a cyclopropylidene group of the formula:

wherein * represent the bonds from the cyclopropylidene group.

It is to be understood that the quinazoline in formula I is unsubstituted at the 2-position on the quinazoline ring.

It is to be understood that certain compounds of the formula I may exist in solvated as well as unsolvated forms such as, for example, hydrated forms. It is to be understood that the invention encompasses all such solvated forms which exhibit an inhibitory effect on an erbB receptor tyrosine kinase.

It is also to be understood that certain compounds of the formula I may exhibit polymorphism, and that the invention encompasses all such forms which exhibit an inhibitory effect on an erbB receptor tyrosine kinase.

It is also to be understood that the invention relates to all tautomeric forms of the compounds of the formula I forms which exhibit an inhibitory effect on an erbB receptor tyrosine kinase.

A suitable pharmaceutically acceptable salt of a compound of the formula I is, for example, an acid-addition salt of a compound of the formula I, for example an acid-addition salt with an inorganic or organic acid such as hydrochloric, hydrobromic, sulfuric, trifluoroacetic, citric or maleic acid; or, for example, a salt of a compound of the formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinazoline derivatives of the formula I, or pharmaceutically acceptable salts thereof, wherein, unless otherwise stated, each of $R^1$, $R^2$, $R^3$, $R^4$, $R^{4a}$, $R^5$, $R^{5a}$, $X^1$, $Q^1$, m, n and A has any of the meanings defined hereinbefore or in paragraphs (a) to (yyyyyy) hereinafter:—

(a) m is 0 or 1 and $R^1$, when present, is located at the 7-position on the quinazoline ring in formula I;

(b) $R^1$ is selected from hydroxy, (1-6C)alkoxy, hydroxy(1-6C)alkoxy, (1-6C)alkoxy-(1-6C)alkoxy, (3-7C)cycloalkyl-oxy and (3-7C)cycloalkyl-(1-6C)alkoxy, and wherein any $CH_2$ or $CH_3$ group within a $R^1$ substituent optionally bears on each said $CH_2$ or $CH_3$ group one or more substituents selected from fluoro and chloro;

(c) m is 0 or 1 and $R^1$, when present, is located at the 7-position on the quinazoline ring and is selected from (1-6C)alkoxy, cyclopropyl-(1-4C)alkoxy, cyclobutyl-(1-4C)alkoxy, cyclopentyl-(1-4C)alkoxy and cyclohexyl-(1-6C)alkoxy, and wherein any $CH_2$ or $CH_3$ group within a $R^1$ substituent optionally bears on each said $CH_2$ or $CH_3$ group one or more fluoro or chloro substituents, or a substituent selected from hydroxy, methoxy and ethoxy;

(d) m is 1 and $R^1$ is located at the 7-position on the quinazoline ring and is (1-4C)alkoxy, for example methoxy or ethoxy, and wherein any $CH_2$ or $CH_3$ group within a $R^1$ substituent optionally bears on each said $CH_2$ or $CH_3$ group one or more fluoro or chloro substituents, or a substituent selected from hydroxy, methoxy and ethoxy;

(e) m is 1 and $R^1$ is located at the 7-position on the quinazoline ring and is selected from methoxy, ethoxy, propyloxy, isopropyloxy, cyclopropylmethoxy, 2-hydroxyethoxy, 2-fluoroethoxy, 2-methoxyethoxy, 2-ethoxyethoxy, trifluoromethoxy, 2,2-difluoroethoxy and 2,2,2-trifluoroethoxy;

(f) m is 1 and $R^1$ is located at the 7-position on the quinazoline ring and is methoxy;

(g) m is 0;

(h) $R^2$ is hydrogen or methyl;

(i) $R^2$ is hydrogen;

(j) n is 0, 1 or 2 and, when present, at least one $R^3$ is in a meta-position (3-position) relative to the nitrogen of the anilino group in formula I;

(k) n is 0, 1 or 2 and, when present, at least one $R^3$ is in a meta-position (3-position) relative to the nitrogen of the anilino group in formula I, and wherein $R^3$ is selected from halogeno, (1-4C)alkyl, (1-4C)alkoxy and (2-4C)alkynyl;

(l) n is 0, 1 or 2 and, when present, at least one $R^3$ is in a meta-position (3-position) relative to the nitrogen of the anilino group in formula I, and wherein $R^3$ is selected from halogeno and (1-4C)alkyl;

(m) n is 0 or 1 and, when present, $R^3$ is in a meta-position (3-position) relative to the nitrogen of the anilino group in formula I, and wherein $R^3$ is selected from halogeno (particularly fluoro or chloro) and (1-4C)alkyl;

(n) n is 0 or 1 and, when present, $R^3$ is in a meta-position (3-position) relative to the nitrogen of the anilino group in formula I, and wherein $R^3$ is selected from cyano, fluoro, chloro, methyl, methoxy and ethynyl (particularly fluoro, chloro, methyl, methoxy and ethynyl);

(o) n is 1 and $R^3$ is in a meta-position (3-position) relative to the nitrogen of the anilino group in formula I, and wherein $R^3$ is selected from halogeno (particularly fluoro or chloro) and (1-4C)alkyl;

(p) n is 1 and $R^3$ is in a meta-position (3-position) relative to the nitrogen of the anilino group in formula I, and wherein $R^3$ is selected from cyano, fluoro, chloro, methyl, methoxy and ethynyl (particularly fluoro, chloro, methyl, methoxy and ethynyl);

(q) n is 1 and $R^3$ is in a meta-position (3-position) relative to the nitrogen of the anilino group in formula I, and wherein $R^3$ is selected from chloro and methyl;

(r) n is 1, $R^3$ chloro and wherein $R^3$ is in a meta-position (3-position) relative to the nitrogen of the anilino group in formula I;

(s) n is 1, $R^3$ is methyl and wherein $R^3$ is in a meta-position (3-position) relative to the nitrogen of the anilino group in formula I;

(t) $X^1$ is selected from O, S, OC($R^7$)$_2$, SC($R^7$)$_2$, SO, SO$_2$, N($R^7$), CO and N($R^7$)C($R^7$)$_2$ wherein each $R^7$, which may be the same or different, is selected from hydrogen or (1-6C)alkyl;

(u) $X^1$ is selected from O, S and OC($R^7$)$_2$ wherein each $R^7$ is, independently, hydrogen or (1-4C)alkyl;

(v) $X^1$ is selected from S and OC($R^7$)$_2$ wherein each $R^7$ is, independently, hydrogen or (1-4C)alkyl;

(w) $X^1$ is selected from O and OC($R^7$)$_2$ wherein each $R^7$ is, independently, hydrogen or (1-4C)alkyl (particularly hydrogen or (1-2C)alkyl);

(x) $X^1$ is selected from O, S, OCH$_2$ and OC(CH$_3$)$_2$;

(y) $X^1$ is selected from O, OCH$_2$ and OC(CH$_3$)$_2$;

(z) $X^1$ is selected from O, S and OCH$_2$;

(aa) $X^1$ is O;

(bb) $X^1$ is S;

(cc) $X^1$ is OCH$_2$;

(dd) $X^1$ is OC(CH$_3$)$_2$;

(ee) $X^1$ is selected from O, OCH$_2$ and OC(CH$_3$)$_2$, n is 0 or 1 and, when present, $R^3$ is selected from halogeno (particularly chloro) and (1-4C)alkyl (particularly methyl);

(ff) $X^1$ is OCH$_2$, n is 0 or 1 and, when present, $R^3$ is halogeno, particularly chloro;

(gg) $X^1$ is OCH$_2$, n is 1, $R^3$ is selected from fluoro, chloro and methyl (particularly chloro and methyl), and wherein $R^3$ is in a meta-position (3-position) relative to the nitrogen of the anilino group in formula I;

(hh) $X^1$ is O, n is 1, $R^3$ is selected from fluoro, chloro and methyl (particularly chloro and methyl), and wherein $R^3$ is in a meta-position (3-position) relative to the nitrogen of the anilino group in formula I;

(ii) $X^1$ is O, n is 1, $R^3$ is methyl, and wherein $R^3$ is in a meta-position (3-position) relative to the nitrogen of the anilino group in formula I;

(jj) $X^1$ is OC(CH$_3$)$_2$, n is 1, $R^3$ is selected from fluoro, chloro and methyl (particularly chloro and methyl), and wherein $R^3$ is in a meta-position (3-position) relative to the nitrogen of the anilino group in formula I;

(kk) $X^1$ is OC(CH$_3$)$_2$, n is 1, $R^3$ is chloro, and wherein $R^3$ is in a meta-position (3-position) relative to the nitrogen of the anilino group in formula I;

(ll) $Q^1$ is selected from phenyl and a 5- or 6-membered monocyclic heteroaryl ring, which ring contains 1, 2 or 3 heteroatoms independently selected from oxygen, nitrogen and sulfur, and wherein $Q^1$ optionally bears one or more substituents (for example 1, 2 or 3), which may be the same or different, selected from halogeno, cyano, nitro, hydroxy, amino, carboxy, carbamoyl, sulfamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (3-6C)alkenoyl, (3-6C)alkynoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, and a group of the formula:

—$X^2$—$R^8$ wherein $X^2$ is a direct bond or is selected from O, CO and N($R^9$), wherein $R^9$ is hydrogen or (1-6C)alkyl, and $R^8$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkylthio-(1-6C)alkyl, (1-6C)alkylsulfinyl-(1-6C)alkyl, (1-6C)alkylsulfonyl-(1-6C)alkyl sulfamoyl(1-6C)alkyl, N-(1-6C)alkylsulfamoyl(1-6C)alkyl, N,N-di-(1-6C)alkylsulfamoyl(1-6C)alkyl, (2-6C)alkanoyl-(1-6C)alkyl, (2-6C)alkanoyloxy-(1-6C)alkyl or (1-6C)alkoxycarbonyl-(1-6C)alkyl, and wherein any CH$_2$ or CH$_3$ group within —$X^1$-$Q^1$ optionally bears on each said CH$_2$ or CH$_3$ group one or more (for example 1, 2, or 3) halogeno or (1-6C)alkyl substituents or a substituent selected from hydroxy, cyano, amino, (1-4C)alkoxy, (1-4C)alkylamino and di-[(1-4C)alkylamino];

(mm) $Q^1$ is selected from phenyl and a 5- or 6-membered monocyclic heteroaryl ring, which ring contains 1 nitrogen heteroatom and optionally 1 additional heteroatom selected from oxygen, nitrogen and sulfur, and wherein $Q^1$ optionally bears one or more substituents (for example 1, 2 or 3), which may be the same or different, as hereinbefore defined in (ll), (nn) $Q^1$ is phenyl, and wherein $Q^1$ optionally bears one or more substituents (for example 1, 2 or 3), which may be the same or different, as hereinbefore defined in (ll);

(oo) $Q^1$ is a 5- or 6-membered monocyclic heteroaryl ring, which ring contains 1 nitrogen heteroatom and optionally 1 additional heteroatom selected from oxygen, nitrogen and sulfur, and wherein $Q^1$ optionally bears one or more substituents (for example 1, 2 or 3), which may be the same or different, as hereinbefore defined in (ll);

(pp) $Q^1$ is selected from phenyl, pyridyl, pyrazinyl, 1,3-thiazolyl, 1H-imidazolyl, 1H-pyrazolyl, 1,3-oxazolyl and isoxazolyl, and wherein $Q^1$ optionally bears one or more substituents (for example 1, 2 or 3), which may be the same or different, as hereinbefore defined in (ll);

(qq) $Q^1$ is selected from phenyl, pyridyl, pyrazinyl, 1,3-thiazolyl and isoxazolyl, and wherein $Q^1$ optionally bears one or more substituents (for example 1, 2 or 3), which may be the same or different, as hereinbefore defined in (ll);

(rr) $Q^1$ is selected from pyridyl, pyrazinyl, 1,3-thiazolyl and isoxazolyl, and wherein $Q^1$ optionally bears one or more substituents (for example 1, 2 or 3), which may be the same or different, as hereinbefore defined in (ll);

(ss) $Q^1$ is selected from phenyl, 2-, 3- or 4-pyridyl, 2-pyrazinyl, 1,3-thiazol-2-yl, 1,3-thiazol-4-yl, 1,3-thiazol-5-yl, 3-isoxazolyl, 4-isoxazolyl and 5-isoxazolyl, and wherein $Q^1$ optionally bears one or more substituents (for example 1, 2 or 3), which may be the same or different, as hereinbefore defined in (ll);

(tt) $Q^1$ is selected from 2-, 3- or 4-pyridyl, 2-pyrazinyl, 1,3-thiazol-2-yl, 1,3-thiazol-4-yl, 1,3-thiazol-5-yl, 3-isoxazolyl, 4-isoxazolyl and 5-isoxazolyl, and wherein $Q^1$ optionally bears one or more substituents (for example 1, 2 or 3), which may be the same or different, as hereinbefore defined in (ll);

(uu) $Q^1$ is selected from phenyl, 2-pyridyl, 3-pyridyl, 2-pyrazinyl, 1,3-thiazol-2-yl, 1,3-thiazol-4-yl and 3-isoxazolyl, and wherein $Q^1$ optionally bears one or more substituents (for example 1, 2 or 3), which may be the same or different, as hereinbefore defined in (ll);

(vv) $Q^1$ is selected from 2-pyridyl, 3-pyridyl, 2-pyrazinyl, 1,3-thiazol-2-yl, 1,3-thiazol-4-yl and 3-isoxazolyl, and wherein $Q^1$ optionally bears one or more substituents (for example 1, 2 or 3), which may be the same or different, as hereinbefore defined in (ll);

(ww) $Q^1$ is selected from 2-pyridyl, 2-pyrazinyl, 1,3-thiazol-4-yl, 1,3-thiazol-5-yl and 3-isoxazolyl, and wherein $Q^1$ optionally bears one or more substituents (for example 1, 2 or 3), which may be the same or different, as hereinbefore defined in (ll);

(xx) $Q^1$ is pyrazinyl (particularly 2-pyrazinyl), which optionally bears one or more substituents (for example 1, 2 or 3), which may be the same or different, as hereinbefore defined in (ll);

(yy) $Q^1$ is isoxazolyl (particularly isoxazol-3-yl), which optionally bears one or more substituents (for example 1, 2 or 3), which may be the same or different, as hereinbefore defined in (ll);

(zz) $Q^1$ is pyridyl (particularly 2-pyridyl or 3-pyridyl, more particularly 2-pyridyl), which optionally bears one or more substituents (for example 1, 2 or 3), which may be the same or different, as hereinbefore defined in (ll);

(aaa) $Q^1$ is 1,3-thiazolyl (particularly 1,3-thiazol-4-yl or 1,3-thiazolyl-2-yl), which optionally bears one or more substituents (for example 1, 2 or 3), which may be the same or different, as hereinbefore defined in (ll);

(bbb) $Q^1$ is selected from phenyl, pyridyl, pyrazinyl, thiazolyl and isoxazolyl, and wherein $Q^1$ optionally bears one or more substituents (for example 1, 2 or 3), which may be the same or different, selected from halogeno, hydroxy, cyano, carboxy, nitro, amino, (1-4C)alkyl, (1-4C)alkoxy, (2-4C)alkenyl, (2-4C)alkynyl, (1-4C)alkylthio, (1-4C)alkylsulfinyl, (1-4C)alkylsulfonyl, (2-4C)alkanoyl, N-(1-4C)alkylamino, N,N-di-[(1-4C)alkyl]amino, (1-4C)alkoxycarbonyl, carbamoyl, N-(1-4C)alkylcarbamoyl, N,N-di-[(1-4C)alkyl]carbamoyl, (2-4C)alkanoyloxy, (2-4C)alkanoylamino, N-(1-4C)alkyl-(2-4C)alkanoylamino, halogeno-(1-4C)alkyl, hydroxy-(1-4C)alkyl, (1-4C)alkoxy-(1-4C)alkyl, cyano-(1-4C)alkyl, carboxy-(1-4C)alkyl, amino-(1-4C)alkyl, N-(1-4C)alkylamino-(1-4C)alkyl and N,N-di-[(1-4C)alkyl]amino-(1-4C)alkyl;

(ccc) $Q^1$ is selected from phenyl and a 5- or 6-membered monocyclic heteroaryl ring, which ring contains 1 nitrogen heteroatom and optionally 1 additional heteroatom selected from oxygen, nitrogen and sulfur, and wherein $Q^1$ optionally bears one or more substituents (for example 1, 2 or 3), which may be the same or different as hereinbefore defined in (bbb), (ddd) $Q^1$ is phenyl, and wherein $Q^1$ optionally bears one or more substituents (for example 1, 2 or 3), which may be the same or different, as hereinbefore defined in (bbb);

(eee) $Q^1$ is selected from pyridyl, pyrazinyl, 1,3-thiazolyl and isoxazolyl, and wherein $Q^1$ optionally bears one or more substituents (for example 1, 2 or 3), which may be the same or different, as hereinbefore defined in (bbb);

(fff) $Q^1$ is selected from phenyl, 2-, 3- or 4-pyridyl, 2-pyrazinyl, 1,3-thiazol-2-yl, 1,3-thiazol-4-yl, 1,3-thiazol-5-yl, 3-isoxazolyl, 4-isoxazolyl and 5-isoxazolyl, and wherein $Q^1$ optionally bears one or more substituents (for example 1, 2 or 3), which may be the same or different, as hereinbefore defined in (bbb);

(ggg) $Q^1$ is selected from phenyl, 2-pyridyl, 3-pyridyl, 2-pyrazinyl, 1,3-thiazol-2-yl, 1,3-thiazol-4-yl and 3-isoxazolyl, and wherein $Q^1$ optionally bears one or more substituents (for example 1, 2 or 3), which may be the same or different, as hereinbefore defined in (bbb);

(hhh) $Q^1$ is selected from 2-pyridyl, 3-pyridyl, 2-pyrazinyl, 1,3-thiazol-2-yl, 1,3-thiazolyl and 3-isoxazolyl, and wherein $Q^1$ optionally bears one or more substituents (for example 1, 2 or 3), which may be the same or different, as hereinbefore defined in (bbb);

(iii) $Q^1$ is pyrazinyl (particularly 2-pyrazinyl), which optionally bears one or more substituents (for example 1, 2 or 3), which may be the same or different, as hereinbefore defined in (bbb);

(jjj) $Q^1$ is isoxazolyl (particularly isoxazol-3-yl), which optionally bears one or more substituents (for example 1, 2 or 3), which may be the same or different, as hereinbefore defined in (bbb);

(kkk) $Q^1$ is pyridyl (particularly 2-pyridyl or 3-pyridyl, more particularly 2-pyridyl), which optionally bears one or more substituents (for example 1, 2 or 3), which may be the same or different, as hereinbefore defined in (bbb);

(lll) $Q^1$ is 1,3-thiazolyl (particularly 1,3-thiazol-4-yl or 1,3-thiazolyl-2-yl), which optionally bears one or more substituents (for example 1, 2 or 3), which may be the same or different, as hereinbefore defined in (bbb);

(mmm) $Q^1$ is selected from phenyl, pyridyl, pyrazinyl, thiazolyl and isoxazolyl, and wherein $Q^1$ optionally bears one or more substituents (for example 1, 2 or 3), which may be the same or different, selected from fluoro, chloro, bromo, hydroxy, carboxy, cyano, nitro, amino, methyl, ethyl, isopropyl, methoxy, ethoxy, vinyl, allyl, ethynyl, 2-propynyl, methylthio, methylsulfinyl, methylsulfonyl, acetyl, propionyl, methylamino, ethylamino, N,N-dimethylamino, N,N-diethylamino, N-methyl-N-ethylamino methoxycarbonyl, ethoxycarbonyl, carbamoyl, N-methylcarbamoyl, N,N-dimethylcarbamoyl, acetoxy, acetamido, fluoromethyl, 2-fluoroethyl, chloromethyl, 2-chloroethyl, hydroxymethyl, 2-hydroxyethyl, methoxymethyl, 2-methoxyethyl, cyanomethyl, 2-cyanoethyl, carboxymethyl, 2-carboxymethyl, aminomethyl, methylaminomethyl, ethylaminomethyl, N,N-dimethylaminomethyl, N,N-diethylaminomethyl, N-methyl-N-ethylaminomethyl, 2-aminoethyl, 2-(methylamino)ethyl, 2-(ethylamino)ethyl, 2-(N,N-dimethylamino)ethyl, 2-(N,N-diethylamino)ethyl, 2-(N-methyl-N-ethylamino)ethyl, carbamoylmethyl, N-methylcarbamoylmethyl and N,N-dimethylcarbamoylmethyl;

(nnn) $Q^1$ is selected from phenyl, 2-pyridyl, 3-pyridyl, 2-pyrazinyl, 1,3-thiazol-2-yl, 1,3-thiazol-4-yl and isoxazol-3-yl, and wherein $Q^1$ optionally bears 1, 2, or 3 substituents, which may be the same or different, as hereinbefore defined in (mmm);

(ooo) Q¹ is selected from phenyl, 2-pyridyl, 2-pyrazinyl, 1,3-thiazol-4-yl, 1,3-thiazol-5-yl and isoxazol-3-yl,
and wherein Q¹ optionally bears 1, 2, or 3 substituents, which may be the same or different, as hereinbefore defined in (mmm);
(ppp) Q¹ is selected from phenyl, 2-pyridyl, 3-pyridyl, 2-pyrazinyl, 1,3-thiazol-2-yl, 1,3-thiazol-4-yl and isoxazol-3-yl,
and wherein Q¹ optionally bears 1, 2, or 3 substituents, which may be the same or different, selected from halogeno (for example fluoro or chloro), hydroxy, (1-4C)alkyl and (1-4C)alkoxy;
(qqq) Q¹ is selected from phenyl, 2-pyridyl, 2-pyrazinyl, 1,3-thiazol-4-yl, 1,3-thiazol-5-yl and isoxazol-3-yl,
and wherein Q¹ optionally bears 1, 2, or 3 substituents, which may be the same or different, selected from halogeno (for example fluoro or chloro), hydroxy, (1-4C)alkyl and (1-4C)alkoxy;
(rrr) Q¹ is selected from phenyl, 2-pyridyl, 3-pyridyl, 2-pyrazinyl, 1,3-thiazol-2-yl, 1,3-thiazol-4-yl and isoxazol-3-yl (particularly phenyl, 2-pyridyl, 3-pyridyl and isoxazol-3-yl),
and wherein Q¹ optionally bears 1, 2, or 3 substituents, which may be the same or different, selected from halogeno (for example fluoro or chloro) and (1-4C)alkyl (for example methyl);
(sss) Q¹ is phenyl which bears 1 or 2 substituents, which may be the same or different, selected from halogeno (particularly fluoro and chloro, more particularly fluoro);
(ttt) Q¹ is selected from 2-fluorophenyl and 3-fluorophenyl;
(uuu) Q¹ is 3-fluorophenyl;
(vvv) Q¹ is 2-fluorophenyl;
(www) Q¹ is pyridyl (for example 2-pyridyl or 3-pyridyl) which optionally bears 1 or 2 substituents, which may be the same or different, selected from fluoro, chloro, hydroxy, (1-4C)alkyl and (1-4C)alkoxy (particularly (1-4C)alkyl, for example methyl);
(xxx) Q¹ is 2-pyridyl which optionally bears 1 or 2 substituents, which may be the same or different, selected from fluoro, chloro, hydroxy, (1-4C)alkyl and (1-4C)alkoxy;
(yyy) Q¹ is selected from 2-pyridyl, 6-methyl-pyrid-2-yl and 6-methyl-pyrid-3-yl;
(zzz) Q¹ is 2-pyridyl;
(aaaa) Q¹ is 6-methyl-pyrid-2-yl;
(bbbb) Q¹ is 6-methyl-pyrid-3-yl;
(cccc) Q¹ is 1,3-thiazolyl (for example 1,3-thiazol-2-yl or 1,3-thiazol-4-yl) which optionally bears 1 or 2 substituents, which may be the same or different, selected from fluoro, chloro, hydroxy, (1-4C)alkyl and (1-4C)alkoxy;
(dddd) Q¹ is 1,3-thiazol-2-yl;
(eeee) Q¹ is 1,3-thiazol-4-yl;
(ffff) Q¹ is pyrazinyl (for example 2-pyrazinyl) which optionally bears 1 or 2 substituents, which may be the same or different, selected from fluoro, chloro, hydroxy, (1-4C)alkyl and (1-4C)alkoxy;
(gggg) Q¹ is 2-pyrazinyl;
(hhhh) Q¹ is isoxazolyl (for example 3-isoxazolyl) which optionally bears 1 or 2 substituents, which may be the same or different, selected from fluoro, chloro, hydroxy, (1-4C)alkyl and (1-4C)alkoxy (particularly (1-4C)alkyl, for example methyl);
(iiii) Q¹ is 5-methyl-isoxazol-3-yl;
(jjjj) Q¹ is selected from phenyl, pyridyl, pyrazinyl, thiazolyl and isoxazolyl (particularly pyridyl, more particularly 2-pyridyl),
and wherein Q¹ optionally bears 1, 2, or 3 substituents, which may be the same or different, selected from fluoro, chloro, hydroxy, cyano, nitro, amino, (1-4C)alkyl, (1-4C)alkoxy, $\underline{N}$-(1-4C)alkylamino and $\underline{N},\underline{N}$-di-[(1-4C)alkyl]amino,
X¹ is selected from OCH₂, O(CH₃)₂ and O, and
n is 0 or 1, R³, when present, is located at the meta-position (3-position) relative to the nitrogen in the anilino group, wherein R³ has any of the values defined above (for example R³ is selected from fluoro, chloro and (1-3C)alkyl (such as methyl));
(kkkk) Q¹ is selected from phenyl, pyridyl, pyrazinyl, thiazolyl and isoxazolyl (particularly pyridyl, more particularly 2-pyridyl),
and wherein Q¹ optionally bears 1, 2, or 3 substituents, which may be the same or different, selected from fluoro, chloro, hydroxy, cyano, nitro, amino, (1-4C)alkyl, (1-4C)alkoxy, $\underline{N}$-(1-4C)alkylamino and $\underline{N},\underline{N}$-di-[(1-4C)alkyl]amino,
X¹ is O(CH₃)₂, and
n is 0 or 1, R³, when present, is located at the meta-position (3-position) relative to the nitrogen in the anilino group, wherein R³ has any of the values defined above (for example R³ is selected from fluoro, chloro and (1-3C)alkyl (such as methyl));
(llll) Q¹ is selected from phenyl, pyridyl, pyrazinyl, thiazolyl and isoxazolyl (particularly pyridyl, more particularly 2-pyridyl),
and wherein Q¹ optionally bears 1, 2, or 3 substituents, which may be the same or different, selected from fluoro, chloro, hydroxy, cyano, nitro, amino, (1-4C)alkyl, (1-4C)alkoxy, $\underline{N}$-(1-4C)alkylamino and $\underline{N},\underline{N}$-di-[(1-4C)alkyl]amino,
X¹ is OCH₂, and
n is 0 or 1, R³, when present, is located at the meta-position (3-position) relative to the nitrogen in the anilino group, wherein R³ has any of the values defined above (for example R³ is selected from fluoro, chloro and (1-3C)alkyl (such a methyl));
(mmmm) Q¹ is selected from phenyl, pyridyl, pyrazinyl, thiazolyl and isoxazolyl,
and wherein Q¹ optionally bears 1, 2, or 3 substituents, which may be the same or different, selected from fluoro, chloro, hydroxy, cyano, nitro, amino, (1-4C)alkyl, (1-4C)alkoxy, $\underline{N}$-(1-4C)alkylamino and $\underline{N},\underline{N}$-di-[(1-4C)alkyl]amino,
X¹ is O, and
n is 0 or 1, R³, when present, is located at the meta-position (3-position) relative to the nitrogen in the anilino group, wherein R³ has any of the values defined above (for example R³ is selected from fluoro, chloro and (1-3C)alkyl (such as methyl));
(nnnn) $R^4$, $R^{4a}$, $R^5$ and $R^{5a}$, which may be the same or different, are selected from hydrogen and (1-3C)alkyl (particularly methyl);
(oooo) $R^4$, $R^{4a}$, $R^5$ and $R^{5a}$, which may be the same or different, are selected from hydrogen and (1-3C)alkyl (particularly methyl), wherein at least one of $R^4$, $R^{4a}$, $R^5$ and $R^{5a}$ is (1-3C)alkyl (particularly methyl);
(pppp) $R^4$, $R^{4a}$ and $R^5$ are all hydrogen and $R^{5a}$ is (1-3C)alkyl (particularly methyl);
(qqqq) $R^4$, $R^5$ and $R^{5a}$ are all hydrogen and $R^{4a}$ is (1-3C)alkyl (particularly methyl);
(rrrr) $R^4$ and $R^{4a}$ are both hydrogen and $R^5$ and $R^{5a}$ are both (1-3C)alkyl (particularly methyl);
(ssss) $R^{4a}$ and $R^{5a}$ are both hydrogen;
(tttt) $R^{4a}$, $R^{5a}$ and $R^4$ are hydrogen and $R^5$ is (1-6C)alkyl, or $R^{4a}$, $R^{5a}$ and $R^5$ are hydrogen and $R^4$ is (1-6C)alkyl, and wherein any $CH_2$ or $CH_3$ group within any of $R^4$ and $R^5$ optionally bears on each said $CH_2$ or $CH_3$ group one or more (for example 1, 2 or 3) halogeno substituents or a substituent selected from hydroxy and (1-6C)alkoxy;

(uuuu) $R^4$ and $R^{4a}$ are hydrogen, and $R^5$ and $R^{5a}$ are both (1-6C)alkyl, or $R^5$ and $R^{5a}$ are hydrogen, and $R^4$ and $R^{4a}$ are both (1-6C)alkyl, and wherein any $CH_2$ or $CH_3$ group within any of $R^4$, $R^{4a}$, $R^5$ and $R^{5a}$ optionally bears on each said $CH_2$ or $CH_3$ group one or more (for example 1, 2 or 3) halogeno substituents or a substituent selected from hydroxy and (1-6C)alkoxy;

(vvvv) $R^5$ and $R^{5a}$ are hydrogen, and $R^4$ and $R^{4a}$ together with the carbon atom to which they are attached form a (3-7C)cycloalkyl ring (for example cyclopropyl, cyclobutyl, cyclopentyl or cyclohexyl), and wherein any $CH_2$ or $CH_3$ group within any of $R^4$ and $R^{4a}$ optionally bears on each said $CH_2$ or $CH_3$ group one or more (for example 1, 2 or 3) halogeno substituents or a substituent selected from hydroxy and (1-6C)alkoxy;

(wwww) $R^4$ and $R^{4a}$ are hydrogen, and $R^5$ and $R^{5a}$ together with the carbon atom to which they are attached form a (3-7C)cycloalkyl ring (for example cyclopropyl, cyclobutyl, cyclopentyl or cyclohexyl), and wherein any $CH_2$ or $CH_3$ group within any of $R^5$ and $R^{5a}$ optionally bears on each said $CH_2$ or $CH_3$ group one or more (for example 1, 2 or 3) halogeno substituents or a substituent selected from hydroxy and (1-6C)alkoxy;

(xxxx) $R^4$, $R^{4a}$, $R^5$ and $R^{5a}$ are all hydrogen;

(yyyy) $R^6$ is selected from hydrogen, (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, and wherein any heterocyclyl group within an $R^6$ substituent optionally bears one or more substituents, which may be the same or different, selected from halogeno, trifluoromethyl, cyano, nitro, hydroxy, amino, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$-X^3-R^{10}$$

wherein $X^3$ is a direct bond or is selected from O and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, amino, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino and di-[(1-6C)alkyl]amino;

(zzzz) $R^6$ is selected from hydrogen, (1-6C)alkyl, hydroxy-(2-6C)alkyl, (1-6C)alkoxy-(2-6C)alkyl, halogeno-(2-6C)alkyl, amino-(2-6C)alkyl, N-(1-6C)alkylamino-(1-6C)alkyl, N,N-di-[(1-6C)alkyl]amino-(1-6C)alkyl, (2-6C)alkenyl, (2-6C)alkynyl, (3-7C)cycloalkyl, (3-7C)cycloalkyl-(1-6C)alkyl, heterocyclyl and heterocyclyl-(1-6C)alkyl, and wherein any heterocyclyl group within an $R^6$ substituent optionally bears one or more substituents, which may be the same or different, selected from halogeno, trifluoromethyl, cyano, nitro, hydroxy, amino, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$-X^3-R^{10}$$

wherein $X^3$ is a direct bond or is selected from O and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo substituents;

(aaaaa) $R^6$ is selected from hydrogen, (1-6C)alkyl, (2-6C)alkenyl, (2-6C)alkynyl, (3-7C)cycloalkyl, (3-7C)cycloalkyl-(1-6C)alkyl, heterocyclyl and heterocyclyl-(1-6C)alkyl, wherein any heterocyclyl group within $R^6$ is a 4, 5, 6 or 7 membered monocyclic saturated or partially saturated heterocyclyl ring containing 1 or 2 heteroatoms selected from oxygen, nitrogen and sulfur, and wherein any heterocyclyl group within an $R^6$ substituent optionally bears one or more substituents, which may be the same or different, selected from halogeno, trifluoromethyl, cyano, nitro, hydroxy, amino, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$-X^3-R^{10}$$

wherein $X^3$ is a direct bond or is selected from O and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, amino, (1-6C)alkoxy, (1-6C)alkylamino and di-[(1-6C)alkyl]amino;

(bbbbb) $R^6$ is selected from hydrogen, (1-6C)alkyl, (2-6C)alkenyl, (2-6C)alkynyl, (3-7C)cycloalkyl, (3-7C)cycloalkyl-(1-6C)alkyl, heterocyclyl and heterocyclyl-(1-6C)alkyl, wherein any heterocyclyl group within $R^6$ is a 4, 5, 6 or 7 membered monocyclic saturated or partially saturated heterocyclyl ring containing 1 or 2 heteroatoms selected from oxygen, nitrogen and sulfur, which heterocyclyl group is linked to the group to which it is attached by a ring carbon atom, and wherein any heterocyclyl group within an $R^6$ substituent optionally bears one or more substituents, which may be the same or different, selected from halogeno, trifluoromethyl, cyano, nitro, hydroxy, amino, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^3$—$R^{10}$ wherein $X^3$ is a direct bond or is selected from O and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, $\underline{N}$-(1-4C)alkylamino-(1-4C)alkyl and $\underline{N}$,$\underline{N}$-di-[(1-4C)alkyl]amino-(1-4C)alkyl, and wherein any heterocyclyl group within an $R^6$ substituent optionally bears 1 or 2 oxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, amino, (1-6C)alkoxy, (1-6C)alkylamino and di-[(1-6C)alkyl]amino;

(ccccc) $R^6$ is selected from hydrogen, (1-3C)alkyl, (2-3C)alkenyl, (2-3C)alkynyl, (3-5C)cycloalkyl, (3-5C)cycloalkyl-(1-3C)alkyl, heterocyclyl and heterocyclyl-(1-3C)alkyl, wherein any heterocyclyl group within $R^6$ is a 4, 5, 6 or 7 membered monocyclic saturated or partially saturated heterocyclyl ring containing 1 or 2 heteroatoms selected from oxygen, nitrogen and sulfur, which heterocyclyl group is linked to the group to which it is attached by a ring carbon atom, and wherein any heterocyclyl group within an $R^6$ substituent optionally bears one or more substituents, which may be the same or different, selected from halogeno, trifluoromethyl, cyano, nitro, hydroxy, amino, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^3$—$R^{10}$ wherein $X^3$ is a direct bond or is selected from O and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, $\underline{N}$-(1-4C)alkylamino-(1-4C)alkyl and $\underline{N}$,$\underline{N}$-di-[(1-4C)alkyl]amino-(1-4C)alkyl, and wherein any heterocyclyl group within an $R^6$ substituent optionally bears 1 or 2 oxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, amino, (1-6C)alkoxy, (1-6C)alkylamino and di-[(1-6C)alkyl]amino;

(ddddd) $R^6$ is selected from hydrogen, methyl, ethyl, propyl, isopropyl, butyl, isobutyl, vinyl, isopropenyl, allyl, but-2-enyl, ethynyl, 2-propynyl, butynyl, cyclopropyl, cyclobutyl, cyclopentyl, cyclohexyl, azetidinyl, pyrrolinyl, pyrrolidinyl, piperidinyl, homopiperidinyl, homopiperazinyl, dihydropyridinyl, tetrahydropyridinyl, dihydropyrimidinyl, tetrahydropyrimidinyl, tetrahydrothienyl, tetrahydrothiopyranyl, tetrahydrofuranyl, tetrahydropyranyl, cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, azetidinylmethyl, pyrrolinylmethyl, pyrrolidinylmethyl, morpholinylmethyl, piperidinylmethyl, homopiperidinylmethyl, piperazinylmethyl, homopiperazinylmethyl, dihydropyridinylmethyl, tetrahydropyridinylmethyl, dihydropyrimidinylmethyl, tetrahydropyrimidinylmethyl, tetrahydrothienylmethyl, tetrahydrothiopyranylmethyl, thiomorpholinylmethyl, tetrahydrofuranylmethyl, tetrahydropyranylmethyl, 2-(azetidinyl)ethyl, 2-(pyrrolinyl)ethyl, 2-(pyrrolidinyl)ethyl, 2-(morpholinyl)ethyl, 2-(piperidinyl)ethyl, 2-(homopiperidinyl)ethyl, 2-(piperazinyl)ethyl, 2-(homopiperazinyl)ethyl, 2-(dihydropyridinyl)ethyl, 2-(tetrahydropyridinyl)ethyl, 2-(dihydropyrimidinyl)ethyl, 2-(tetrahydropyrimidinyl)ethyl, 2-(tetrahydrothienyl)ethyl, 2-(tetrahydrothiopyranyl)ethyl, 2-(thiomorpholinyl)ethyl, 2-(tetrahydrofuranyl)ethyl, 2-(tetrahydropyranyl)ethyl, and wherein any $CH_2$ or $CH_3$ group within a $R^6$ substituent, other than a $CH_2$ group within a heterocyclyl group, optionally bears on each said $CH_2$ or $CH_3$ group one or more substituents, which may be the same or different, selected from fluoro, chloro, bromo, methyl, ethyl, propyl and isopropyl, or a substituent selected from hydroxy, amino, methoxy, ethoxy, methylamino, ethylamino, di-methylamino, di-ethylamino and $\underline{N}$-methyl-$\underline{N}$-ethylamino, and wherein any heterocyclyl group within $R^6$ optionally bears one or more substituents, which may be the same or different, selected from fluoro, chloro, bromo, oxo, hydroxy, methyl, ethyl, propyl, butyl, isopropyl, isobutyl, trifluoromethyl, vinyl, isopropenyl, allyl, but-2-enyl, ethynyl, 2-propynyl, butynyl, methoxy, ethoxy, propoxy, isopropoxy, trifluoromethoxy, acetyl, propionyl, hydroxymethyl, methoxymethyl, ethoxymethyl, 2-hydroxyethyl, 2-methoxyethyl and 2-ethoxyethyl;

(eeeee) $R^6$ is selected from hydrogen, methyl, ethyl, 2-hydroxyethyl, 2-methoxyethyl, propyl, 3-hydroxypropyl, 2-hydroxypropyl, 3-methoxypropyl, 2-methoxypropyl, isopropyl, vinyl, isopropenyl, allyl, but-2-enyl, ethynyl, 2-propynyl, cyclopropyl, cyclobutyl, cyclopentyl, cyclohexyl, azetidinyl, pyrrolinyl, pyrrolidinyl, piperidinyl, homopiperidinyl, tetrahydrofuranyl, tetrahydropyranyl, cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, azetidinylmethyl, pyrrolidinylmethyl, piperidinylmethyl, homopiperidinylmethyl, tetrahydrothiopyranylmethyl, tetrahydrofuranylmethyl, tetrahydropyranylmethyl, 2-(azetidinyl)ethyl, 2-(pyrrolidinyl)ethyl, 2-(piperidinyl)ethyl, 2-(homopiperidinyl)ethyl, 2-(tetrahydrothienyl)ethyl, 2-(tetrahydrothiopyranyl)ethyl, 2-(thiomorpholinyl)ethyl, 2-(tetrahydrofuranyl)ethyl and 2-(tetrahydropyranyl)ethyl, and wherein any $CH_2$ group within a cycloalkyl group within $R^6$ optionally bears on each $CH_2$ group 1 or 2 substituents selected from hydroxy, methyl, ethyl, methoxy and ethoxy, and wherein any $CH_2$ or $CH_3$ group within a $R^6$ substituent, other than a $CH_2$ group within a heterocyclyl group, optionally bears on each said $CH_2$ or $CH_3$ group one or more fluoro substituents, and wherein any heterocyclyl group within $R^6$ optionally bears one or more substituents, which may be the same or different, selected from fluoro, chloro, bromo, oxo, hydroxy, methyl, ethyl, propyl, isopropyl, trifluoromethyl, methoxy, ethoxy, propoxy, isopropoxy and trifluoromethoxy;

(fffff) $R^6$ is selected from hydrogen, methyl, ethyl, 2-hydroxyethyl, 2-methoxyethyl, propyl, 3-hydroxypropyl, 2-hydroxypropyl, 3-methoxypropyl, 2-methoxypropyl, isopropyl, allyl, but-2-enyl, 2-propynyl, cyclopropyl, cyclobutyl, cyclopentyl, cyclohexyl, azetidinyl, pyrrolinyl, pyrrolidinyl, piperidinyl, tetrahydrofuranyl, tetrahydropyranyl, cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, azetidinylmethyl, pyrrolidinylmethyl, piperidinylmethyl, tetrahydrofuranylmethyl, tetrahydropyranylmethyl, 2-(azetidinyl)ethyl, 2-(pyrrolidinyl)ethyl, 2-(piperidinyl)ethyl, 2-(tetrahydrofuranyl)ethyl and 2-(tetrahydropyranyl)ethyl, and wherein any $CH_2$ group within a cycloalkyl group within $R^6$ optionally bears on each $CH_2$ group 1 or 2 substituents selected from hydroxy, methyl, ethyl, methoxy and ethoxy, and wherein any heterocyclyl group within $R^6$ optionally bears one or more substituents, which may be the same or different, selected from fluoro, chloro, bromo, oxo, hydroxy, methyl, ethyl, propyl, isopropyl, trifluoromethyl, methoxy, ethoxy, propoxy, isopropoxy and trifluoromethoxy;

(ggggg) $R^6$ is selected from hydrogen, methyl, ethyl, 2-hydroxyethyl, 2-methoxyethyl, propyl, isopropyl, allyl, 2-propynyl, cyclopropyl, cyclobutyl, piperidinyl, tetrahydropyranyl and cyclopropylmethyl, and wherein any $CH_2$ group within a cycloalkyl group within $R^6$ optionally bears on each $CH_2$ group 1 or 2 substituents selected from hydroxy, methyl, ethyl, methoxy and ethoxy, and wherein any heterocyclyl group within $R^6$ optionally bears one or more substituents, which may be the same or different, selected from fluoro, chloro, bromo, oxo, hydroxy, methyl, ethyl, propyl, isopropyl, trifluoromethyl, methoxy, ethoxy, propoxy, isopropoxy and trifluoromethoxy;

(hhhhh) $R^6$ is selected from hydrogen and (1-3C)alkyl (for example $R^6$ is hydrogen or methyl);

(iiiii) $R^6$ is hydrogen;

(jjjjj) $R^6$ is (1-3C)alkyl (for example methyl);

(kkkkk) $R^6$ is (1-3C)alkyl, and wherein any $CH_2$ or $CH_3$ group within a $R^6$ substituent, other than a $CH_2$ group within a heterocyclyl ring, optionally bears on each said $CH_2$ or $CH_3$ group one or more substituents selected from hydroxy and (1-6C)alkoxy (for example methoxy);

(lllll) $R^6$ is (2-6C)alkenyl (for example allyl);

(mmmmm) $R^6$ is (2-6C)alkynyl (for example 2-propynyl);

(nnnnn) $R^6$ is selected from (3-7C)cycloalkyl and (3-7C)cycloalkyl-(1-6C)alkyl (for example $R^6$ is selected from cyclopropyl, cyclobutyl, cyclopropyl-methyl and cyclobutyl-methyl);

(ooooo) $R^6$ is heterocyclyl (for example $R^6$ is selected from piperidinyl and tetrahydropyranyl);

(ppppp) A is selected from a group of the formula Z-$(CR^{12}R^{13})_p$— and $R^{14}$, wherein p is 1, 2, 3, or 4, each $R^{12}$ and $R^{13}$, which may be the same or different, is selected from hydrogen, (1-6C)alkyl, (2-6C)alkenyl and (2-6C)alkynyl, or an $R^{12}$ and an $R^{13}$ group attached to the same carbon atom form a (3-7C)cycloalkyl or (3-7C)cycloalkenyl ring, and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkyl]amino, Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-6C)alkyl, (2-6C)alkenyl, (2-6C)alkynyl and (1-6C)alkoxycarbonyl, $R^{14}$ is selected from $OR^{19}$ and $NR^{16}R^{17}$, wherein $R^{19}$ is selected from (1-6C)alkyl, (2-6C)alkenyl and (2-6C)alkynyl, and wherein $R^{16}$ and $R^{17}$ are as defined above, or $R^{14}$ is $Q^4$ wherein $Q^4$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein adjacent carbon atoms in any (2-6C)alkylene chain within a Z or $R^{14}$ substituent are optionally separated by the insertion into the chain of a group selected from O, S, SO, $SO_2$, $N(R^{21})$, CO, —C=C— and —C≡C—, wherein $R^{21}$ is hydrogen or (1-6C)alkyl, and wherein any heterocyclyl group within a Z or $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$ wherein $X^6$ is a direct bond or is selected from O, CO, $SO_2$ and $N(R^{23})$, wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within a Z or $R^{14}$ substituent optionally bears 1 or 2 oxo or thioxo substituents, and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

(qqqqq) A is selected from a group of the formula Z-$(CR^{12}R^{13})_p$— and $R^{14}$, wherein p is 1, 2 or 3, each $R^{12}$ and $R^{13}$, which may be the same or different, is selected from hydrogen and (1-6C)alkyl, or an $R^{12}$ and an $R^{13}$ group attached to the same carbon atom form a (3-7C)cycloalkyl ring, and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy, cyano, (1-6C)alkyl and (1-6C)alkoxy, Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-6C)alkyl and (1-6C)alkoxycarbonyl, $R^{14}$ is selected from $OR^{19}$ and $NR^{16}R^{17}$, wherein $R^{19}$ is selected from (1-6C)alkyl and wherein $R^{16}$ and $R^{17}$ are as defined above, or $R^{14}$ is $Q^4$ wherein $Q^4$ is (3-7C)cycloalkyl, (3-7C)cycloalkyl-(1-6C)alkyl, heterocyclyl or heterocyclyl-(1-6C)alkyl, and wherein adjacent carbon atoms in any (2-6C)alkylene chain within a Z or $R^{14}$ substituent are optionally separated by the insertion into the chain of a group selected from O, S, SO, $SO_2$, $N(R^{21})$, Co, —C=C— and —C≡C—, wherein $R^{21}$ is hydrogen or (1-6C)alkyl, and wherein any heterocyclyl group within a Z or $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$—X^6—R^{22}$$

wherein $X^6$ is a direct bond or is selected from O, CO, $SO_2$ and $N(R^{23})$, wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within a Z or $R^{14}$ substituent optionally bears 1 or 2 oxo or thioxo substituents, and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

(rrrrr) A is selected from a group of the formula $Z-(CR^{12}R^{13})_p—$ and $R^{14}$, wherein p is 1, 2 or 3 (particularly 1 or 2), each $R^{12}$ and $R^{13}$, which may be the same or different, is selected from hydrogen and (1-6C)alkyl, and wherein any $CH_2$ or $CH_3$ group within any of $R^{12}$ and $R^{13}$ optionally bears on each said $CH_2$ or $CH_3$ group one or more (for example 1, 2 or 3) halogeno substituents or a substituent selected from hydroxy and (1-6C)alkoxy (particularly hydroxy), Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-6C)alkyl and (1-6C)alkoxycarbonyl, $R^{14}$ is selected from $OR^{19}$ and $NR^{16}R^{17}$, wherein $R^{19}$ is selected from (1-6C)alkyl and wherein $R^{16}$ and $R^{17}$ are as defined above, or $R^{14}$ is $Q^4$ wherein $Q^4$ is (3-7C)cycloalkyl, heterocyclyl or heterocyclyl-(1-6C)alkyl, and wherein any heterocyclyl group within a Z or $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl and (1-6C)alkoxy, and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl and (1-6C)alkoxy;

(sssss) A is selected from a group of the formula $Z-(CR^{12}R^{13})_p—$ and $R^{14}$, wherein p is 1, 2 or 3 (particularly 1 or 2), each $R^{12}$ and $R^{13}$, which may be the same or different, is selected from hydrogen and (1-6C)alkyl, and wherein any $CH_2$ or $CH_3$ group within any of $R^{12}$ and $R^{13}$ optionally bears on each said $CH_2$ or $CH_3$ group one or more (for example 1, 2 or 3) halogeno substituents or a substituent selected from hydroxy and (1-6C)alkoxy (particularly hydroxy), Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-6C)alkyl and (1-6C)alkoxycarbonyl, $R^{14}$ is selected from $OR^{19}$ and $NR^{16}R^{17}$, wherein $R^{19}$ is selected from (1-6C)alkyl and wherein $R^{16}$ and $R^{17}$ are as defined above, or $R^{14}$ is $Q^4$ wherein $Q^4$ is (3-7C)cycloalkyl, heterocyclyl or heterocyclyl-(1-6C)alkyl, and wherein any heterocyclyl group within a Z or $R^{14}$ substituent optionally bears one or more (for example 1, 2 or 3) substituents, which may be the same or different, selected from halogeno, hydroxy, (1-6C)alkyl and (1-6C)alkoxy (particularly (1-6C)alkyl), and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy and (1-6C)alkoxy (particularly a substituent selected from halogeno and hydroxy);

(ttttt) A is selected from a group of the formula $Z-(CR^{12}R^{13})_p—$ and $R^{14}$, wherein p is 1, 2, 3, or 4, each $R^{12}$ and $R^{13}$, which may be the same or different, is selected from hydrogen, (1-6C)alkyl, (2-6C)alkenyl and (2-6C)alkynyl, or an $R^{12}$ and an $R^{13}$ group attached to the same carbon atom form a (3-7C)cycloalkyl or (3-7C)cycloalkenyl ring, and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkylamino], and wherein Z is selected from hydrogen, $OR^{15}$, $NR^{16}R^{17}$, wherein each of $R^{15}$, $R^{16}$ and $R^{17}$, which may be the same or different, is selected from hydrogen, (1-6C)alkyl, (2-6C)alkenyl and (2-6C)alkynyl, and wherein $R^{14}$ is $Q^4$ wherein $Q^4$ is heterocyclyl,
and wherein adjacent carbon atoms in any (2-6C)alkylene chain within a Z or $R^{14}$ substituent are optionally separated by the insertion into the chain of a group selected from O, S, SO, $SO_2$ N($R^{21}$), CO, —C=C— and —C≡C—, wherein $R^{21}$ is hydrogen or (1-6C)alkyl,
and wherein any heterocyclyl group within a $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$ wherein $X^6$ is a direct bond or is selected from O, CO, $SO_2$ and N($R^{23}$), wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^{14}$ substituent optionally bears 1 or 2 oxo substituents,
and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

(uuuuu) A is selected from a group of the formula Z-($CR^{12}R^{13}$)$_p$— and $R^{14}$,
wherein p is 1 or 2,
each $R^{12}$ and $R^{13}$, which may be the same or different, is selected from hydrogen and (1-6C)alkyl,
or an $R^{12}$ and an $R^{13}$ group attached to the same carbon atom form a (3-7C)cycloalkyl ring,
and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy and (1-6C)alkoxy,
and wherein Z is selected from hydrogen, $OR^{15}$, $NR^{16}R^{17}$, wherein each of $R^{15}$, $R^{16}$ and $R^{17}$, which may be the same or different, is selected from hydrogen, (1-6C)alkyl, (2-6C)alkenyl and (2-6C)alkynyl,
and wherein $R^{14}$ is $Q^4$ wherein $Q^4$ is a 4, 5, 6 or 7 membered saturated or partially saturated monocyclic heterocyclyl ring containing 1 nitrogen or oxygen heteroatom and optionally 1 further heteroatom selected from oxygen, nitrogen and sulfur,
and wherein $Q^4$ optionally bears one or more (for example 1, 2 or 3) substituents, which may be the same or different, selected from halogeno, trifluoromethyl, cyano, nitro, hydroxy, amino, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$ wherein $X^6$ is a direct bond or is selected from O and N($R^{23}$), wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl,
and wherein $Q^4$ optionally bears 1 or 2 oxo substituents,
and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, (1-6C)alkoxy, (1-6C)alkylamino and di-[(1-6C)alkyl]amino;

(vvvvv) A is selected from a group of the formula Z-($CR^{12}R^{13}$)$_p$— and $R^{14}$,
wherein p is 1 or 2,
each $R^{12}$ and $R^{13}$, which may be the same or different, is selected from hydrogen and (1-6C)alkyl,
or an $R^{12}$ and an $R^{13}$ group attached to the same carbon atom form a (3-7C)cycloalkyl ring,
and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy and (1-6C)alkoxy,
and wherein Z is selected from hydrogen, $OR^{15}$, $NR^{16}R^{17}$, wherein each of $R^{15}$, $R^{16}$ and $R^{17}$, which may be the same or different, is selected from hydrogen, (1-6C)alkyl, (2-6C)alkenyl and (2-6C)alkynyl,
and wherein $R^{14}$ is $Q^4$ wherein $Q^4$ is a 4, 5, 6 or 7 membered saturated or partially saturated monocyclic heterocyclyl ring containing 1 nitrogen or oxygen heteroatom and optionally 1 further heteroatom selected from oxygen, nitrogen and sulfur, which ring is linked to the carbonyl group in formula I by a ring carbon atom,
and wherein $Q^4$ optionally bears one or more (for example 1, 2 or 3) substituents, which may be the same or different, selected from halogeno, trifluoromethyl, cyano, nitro, hydroxy, amino, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$ wherein $X^6$ is a direct bond or is selected from O and N($R^{23}$), wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl,
and wherein $Q^4$ optionally bears 1 or 2 oxo substituents,
and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, (1-6C)alkoxy, (1-6C)alkylamino and di-[(1-6C)alkyl]amino;

(wwwww) A is a group of the formula Z-($CR^{12}R^{13}$)$_p$—,
wherein p is 1 or 2,
each $R^{12}$ and $R^{13}$, which may be the same or different, is selected from hydrogen and (1-6C)alkyl, or an $R^{12}$ and an $R^{13}$ group attached to the same carbon atom form a (3-7C)cycloalkyl ring, and wherein Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-6C)alkyl and (1-6C)alkoxycarbonyl, and wherein any $CH_2$ or $CH_3$ group within any of $R^{12}$, $R^{13}$ and Z, optionally bears on each said $CH_2$ or $CH_3$ group one or more (for example 1, 2 or 3) halogeno or (1-6C) alkyl substituents or a substituent selected from hydroxy and (1-6C)alkoxy;

(xxxxx) A is a group of the formula Z-$(CR^{12}R^{13})_p$—,
  wherein p is 1 or 2,
  each $R^{12}$ and $R^{13}$, which may be the same or different, is selected from hydrogen and (1-6C)alkyl,
  and wherein Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-6C)alkyl and (1-6C)alkoxycarbonyl,
  and wherein any $CH_2$ or $CH_3$ group within any of $R^{12}$, $R^{13}$ and Z, optionally bears on each said $CH_2$ or $CH_3$ group one or more (for example 1, 2 or 3) halogeno, (1-6C) alkyl or hydroxy substituents;

(yyyyy) A is a group of the formula Z-$(CR^{12}R^{13})_p$—,
  wherein p is 1 or 2,
  each $R^{12}$ and $R^{13}$, which may be the same or different, is selected from hydrogen and (1-4C)alkyl,
  or an $R^{12}$ and an $R^{13}$ group attached to the same carbon atom form a (3-7C)cycloalkyl ring,
  and wherein Z is selected from hydrogen, $OR^{15}$, $NR^{16}R^{17}$, wherein each of $R^{15}$, $R^{16}$ and $R^{17}$, which may be the same or different, is selected from hydrogen, (1-6C) alkyl, (2-6C)alkenyl and (2-6C)alkynyl,
  and wherein any $CH_2$ or $CH_3$ group within any of $R^{12}$, $R^{13}$ and Z, optionally bears on each said $CH_2$ or $CH_3$ group one or more (for example 1, 2 or 3) halogeno or (1-6C) alkyl substituents or a substituent selected from hydroxy and (1-6C)alkoxy;

(zzzzz) A is a group of the formula Z-$(CR^{12}R^{13})_p$—,
  wherein p is 1 or 2,
  each $R^{12}$ and $R^{13}$, which may be the same or different, is selected from hydrogen and (1-4C)alkyl,
  or an $R^{12}$ and an 13 group attached to the same carbon atom form a (3-6C)cycloalkyl ring,
  and wherein Z is selected from hydrogen and $OR^{15}$, wherein $R^{15}$ is selected from hydrogen and (1-6C)alkyl,
  and wherein any $CH_2$ or $CH_3$ group within any of $R^{12}$, $R^{13}$ and Z, optionally bears on each said $CH_2$ or $CH_3$ group one or more (for example 1, 2 or 3) halogeno or (1-4C) alkyl substituents or a substituent selected from hydroxy and (1-4C)alkoxy;

(aaaaaa) A is a group of the formula Z-$(CR^{12}R^{13})_p$—,
  wherein p is 1 or 2,
  each $R^{12}$ and $R^{13}$, which may be the same or different, is selected from hydrogen and (1-4C)alkyl,
  or an $R^{12}$ and an $R^{13}$ group attached to the same carbon atom form a (3-6C)cycloalkyl ring,
  and wherein any $CH_2$ or $CH_3$ group within any of $R^{12}$ and $R^{13}$ optionally bears on each said $CH_2$ or $CH_3$ group one or more (for example 1, 2 or 3) halogeno or (1-4C)alkyl substituents or a substituent selected from hydroxy and (1-4C)alkoxy,
  and wherein Z is hydroxy;

(bbbbbb) A is a group of the formula Z-$(CR^{12}R^{13})_p$—,
  wherein p is 1 or 2,
  each $R^{12}$ and $R^{13}$, which may be the same or different, is selected from hydrogen and (1-4C)alkyl,
  or an $R^{12}$ and an $R^{13}$ group attached to the same carbon atom form a (3-7C)cycloalkyl ring,
  and wherein Z is $NR^{16}R^{17}$, wherein each of $R^{16}$ and $R^{17}$, which may be the same or different, is selected from hydrogen, (1-6C)alkyl, (2-6C)alkenyl and (2-6C)alkynyl,
  and wherein any $CH_2$ or $CH_3$ group within any of $R^{12}$, $R^{13}$ and Z, optionally bears on each said $CH_2$ or $CH_3$ group one or more (for example 1, 2 or 3) halogeno or (1-6C) alkyl substituents or a substituent selected from hydroxy and (1-6C)alkoxy;

(cccccc) A is a group of the formula Z-$(CR^{12}R^{13})_p$—,
  wherein p is 1 or 2,
  each $R^{12}$ and $R^{13}$, which may be the same or different, is selected from hydrogen and (1-4C)alkyl,
  or an $R^{12}$ and an $R^{13}$ group attached to the same carbon atom form a (3-6C)cycloalkyl ring,
  provided (i) that at least one of the $R^{12}$ or $R^{13}$ groups is (1-4C)alkyl, or (ii) that an $R^{12}$ and an $R^{13}$ group attached to the same carbon atom form a (3-6C)cycloalkyl ring,
  and wherein Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-6C)alkyl, (2-6C)alkenyl, (2-6C)alkynyl and (1-6C)alkoxycarbonyl,
  and wherein any $CH_2$ or $CH_3$ group within any of $R^{12}$, $R^{13}$ and Z, optionally bears on each said $CH_2$ or $CH_3$ group one or more (for example 1, 2 or 3) halogeno or (1-6C) alkyl substituents or a substituent selected from hydroxy and (1-6C)alkoxy;

(dddddd) A is a group of the formula Z-$(CR^{12}R^{13})_p$—,
  wherein p is 1 or 2,
  each $R^{12}$ and $R^{13}$, which may be the same or different, is selected from hydrogen and (1-4C)alkyl,
  or an $R^{12}$ and an $R^{13}$ group attached to the same carbon atom form a (3-6C)cycloalkyl ring,
  provided (i) that at least one of the $R^{12}$ or $R^{13}$ groups is (1-4C)alkyl, or (ii) that an $R^{12}$ and an $R^{13}$ group attached to the same carbon atom form a (3-6C)cycloalkyl ring,
  and wherein Z is selected from hydrogen, $OR^{15}$, $NR^{16}R^{17}$, wherein each of $R^{15}$, $R^{16}$ and $R^{17}$, which may be the same or different, is selected from hydrogen, (1-6C) alkyl, (2-6C)alkenyl and (2-6C)alkynyl,
  and wherein any $CH_2$ or $CH_3$ group within any of $R^{12}$, $R^{13}$ and Z, optionally bears on each said $CH_2$ or $CH_3$ group one or more (for example 1, 2 or 3) halogeno or (1-6C) alkyl substituents or a substituent selected from hydroxy and (1-6C)alkoxy;

(eeeeee) A is $R^{14}$, wherein $R^{14}$ is selected from $OR^{19}$ and $NR^{16}R^{17}$, wherein each of $R^{16}$ and $R^{17}$, which may be the same or different, is selected from hydrogen, (1-6C)alkyl, (2-6C)alkenyl, (2-6C)alkynyl and (1-6C)alkoxycarbonyl, and wherein $R^{19}$ is selected from (1-6C)alkyl, (2-6C)alkenyl and (2-6C)alkynyl,
  or $R^{14}$ is $Q^4$ wherein $Q^4$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl,
  and wherein adjacent carbon atoms in any (2-6C)alkylene chain within a $R^{14}$ group are optionally separated by the insertion into the chain of a group selected from O, S, SO, $SO_2$, $N(R^{21})$, CO, —C=C— and —C≡C—, wherein $R^{21}$ is hydrogen or (1-6C)alkyl,
  and wherein any heterocyclyl group within a $R^{14}$ group optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)
alkenyl, (2-6C)alkynyl, (1-6C)alkoxy, (1-6C)alkylthio,
(1-6C)alkylsulfinyl, (1-6C)alkylsulfonyl, (1-6C)alky-
lamino, di-[(1-6C)alkyl]amino, (2-6C)alkanoyl, (2-6C)
alkanoyloxy and from a group of the formula:

—$X^6$—$R^{22}$ wherein $X^6$ is a direct bond or is selected from O, CO, $SO_2$
and N($R^{23}$), wherein $R^{23}$ is hydrogen or (1-4C)alkyl, and
$R^{22}$ is halogeno-(1-4C)alkyl, hydroxy-(1-4C)alkyl,
(1-4C)alkoxy-(1-4C)alkyl, cyano-(1-4C)alkyl, amino-
(1-4C)alkyl, N-(1-4C)alkylamino-(1-4C)alkyl and N,
N-di-[(1-4C)alkyl]amino-(1-4C)alkyl, and wherein any heterocyclyl group within a $R^{14}$ group
optionally bears 1 or 2 oxo or thioxo substituents, and wherein any $CH_2$ or $CH_3$ group within a $R^{14}$ group,
other than a $CH_2$ group within a heterocyclyl ring,
optionally bears on each said $CH_2$ or $CH_3$ group one or
more halogeno or (1-6C)alkyl substituents or a substitu-
ent selected from hydroxy, cyano, amino, carboxy, car-
bamoyl, sulfamoyl, (2-6C)alkenyl, (2-6C)alkynyl,
(1-6C)alkoxy, (1-6C)alkylthio, (1-6C)alkylsulfinyl,
(1-6C)alkylsulfonyl, (1-6C)alkylamino, di-[(1-6C)
alkyl]amino, N-(1-6C)alkylcarbamoyl, N,
N-di-[(1-6C)alkyl]carbamoyl, (2-6C)alkanoyl, (2-6C)
alkanoyloxy, (2-6C)alkanoylamino,
N-(1-6C)alkyl-(2-6C)alkanoylamino,
N-(1-6C)alkylsulfamoyl, N,
N-di-[(1-6C)alkyl]sulfamoyl, (1-6C)alkanesulfony-
lamino and N-(1-6C)alkyl-(1-6C)alkanesulfonylamino;

(ffffff) A is $R^{14}$, wherein $R^{14}$ is selected from $OR^{19}$ and
$NR^{16}R^{17}$, wherein each of $R^{16}$ and $R^{17}$, which may be the
same or different, is selected from hydrogen, (1-6C)alkyl
and (1-6C)alkoxycarbonyl, and wherein $R^{19}$ is selected
from (1-6C)alkyl,
or $R^{14}$ is $Q^4$ wherein $Q^4$ is (3-7C)cycloalkyl, (3-7C)cy-
cloalkyl-(1-6C)alkyl, heterocyclyl or heterocyclyl-(1-
6C)alkyl,
and wherein any heterocyclyl group within a $R^{14}$ group
optionally bears one or more (for example 1, 2 or 3)
substituents, which may be the same or different,
selected from halogeno, trifluoromethyl, cyano, nitro,
hydroxy, amino, formyl, mercapto, (1-6C)alkyl, (2-6C)
alkenyl, (2-6C)alkynyl and (1-6C)alkoxy,
and wherein any heterocyclyl group within a $R^{14}$ group
optionally bears 1 or 2 oxo or thioxo substituents,
and wherein any $CH_2$ or $CH_3$ group within a $R^{14}$ group,
other than a $CH_2$ group within a heterocyclyl ring,
optionally bears on each said $CH_2$ or $CH_3$ group one or
more halogeno or (1-6C)alkyl substituents or a substitu-
ent selected from hydroxy and (1-6C)alkoxy;

(gggggg) A is $R^{14}$, wherein $R^{14}$ is $OR^{19}$, wherein $R^{19}$ is
(1-6C)alkyl (particularly (1-3C)alkyl, such as methyl);

(hhhhhh) A is $R^{14}$, wherein $R^{14}$ is $NR^{16}R^{17}$, wherein each of
$R^{16}$ and $R^{17}$, which may be the same or different, is selected
from hydrogen, (1-6C)alkyl and (1-6C)alkoxycarbonyl,
and wherein any $CH_2$ or $CH_3$ group within a $R^{16}$ or a $R^{17}$
group, optionally bears on each said $CH_2$ or $CH_3$ group
one or more halogeno or (1-6C)alkyl substituents or a
substituent selected from hydroxy and (1-6C)alkoxy;

(iiiiii) A is $R^{14}$, wherein $R^{14}$ is $Q^4$ wherein $Q^4$ is (3-7C)
cycloalkyl, heterocyclyl or heterocyclyl-(1-6C)alkyl,
and wherein any heterocyclyl group within a $R^{14}$ group
optionally bears one or more (for example 1, 2 or 3)
substituents, which may be the same or different,
selected from halogeno, trifluoromethyl, cyano, nitro,
hydroxy, amino, formyl, mercapto, (1-6C)alkyl, (2-6C)
alkenyl, (2-6C)alkynyl and (1-6C)alkoxy,
and wherein any heterocyclyl group within a $R^{14}$ group
optionally bears 1 or 2 oxo or thioxo substituents,
and wherein any $CH_2$ or $CH_3$ group within a $R^{14}$ group,
other than a $CH_2$ group within a heterocyclyl ring,
optionally bears on each said $CH_2$ or $CH_3$ group one or
more halogeno or (1-6C)alkyl substituents or a substitu-
ent selected from hydroxy and (1-6C)alkoxy;

(jjjjjj) A is $Q^4$ wherein $Q^4$ is a 4, 5, 6 or 7 membered saturated
or partially saturated monocyclic heterocyclyl ring con-
taining 1 nitrogen or oxygen heteroatom and optionally 1
further heteroatom selected from oxygen, nitrogen and
sulfur,
and wherein $Q^4$ optionally bears one or more (for example
1, 2 or 3) substituents, which may be the same or differ-
ent, selected from halogeno, trifluoromethyl, cyano,
hydroxy, amino, (1-6C)alkyl, (2-6C)alkenyl, (2-6C)
alkynyl, (1-6C)alkoxy, (1-6C)alkylthio, (1-6C)alkyl-
sulfinyl, (1-6C)alkylsulfonyl, (1-6C)alkylamino, di-[(1-
6C)alkyl]amino and (2-6C)alkanoyl, (2-6C)
alkanoyloxy and from a group of the formula:

—$X^6$—$R^{22}$ wherein $X^6$ is a direct bond or is selected from O and
N($R^{23}$), wherein $R^{23}$ is hydrogen or (1-4C)alkyl, and $R^{22}$
is halogeno-(1-4C)alkyl, hydroxy-(1-4C)alkyl, (1-4C)
alkoxy-(1-4C)alkyl, cyano-(1-4C)alkyl, amino-(1-4C)
alkyl, N-(1-4C)alkylamino-(1-4C)alkyl and N,
N-di-[(1-4C)alkyl]amino-(1-4C)alkyl,
and wherein $Q^4$ optionally bears 1 or 2 oxo substituents;

(kkkkkk) A is $Q^4$ wherein $Q^4$ is a 5 or 6 membered saturated
or partially saturated monocyclic heterocyclyl ring con-
taining 1 nitrogen or oxygen heteroatom and optionally 1
further heteroatom selected from oxygen, nitrogen and
sulfur,
and wherein $Q^4$ optionally bears one or more (for example
1, 2 or 3) substituents, which may be the same or differ-
ent, selected from halogeno, trifluoromethyl, cyano,
hydroxy, amino, (1-6C)alkyl, (2-6C)alkenyl, (2-6C)
alkynyl and (1-6C)alkoxy,
and wherein $Q^4$ optionally bears 1 or 2 oxo substituents;

(llllll) A is selected from cyclopropyl, cyclobutyl, cyclopen-
tyl, cyclohexyl, azetidinyl, pyrrolinyl, pyrrolidinyl, pip-
eridinyl, piperazinyl, morpholinyl, homopiperidinyl,
homopiperazinyl, dihydropyridinyl, tetrahydropyridinyl,
dihydropyrimidinyl, tetrahydropyrimidinyl, tetrahydro-
furanyl and tetrahydropyranyl,
and wherein A optionally bears one or more substituents,
which may be the same or different, selected from
fluoro, chloro, bromo, oxo, hydroxy, methyl, ethyl, pro-
pyl, butyl, isopropyl, isobutyl, trifluoromethyl, vinyl,
isopropenyl, allyl, but-2-enyl, ethynyl, 2-propynyl,
butynyl, methoxy, ethoxy, propoxy, isopropoxy, trifluo-
romethoxy, acetyl, propionyl, hydroxymethyl, meth-
oxymethyl, ethoxymethyl, 2-hydroxyethyl, 2-methoxy-
ethyl and 2-ethoxyethyl;

(mmmmmm) A is selected from cyclopropyl, pyrrolidinyl,
piperazinyl, morpholinyl and tetrahydrofuranyl,
and wherein A optionally bears one or more substituents,
which may be the same or different, selected from
methyl, ethyl, propyl, butyl, isopropyl and isobutyl (par-
ticularly methyl);

(nnnnnn) A is selected from azetidinyl, pyrrolidinyl, piperidi-
nyl, piperazinyl, morpholinyl, homopiperidinyl, homopip-
erazinyl, tetrahydrofuranyl and tetrahydropyranyl, and wherein A optionally bears one or more substituents, which may be the same or different, selected from fluoro, chloro, bromo, oxo, hydroxy, methyl, ethyl, propyl, isopropyl, trifluoromethyl, vinyl, allyl, ethynyl, 2-propynyl, methoxy, ethoxy, propoxy, isopropoxy, trifluoromethoxy and acetyl;

(oooooo) A is selected from methyl, ethyl, propyl, isopropyl, hydroxymethyl, 2-hydroxyethyl, 1-hydroxyethyl, 3-hydroxypropyl, 1-hydroxypropyl, 2-hydroxypropyl, 2-hydroxyprop-2-yl, 1,3-dihydroxypropyl, 2-(hydroxymethyl) prop-2-yl, 2-hydroxy-2-methylpropyl, methoxymethyl, 2-methoxyethyl, 1-methoxyethyl, 3-methoxypropyl, 1-methoxypropyl, 2-methoxypropyl, 2-methoxyprop-2-yl, 2-(methoxymethyl)prop-2-yl, 2-methoxy-2-methylpropyl, ethoxymethyl, 2-ethoxyethyl, 1-ethoxyethyl, 1-hydroxy-3-bromopropyl, (methylsulfonyl)methyl, aminomethyl, 2-aminoethyl, 1-aminoethyl, 3-aminopropyl, 1-aminopropyl, 2-aminopropyl, 2-aminoprop-2-yl, 2-(aminomethyl)prop-2-yl, 2-amino-2-methylpropyl, $\underline{N}$-methylaminomethyl, 2-($\underline{N}$-methylamino)ethyl, 1-1-methylamino)ethyl, 3-($\underline{N}$-methylamino)propyl, 1-($\underline{N}$- methylamino)propyl, 2-($\underline{N}$-methylamino)propyl, 2-($\underline{N}$- methylamino)prop-2-yl, 2-($\underline{N}$-methylaminomethyl) prop-2-yl, [($\underline{N}$-methyl)-(N-tert-butoxycarbonyl)amino] methyl, 2-$\underline{N}$-methylamino)-2-methylpropyl, $\underline{N}$,$\underline{N}$-dimethylaminomethyl, 2-($\underline{N},\underline{N}$-dimethylamino)ethyl, 1-($\underline{N},\underline{N}$-dimethylamino)ethyl, 3-($\underline{N},\underline{N}$-dimethylamino) propyl, 1-($\underline{N},\underline{N}$-dimethylamino)propyl, 2-($\underline{N}$,$\underline{N}$-dimethylamino)propyl, 2-($\underline{N}$,$\underline{N}$-dimethylamino)prop-2-yl, 2-($\underline{N}$,$\underline{N}$-dimethylaminomethyl)prop-2-yl, 2-($\underline{N}$,$\underline{N}$-dimethylamino)-2-methylpropyl, methylamino, dimethylamino, ethylamino, diethylamino, (2-chloroethyl)amino, methoxy, ethoxy, propoxy, butoxy, cyclopropyl, cyclobutyl, cyclopentyl, cyclohexyl, 1-hydroxycyclopropyl, 1-hydroxycyclobutyl, 1-hydroxycyclopentyl, 1-hydroxycyclohexyl, 1-hydroxymethylcyclopropyl, 1-hydroxymethylcyclobutyl, 1-hydroxymethylcyclopentyl, 1-hydroxymethylcyclohexyl, tetrahydrofuran-2-yl, tetrahydrofuran-3-yl, tetrahydropyran-2-yl, tetrahydropyran-3-yl, tetrahydropyran-4-yl, azetidin-2-yl, azetidin-3-yl, 1r-methylazetidin-2-yl, 1-methylazetidin-3-yl, pyrrolidin-2-yl, pyrrolidin-3-yl, 1-methylpyrrolidin-2-yl, 1-methylpyrrolidin-3-yl, pyrrolidin-1-ylmethyl, piperidin-2-yl, piperidin-3-yl, piperidin-4-yl, 1-methylpiperidin-2-yl, 1-methylpiperidin-3-yl, 1-methylpiperidin-4-yl, morpholin-4-yl, morpholin-4-ylmethyl, 1-methylpiperazin-4-ylmethyl;

(pppppp) A is selected from methyl, ethyl, propyl, isopropyl, hydroxymethyl, 2-hydroxyethyl, 1-hydroxyethyl, 3-hydroxypropyl, 1-hydroxypropyl, 2-hydroxypropyl, 2-hydroxyprop-2-yl, 2-(hydroxymethyl)prop-2-yl, 2-hydroxy-2-methylpropyl, methoxymethyl, 2-methoxyethyl, 1-methoxyethyl, 3-methoxypropyl, 1-methoxypropyl, 2-methoxypropyl, 2-methoxyprop-2-yl, 2-(methoxymethyl)prop-2-yl, 2-methoxy-2-methylpropyl, ethoxymethyl, 2-ethoxyethyl, 1-ethoxyethyl, aminomethyl, 2-aminoethyl, 1-aminoethyl, 3-aminopropyl, 1-aminopropyl, 2-aminopropyl, 2-aminoprop-2-yl, 2-(aminomethyl)prop-2-yl, 2-amino-2-methylpropyl, $\underline{N}$-methylaminomethyl, 2-($\underline{N}$-methylamino)ethyl, 1-($\underline{N}$-methylamino)ethyl, 3-($\underline{N}$-methylamino)propyl, 1-($\underline{N}$-methylamino)propyl, 2-($\underline{N}$-methylamino)propyl, 2-($\underline{N}$-methylamino)prop-2-yl, 2-($\underline{N}$-methylaminomethyl)prop-2-yl, 2-($\underline{N}$-methylamino)-2- methylpropyl, $\underline{N}$,$\underline{N}$-dimethylaminomethyl, 2-($\underline{N}$,$\underline{N}$-dimethylamino)ethyl, 1-($\underline{N}$,$\underline{N}$-dimethylamino)ethyl, 3-($\underline{N}$,$\underline{N}$-dimethylamino)propyl, 1-($\underline{N}$,$\underline{N}$-dimethylamino) propyl, 2-($\underline{N}$,$\underline{N}$-dimethylamino)propyl, 2-($\underline{N}$,$\underline{N}$-dimethylamino)prop-2-yl, 2-($\underline{N}$,$\underline{N}$-dimethylaminomethyl)prop-2-yl, 2-($\underline{N}$,$\underline{N}$-dimethylamino)-2-methylpropyl, cyclopropyl, cyclobutyl, cyclopentyl, cyclohexyl, 1-hydroxycyclopropyl, 1-hydroxycyclobutyl, 1-hydroxycyclopentyl, 1-hydroxycyclohexyl, 1-hydroxymethylcyclopropyl, 1-hydroxymethylcyclobutyl, 1-hydroxymethylcyclopentyl, 1-hydroxymethylcyclohexyl, tetrahydrofuran-2-yl, tetrahydrofuran-3-yl, tetrahydropyran-2-yl, tetrahydropyran-3-yl, tetrahydropyran-4-yl, azetidin-2-yl, azetidin-3-yl, 1-methylazetidin-2-yl, 1-methylazetidin-3-yl, pyrrolidin-2-yl, pyrrolidin-3-yl, 1-methylpyrrolidin-2-yl, 1-methylpyrrolidin-3-yl, piperidin-2-yl, piperidin-3-yl, piperidin-4-yl, 1-methylpiperidin-2-yl, 1-methylpiperidin-3-yl and 1-methylpiperidin-4-yl;

(qqqqqq) A is selected from methyl, ethyl, propyl, isopropyl, hydroxymethyl, 2-hydroxyethyl, 1-hydroxyethyl, 3-hydroxypropyl, 1-hydroxypropyl, 2-hydroxypropyl, 2-hydroxyprop-2-yl, 1,3-dihydroxypropyl, 2-(hydroxymethyl) prop-2-yl, 2-hydroxy-2-methylpropyl, methoxymethyl, 2-methoxyethyl, 1-methoxyethyl, 3-methoxypropyl, 1-methoxypropyl, 2-methoxypropyl, 2-methoxyprop-2-yl, 1-hydroxy-3-bromopropyl, (methylsulfonyl)methyl, aminomethyl, 2-aminoethyl, 1-aminoethyl, 3-aminopropyl, 1-aminopropyl, 2-aminopropyl, 2-aminoprop-2-yl, 2-(aminomethyl)prop-2-yl, 2-amino-2-methylpropyl, $\underline{N}$-methylaminomethyl, 2-($\underline{N}$-methylamino)ethyl, 1-($\underline{N}$-methylamino)ethyl, [($\underline{N}$-methyl)-(N-tert- butoxycarbonyl)amino]methyl, $\underline{N},\underline{N}$-dimethylaminomethyl, 2-($\underline{N},\underline{N}$-dimethylamino)ethyl, 1-($\underline{N}$,$\underline{N}$-dimethylamino)ethyl, methylamino, dimethylamino, ethylamino, diethylamino, (2-chloroethyl)amino, methoxy, ethoxy, cyclopropyl, cyclobutyl, 1-hydroxycyclopropyl, 1-hydroxycyclobutyl, 1-hydroxymethylcyclopropyl, 1-hydroxymethylcyclobutyl, tetrahydrofuran-2-yl, tetrahydrofuran-3-yl, tetrahydropyran-2-yl, tetrahydropyran-3-yl, tetrahydropyran-4-yl, pyrrolidin-2-yl, pyrrolidin-3-yl, 1-methylpyrrolidin-2-yl, 1-methylpyrrolidin-3-yl, pyrrolidin-1-ylmethyl, morpholin-4-yl, morpholin-4-ylmethyl, 1-methylpiperazin-4-ylmethyl;

(rrrrrr) A is selected from methyl, hydroxymethyl, 2-hydroxyethyl, 1-hydroxyethyl, 3-hydroxypropyl, 1,3-dihydroxypropyl, 2-(hydroxymethyl)prop-2-yl, methoxymethyl, 1-methoxyethyl, 1-hydroxy-3-bromopropyl, (methylsulfonyl)methyl, aminomethyl, $\underline{N}$-methylaminomethyl, [(N-methyl)-(N-tert-butoxycarbonyl)amino]methyl, methylamino, (2-chloroethyl) amino, methoxy, 1-hydroxycyclopropyl, tetrahydrofuran-2-yl, 1-methylpyrrolidin-2-yl, pyrrolidin-1-ylmethyl, morpholin-4-ylmethyl, 1-methylpiperazin-4-ylmethyl;

(ssssss) A is selected from hydroxymethyl, 2-hydroxyethyl, 1-hydroxyethyl, 3-hydroxypropyl, 1-hydroxypropyl, 2-hydroxypropyl, 2-hydroxyprop-2-yl, 2-(hydroxymethyl)prop-2-yl and 2-hydroxy-2-methylpropyl;

(tttttt) A is selected from methyl, hydroxymethyl, 2-hydroxyethyl, 1-hydroxyethyl and 2-hydroxyprop-2-yl;

(uuuuuu) A is selected from methyl and hydroxymethyl;

(vvvvvv) A is hydroxymethyl;

(wwwwww) A is a group of the formula Z-$(CR^{12}R^{13})_p$—,
wherein p is 1 or 2,
each $R^{12}$ and $R^{13}$, which may be the same or different, is selected from hydrogen and (1-3C)alkyl, and wherein Z is a group of the formula NR$^{16}$R$^{17}$, wherein each of R$^{16}$ and R$^{17}$, which may be the same or different, is selected from hydrogen and (1-6C)alkyl, and wherein any CH$_2$ or CH$_3$ group within any of R$^{12}$, R$^{13}$ and Z, optionally bears on each said CH$_2$ or CH$_3$ group one or more (for example 1, 2 or 3) halogeno or (1-6C) alkyl substituents, and wherein any CH$_2$ or CH$_3$ group within any of R$^{12}$, R$^{13}$ and Z which is not attached to a nitrogen atom optionally bears on each said CH$_2$ or CH$_3$ group a substituent selected from hydroxy and (1-6C)alkoxy;

(xxxxxx) A is selected from aminomethyl, 2-aminoethyl, 1-aminoethyl, 3-aminopropyl, 1-aminopropyl, 2-aminopropyl, 2-aminoprop-2-yl, 2-(aminomethyl)prop-2-yl, 2-amino-2-methylpropyl, N-methylaminomethyl, 2-(N-methylamino)ethyl, 1-(N-methylamino)ethyl, 3-(N-methylamino)propyl, 1-(N-methylamino)propyl, 2-(N-methylamino)propyl, 2-(N-methylamino)prop-2-yl, 2-(N-methylaminomethyl)prop-2-yl, 2-(N-methylamino)-2-methylpropyl, N,N-dimethylaminomethyl, 2-(N,N-dimethylamino)ethyl, 1-(N,N-dimethylamino) ethyl, 3-(N,N-dimethylamino)propyl, 1-(N,N-dimethylamino)propyl, 2-(N,N-dimethylamino)propyl, 2-(N,N-dimethylamino)prop-2-yl, 2-(N,N-dimethylaminomethyl)prop-2-yl, 2-(N,N-dimethylamino)-2-methylpropyl and [(N-methyl)-(N-tert-butoxycarbonyl)amino]methyl; and (yyyyyy) A is selected from aminomethyl, 2-aminoethyl, N-methylaminomethyl, 2-(N-methylamino)ethyl, N,N-dimethylaminomethyl, 2-(N,N-dimethylamino)ethyl and [(N-methyl)-(N-tert-butoxycarbonyl)amino]methyl (particularly A is N,N-dimethylaminomethyl).

A particular embodiment of the present invention is a quinazoline derivative of the formula I of the formula Ia:

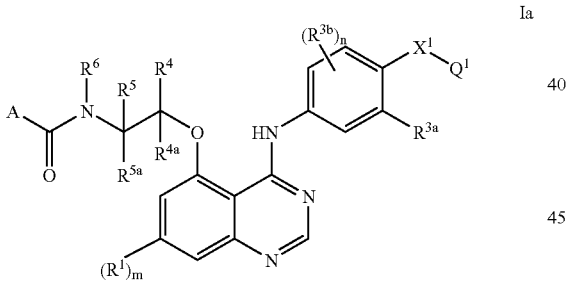

wherein:
m is 0, 1 or 2;
each R$^1$, which may be the same or different, is selected from hydroxy, (1-6C)alkoxy, (3-7C)cycloalkyl-oxy and (3-7C)cycloalkyl-(1-6C)alkoxy,
and wherein any CH$_2$ or CH$_3$ group within a R$^1$ substituent optionally bears on each said CH$_2$ or CH$_3$ group one or more halogeno or (1-6C)alkyl substituents, or a substituent selected from hydroxy and (1-6C)alkoxy,
R$^{3a}$ is selected from cyano, halogeno, (1-4C)alkyl, trifluoromethyl, (1-4C)alkoxy, (2-4C)alkenyl and (2-4C)alkynyl;
n is 0, 1 or 2;
each R$^{3b}$, which may be the same or different, is selected from cyano, halogeno, (1-4C)alkyl, trifluoromethyl, (1-4C)alkoxy, (2-4C)alkenyl and (2-4C)alkynyl (particularly halogeno and (1-4C)alkyl);

X$^1$ is selected from O, S, SO, SO$_2$, N(R$^7$), CH(OR$^7$), CON (R$^7$), N(R$^7$)CO, SO$_2$N(R$^7$), N(R$^7$)SO$_2$, OC(R$^7$)$_2$, C(R$^7$)$_2$O, SC(R$^7$)$_2$, C(R$^7$)$_2$S, CO, C(R$^7$)$_2$N(R$^7$) and N(R$^7$)C(R$^7$)$_2$, wherein each R$^7$, which may be the same or different, is hydrogen or (1-6C)alkyl;

Q$^1$ is aryl, or heteroaryl, and wherein Q$^1$ optionally bears one or more substituents (for example 1, 2 or 3), which may be the same or different, selected from halogeno, cyano, nitro, hydroxy, amino, carboxy, carbamoyl, sulfamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C) alkoxycarbonyl, N-(1-6C)alkylcarbamoyl, N, N-di-[(1-6C)alkyl]carbamoyl, (2-6C)alkanoyl, (3-6C) alkenoyl, (3-6C)alkynoyl, (2-6C)alkanoyloxy, (2-6C) alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N, N-di-[(1-6C)alkyl]sulfamoyl, (1-6C)alkanesulfonylamino, N-(1-6C)alkyl-(1-6C)alkanesulfonylamino, and a group of the formula:

—X$^2$—R$^8$ wherein X$^2$ is a direct bond or is selected from O, CO and N(R$^9$), wherein R$^9$ is hydrogen or (1-6C)alkyl, and R$^8$ is halogeno-(1-6C)alkyl, hydroxy-(1-6C)alkyl, carboxy-(1-6C)alkyl, (1-6C)alkoxy-(1-6C)alkyl, cyano-(1-6C) alkyl, amino-(1-6C)alkyl, N-(1-6C)alkylamino-(1-6C)alkyl, N, N-di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N, N-di-[(1-6C)alkyl]carbamoyl-(1-6C)alkyl, (1-6C)alkylthio-(1-6C)alkyl, (1-6C)alkylsulfinyl-(1-6C)alkyl, (1-6C)alkylsulfonyl-(1-6C)alkyl sulfamoyl(1-6C)alkyl, N-(1-6C)alkylsulfamoyl(1-6C)alkyl, N, N-di-(1-6C)alkylsulfamoyl(1-6C)alkyl, (2-6C)alkanoyl-(1-6C)alkyl, (2-6C)alkanoyloxy-(1-6C)alkyl or (1-6C)alkoxycarbonyl-(1-6C)alkyl, and wherein any CH$_2$ or CH$_3$ group within —X$^1$-Q$^1$ optionally bears on each said CH$_2$ or CH$_3$ group one or more (for example 1, 2, or 3) halogeno or (1-6C)alkyl substituents or a substituent selected from hydroxy, cyano, amino, (1-4C)alkoxy, (1-4C)alkylamino and di-[(1-4C)alkylamino];

R$^4$, R$^{4a}$, R$^5$ and R$^{5a}$, which may be the same or different, are selected from hydrogen and (1-6C)alkyl, or R$^4$ and R$^{4a}$ together with the carbon atom to which they are attached form a (3-7C)cycloalkyl ring, or R$^5$ and R$^{5a}$ together with the carbon atom to which they are attached form a (3-7C)cycloalkyl ring, and wherein any CH$_2$ or CH$_3$ group within any of R$^4$, R$^{4a}$, R$^5$ and R$^{5a}$ optionally bears on each said CH$_2$ or CH$_3$ group one or more (for example 1, 2 or 3) halogeno substituents or a substituent selected from hydroxy, cyano, (1-6C)alkoxy, amino, (2-6C)alkanoyl, (1-6C) alkylamino and di-[(1-6C)alkylamino];

R$^6$ is selected from hydrogen, (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, and wherein any heterocyclyl group within an $R^6$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^3$—$R^{10}$ wherein $X^3$ is a direct bond or is selected from O, CO, $SO_2$ and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo or thioxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

A is selected from hydrogen, a group of the formula Z-$(CR^{12}R^{13})_p$— and $R^{14}$,
  wherein p is 1, 2, 3, or 4,
  each $R^{12}$ and $R^{13}$, which may be the same or different, is selected from hydrogen, (1-6C)alkyl, (2-6C)alkenyl and (2-6C)alkynyl,
  or an $R^{12}$ and an $R^{13}$ group attached to the same carbon atom form a (3-7C)cycloalkyl or (3-7C)cycloalkenyl ring,
  and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkyl]amino,
  Z is selected from hydrogen, $OR^{15}$, $NR^{16}R^{17}$, (1-6C)alkylsulfonyl, (1-6C)alkanesulfonylamino and N-(1-6C)alkyl-(1-6C)alkanesulfonylamino, wherein each of $R^{15}$, $R^{16}$ and $R^{17}$, which may be the same or different, is selected from hydrogen, (1-6C)alkyl, (2-6C)alkenyl, (2-6C)alkynyl and (1-6C)alkoxycarbonyl,
  or Z is a group of the formula:

$Q^2$-$X^4$— wherein $X^4$ is selected from O, $N(R^{18})$, $SO_2$ and $SO_2N(R^{18})$, wherein $R^{18}$ is hydrogen or (1-6C)alkyl, and $Q^2$ is (3-7C)cycloalkyl, (3-7C)cycloalkenyl or heterocyclyl, $R^{14}$ is selected from hydrogen, $OR^{19}$ and $NR^{16}R^{17}$, wherein $R^{19}$ is selected from (1-6C)alkyl, (2-6C)alkenyl and (2-6C)alkynyl, and wherein $R^{16}$ and $R^{17}$ are as defined above, or $R^{14}$ is a group of the formula:

$Q^3$-$X^5$— wherein $X^5$ is selected from O and $N(R^{20})$, wherein $R^{20}$ is hydrogen or (1-6C)alkyl, and $Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, or $R^{14}$ is $Q^4$ wherein $Q^4$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein adjacent carbon atoms in any (2-6C)alkylene chain within a Z or $R^{14}$ substituent are optionally separated by the insertion into the chain of a group selected from O, S, SO, $SO_2$, $N(R^{21})$, CO, —C=C— and —C≡C—, wherein $R^{21}$ is hydrogen or (1-6C)alkyl, and wherein any heterocyclyl group within a Z or $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$ wherein $X^6$ is a direct bond or is selected from O, CO, $SO_2$ and $N(R^{23})$, wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within a Z or $R^{14}$ substituent optionally bears 1 or 2 oxo or thioxo substituents, and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

or a pharmaceutically acceptable salt thereof.

Another embodiment of the present invention is a quinazoline derivative of the formula Ia, wherein:
  m is 0 or 1;
  $R^1$ is selected from (1-4C)alkoxy (for example methoxy or ethoxy),
  and wherein any $CH_2$ or $CH_3$ group within a $R^1$ substituent optionally bears on each said $CH_2$ or $CH_3$ group one or more fluoro or chloro substituents, or a substituent selected from hydroxy and (1-3C)alkoxy;
  $R^{3a}$ is selected from hydrogen, halogeno, trifluoromethyl, (1-4C)alkyl, (1-4C) alkoxy, (2-4C)alkenyl and (2-4C)alkynyl;
  n is 0, 1 or 2;
  each $R^{3b}$, which may be the same or different, is selected from halogeno and (1-4C)alkyl;

$X^1$ is selected from O, S and $OC(R^7)_2$, wherein each $R^7$, which may be the same or different, is hydrogen or (1-6C)alkyl;

$Q^1$ is aryl, or heteroaryl, and wherein $Q^1$ optionally bears one or more substituents (for example 1, 2 or 3), which may be the same or different, selected from halogeno, cyano, nitro, hydroxy, amino, carboxy, carbamoyl, sulfamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (3-6C)alkenoyl, (3-6C)alkynoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, and a group of the formula:

—$X^2$—$R^8$ wherein $X^2$ is a direct bond or is selected from O, CO and $N(R^9)$, wherein $R^9$ is hydrogen or (1-6C)alkyl, and $R^8$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkylthio-(1-6C)alkyl, (1-6C)alkylsulfinyl-(1-6C)alkyl, (1-6C)alkylsulfonyl-(1-6C)alkyl sulfamoyl(1-6C)alkyl, N-(1-6C)alkylsulfamoyl(1-6C)alkyl, N,N-di-(1-6C)alkylsulfamoyl(1-6C)alkyl, (2-6C)alkanoyl-(1-6C)alkyl, (2-6C)alkanoyloxy-(1-6C)alkyl or (1-6C)alkoxycarbonyl-(1-6C)alkyl, and wherein any $CH_2$ or $CH_3$ group within —$X^1$-$Q^1$ optionally bears on each said $CH_2$ or $CH_3$ group one or more (for example 1, 2, or 3) halogeno or (1-6C)alkyl substituents or a substituent selected from hydroxy, cyano, amino, (1-4C)alkoxy, (1-4C)alkylamino and di-[(1-4C)alkylamino];

$R^4$, $R^{4a}$, $R^5$ and $R^{5a}$, which may be the same or different, are selected from hydrogen and (1-6C)alkyl, or $R^4$ and $R^{4a}$ together with the carbon atom to which they are attached form a (3-7C)cycloalkyl ring, or $R^5$ and $R^{5a}$ together with the carbon atom to which they are attached form a (3-7C)cycloalkyl ring, and wherein any $CH_2$ or $CH_3$ group within any of $R^4$, $R^{4a}$, $R^5$ and $R^{5a}$ optionally bears on each said $CH_2$ or $CH_3$ group one or more (for example 1, 2 or 3) halogeno substituents or a substituent selected from hydroxy, cyano, (1-6C)alkoxy, amino, (2-6C)alkanoyl, (1-6C)alkylamino and di-[(1-6C)alkylamino];

$R^6$ is selected from hydrogen, (1-6C)alkyl, (2-6C)alkenyl, (2-6C)alkynyl, (3-7C)cycloalkyl, (3-7C)cycloalkyl-(1-6C)alkyl, heterocyclyl and heterocyclyl-(1-6C)alkyl, and wherein any heterocyclyl group within an $R^6$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^3$—$R^{10}$ wherein $X^3$ is a direct bond or is selected from O, CO, $SO_2$ and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo or thioxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

A is selected from a group of the formula Z-$(CR^{12}R^{13})_p$— and $R^{14}$, wherein p is 1, 2 or 3, each $R^{12}$ and $R^{13}$, which may be the same or different, is selected from hydrogen, (1-6C)alkyl, (2-6C)alkenyl and (2-6C)alkynyl, or an $R^{12}$ and an $R^{13}$ group attached to the same carbon atom form a (3-7C)cycloalkyl ring, and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkylamino], Z is selected from hydrogen, $OR^{15}$, $NR^{16}R^{17}$ and $R^{14}$ wherein each of $R^{15}$, $R^{16}$ and $R^{17}$, which may be the same or different, is selected from hydrogen, (1-6C)alkyl, (2-6C)alkenyl and (2-6C)alkynyl, $R^{14}$ is a 4, 5, 6 or 7 membered saturated or partially saturated monocyclic heterocyclyl ring containing 1 nitrogen or oxygen heteroatom and optionally 1 further heteroatom selected from oxygen, nitrogen and sulfur, and wherein any heterocyclyl group within a $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$ wherein $X^6$ is a direct bond or is selected from O, CO, $SO_2$ and $N(R^{23})$, wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within a $R^{14}$ substituent optionally bears 1 or 2 oxo or thioxo substituents, and wherein any $CH_2$ or $CH_3$ group within a Z group optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

or a pharmaceutically acceptable salt thereof.

In an embodiment, in the compound of formula Ia m is 0 or m is 1 and $R^1$ is (1-3C)alkoxy, for example methoxy. Particularly m is 0.

In another embodiment, in the compound of formula Ia, n is 0 and $R^{3a}$ is selected from halogeno, trifluoromethyl, (1-4C)alkyl, (1-4C)alkoxy, (2-4C)alkenyl and (2-4C)alkynyl. Particularly $R^{3a}$ is selected from halogeno and (1-3C)alkyl, more particularly $R^{3a}$ is selected from chloro and methyl, still more particularly $R^{3a}$ is chloro. In this embodiment n is suitably 0 or 1. Particularly n is 0.

In another embodiment, in the compound of formula Ia, $X^1$ is selected from O, S and $OC(R^7)_2$, wherein $R^7$ is hydrogen or (1-3C)alkyl, more particularly $X^1$ is selected from O and $OC(R^7)_2$, for example $X^1$ is selected from O, $OCH_2$ and $OC(CH_3)_2$. In another embodiment, in the compound of formula Ia, $X^1$ is selected from S and $OC(R^7)_2$, wherein $R^7$ is hydrogen or (1-3C)alkyl, more particularly $X^1$ is $OC(R^7)_2$, for example $X^1$ is $OCH_2$.

In another embodiment, in the compound of formula Ia, $Q^1$ is selected from phenyl and a 5- or 6-membered monocyclic heteroaryl ring, which ring contains 1 nitrogen heteroatom and optionally 1 additional heteroatom selected from oxygen, nitrogen and sulfur, and wherein $Q^1$ optionally bears one or more substituents (for example 1, 2 or 3), which may be the same or different selected from halogeno, hydroxy, cyano, carboxy, nitro, amino, (1-4C)alkyl, (1-4C)alkoxy, (2-4C)alkenyl, (2-4C)alkynyl, (1-4C)alkylthio, (1-4C)alkylsulfinyl, (1-4C)alkylsulfonyl, (2-4C)alkanoyl, N-(1-4C)alkylamino, N,N-di-[(1-4C)alkyl]amino, (1-4C)alkoxycarbonyl, carbamoyl, N-(1-4C)alkylcarbamoyl, N,N-di-[(1-4C)alkyl]carbamoyl, (2-4C)alkanoyloxy, (2-4C)alkanoylamino, N-(1-4C)alkyl-(2-4C)alkanoylamino, halogeno-(1-4C)alkyl, hydroxy-(1-4C)alkyl, (1-4C)alkoxy-(1-4C)alkyl, cyano-(1-4C)alkyl, carboxy-(1-4C)alkyl, amino-(1-4C)alkyl, N-(1-4C)alkylamino-(1-4C)alkyl and N,N-di-[(1-4C)alkyl]amino-(1-4C)alkyl.

In another embodiment, in the compound of formula Ia, $Q^1$ is selected from phenyl, pyridyl, pyrazinyl, thiazolyl and isoxazolyl, optionally substituted by 1, 2, or 3 substituents, which may be the same or different, selected from halogeno (for example fluoro or chloro), hydroxy, (1-4C)alkyl and (1-4C)alkoxy. For example $Q^1$ is selected from phenyl optionally substituted with 1 or 2 substituents selected from fluoro and chloro or $Q^1$ is selected from 2-pyridyl, 3-pyridyl, 2-pyrazinyl, 1,3-thiazol-2-yl, 1,3-thiazol-4-yl, 1,3-thiazol-5-yl and isoxazol-3-yl (particularly 2-pyridyl, 3-pyridyl, 2-pyrazinyl, 1,3-thiazol-2-yl, 1,3-thiazol-4-yl and isoxazol-3-yl), and wherein any heterocyclic group in $Q^1$ optionally bears 1, 2, or 3 substituents, which may be the same or different, selected from halogeno (for example fluoro or chloro), hydroxy, (1-4C)alkyl and (1-4C)alkoxy.

In another embodiment, in the compound of formula Ia, $Q^1$ is pyridyl (for example 2-pyridyl or 3-pyridyl, particularly 2-pyridyl), which optionally bears 1, 2, or 3 substituents, which may be the same or different, selected from halogeno (for example fluoro or chloro), hydroxy, (1-4C)alkyl and (1-4C)alkoxy. For example, $Q^1$ is particularly pyridyl, optionally substituted by 1 or 2 (1-4C)alkyl substituents (for example by 1 or 2 methyl substituents).

In another embodiment, in the compound of formula Ia, $R^4$, $R^{4a}$, $R^5$ and $R^{5a}$ are selected from hydrogen and (1-3C)alkyl, for example $R^4$, $R^{4a}$, $R^5$ and $R^{5a}$ are selected from hydrogen and methyl.

In another embodiment, in the compound of formula Ia, $R^4$, $R^{4a}$, $R^5$ and $R^{5a}$ are all hydrogen.

In another embodiment, in the compound of formula Ia, $R^{4a}$, $R^5$ and $R^{5a}$ are hydrogen and $R^4$ is (1-3C)alkyl, for example methyl.

In another embodiment, in the compound of formula Ia, $R^4$, $R^{4a}$ and $R^{5a}$ are hydrogen and $R^5$ is (1-3C)alkyl, for example methyl.

In another embodiment, in the compound of formula Ia, $R^4$ and $R^{4a}$ are both hydrogen and $R^5$ and $R^{5a}$ are both (1-3C)alkyl, for example methyl.

In another embodiment, in the compound of formula Ia, $R^6$ is selected from hydrogen, (1-6C)alkyl, (2-6C)alkenyl, (2-6C)alkynyl, (3-7C)cycloalkyl, (3-7C)cycloalkyl-(1-6C)alkyl, heterocyclyl and heterocyclyl-(1-6C)alkyl, wherein any heterocyclyl group within $R^6$ is a 4, 5, 6 or 7 membered monocyclic saturated or partially saturated heterocyclyl ring containing 1 or 2 heteroatoms selected from oxygen, nitrogen and sulfur, and wherein any heterocyclyl group within an $R^6$ substituent optionally bears one or more substituents, which may be the same or different, selected from halogeno, trifluoromethyl, hydroxy, amino, (1-6C)alkyl, (2-6C)alkenyl, (2-6C)alkynyl, (1-6C)alkoxy, (1-6C)alkylamino, di-[(1-6C)alkyl]amino, (2-6C)alkanoyl, and from a group of the formula:

—$X^3$—$R^{10}$ wherein $X^3$ is a direct bond or is selected from O and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo substituents.

In another embodiment, in the compound of formula Ia, $R^6$ is selected from hydrogen, (1-6C)alkyl, (2-6C)alkenyl, (2-6C)alkynyl, (3-7C)cycloalkyl, (3-7C)cycloalkyl-(1-4C)alkyl, heterocyclyl and heterocyclyl-(1-4C)alkyl, wherein any heterocyclyl group within $R^6$ is a 4, 5, 6 or 7 membered monocyclic saturated or partially saturated heterocyclyl ring containing 1 or 2 heteroatoms selected from oxygen, nitrogen and sulfur, and wherein any heterocyclyl group within an $R^6$ substituent optionally bears one or more substituents, which may be the same or different, selected from fluoro, chloro, bromo, hydroxy, (1-4C)alkyl, (2-4C)alkenyl, (2-4C)alkynyl and (1-4C)alkoxy, and wherein any heterocyclyl group within an $R^6$ substituent optionally bears 1 oxo substituent, and wherein any $CH_2$ or $CH_3$ group within a $R^6$ substituent, other than a $CH_2$ group within a heterocyclyl ring, optionally bears on each said $CH_2$ or $CH_3$ group one or more substituents selected from fluoro and chloro, or a substituent selected from hydroxy and (1-4C)alkoxy, (1-6C)alkylamino and di-[(1-6C)alkyl]amino.

In another embodiment, in the compound of formula Ia, $R^6$ is selected from hydrogen and (1-4C)alkyl. For example $R^6$ is (1-3C)alkyl such as methyl.

In another embodiment, in the compound of formula Ia, $R^6$ is selected from hydrogen, methyl, ethyl, 2-hydroxyethyl, 2-methoxyethyl, propyl, isopropyl, allyl, 2-propynyl, cyclopropyl, cyclobutyl, piperidinyl, tetrahydropyranyl and cyclopropylmethyl, and wherein any $CH_2$ group within a cycloalkyl group within $R^6$ optionally bears on each $CH_2$ group 1 or 2 substituents selected from hydroxy, methyl, ethyl, methoxy and ethoxy, and wherein any heterocyclyl group within $R^6$ optionally bears one or more substituents, which may be the same or different, selected from fluoro, chloro, bromo, oxo, hydroxy, methyl, ethyl, propyl, isopropyl, trifluoromethyl, methoxy, ethoxy, propoxy, isopropoxy and trifluoromethoxy.

In another embodiment, in the compound of formula Ia, A is a group of the formula $Z\text{-}(CR^{12}R^{13})_p\text{—}$, wherein p is 1 or 2, each $R^{12}$ and $R^{13}$, which may be the same or different, is selected from hydrogen and (1-4C)alkyl, or an $R^{12}$ and an $R^{13}$ group attached to the same carbon atom form a (3-6C)cycloalkyl ring, and wherein any $CH_2$ or $CH_3$ group within any of $R^{12}$ and $R^{13}$, optionally bears on each said $CH_2$ or $CH_3$ group one or more (for example 1, 2 or 3) halogeno or (1-4C)alkyl substituents or a substituent selected from hydroxy and (1-4C)alkoxy, and wherein Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-4C)alkyl and (1-4C)alkoxycarbonyl.

For example, in an embodiment, Z is selected from hydrogen, hydroxy, methoxy, N-methylamino, N,N-dimethylamino, (N-methyl)-(N-tert-butoxycarbonyl)amino and methylsulfonyl (particularly Z is hydroxy).

In another embodiment, in the compound of formula Ia, A is a group of the formula $Z\text{-}(CR^{12}R^{13})_p\text{—}$, wherein p is 1 or 2, each $R^{12}$ and $R^{13}$, which may be the same or different, is selected from hydrogen and (1-4C)alkyl, or an $R^{12}$ and an $R^{13}$ group attached to the same carbon atom form a (3-6C)cycloalkyl ring, and wherein any $CH_2$ or $CH_3$ group within any of $R^{12}$ and $R^{13}$, optionally bears on each said $CH_2$ or $CH_3$ group one or more (for example 1, 2 or 3) halogeno or (1-4C)alkyl substituents or a substituent selected from hydroxy and (1-4C)alkoxy, and wherein Z is selected from hydrogen, hydroxy and (1-3C)alkoxy. For example Z is hydrogen or hydroxy, particularly Z is hydroxy.

In another embodiment, in the compound of formula Ia, A is selected from methyl, hydroxymethyl, 2-hydroxyethyl, 1-hydroxyethyl and 2-hydroxyprop-2-yl. Particularly A is hydroxymethyl.

In another embodiment, in the compound of formula Ia:
m is 0;

$R^{3a}$ is selected from fluoro, chloro and (1-3C)alkyl (for example $R^{3a}$ is chloro or methyl, particularly $R^{3a}$ is chloro);

n is 0;

$X^1$ is selected from O and $OCH_2$ (for example $X^1$ is $OCH_2$);

$R^4$, $R^{4a}$, $R^5$ and $R^{5a}$ are selected from hydrogen and (1-3C)alkyl, for example $R^4$, $R^{4a}$, $R^5$ and $R^{5a}$ are selected from hydrogen and methyl (for example $R^{4a}$ and $R^{5a}$ are hydrogen and one of $R^4$ and $R^5$ is methyl and the other of $R^4$ and $R^5$ is hydrogen or $R^4$ and $R^{4a}$ are both hydrogen and $R^5$ and $R^{5a}$ are both methyl); or $R^4$ and $R^{4a}$ together with the carbon atom to which they are attached form a (3-6C)cycloalkyl ring, or $R^5$ and $R^{5a}$ together with the carbon atom to which they are attached form a (3-6C)cycloalkyl ring;

$R^6$ is hydrogen or (1-3C)alkyl, for example $R^6$ is hydrogen or methyl (a particular value for $R^6$ is methyl);

A is a group of the formula $Z\text{-}(CR^{12}R^{13})_p\text{—}$, wherein p is 1 or 2, each $R^{12}$ and $R^{13}$, which may be the same or different, is selected from hydrogen and (1-3C)alkyl, or an $R^{12}$ and an $R^{13}$ group attached to the same carbon atom form a (3-6C)cycloalkyl ring, and wherein Z is selected from hydrogen, hydroxy and (1-3C)alkoxy (for example Z is hydrogen or hydroxy, particularly Z is hydroxy).

In another embodiment, in the compound of formula Ia:
m is 0;

$R^{3a}$ is selected from fluoro, chloro and (1-3C)alkyl (for example $R^{3a}$ is chloro or methyl, particularly $R^{3a}$ is chloro);

n is 0;

$X^1$ is selected from O, $OCH_2$ and $OC(CH_3)_2$ (for example $X^1$ is $OCH_2$);

$R^4$, $R^{4a}$, $R^5$ and $R^{5a}$ are selected from hydrogen and (1-3C)alkyl, for example $R^4$, $R^{4a}$, $R^5$ and $R^{5a}$ are selected from hydrogen and methyl (for example $R^4$, $R^{4a}$, $R^5$ and $R^{5a}$ are all hydrogen, or $R^{4a}$ and $R^{5a}$ are both hydrogen and one of $R^4$ and $R^5$ is methyl and the other of $R^4$ and $R^5$ is hydrogen, or $R^4$ and $R^{4a}$ are both hydrogen and $R^5$ and $R^{5a}$ are both methyl);

$R^6$ is selected from hydrogen, (1-3C)alkyl, (2-3C)alkenyl, (2-3C)alkynyl, (3-5C)cycloalkyl, (3-5C)cycloalkyl-(1-3C)alkyl and heterocyclyl, and wherein any heterocyclyl group within an $R^6$ substituent optionally bears one or more (1-6C)alkyl substituents (for example $R^6$ is hydrogen or methyl (a particular value for $R^6$ is methyl));

A is selected from a group of the formula $Z\text{-}(CR^{12}R^{13})_p\text{—}$ and $R^{14}$, wherein p is 1 or 2, each $R^2$ and $R^{13}$, which may be the same or different, is selected from hydrogen and (1-6C)alkyl, and wherein any $CH_2$ or $CH_3$ group within any of $R^{12}$ and $R^{13}$, optionally bears on each said $CH_2$ or $CH_3$ group one or more (for example 1, 2 or 3) halogeno substituents or a substituent selected from hydroxy and (1-6C)alkoxy (particularly hydroxy), Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-6C)alkyl and (1-6C)alkoxycarbonyl, $R^{14}$ is selected from $OR^{19}$ and $NR^{16}R^{17}$, wherein $R^{19}$ is selected from (1-6C)alkyl and wherein $R^{16}$ and $R^{17}$ are as defined above, or $R^{14}$ is $Q^4$ wherein $Q^4$ is (3-7C)cycloalkyl, heterocyclyl or heterocyclyl-(1-6C)alkyl, and wherein any heterocyclyl group within a Z or R$^{14}$ substituent optionally bears one or more (for example 1, 2 or 3) substituents, which may be the same or different, selected from halogeno, hydroxy, (1-6C)alkyl and (1-6C)alkoxy (particularly (1-6C)alkyl), and wherein any CH$_2$ or CH$_3$ group within a Z or R$^{14}$ group, other than a CH$_2$ group within a heterocyclyl ring, optionally bears on each said CH$_2$ or CH$_3$ group one or more halogeno or (1-6C)alkyl substituents or a substituent selected from hydroxy and (1-6C)alkoxy (particularly a substituent selected from halogeno and hydroxy).

Another particular embodiment of the present invention is a quinazoline derivative of the formula I of the formula Ib:

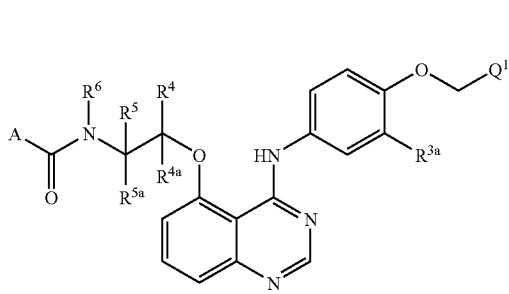

wherein:
R$^{3a}$ is selected from cyano, halogeno, (1-4C)alkyl, trifluoromethyl, (1-4C)alkoxy, (2-4C)alkenyl and (2-4C)alkynyl;

Q$^1$ is aryl, or heteroaryl, and wherein Q$^1$ optionally bears one or more substituents (for example 1, 2 or 3), which may be the same or different, selected from halogeno, cyano, nitro, hydroxy, amino, carboxy, carbamoyl, sulfamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (3-6C)alkenoyl, (3-6C)alkynoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, and a group of the formula:

—X$^2$—R$^8$ wherein X$^2$ is a direct bond or is selected from O, CO and N(R$^9$), wherein R$^9$ is hydrogen or (1-6C)alkyl, and R$^8$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkylthio-(1-6C)alkyl, (1-6C)alkylsulfinyl-(1-6C)alkyl, (1-6C)alkylsulfonyl-(1-6C)alkyl sulfamoyl(1-6C)alkyl, N-(1-6C)alkylsulfamoyl(1-6C)alkyl, N,N-di-(1-6C)alkylsulfamoyl(1-6C)alkyl, (2-6C)alkanoyl-(1-6C)alkyl, (2-6C)alkanoyloxy-(1-6C)alkyl or (1-6C)alkoxycarbonyl-(1-6C)alkyl, and wherein any CH$_2$ or CH$_3$ group within —X$^1$-Q$^1$ optionally bears on each said CH$_2$ or CH$_3$ group one or more (for example 1, 2, or 3) halogeno or (1-6C)alkyl substituents or a substituent selected from hydroxy, cyano, amino, (1-4C)alkoxy, (1-4C)alkylamino and di-[(1-4C)alkylamino];

R$^4$, R$^{4a}$, R$^5$ and R$^{5a}$, which may be the same or different, are selected from hydrogen and (1-6C)alkyl, and wherein any CH$_2$ or CH$_3$ group within any of R$^4$, R$^{4a}$, R$^5$ and R$^{5a}$ optionally bears on each said CH$_2$ or CH$_3$ group one or more (for example 1, 2 or 3) halogeno substituents or a substituent selected from hydroxy, cyano, (1-6C)alkoxy, amino, (2-6C)alkanoyl, (1-6C)alkylamino and di-[(1-6C)alkylamino];

R$^6$ is selected from hydrogen, (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, and wherein any heterocyclyl group within an R$^6$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—X$^3$—R$^{10}$ wherein X$^3$ is a direct bond or is selected from O, CO, SO$_2$ and N(R$^{11}$), wherein R$^{11}$ is hydrogen or (1-4C)alkyl, and R$^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an R$^6$ substituent optionally bears 1 or 2 oxo or thioxo substituents;

and wherein any CH$_2$ or CH$_3$ group within a R$^6$ substituent, other than a CH$_2$ group within a heterocyclyl group, optionally bears on each said CH$_2$ or CH$_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

A is selected from hydrogen, a group of the formula Z-(CR$^{12}$R$^{13}$)$_p$— and R$^{14}$, wherein p is 1, 2, 3, or 4, each R$^{12}$ and R$^{13}$, which may be the same or different, is selected from hydrogen, (1-6C)alkyl, (2-6C)alkenyl and (2-6C)alkynyl, or an R$^{12}$ and an R$^{13}$ group attached to the same carbon atom form a (3-7C)cycloalkyl or (3-7C)cycloalkenyl ring, and wherein any $CH_2$ or $CH_3$ group within any of $R^{12}$ and $R^{13}$ optionally bears on each said $CH_2$ or $CH_3$ group one or more (for example 1, 2 or 3) halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkyl]amino, Z is selected from hydrogen, $OR^{15}$, $NR^{16}R^{17}$, (1-6C)alkylsulfonyl, (1-6C)alkanesulfonylamino and N-(1-6C)alkyl-(1-6C)alkanesulfonylamino, wherein each of $R^{15}$, $R^{16}$ and $R^{17}$, which may be the same or different, is selected from hydrogen, (1-6C)alkyl, (2-6C)alkenyl, (2-6C)alkynyl and (1-6C)alkoxycarbonyl, or Z is a group of the formula:

$$Q^2-X^4-$$

wherein $X^4$ is selected from O, $N(R^{18})$, $SO_2$ and $SO_2N(R^{18})$, wherein $R^{18}$ is hydrogen or (1-6C)alkyl, and $Q^2$ is (3-7C)cycloalkyl, (3-7C)cycloalkenyl or heterocyclyl, $R^{14}$ is selected from hydrogen, $OR^{19}$ and $NR^{16}R^{17}$, wherein $R^{19}$ is selected from (1-6C)alkyl, (2-6C)alkenyl and (2-6C)alkynyl, and wherein $R^{16}$ and $R^{17}$ are as defined above, or $R^{14}$ is a group of the formula:

$$Q^3-X^5-$$

wherein $X^5$ is selected from O and $N(R^{20})$, wherein $R^{20}$ is hydrogen or (1-6C)alkyl, and $Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, or $R^{14}$ is $Q^4$ wherein $Q^4$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein adjacent carbon atoms in any (2-6C)alkylene chain within a Z or $R^{14}$ substituent are optionally separated by the insertion into the chain of a group selected from O, S, SO, $SO_2$, $N(R^{21})$, CO, —C=C— and —C≡C—, wherein $R^{21}$ is hydrogen or (1-6C)alkyl, and wherein any heterocyclyl group within a Z or $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$-X^6-R^{22}$$

wherein $X^6$ is a direct bond or is selected from O, CO, $SO_2$ and N(23), wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within a Z or $R^{14}$ substituent optionally bears 1 or 2 oxo or thioxo substituents, and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

or a pharmaceutically acceptable salt thereof.

Another particular embodiment of the present invention is a quinazoline derivative of the formula I of the formula Ib, wherein:

$R^{3a}$ is selected from hydrogen, fluoro, chloro, trifluoromethyl, (1-3C)alkyl, (1-3C)alkoxy, (2-4C)alkenyl and (2-4C)alkynyl;

$Q^1$ is selected from phenyl, pyridyl, pyrazinyl, thiazolyl and isoxazolyl, optionally substituted by 1, 2, or 3 substituents, which may be the same or different, selected from halogeno (for example fluoro or chloro), hydroxy, (1-4C)alkyl and (1-4C)alkoxy;

$R^4$, $R^{4a}$, $R^5$ and $R^{5a}$, which may be the same or different, are selected from hydrogen and (1-3C)alkyl, and wherein any $CH_2$ or $CH_3$ group within any of $R^4$, $R^{4a}$, $R^5$ and $R^{5a}$ optionally bears on each said $CH_2$ or $CH_3$ group one or more (for example 1, 2 or 3) halogeno substituents or a substituent selected from hydroxy and (1-3C)alkoxy;

$R^6$ is selected from hydrogen and (1-4C)alkyl;

A is a group of the formula $Z-(CR^{12}R^{13})_p-$, wherein p is 1 or 2, each $R^{12}$ and $R^{13}$, which may be the same or different, is selected from hydrogen and (1-4C)alkyl, or an $R^{12}$ and an $R^{13}$ group attached to the same carbon atom form a (3-6C)cycloalkyl ring, and wherein any $CH_2$ or $CH_3$ group within any of $R^{12}$ and $R^{13}$ optionally bears on each said $CH_2$ or $CH_3$ group one or more (for example 1, 2 or 3) halogeno substituents or a substituent selected from hydroxy, and (1-3C)alkoxy, Z is selected from hydrogen, $OR^{15}$ and $NR^{16}R^{17}$, wherein each of $R^{15}$, $R^{16}$ and $R^{17}$, which may be the same or different, is selected from hydrogen and (1-6C)alkyl, and wherein any $CH_2$ or $CH_3$ group within a Z group optionally bears on each said $CH_2$ or $CH_3$ group one or more fluoro or chloro substituents or a substituent selected from hydroxy, (2-4C)alkenyl, (2-4C)alkynyl and (1-4C)alkoxy;

or a pharmaceutically acceptable salt thereof.

In an embodiment, in the compound of formula Ib, $R^{3a}$ is selected from hydrogen, chloro and (1-3C)alkyl, particularly $R^{3a}$ is chloro or (1-3C)alkyl (such as methyl), more particularly $R^{3a}$ is chloro.

In another embodiment, in the compound of formula Ib, $Q^1$ is selected from phenyl optionally substituted with 1 or 2 substituents selected from fluoro and chloro, or $Q^1$ is selected from 2-pyridyl, 3-pyridyl, 2-pyrazinyl, 1,3-thiazol-2-yl, 1,3-thiazol-4-yl, 1,3-thiazol-5-yl and isoxazol-3-yl (particularly 2-pyridyl, 3-pyridyl, 2-pyrazinyl, 1,3-thiazol-2-yl, 1,3-thiazol-4-yl and isoxazol-3-yl), and wherein $Q^1$ optionally bears 1, 2, or 3 substituents, which may be the same or different, selected from halogeno (for example fluoro or chloro), hydroxy, (1-4C)alkyl and (1-4C)alkoxy.

In another embodiment, in the compound of formula Ib, $Q^1$ is pyridyl (for example 2-pyridyl or 3-pyridyl, particularly 2-pyridyl).

In another embodiment, in the compound of formula Ib, $R^4$, $R^{4a}$, $R^5$ and $R^{5a}$ are selected from hydrogen and (1-3C) alkyl, for example $R^4$, $R^{4a}$, $R^5$ and $R^{5a}$ are selected from hydrogen and methyl.

In another embodiment, in the compound of formula Ib, $R^4$, $R^{4a}$, $R^5$ and $R^{5a}$ are all hydrogen.

In another embodiment, in the compound of formula Ib, $R^{4a}$, $R^5$ and $R^{5a}$ are hydrogen and $R^4$ is (1-3C)alkyl, for example methyl.

In another embodiment, in the compound of formula Ib, $R^4$, $R^{4a}$ and $R^{5a}$ are hydrogen and $R^5$ is (1-3C)alkyl, for example methyl.

In another embodiment, in the compound of formula Ib, $R^4$ and $R^{4a}$ are both hydrogen and $R^5$ and $R^{5a}$ are both (1-3C) alkyl, for example methyl.

In another embodiment, in the compound of formula Ib, $R^6$ is selected from hydrogen, methyl, ethyl, 2-hydroxyethyl, 2-methoxyethyl, propyl, isopropyl, allyl, 2-propynyl, cyclopropyl, cyclobutyl, piperidinyl, tetrahydropyranyl and cyclopropylmethyl, and wherein any $CH_2$ group within a cycloalkyl group within $R^6$ optionally bears on each $CH_2$ group 1 or 2 substituents selected from hydroxy, methyl, ethyl, methoxy and ethoxy, and wherein any heterocyclyl group within $R^6$ optionally bears one or more substituents, which may be the same or different, selected from fluoro, chloro, bromo, oxo, hydroxy, methyl, ethyl, propyl, isopropyl, trifluoromethyl, methoxy, ethoxy, propoxy, isopropoxy and trifluoromethoxy.

In another embodiment, in the compound of formula Ib, A is a group of the formula Z-$(CR^{12}R^{13})_p$—, wherein p is 1 or 2, each $R^{12}$ and $R^{13}$, which may be the same or different, is selected from hydrogen and (1-4C)alkyl, or an $R^{12}$ and an $R^{13}$ group attached to the same carbon atom form a (3-6C)cycloalkyl ring, and wherein any $CH_2$ or $CH_3$ group within any of $R^{12}$ and $R^{13}$, optionally bears on each said $CH_2$ or $CH_3$ group one or more (for example 1, 2 or 3) halogeno or (1-4C)alkyl substituents or a substituent selected from hydroxy and (1-4C)alkoxy, and wherein Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-4C)alkyl and (1-4C)alkoxycarbonyl.

For example, in an embodiment, Z is selected from hydrogen, hydroxy, methoxy, N-methylamino, N,N-dimethylamino, (N-methyl)-(N-tert-butoxycarbonyl)amino and methylsulfonyl (particularly Z is hydroxy).

In another embodiment, in the compound of formula Ib, A is a group of the formula Z-$(CR^{12}R^{13})_p$—, wherein p is 1 or 2, each $R^{12}$ and $R^{13}$, which may be the same or different, is selected from hydrogen and (1-4C)alkyl, or an $R^{12}$ and an $R^{13}$ group attached to the same carbon atom form a (3-6C)cycloalkyl ring, and wherein any $CH_2$ or $CH_3$ group within any of $R^{12}$ and $R^{13}$, optionally bears on each said $CH_2$ or $CH_3$ group one or more (for example 1, 2 or 3) halogeno or (1-4C)alkyl substituents or a substituent selected from hydroxy and (1-4C)alkoxy, and wherein Z is selected from hydrogen, hydroxy and (1-3C)alkoxy. For example Z is hydrogen or hydroxy, particularly Z is hydroxy.

In another embodiment, in the compound of formula Ib, A is selected from methyl and hydroxymethyl. Particularly A is hydroxymethyl.

In another embodiment, in the compound of formula Ib, A is a group of the formula Z-$(CR^{12}R^{13})_p$—, wherein p is 1 or 2, each $R^{12}$ and $R^{13}$, which may be the same or different, is selected from hydrogen and (1-4C)alkyl, or an $R^{12}$ and an $R^{13}$ group attached to the same carbon atom form a (3-6C)cycloalkyl ring, and wherein Z is $NR^{16}R^{17}$, wherein each of $R^{16}$ and $R^{17}$, which may be the same or different, is selected from hydrogen and (1-4C)alkyl (for example Z is selected from amino, N-methylamino and N,N-dimethylamino, particularly Z is N,N-dimethylamino).

In another embodiment, in the compound of formula Ib:

$Q^1$ is pyridyl (for example 2-pyridyl);

$R^{3a}$ is selected from chloro and methyl (particularly $R^{3a}$ is chloro);

$R^4$, $R^{4a}$, $R^5$ and $R^{5a}$, which may be the same or different, are selected from hydrogen and methyl; and A is a group of the formula Z-$(CR^{12}R^{13})_p$—, wherein p is 1 or 2, each $R^{12}$ and $R^{13}$, which may be the same or different, is selected from hydrogen and (1-3C)alkyl (for example $R^{12}$ and $R^{13}$ are selected from hydrogen and methyl), and Z is selected from hydrogen, and hydroxy (particularly Z is hydroxy).

A particular embodiment of the present invention is a quinazoline derivative of the formula I of the formula Ic:

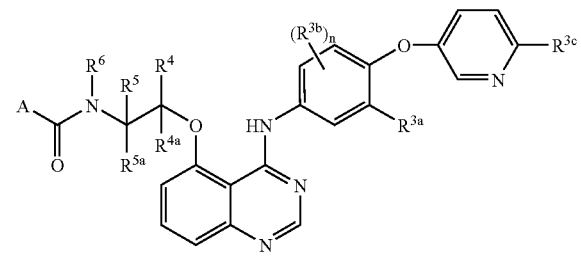

Ic wherein:

$R^{3a}$ is selected from cyano, halogeno, (1-4C)alkyl, trifluoromethyl, (1-4C)alkoxy, (2-4C)alkenyl and (2-4C)alkynyl;

n is 0, 1 or 2;

each $R^{3b}$, which may be the same or different, is selected from cyano, halogeno, (1-4C)alkyl, trifluoromethyl, (1-4C)alkoxy, (2-4C)alkenyl and (2-4C)alkynyl;

$R^{3a}$ is selected from halogeno and (1-4C)alkyl;

$R^4$, $R^{4a}$, $R^5$ and $R^{5a}$, which may be the same or different, are selected from hydrogen and (1-6C)alkyl, or $R^4$ and $R^{4a}$ together with the carbon atom to which they are attached form a (3-7C)cycloalkyl ring, or $R^5$ and $R^{5a}$ together with the carbon atom to which they are attached form a (3-7C)cycloalkyl ring, and wherein any $CH_2$ or $CH_3$ group within any of $R^4$, $R^{4a}$, $R^5$ and $R^{5a}$ optionally bears on each said $CH_2$ or $CH_3$ group one or more (for example 1, 2 or 3) halogeno substituents or a substituent selected from hydroxy, cyano, (1-6C)alkoxy, amino, (2-6C)alkanoyl, (1-6C)alkylamino and di-[(1-6C)alkylamino];

$R^6$ is selected from hydrogen, (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, and wherein any heterocyclyl group within an $R^6$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$-X^3-R^{10}$$

wherein $X^3$ is a direct bond or is selected from O, CO, $SO_2$ and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo or thioxo substituents;

and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

A is selected from hydrogen, a group of the formula $Z-(CR^{12}R^{13})_p-$ and $R^{14}$, wherein p is 1, 2, 3, or 4, each $R^{12}$ and $R^{13}$, which may be the same or different, is selected from hydrogen, (1-6C)alkyl, (2-6C)alkenyl and (2-6C)alkynyl, or an $R^{12}$ and an $R^{13}$ group attached to the same carbon atom form a (3-7C)cycloalkyl or (3-7C)cycloalkenyl ring, and wherein any $CH_2$ or $CH_3$ group within any of $R^{12}$ and $R^{13}$, optionally bears on each said $CH_2$ or $CH_3$ group one or more (for example 1, 2 or 3) halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkyl]amino, Z is selected from hydrogen, $OR^{15}$, $NR^{16}R^{17}$, (1-6C)alkylsulfonyl, (1-6C)alkanesulfonylamino and N-(1-6C)alkyl-(1-6C)alkanesulfonylamino, wherein each of $R^{15}$, $R^{16}$ and $R^{17}$, which may be the same or different, is selected from hydrogen, (1-6C)alkyl, (2-6C)alkenyl, (2-6C)alkynyl and (1-6C)alkoxycarbonyl, or Z is a group of the formula:

$$Q^2-X^4-$$

wherein $X^4$ is selected from O, $N(R^{18})$, $SO_2$ and $SO_2N(R^{18})$, wherein $R^{18}$ is hydrogen or (1-6C)alkyl, and $Q^2$ is (3-7C)cycloalkyl, (3-7C)cycloalkenyl or heterocyclyl, $R^{14}$ is selected from hydrogen, $OR^{19}$ and $NR^{16}R^{17}$, wherein $R^{19}$ is selected from (1-6C)alkyl, (2-6C)alkenyl and (2-6C)alkynyl, and wherein $R^{16}$ and $R^{17}$ are as defined above, or $R^{14}$ is a group of the formula:

$$Q^3-X^5-$$

wherein $X^5$ is selected from O and $N(R^{20})$, wherein $R^{20}$ is hydrogen or (1-6C)alkyl, and $Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, or $R^{14}$ is $Q^4$ wherein $Q^4$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein adjacent carbon atoms in any (2-6C)alkylene chain within a Z or $R^{14}$ substituent are optionally separated by the insertion into the chain of a group selected from O, S, SO, $SO_2$, $N(R^{21})$, CO, —C≡C— and —C≡C—, wherein $R^{21}$ is hydrogen or (1-6C)alkyl, and wherein any heterocyclyl group within a Z or $R^{14}$ substituent optionally bears one or more (for example 1, 2 or 3) substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$-X^6-R^{22}$$

wherein $X^6$ is a direct bond or is selected from O, CO, $SO_2$ and $N(R^{23})$, wherein $R^{23}$ is hydrogen or (1-4C)alkyl, and $R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within a Z or $R^{14}$ substituent optionally bears 1 or 2 oxo or thioxo substituents, and wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

or a pharmaceutically acceptable salt thereof.

In another embodiment, in the compound of formula Ic, n is 0 and $R^{3a}$ is selected from halogeno, trifluoromethyl, (1-4C)alkyl, (1-4C)alkoxy, (2-4C)alkenyl and (2-4C)alkynyl. Particularly $R^{3a}$ is selected from halogeno and (1-3C)alkyl, more particularly $R^{3a}$ is selected from chloro and methyl, still more particularly $R^{3a}$ is chloro. In this embodiment n is suitably 0 or 1. Particularly n is 0.

In another embodiment, in the compound of formula Ic, $R^{3c}$ is (1-4C)alkyl, particularly methyl.

In another embodiment, in the compound of formula Ic, $R^4$, $R^{4a}$, $R^5$ and $R^{5a}$ are selected from hydrogen and (1-3C)alkyl, for example $R^4$, $R^{4a}$, $R^5$ and $R^{5a}$ are selected from hydrogen and methyl.

In another embodiment, in the compound of formula Ic, $R^4$, $R^{4a}$, $R^5$ and $R^{5a}$ are all hydrogen.

In another embodiment, in the compound of formula Ic, $R^{4a}$, $R^5$ and $R^{5a}$ are hydrogen and $R^4$ is (1-3C)alkyl, for example methyl.

In another embodiment, in the compound of formula Ic, $R^4$, $R^{4a}$ and $R^{5a}$ are hydrogen and $R^5$ is (1-3C)alkyl, for example methyl.

In another embodiment, in the compound of formula Ic, $R^4$ and $R^{4a}$ are both hydrogen and $R^5$ and $R^{5a}$ are both (1-3C)alkyl, for example methyl.

In another embodiment, in the compound of formula Ic, $R^6$ is selected from hydrogen, (1-6C)alkyl, (2-6C)alkenyl, (2-6C)alkynyl, (3-7C)cycloalkyl, (3-7C)cycloalkyl-(1-6C)alkyl, heterocyclyl and heterocyclyl-(1-6C)alkyl, wherein any heterocyclyl group within $R^6$ is a 4, 5, 6 or 7 membered monocyclic saturated or partially saturated heterocyclyl ring containing 1 or 2 heteroatoms selected from oxygen, nitrogen and sulfur, and wherein any heterocyclyl group within an $R^6$ substituent optionally bears one or more substituents, which may be the same or different, selected from halogeno, trifluoromethyl, hydroxy, amino, (1-6C)alkyl, (2-6C)alkenyl, (2-6C)alkynyl, (1-6C)alkoxy, (1-6C)alkylamino, di-[(1-6C)alkyl]amino, (2-6C)alkanoyl, and from a group of the formula:

$-X^3-R^{10}$ wherein $X^3$ is a direct bond or is selected from O and $N(R^{11})$, wherein $R^{11}$ is hydrogen or (1-4C)alkyl, and $R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within an $R^6$ substituent optionally bears 1 or 2 oxo substituents.

In another embodiment, in the compound of formula Ic, $R^6$ is selected from hydrogen, (1-6C)alkyl, (2-6C)alkenyl, (2-6C)alkynyl, (3-7C)cycloalkyl, (3-7C)cycloalkyl-(1-4C)alkyl, heterocyclyl and heterocyclyl-(1-4C)alkyl, wherein any heterocyclyl group within $R^6$ is a 4, 5, 6 or 7 membered monocyclic saturated or partially saturated heterocyclyl ring containing 1 or 2 heteroatoms selected from oxygen, nitrogen and sulfur, and wherein any heterocyclyl group within an $R^6$ substituent optionally bears one or more substituents, which may be the same or different, selected from fluoro, chloro, bromo, hydroxy, (1-4C)alkyl, (2-4C)alkenyl, (2-4C)alkynyl and (1-4C)alkoxy, and wherein any heterocyclyl group within an $R^6$ substituent optionally bears 1 oxo substituent, and wherein any $CH_2$ or $CH_3$ group within a $R^6$ substituent, other than a $CH_2$ group within a heterocyclyl group, optionally bears on each said $CH_2$ or $CH_3$ group one or more substituents selected from fluoro and chloro, or a substituent selected from hydroxy and (1-4C)alkoxy, (1-6C)alkylamino and di-[(1-6C)alkyl]amino.

In another embodiment, in the compound of formula Ic, $R^6$ is selected from hydrogen, methyl, ethyl, 2-hydroxyethyl, 2-methoxyethyl, propyl, isopropyl, allyl, 2-propynyl, cyclopropyl, cyclobutyl, piperidinyl, tetrahydropyranyl and cyclopropylmethyl, and wherein any $CH_2$ group within a cycloalkyl group within $R^6$ optionally bears on each $CH_2$ group 1 or 2 substituents selected from hydroxy, methyl, ethyl, methoxy and ethoxy, and wherein any heterocyclyl group within $R^6$ optionally bears one or more substituents, which may be the same or different, selected from fluoro, chloro, bromo, oxo, hydroxy, methyl, ethyl, propyl, isopropyl, trifluoromethyl, methoxy, ethoxy, propoxy, isopropoxy and trifluoromethoxy.

In another embodiment, in the compound of formula Ic, A is a group of the formula $Z-(CR^{12}R^{13})_p-$, wherein p is 1 or 2, each $R^{12}$ and $R^{13}$, which may be the same or different, is selected from hydrogen and (1-4C)alkyl, or an $R^{12}$ and an $R^{13}$ group attached to the same carbon atom form a (3-6C)cycloalkyl ring, and wherein any $CH_2$ or $CH_3$ group within any of $R^{12}$ and $R^{13}$, optionally bears on each said $CH_2$ or $CH_3$ group one or more (for example 1, 2 or 3) halogeno or (1-4C)alkyl substituents or a substituent selected from hydroxy and (1-4C)alkoxy, and wherein Z is selected from hydrogen, $OR^{15}$, $NR^{16}R^{17}$ and (1-6C)alkylsulfonyl, wherein each of $R^{15}$, $R^{16}$ and $R^{17}$, which may be the same or different, is selected from hydrogen, (1-4C)alkyl and (1-4C)alkoxycarbonyl.

For example, in an embodiment, Z is selected from hydrogen, hydroxy, methoxy, N-methylamino, N,N-dimethylamino, (N-methyl)-(N-tert-butoxycarbonyl)amino and methylsulfonyl (particularly Z is hydroxy).

A particular compound of the invention is, for example, one or more quinazoline derivatives of the formula I selected from:

N-{2-[(4-{3-chloro-4-(pyridin-2-ylmethoxy)anilino}quinazolin-5-yl)oxy]ethyl}-2-methoxy-N-methylacetamide;

N-{2-[(4-{3-chloro-4-(pyridin-2-ylmethoxy)anilino}quinazolin-5-yl)oxy]ethyl}-2-(dimethylamino)-N-methylacetamide;

N-{(2R)-2-[(4-{3-chloro-4-(pyridin-2-ylmethoxy)anilino}quinazolin-5-yl)oxy]propyl}-2-methoxy-N-methylacetamide);

2-hydroxy-N-methyl-N-{2-[(4-{3-methyl-4-(pyrazin-2-ylmethoxy)anilino}quinazolin-5-yl)oxy]ethyl}acetamide;

2-hydroxy-N-methyl-N-{2-[(4-{3-methyl-(1,3-thiazol-4-ylmethoxy)anilino}quinazolin-5-yl)oxy]ethyl}acetamide;

2-hydroxy-N-methyl-N-(2-{[4-(3-methyl-4-[(5-methylisoxazol-3-yl)methoxy]anilino)quinazolin-5-yl]oxy}ethyl)acetamide;

N-{(2R)-2-[(4-{3-chloro-4-(pyridin-2-ylmethoxy)anilino}quinazolin-5-yl)oxy]propyl}-2-methoxyacetamide;

N-(2-{[4-(3-chloro-4-[(6-methylpyridin-2-yl)methoxy]anilino)quinazolin-5-yl]oxy}ethyl)-2-hydroxy-N-methylacetamide;

N-((2R)-2-{[4-(3-chloro-4-[(6-methylpyridin-2-yl)methoxy]anilino)quinazolin-5-yl]oxy}propyl)-2-hydroxy-N-methylacetamide;

N-(2-{[4-(3-chloro-4-[(6-methylpyridin-2-yl)methoxy]anilino)quinazolin-5-yl]oxy}ethyl)-N-methylacetamide;

N-(2-{[4-(3-chloro-4-[(2-fluorobenzyl)oxy]anilino)quinazolin-5-yl]oxy}ethyl)-N-methylacetamide;

N-(2-{[4-(3-chloro-4-[(3-fluorobenzyl)oxy]anilino)quinazolin-5-yl]oxy}ethyl)-N-methylacetamide;

N-{2-[(4-{3-chloro-4-(1,3-thiazol-4-ylmethoxy)anilino}quinazolin-5-yl)oxy]ethyl}-N-methylacetamide;

N-{2-[(4-{3-chloro-4-(pyrazin-2-ylmethoxy)anilino}quinazolin-5-yl)oxy]ethyl}-N-methylacetamide;

N-{(2R)-2-[(4-{3-chloro-4-(pyridin-2-ylmethoxy)anilino}quinazolin-5-yl)oxy]propyl}-2-hydroxyacetamide;

N-{2-[(4-{3-chloro-4-(pyridin-2-ylmethoxy)anilino}quinazolin-5-yl)oxy]ethyl}-N-methylacetamide;

2-hydroxy-N-methyl-N-{2-[(4-{3-methyl-4-(pyridin-2-ylmethoxy)anilino}quinazolin-5-yl)oxy]ethyl}acetamide;

N-{(1R)-2-[(4-{3-chloro-4-(pyridin-2-ylmethoxy)anilino}quinazolin-5-yl)oxy]-1-methylethyl}acetamide;

N-{(1R)-2-[(4-{3-chloro-4-(pyridin-2-ylmethoxy)anilino}quinazolin-5-yl)oxy]-1-methylethyl}-2-hydroxyacetamide;

N-{2-[(4-{3-chloro-4-(pyridin-2-ylmethoxy)anilino}quinazolin-5-yl)oxy]ethyl}-2-hydroxy-N-methylacetamide;

N-(2-{[4-(3-chloro-4-[(3-fluorobenzyl)oxy]anilino)quinazolin-5-yl]oxy}ethyl)-2-hydroxy-N-methylacetamide;

N-{2-[(4-{3-chloro-4-(1,3-thiazol-4-ylmethoxy)anilino}quinazolin-5-yl)oxy]ethyl}-2-hydroxy-N-methylacetamide;

N-{2-[(4-{3-chloro-4-(pyrazin-2-ylmethoxy)anilino}quinazolin-5-yl)oxy]ethyl}-2-hydroxy-N-methylacetamide;

N-{2-[(4-{3-chloro-4-(pyridin-2-ylmethoxy)anilino}quinazolin-5-yl)oxy]ethyl}acetamide;

N-{(2R)-2-[(4-{3-chloro-4-(pyridin-2-ylmethoxy)anilino}quinazolin-5-yl)oxy]propyl}acetamide;

N-{(2R)-2-[(4-{3-chloro-4-(pyridin-2-ylmethoxy)anilino}quinazolin-5-yl)oxy]propyl}-2-hydroxy-N-methylacetamide;

N-{(2R)-2-[(4-{3-chloro-4-(pyrazin-2-ylmethoxy)anilino}quinazolin-5-yl)oxy]propyl}-2-hydroxy-N-methylacetamide;

N-((2R)-2-{[4-(3-chloro-4-[(3-fluorobenzyl)oxy]anilino)quinazolin-5-yl]oxy}propyl)-2-hydroxy-N-methylacetamide;

N-{(2R)-2-[(4-{3-chloro-4-(1,3-thiazol-4-ylmethoxy)anilino}quinazolin-5-yl)oxy]propyl}-2-hydroxy-N-methylacetamide;

N-{(2R)-2-[(4-{3-chloro-4-(pyridin-2-ylmethoxy)anilino}quinazolin-5-yl)oxy]propyl}-N-methylacetamide;

N-{2-[(4-{[3-chloro-4-(pyridin-2-ylmethoxy)phenyl]amino}quinazolin-5-yl)oxy]ethyl}-N-ethylacetamide;

N-{2-[(4-{[3-chloro-4-(pyridin-2-ylmethoxy)phenyl]amino}quinazolin-5-yl)oxy]ethyl}-N-ethyl-2-hydroxyacetamide;

N-{2-[(4-{[3-chloro-4-(pyridin-2-ylmethoxy)phenyl]amino}quinazolin-5-yl)oxy]ethyl}-N-propylacetamide;

N-{2-[(4-{[3-chloro-4-(pyridin-2-ylmethoxy)phenyl]amino}quinazolin-5-yl)oxy]ethyl}-2-hydroxy-N-propylacetamide;

N-{2-[(4-{[3-chloro-4-(pyridin-2-ylmethoxy)phenyl]amino}quinazolin-5-yl)oxy]ethyl}-N-isopropylacetamide;

N-{2-[(4-{[3-chloro-4-(pyridin-2-ylmethoxy)phenyl]amino}quinazolin-5-yl)oxy]ethyl}-2-hydroxy-N-isopropylacetamide;

N-allyl-N-{2-[(4-{[3-chloro-4-(pyridin-2-ylmethoxy)phenyl]amino}quinazolin-5-yl)oxy]ethyl}acetamide;

N-allyl-N-{2-[(4-{[3-chloro-4-(pyridin-2-ylmethoxy)phenyl]amino}quinazolin-5-yl)oxy]ethyl}-2-hydroxyacetamide;

N-{2-[(4-{[3-chloro-4-(pyridin-2-ylmethoxy)phenyl]amino}quinazolin-5-yl)oxy]ethyl}-N-cyclopropylacetamide;

N-{2-[(4-{[3-chloro-4-(pyridin-2-ylmethoxy)phenyl]amino}quinazolin-5-yl)oxy]ethyl}-N-cyclopropyl-2-hydroxyacetamide;

N-{2-[(4-{[3-chloro-4-(pyridin-2-ylmethoxy)phenyl]amino}quinazolin-5-yl)oxy]ethyl}-N-(cyclopropylmethyl)acetamide;

N-{2-[(4-{[3-chloro-4-(pyridin-2-ylmethoxy)phenyl]amino}quinazolin-5-yl)oxy]ethyl}-N-(cyclopropylmethyl)-2-hydroxyacetamide;

N-{2-[(4-{[3-chloro-4-(pyridin-2-ylmethoxy)phenyl]amino}quinazolin-5-yl)oxy]ethyl}-N-cyclobutylacetamide;

N-{2-[(4-{[3-chloro-4-(pyridin-2-ylmethoxy)phenyl]amino}quinazolin-5-yl)oxy]ethyl}-N-cyclobutyl-2-hydroxyacetamide;

N-{2-[(4-{[3-chloro-4-(pyridin-2-ylmethoxy)phenyl]amino}quinazolin-5-yl)oxy]ethyl}-N-(1-methylpiperidin-4-yl)acetamide;

N-{2-[(4-{[3-chloro-4-(pyridin-2-ylmethoxy)phenyl]amino}quinazolin-5-yl)oxy]ethyl}-N-(tetrahydro-2H-pyran-4-yl)acetamide;

N-{2-[(4-{[3-chloro-4-(pyridin-2-ylmethoxy)phenyl]amino}quinazolin-5-yl)oxy]ethyl}-2-hydroxy-N-(tetrahydro-2H-pyran-4-yl)acetamide;

N-{2-[(4-{[3-chloro-4-(pyridin-2-ylmethoxy)phenyl]amino}quinazolin-5-yl)oxy]ethyl}-N-(2-hydroxyethyl)acetamide;

N-{2-[(4-{[3-chloro-4-(pyridin-2-ylmethoxy)phenyl]amino}quinazolin-5-yl)oxy]ethyl}-2-hydroxy-N-(2-hydroxyethyl)acetamide;

N-{2-[(4-{[3-chloro-4-(pyridin-2-ylmethoxy)phenyl]amino}quinazolin-5-yl)oxy]ethyl}-N-(2-methoxyethyl)acetamide;

N-{2-[(4-{[3-chloro-4-(pyridin-2-ylmethoxy)phenyl]amino}quinazolin-5-yl)oxy]ethyl}-2-hydroxy-N-(2-methoxyethyl)acetamide;

N-{2-[(4-{[3-chloro-4-(pyridin-2-ylmethoxy)phenyl]amino}quinazolin-5-yl)oxy]ethyl}-N-prop-2-yn-1-ylacetamide;

N-{2-[(4-{[3-chloro-4-(pyridin-2-ylmethoxy)phenyl]amino}quinazolin-5-yl)oxy]ethyl}-2-hydroxy-N-prop-2-yn-1-ylacetamide;

N-{2-[(4-{[3-chloro-4-(pyridin-2-ylmethoxy)phenyl]amino}quinazolin-5-yl)oxy]ethyl}-2-hydroxy-N-methylpropanamide;

N-{2-[(4-{[3-chloro-4-(pyridin-2-ylmethoxy)phenyl]amino}quinazolin-5-yl)oxy]ethyl}-N-methyl-tetrahydrofuranyl-2-carboxamide;

N-{2-[(4-{[3-chloro-4-(pyridin-2-ylmethoxy)phenyl]amino}quinazolin-5-yl)oxy]ethyl}-N,1-dimethylprolinamide;

N-{2-[(4-{[3-chloro-4-(pyridin-2-ylmethoxy)phenyl]amino}quinazolin-5-yl)oxy]ethyl}-2-hydroxy-N,2-dimethylpropanamide;

N-{2-[(4-{[3-chloro-4-(pyridin-2-ylmethoxy)phenyl]amino}quinazolin-5-yl)oxy]ethyl}-1-hydroxy-N-methylcyclopropanecarboxamide;

$N^1$-{2-[(4-{[3-chloro-4-(pyridin-2-ylmethoxy)phenyl]amino}quinazolin-5-yl)oxy]ethyl}-$N^1$,$N^2$-dimethylglycinamide;

N-{2-[(4-{[3-chloro-4-(pyridin-2-ylmethoxy)phenyl]amino}quinazolin-5-yl)oxy]ethyl}-3-hydroxy-N,2,2-trimethylpropanamide;

N-{2-[(4-{[3-chloro-4-(pyridin-2-ylmethoxy)phenyl]
amino}quinazolin-5-yl)oxy]ethyl}-3-hydroxy-N-methyl-
propanamide;
N-{(2S)-2-[(4-{[3-chloro-4-(pyridin-2-ylmethoxy)phenyl]
amino}quinazolin-5-yl)oxy]propyl}acetamide;
N-{(2S)-2-[(4-{[3-chloro-4-(pyridin-2-ylmethoxy)phenyl]
amino}quinazolin-5-yl)oxy]propyl}-2-hydroxyaceta-
mide;
$N^1$-{(2S)-2-[(4-{[3-chloro-4-(pyridin-2-ylmethoxy)phenyl]
amino}quinazolin-5-yl)oxy]propyl}-$N^2$,$N^2$-dimethylgly-
cinamide;
N-{(2S)-2-[(4-{[3-chloro-4-(pyridin-2-ylmethoxy)phenyl]
amino}quinazolin-5-yl)oxy]propyl}-2-methoxyaceta-
mide;
N-{(2S)-2-[(4-{[3-chloro-4-(pyridin-2-ylmethoxy)phenyl]
amino}quinazolin-5-yl)oxy]propyl}-2-(methylsulfonyl)
acetamide;
N-{2-[(4-{[3-chloro-4-(pyridin-2-ylmethoxy)phenyl]
amino}quinazolin-5-yl)oxy]ethyl}-2-hydroxyacetamide;
$N^1$-{2-[(4-{[3-chloro-4-(pyridin-2-ylmethoxy)phenyl]
amino}quinazolin-5-yl)oxy]ethyl}-$N^2$,$N^2$-dimethylglyci-
namide;
N-{2-[(4-{[3-chloro-4-(pyridin-2-ylmethoxy)phenyl]
amino}quinazolin-5-yl)oxy]ethyl}-2-methoxyacetamide;
N-{2-[(4-{[3-chloro-4-(pyridin-2-ylmethoxy)phenyl]
amino}quinazolin-5-yl)oxy]ethyl}-2-(methylsulfonyl)ac-
etamide;
N-{(2S)-2-[(4-{[3-chloro-4-(pyridin-2-ylmethoxy)phenyl]
amino}quinazolin-5-yl)oxy]propyl}-N-methylacetamide;
N-{(2S)-2-[(4-{[3-chloro-4-(pyridin-2-ylmethoxy)phenyl]
amino}quinazolin-5-yl)oxy]propyl}-2-hydroxy-N-me-
thylacetamide;
$N^1$-{(2S)-2-[(4-{[3-chloro-4-(pyridin-2-ylmethoxy)phenyl]
amino}quinazolin-5-yl)oxy]propyl}-$N^1$,$N^2$,$N^2$-trimeth-
ylglycinamide;
N-{(2S)-2-[(4-{[3-chloro-4-(pyridin-2-ylmethoxy)phenyl]
amino}quinazolin-5-yl)oxy]propyl}-2-methoxy-N-me-
thylacetamide;
N-{(2S)-2-[(4-{[3-chloro-4-(pyridin-2-ylmethoxy)phenyl]
amino}quinazolin-5-yl)oxy]propyl}-N-methyl-2-(meth-
ylsulfonyl)acetamide;
N-{(2R)-2-[(4-{[3-chloro-4-(pyrazin-2-ylmethoxy)phenyl]
amino}quinazolin-5-yl)oxy]propyl}-N-methylacetamide;
N-{(2R)-2-[(4-{[3-chloro-4-(1,3-thiazol-4-ylmethoxy)phe-
nyl]amino}quinazolin-5-yl)oxy]propyl}-N-methylaceta-
mide;
N-((2R)-2-{[4-({3-chloro-4-[(3-fluorobenzyl)oxy]
phenyl}amino)quinazolin-5-yl]oxy}propyl)-N-methylac-
etamide;
N-((2R)-2-{[4-({3-chloro-4-[(2-fluorobenzyl)oxy]
phenyl}amino)quinazolin-5-yl]oxy}propyl)-N-methylac-
etamide;
N-{(1R)-2-[(4-{[3-chloro-4-(pyridin-2-ylmethoxy)phenyl]
amino}quinazolin-5-yl)oxy]-1-methylethyl}-2-hydroxy-
N-methylacetamide;
N-{(1R)-2-[(4-{[3-chloro-4-(pyridin-2-ylmethoxy)phenyl]
amino}quinazolin-5-yl)oxy]-1-methylethyl}-N-methy-
lacetamide;
N-{(1S)-2-[(4-{[3-chloro-4-(pyridin-2-ylmethoxy)phenyl]
amino}quinazolin-5-yl)oxy]-1-methylethyl}-2-hydroxy-
N-methylacetamide;
N-{(1S)-2-[(4-{[3-chloro-4-(pyridin-2-ylmethoxy)phenyl]
amino}quinazolin-5-yl)oxy]-1-methylethyl}-N-methy-
lacetamide;
N-{(1S)-2-[(4-{[3-chloro-4-(pyridin-2-ylmethoxy)phenyl]
amino}quinazolin-5-yl)oxy]-1-methylethyl}-2-methoxy-
N-methylacetamide;
N-{(1S)-2-[(4-{[3-chloro-4-(pyridin-2-ylmethoxy)phenyl]
amino}quinazolin-5-yl)oxy]-1-methylethyl}-2-hydroxy-
acetamide;
N-{(1S)-2-[(4-{[3-chloro-4-(pyridin-2-ylmethoxy)phenyl]
amino}quinazolin-5-yl)oxy]-1-methylethyl}acetamide;
$N^1$-{(1S)-2-[(4-{[3-chloro-4-(pyridin-2-ylmethoxy)phenyl]
amino}quinazolin-5-yl)oxy]-1-methylethyl}-$N^2$,$N^2$-dim-
ethylglycinamide;
$N^1$-{(2R)-2-[(4-{[3-chloro-4-(pyridin-2-ylmethoxy)phenyl]
amino}quinazolin-5-yl)oxy]propyl}-$N^2$,$N^2$-dimethylgly-
cinamide;
(2S)-N-{2-[(4-{[3-chloro-4-(pyridin-2-ylmethoxy)phenyl]
amino}quinazolin-5-yl)oxy]ethyl}-2,4-dihydroxybutana-
mide;
(2R)-N-{2-[(4-{[3-chloro-4-(pyridin-2-ylmethoxy)phenyl]
amino}quinazolin-5-yl)oxy]ethyl}-2,4-dihydroxybutana-
mide;
(2R)-N-{(2R)-2-[(4-{[3-chloro-4-(pyridin-2-ylmethoxy)
phenyl]amino}quinazolin-5-yl)oxy]propyl}-2,4-dihy-
droxybutanamide;
(2S)-N-{(2R)-2-[(4-{[3-chloro-4-(pyridin-2-ylmethoxy)
phenyl]amino}quinazolin-5-yl)oxy]propyl}-2,4-dihy-
droxybutanamide;
(2R)-N-{(2S)-2-[(4-{[3-chloro-4-(pyridin-2-ylmethoxy)
phenyl]amino}quinazolin-5-yl)oxy]propyl}-2,4-dihy-
droxybutanamide;
(2S)-N-{(2S)-2-[(4-{[3-chloro-4-(pyridin-2-ylmethoxy)
phenyl]amino}quinazolin-5-yl)oxy]propyl}-2,4-dihy-
droxybutanamide;
(2S)-N-{(1R)-2-[(4-{[3-chloro-4-(pyridin-2-ylmethoxy)
phenyl]amino}quinazolin-5-yl)oxy]-1-methylethyl}-2,4-
dihydroxybutanamide;
(2R)-N-{(1R)-2-[(4-{[3-chloro-4-(pyridin-2-ylmethoxy)
phenyl]amino}quinazolin-5-yl)oxy]-1-methylethyl}-2,4-
dihydroxybutanamide;
(2R)-N-{2-[(4-{[3-chloro-4-(1,3-thiazol-4-ylmethoxy)phe-
nyl]amino}quinazolin-5-yl)oxy]ethyl}-2,4-dihydroxybu-
tanamide;
(2S)-N-{2-[(4-{[3-chloro-4-(1,3-thiazol-4-ylmethoxy)phe-
nyl]amino}quinazolin-5-yl)oxy]ethyl}-2,4-dihydroxybu-
tanamide;
(2R)-N-{(1R)-2-[(4-{[3-chloro-4-(1,3-thiazol-4-ylmethoxy)
phenyl]amino}quinazolin-5-yl)oxy]-1-methylethyl}-2,4-
dihydroxybutanamide;
(2S)-N-{(1R)-2-[(4-{[3-chloro-4-(1,3-thiazol-4-ylmethoxy)
phenyl]amino}quinazolin-5-yl)oxy]-1-methylethyl}-2,4-
dihydroxybutanamide;
N-methyl-N-{2-[(4-{[3-methyl-4-(pyridin-2-ylmethoxy)
phenyl]amino}quinazolin-5-yl)oxy]ethyl}acetamide;
N-methyl-N-{2-[(4-{[3-methyl-4-(1,3-thiazol-4-yl-
methoxy)phenyl]amino}quinazolin-5-yl)oxy]
ethyl}acetamide;
N-methyl-N-(2-{[4-({3-methyl-4-[(5-methylisoxazol-3-yl)
methoxy]phenyl}amino) quinazolin-5-yl]oxy}ethyl)ac-
etamide;
2-hydroxy-N-methyl-N-{2-[(4-{[3-methyl-4-(1,3-thiazol-2-
ylmethoxy)phenyl]amino}quinazolin-5-yl)oxy]
ethyl}acetamide;
2-hydroxy-N-{2-[(4-{[3-methyl-4-(pyridin-2-ylmethoxy)
phenyl]amino}quinazolin-5-yl)oxy]ethyl}acetamide;
2-hydroxy-N-{2-[(4-{[3-methyl-4-(1,3-thiazol-4-yl-
methoxy)phenyl]amino}quinazolin-5-yl)oxy]
ethyl}acetamide;
N-{2-[(4-{[3-chloro-4-(pyridin-2-ylmethoxy)phenyl]
amino}quinazolin-5-yl)oxy]-1,1-dimethylethyl}-2-hy-
droxyacetamide;

2-hydroxy-N-{(2R)-2-[(4-{[3-methyl-4-(pyridin-2-yl-methoxy)phenyl]amino}quinazolin-5-yl)oxy]propyl}acetamide;

2-hydroxy-N-{(2R)-2-[(4-{[3-methyl-4-(1,3-thiazol-4-yl-methoxy)phenyl]amino}quinazolin-5-yl)oxy]propyl}acetamide;

N-((2R)-2-{[4-({4-[(3-fluorobenzyl)oxy]-3-methylphenyl}amino)quinazolin-5-yl]oxy}propyl)-2-hydroxyacetamide;

2-hydroxy-N-{(2R)-2-[(4-{[3-methyl-4-(1,3-thiazol-2-yl-methoxy)phenyl]amino}quinazolin-5-yl)oxy]propyl}acetamide;

N-{(2R)-2-[(4-{[3-methyl-4-(pyridin-2-ylmethoxy)phenyl]amino}quinazolin-5-yl)oxy]propyl}acetamide;

N-{(2R)-2-[(4-{[3-methyl-4-(1,3-thiazol-4-ylmethoxy)phenyl]amino}quinazolin-5-yl)oxy]propyl}acetamide;

N-((2R)-2-{[4-({4-[(3-fluorobenzyl)oxy]-3-methylphenyl}amino)quinazolin-5-yl]oxy}propyl)acetamide;

N-{(2R)-2-[(4-{[3-methyl-4-(1,3-thiazol-2-ylmethoxy)phenyl]amino}quinazolin-5-yl)oxy]propyl}acetamide;

2-hydroxy-N-methyl-N-{(2R)-2-[(4-{[3-methyl-4-(pyridin-2-ylmethoxy)phenyl]amino}quinazolin-5-yl)oxy]propyl}acetamide;

2-hydroxy-N-methyl-N-{(2R)-2-[(4-{[3-methyl-4-(1,3-thiazol-4-ylmethoxy)phenyl]amino}quinazolin-5-yl)oxy]propyl}acetamide;

2-hydroxy-N-methyl-N-((2R)-2-{[4-({3-methyl-4-[(5-methylisoxazol-3-yl)methoxy]phenyl}amino)quinazolin-5-yl]oxy}propyl)acetamide;

N-methyl-N-{(1R)-1-methyl-2-[(4-{[3-methyl-4-(pyridin-2-ylmethoxy)phenyl]amino}quinazolin-5-yl)oxy]ethyl}acetamide;

N-methyl-N-{(1R)-1-methyl-2-[(4-{[3-methyl-4-(1,3-thiazol-4-ylmethoxy)phenyl]amino}quinazolin-5-yl)oxy]ethyl}acetamide;

N-{(1R)-2-[(4-{[3-chloro-4-(1,3-thiazol-4-ylmethoxy)phenyl]amino}quinazolin-5-yl)oxy]-1-methylethyl}-2-hydroxy-N-methylacetamide;

2-hydroxy-N-methyl-N-{(1R)-1-methyl-2-[(4-{[3-methyl-4-(pyridin-2-ylmethoxy)phenyl]amino}quinazolin-5-yl)oxy]ethyl}acetamide;

2-hydroxy-N-methyl-N-{(1R)-1-methyl-2-[(4-{[3-methyl-4-(1,3-thiazol-4-ylmethoxy)phenyl]amino}quinazolin-5-yl)oxy]ethyl}acetamide;

N-{(2R)-2-[(4-{[3-chloro-4-(pyridin-2-ylmethoxy)phenyl]amino}quinazolin-5-yl)oxy]propyl}-1-hydroxy-N-methylcyclopropanecarboxamide;

(2S)-N-{(2R)-2-[(4-{[3-chloro-4-(pyridin-2-ylmethoxy)phenyl]amino}quinazolin-5-yl)oxy]propyl}-2-hydroxy-N-methylpropanamide;

N-{(2R)-2-[(4-{[3-chloro-4-(pyridin-2-ylmethoxy)phenyl]amino}quinazolin-5-yl)oxy]propyl}-2-hydroxy-N,2-dimethylpropanamide;

(2R)-N-{(2R)-2-[(4-{[3-chloro-4-(pyridin-2-ylmethoxy)phenyl]amino}quinazolin-5-yl)oxy]propyl}-2-hydroxy-N-methylpropanamide;

(2R)-N-{(2R)-2-[(4-{[3-chloro-4-(pyridin-2-ylmethoxy)phenyl]amino}quinazolin-5-yl)oxy]propyl}-2-methoxy-N-methylpropanamide;

2-hydroxy-N-methyl-N-((2R)-2-{[4-({3-methyl-4-[(6-methylpyridin-3-yl)oxy]phenyl}amino)quinazolin-5-yl]oxy}propyl)acetamide;

N-methyl-N-((2R)-2-{[4-({3-methyl-4-[(6-methylpyridin-3-yl)oxy]phenyl}amino)quinazolin-5-yl]oxy}propyl)acetamide;

$N^1,N^2,N^2$-trimethyl-$N^1$-((2R)-2-{[4-({3-methyl-4-[(6-methylpyridin-3-yl)oxy]phenyl}amino)quinazolin-5-yl]oxy}propyl)glycinamide;

N-methyl-N-((2R)-2-{[4-({3-methyl-4-[(6-methylpyridin-3-yl)oxy]phenyl}amino)quinazolin-5-yl]oxy}propyl)-2-pyrrolidin-1-ylacetamide;

N-methyl-N-((2R)-2-{[4-({3-methyl-4-[(6-methylpyridin-3-yl)oxy]phenyl}amino)quinazolin-5-yl]oxy}propyl)-2-morpholin-4-ylacetamide;

N-methyl-N-((2R)-2-{[4-({3-methyl-4-[(6-methylpyridin-3-yl)oxy]phenyl}amino)quinazolin-5-yl]oxy}propyl)-2-(4-methylpiperazin-1-yl)acetamide;

2-hydroxy-N-methyl-N-((2S)-2-{[4-({3-methyl-4-[(6-methylpyridin-3-yl)oxy]phenyl}amino)quinazolin-5-yl]oxy}propyl)acetamide;

N-methyl-N-((2S)-2-{[4-({3-methyl-4-[(6-methylpyridin-3-yl)oxy]phenyl}amino)quinazolin-5-yl]oxy}propyl)acetamide;

N-methyl-N-((2S)-2-{[4-({3-methyl-4-[(6-methylpyridin-3-yl)oxy]phenyl}amino)quinazolin-5-yl]oxy}propyl)-2-pyrrolidin-1-ylacetamide;

(2S)-2,4-dihydroxy-N-((2R)-2-{[4-({3-methyl-4-[(6-methylpyridin-3-yl)oxy]phenyl}amino)quinazolin-5-yl]oxy}propyl)butanamide;

(2S)-4-bromo-2-hydroxy-N-((2R)-2-{[4-({3-methyl-4-[(6-methylpyridin-3-yl)oxy]phenyl}amino)quinazolin-5-yl]oxy}propyl)butanamide;

N-(2-chloroethyl)-N'-((2R)-2-{[4-({3-methyl-4-[(6-methylpyridin-3-yl)oxy]phenyl}amino)quinazolin-5-yl]oxy}propyl)urea;

2-hydroxy-N-methyl-N-((1R)-1-methyl-2-{[4-({3-methyl-4-[(6-methylpyridin-3-yl)oxy]phenyl}amino)quinazolin-5-yl]oxy}ethyl)acetamide;

N-methyl-N-((1R)-1-methyl-2-{[4-({3-methyl-4-[(6-methylpyridin-3-yl)oxy]phenyl}amino)quinazolin-5-yl]oxy}ethyl)acetamide;

2-hydroxy-N-methyl-N-((1S)-1-methyl-2-{[4-({3-methyl-4-[(6-methylpyridin-3-yl)oxy]phenyl}amino)quinazolin-5-yl]oxy}ethyl)acetamide;

N-methyl-N-((1S)-1-methyl-2-{[4-({3-methyl-4-[(6-methylpyridin-3-yl)oxy]phenyl}amino)quinazolin-5-yl]oxy}ethyl)acetamide;

methyl-{2-[(4-{[3-chloro-4-(pyridin-2-ylmethoxy)phenyl]amino}quinazolin-5-yl)oxy]ethyl}methylcarbamate;

N-{2-[(4-{[3-chloro-4-(pyridin-2-ylmethoxy)phenyl]amino}quinazolin-5-yl)oxy]ethyl}-N,N'-dimethylurea;

N'-(2-chloroethyl)-N-{2-[(4-{[3-chloro-4-(pyridin-2-ylmethoxy)phenyl]amino}quinazolin-5-yl)oxy]ethyl}-N-methylurea;

N-{(2R)-2-[(4-{[3-chloro-4-(pyridin-2-ylmethoxy)phenyl]amino}quinazolin-5-yl)oxy]propyl}-N'-methylurea;

[((R)-2-{4-[3-chloro-4-(pyridin-2-ylmethoxy)phenylamino]quinazolin-5-yloxy}propylcarbamoyl)methyl]methylcarbamic acid tert-butyl ester;

$N^1$-{(2R)-2-[(4-{[3-chloro-4-(pyridin-2-ylmethoxy)phenyl]amino}quinazolin-5-yl)oxy]propyl}-$N^2$-methylglycinamide;

2-hydroxy-N-methyl-N-(2-{[4-({3-methyl-4-[(6-methylpyridin-3-yl)oxy]phenyl}amino)quinazolin-5-yl]oxy}ethyl)acetamide;

N-methyl-N-(2-{[4-({3-methyl-4-[(6-methylpyridin-3-yl)oxy]phenyl}amino)quinazolin-5-yl]oxy}ethyl)acetamide; and N-{2-[(4-{[3-chloro-4-(1-methyl-1-pyridin-2-ylethoxy)phenyl]amino}quinazolin-5-yl)oxy]ethyl}-N-methylacetamide;

or a pharmaceutically acceptable salt thereof.

A particular compound of the invention is, for example, one or more quinazoline derivatives of the formula Ia selected from:

N-{2-[(4-{3-chloro-4-(pyridin-2-ylmethoxy)anilino}quinazolin-5-yl)oxy]ethyl}-2-methoxy-N-methylacetamide;

N-{2-[(4-{3-chloro-4-(pyridin-2-ylmethoxy)anilino}quinazolin-5-yl)oxy]ethyl}-2-(dimethylamino)-N-methylacetamide;

N-{(2R)-2-[(4-{3-chloro-4-(pyridin-2-ylmethoxy)anilino}quinazolin-5-yl)oxy]propyl}-2-methoxy-N-methylacetamide);

2-hydroxy-N-methyl-N-{2-[(4-{3-methyl-4-(pyrazin-2-ylmethoxy)anilino}quinazolin-5-yl)oxy]ethyl}acetamide;

2-hydroxy-N-methyl-N-{2-[(4-{3-methyl-4-(1,3-thiazol-4-ylmethoxy)anilino}quinazolin-5-yl)oxy]ethyl}acetamide;

2-hydroxy-N-methyl-N-(2-{[4-(3-methyl-4-[(5-methylisoxazol-3-yl)methoxy]anilino)quinazolin-5-yl]oxy}ethyl)acetamide;

N-{(2R)-2-[(4-{3-chloro-4-(pyridin-2-ylmethoxy)anilino}quinazolin-5-yl)oxy]propyl}-2-methoxyacetamide;

N-(2-{[4-(3-chloro-4-[(6-methylpyidin-2-yl)methoxy]anilino)quinazolin-5-yl]oxy}ethyl)-2-hydroxy-N-methylacetamide;

N-((2R)-2-{[4-(3-chloro-4-[(6-methylpyridin-2-yl)methoxy]anilino)quinazolin-5-yl]oxy}propyl)-2-hydroxy-N-methylacetamide;

N-(2-{[4-(3-chloro-4-[(6-methylpyridin-2-yl)methoxy]anilino)quinazolin-5-yl]oxy}ethyl)-N-methylacetamide;

N-(2-{[4-(3-chloro-4-[(2-fluorobenzyl)oxy]anilino)quinazolin-5-yl]oxy}ethyl)-N-methylacetamide;

N-(2-{[4-(3-chloro-4-[(3-fluorobenzyl)oxy]anilino)quinazolin-5-yl]oxy}ethyl)-N-methylacetamide;

N-{2-[(4-{3-chloro-4-(1,3-thiazol-4-ylmethoxy)anilino}quinazolin-5-yl)oxy]ethyl}-N-methylacetamide;

N-{2-[(4-{3-chloro-4-(pyrazin-2-ylmethoxy)anilino}quinazolin-5-yl)oxy]ethyl}-N-methylacetamide;

N-{(2R)-2-[(4-{3-chloro-4-(pyridin-2-ylmethoxy)anilino}quinazolin-5-yl)oxy]propyl}-2-hydroxyacetamide;

N-{2-[(4-{3-chloro-4-(pyridin-2-ylmethoxy)anilino}quinazolin-5-yl)oxy]ethyl}-N-methylacetamide;

2-hydroxy-N-methyl-N-{2-[(4-{3-methyl-4-(pyridin-2-ylmethoxy)anilino}quinazolin-5-yl)oxy]ethyl}acetamide;

N-{(1R)-2-[(4-{3-chloro-4-(pyridin-2-ylmethoxy)anilino}quinazolin-5-yl)oxy]-1-methylethyl}acetamide;

N-{(1R)-2-[(4-{3-chloro-4-(pyridin-2-ylmethoxy)anilino}quinazolin-5-yl)oxy]-1-methylethyl}-2-hydroxyacetamide;

N-{2-[(4-{3-chloro-4-(pyridin-2-ylmethoxy)anilino}quinazolin-5-yl)oxy]ethyl}-2-hydroxy-N-methylacetamide;

N-(2-{[4-(3-chloro-4-[(3-fluorobenzyl)oxy]anilino)quinazolin-5-yl]oxy}ethyl)-2-hydroxy-N-methylacetamide;

N-{2-[(4-{3-chloro-4-(1,3-thiazol-4-ylmethoxy)anilino}quinazolin-5-yl)oxy]ethyl}-2-hydroxy-N-methylacetamide;

N-{2-[(4-{3-chloro-4-(pyrazin-2-ylmethoxy)anilino}quinazolin-5-yl)oxy]ethyl}-2-hydroxy-N-methylacetamide;

N-{2-[(4-{3-chloro-4-(pyridin-2-ylmethoxy)anilino}quinazolin-5-yl)oxy]ethyl}acetamide;

N-{(2R)-2-[(4-{3-chloro-4-(pyridin-2-ylmethoxy)anilino}quinazolin-5-yl)oxy]propyl}acetamide;

N-{(2R)-2-[(4-{3-chloro-4-(pyridin-2-ylmethoxy)anilino}quinazolin-5-yl)oxy]propyl}-2-hydroxy-N-methylacetamide;

N-{(2R)-2-[(4-{3-chloro-4-(pyrazin-2-ylmethoxy)anilino}quinazolin-5-yl)oxy]propyl}-2-hydroxy-N-methylacetamide;

N-((2R)-2-{[4-(3-chloro-4-[(3-fluorobenzyl)oxy]anilino)quinazolin-5-yl]oxy}propyl)-2-hydroxy-N-methylacetamide;

N-{(2R)-2-[(4-{3-chloro-4-(1,3-thiazol-4-ylmethoxy)anilino}quinazolin-5-yl)oxy]propyl}-2-hydroxy-N-methylacetamide;

N-{(2R)-2-[(4-{3-chloro-4-(pyridin-2-ylmethoxy)anilino}quinazolin-5-yl)oxy]propyl}-N-methylacetamide;

N-{2-[(4-{[3-chloro-4-(pyridin-2-ylmethoxy)phenyl]amino}quinazolin-5-yl)oxy]ethyl}-N-ethylacetamide;

N-{2-[(4-{[3-chloro-4-(pyridin-2-ylmethoxy)phenyl]amino}quinazolin-5-yl)oxy]ethyl}-N-ethyl-2-hydroxyacetamide;

N-{2-[(4-{[3-chloro-4-(pyridin-2-ylmethoxy)phenyl]amino}quinazolin-5-yl)oxy]ethyl}-N-propylacetamide;

N-{2-[(4-{[3-chloro-4-(pyridin-2-ylmethoxy)phenyl]amino}quinazolin-5-yl)oxy]ethyl}-2-hydroxy-N-propylacetamide;

N-{2-[(4-{[3-chloro-4-(pyridin-2-ylmethoxy)phenyl]amino}quinazolin-5-yl)oxy]ethyl}-N-isopropylacetamide;

N-{2-[(4-{[3-chloro-4-(pyridin-2-ylmethoxy)phenyl]amino}quinazolin-5-yl)oxy]ethyl}-2-hydroxy-N-isopropylacetamide;

N-allyl-N-{2-[(4-{[3-chloro-4-(pyridin-2-ylmethoxy)phenyl]amino}quinazolin-5-yl)oxy]ethyl}acetamide;

N-allyl-N-{2-[(4-{[3-chloro-4-(pyridin-2-ylmethoxy)phenyl]amino}quinazolin-5-yl)oxy]ethyl}-2-hydroxyacetamide;

N-{2-[(4-{[3-chloro-4-(pyridin-2-ylmethoxy)phenyl]amino}quinazolin-5-yl)oxy]ethyl}-N-cyclopropylacetamide;

N-{2-[(4-{[3-chloro-4-(pyridin-2-ylmethoxy)phenyl]amino}quinazolin-5-yl)oxy]ethyl}-N-cyclopropyl-2-hydroxyacetamide;

N-{2-[(4-{[3-chloro-4-(pyridin-2-ylmethoxy)phenyl]amino}quinazolin-5-yl)oxy]ethyl}-N-(cyclopropylmethyl)acetamide;

N-{2-[(4-{[3-chloro-4-(pyridin-2-ylmethoxy)phenyl]amino}quinazolin-5-yl)oxy]ethyl}-N-(cyclopropylmethyl)-2-hydroxyacetamide;

N-{2-[(4-{[3-chloro-4-(pyridin-2-ylmethoxy)phenyl]amino}quinazolin-5-yl)oxy]ethyl}-N-cyclobutylacetamide;

N-{2-[(4-{[3-chloro-4-(pyridin-2-ylmethoxy)phenyl]amino}quinazolin-5-yl)oxy]ethyl}-N-cyclobutyl-2-hydroxyacetamide;

N-{2-[(4-{[3-chloro-4-(pyridin-2-ylmethoxy)phenyl]amino}quinazolin-5-yl)oxy]ethyl}-N-(1-methylpiperidin-4-yl)acetamide;

N-{2-[(4-{[3-chloro-4-(pyridin-2-ylmethoxy)phenyl]amino}quinazolin-5-yl)oxy]ethyl}-N-(tetrahydro-2H-pyran-4-yl)acetamide;

N-{2-[(4-{[3-chloro-4-(pyridin-2-ylmethoxy)phenyl]amino}quinazolin-5-yl)oxy]ethyl}-2-hydroxy-N-(tetrahydro-2H-pyran-4-yl)acetamide;

N-{2-[(4-{[3-chloro-4-(pyridin-2-ylmethoxy)phenyl]amino}quinazolin-5-yl)oxy]ethyl}-N-(2-hydroxyethyl)acetamide;
N-{2-[(4-{[3-chloro-4-(pyridin-2-ylmethoxy)phenyl]amino}quinazolin-5-yl)oxy]ethyl}-2-hydroxy-N-(2-hydroxyethyl)acetamide;
N-{2-[(4-{[3-chloro-4-(pyridin-2-ylmethoxy)phenyl]amino}quinazolin-5-yl)oxy]ethyl}-N-(2-methoxyethyl)acetamide;
N-{2-[(4-{[3-chloro-4-(pyridin-2-ylmethoxy)phenyl]amino}quinazolin-5-yl)oxy]ethyl}-2-hydroxy-N-(2-methoxyethyl)acetamide;
N-{2-[(4-{[3-chloro-4-(pyridin-2-ylmethoxy)phenyl]amino}quinazolin-5-yl)oxy]ethyl}-N-prop-2-yn-1-ylacetamide;
N-{2-[(4-{[3-chloro-4-(pyridin-2-ylmethoxy)phenyl]amino}quinazolin-5-yl)oxy]ethyl}-2-hydroxy-N-prop-2-yn-1-ylacetamide;
N-{2-[(4-{[3-chloro-4-(pyridin-2-ylmethoxy)phenyl]amino}quinazolin-5-yl)oxy]ethyl}-2-hydroxy-N-methylpropanamide;
N-{2-[(4-{[3-chloro-4-(pyridin-2-ylmethoxy)phenyl]amino}quinazolin-5-yl)oxy]ethyl}-N-methyl-tetrahydrofuranyl-2-carboxamide;
N-{2-[(4-{[3-chloro-4-(pyridin-2-ylmethoxy)phenyl]amino}quinazolin-5-yl)oxy]ethyl}-N,1-dimethylprolinamide;
N-{2-[(4-{[3-chloro-4-(pyridin-2-ylmethoxy)phenyl]amino}quinazolin-5-yl)oxy]ethyl}-2-hydroxy-N,2-dimethylpropanamide;
N-{2-[(4-{[3-chloro-4-(pyridin-2-ylmethoxy)phenyl]amino}quinazolin-5-yl)oxy]ethyl}-1-hydroxy-N-methylcyclopropanecarboxamide;
$N^1$-{2-[(4-{[3-chloro-4-(pyridin-2-ylmethoxy)phenyl]amino}quinazolin-5-yl)oxy]ethyl}-$N^{11}$,$N^2$-dimethylglycinamide;
N-{2-[(4-{[3-chloro-4-(pyridin-2-ylmethoxy)phenyl]amino}quinazolin-5-yl)oxy]ethyl}-3-hydroxy-N,2,2-trimethylpropanamide;
N-{2-[(4-{[3-chloro-4-(pyridin-2-ylmethoxy)phenyl]amino}quinazolin-5-yl)oxy]ethyl}-3-hydroxy-N-methylpropanamide;
N-{(2S)-2-[(4-{[3-chloro-4-(pyridin-2-ylmethoxy)phenyl]amino}quinazolin-5-yl)oxy]propyl}acetamide;
N-{(2S)-2-[(4-{[3-chloro-4-(pyridin-2-ylmethoxy)phenyl]amino}quinazolin-5-yl)oxy]propyl}-2-hydroxyacetamide;
$N^1$-{(2S)-2-[(4-{[3-chloro-4-(pyridin-2-ylmethoxy)phenyl]amino}quinazolin-5-yl)oxy]propyl}-$N^2$,N-dimethylglycinamide;
N-{(2S)-2-[(4-{[3-chloro-4-(pyridin-2-ylmethoxy)phenyl]amino}quinazolin-5-yl)oxy]propyl}-2-methoxyacetamide;
N-{(2S)-2-[(4-{[3-chloro-4-(pyridin-2-ylmethoxy)phenyl]amino}quinazolin-5-yl)oxy]propyl}-2-(methylsulfonyl)acetamide;
N-{2-[(4-{[3-chloro-4-(pyridin-2-ylmethoxy)phenyl]amino}quinazolin-5-yl)oxy]ethyl}-2-hydroxyacetamide;
$N^1$-{2-[(4-{[3-chloro-4-(pyridin-2-ylmethoxy)phenyl]amino}quinazolin-5-yl)oxy]ethyl}-$N^2$,$N^2$-dimethylglycinamide;
N-{2-[(4-{[3-chloro-4-(pyridin-2-ylmethoxy)phenyl]amino}quinazolin-5-yl)oxy]ethyl}-2-methoxyacetamide;
N-{2-[(4-{[3-chloro-4-(pyridin-2-ylmethoxy)phenyl]amino}quinazolin-5-yl)oxy]ethyl}-2-(methylsulfonyl)acetamide;
N-{(2S)-2-[(4-{[3-chloro-4-(pyridin-2-ylmethoxy)phenyl]amino}quinazolin-5-yl)oxy]propyl}-N-methylacetamide;
N-{(2S)-2-[(4-{[3-chloro-4-(pyridin-2-ylmethoxy)phenyl]amino}quinazolin-5-yl)oxy]propyl}-2-hydroxy-N-methylacetamide;
$N^1$-{(2S)-2-[(4-{[3-chloro-4-(pyridin-2-ylmethoxy)phenyl]amino}quinazolin-5-yl)oxy]propyl}-$N^1$,$N^2$,$N^2$-trimethylglycinamide;
N-{(2S)-2-[(4-{[3-chloro-4-(pyridin-2-ylmethoxy)phenyl]amino}quinazolin-5-yl)oxy]propyl}-2-methoxy-N-methylacetamide;
N-{(2S)-2-[(4-{[3-chloro-4-(pyridin-2-ylmethoxy)phenyl]amino}quinazolin-5-yl)oxy]propyl}-N-methyl-2-(methylsulfonyl)acetamide;
N-{(2R)-2-[(4-{[3-chloro-4-(pyrazin-2-ylmethoxy)phenyl]amino}quinazolin-5-yl)oxy]propyl}-N-methylacetamide;
N-{(2R)-2-[(4-{[3-chloro-4-(1,3-thiazol-4-ylmethoxy)phenyl]amino}quinazolin-5-yl)oxy]propyl}-N-methylacetamide;
N-((2R)-2-{[4-({3-chloro-4-[(3-fluorobenzyl)oxy]phenyl}amino)quinazolin-5-yl]oxy}propyl)-N-methylacetamide;
N-((2R)-2-{[4-({3-chloro-4-[(2-fluorobenzyl)oxy]phenyl}amino)quinazolin-5-yl]oxy}propyl)-N-methylacetamide;
N-{(1R)-2-[(4-{[3-chloro-4-(pyridin-2-ylmethoxy)phenyl]amino}quinazolin-5-yl)oxy]-1-methylethyl}-2-hydroxy-N-methylacetamide;
N-{(1R)-2-[(4-{[3-chloro-4-(pyridin-2-ylmethoxy)phenyl]amino}quinazolin-5-yl)oxy]-1-methylethyl}-N-methylacetamide;
N-{(1S)-2-[(4-{[3-chloro-4-(pyridin-2-ylmethoxy)phenyl]amino}quinazolin-5-yl)oxy]-1-methylethyl}-2-hydroxy-N-methylacetamide;
N-{(1S)-2-[(4-{[3-chloro-4-(pyridin-2-ylmethoxy)phenyl]amino}quinazolin-5-yl)oxy]-1-methylethyl}-N-methylacetamide;
N-{(1S)-2-[(4-{[3-chloro-4-(pyridin-2-ylmethoxy)phenyl]amino}quinazolin-5-yl)oxy]-1-methylethyl}-2-methoxy-N-methylacetamide;
N-{(1S)-2-[(4-{[3-chloro-4-(pyridin-2-ylmethoxy)phenyl]amino}quinazolin-5-yl)oxy]-1-methylethyl}-2-hydroxyacetamide;
N-{(1S)-2-[(4-{[3-chloro-4-(pyridin-2-ylmethoxy)phenyl]amino}quinazolin-5-yl)oxy]-1-methylethyl}acetamide;
$N^1$-{(1S)-2-[(4-{[3-chloro-4-(pyridin-2-ylmethoxy)phenyl]amino}quinazolin-5-yl)oxy]-1-methylethyl}-$N^2$,$N^2$-dimethylglycinamide;
$N^1$-{(2R)-2-[(4-{[3-chloro-4-(pyridin-2-ylmethoxy)phenyl]amino}quinazolin-5-yl)oxy]propyl}-$N^2$,$N^2$-dimethylglycinamide;
(2S)-N-{2-[(4-{[3-chloro-4-(pyridin-2-ylmethoxy)phenyl]amino}quinazolin-5-yl)oxy]ethyl}-2,4-dihydroxybutanamide;
(2R)-N-{2-[(4-{[3-chloro-4-(pyridin-2-ylmethoxy)phenyl]amino}quinazolin-5-yl)oxy]ethyl}-2,4-dihydroxybutanamide;
(2R)-N-{(2R)-2-[(4-{[3-chloro-4-(pyridin-2-ylmethoxy)phenyl]amino}quinazolin-5-yl)oxy]propyl}-2,4-dihydroxybutanamide;
(2S)-N-{(2R)-2-[(4-{[3-chloro-4-(pyridin-2-ylmethoxy)phenyl]amino}quinazolin-5-yl)oxy]propyl}-2,4-dihydroxybutanamide;
(2R)-N-{(2S)-2-[(4-{[3-chloro-4-(pyridin-2-ylmethoxy)phenyl]amino}quinazolin-5-yl)oxy]propyl}-2,4-dihydroxybutanamide;

(2S)-N-{(2S)-2-[(4-{[3-chloro-4-(pyridin-2-ylmethoxy)phenyl]amino}quinazolin-5-yl)oxy]propyl}-2,4-dihydroxybutanamide;

(2S)-N-{(1R)-2-[(4-{[3-chloro-4-(pyridin-2-ylmethoxy)phenyl]amino}quinazolin-5-yl)oxy]-1-methylethyl}-2,4-dihydroxybutanamide;

(2R)-N-{(1R)-2-[(4-{[3-chloro-4-(pyridin-2-ylmethoxy)phenyl]amino}quinazolin-5-yl)oxy]-1-methylethyl}-2,4-dihydroxybutanamide;

(2R)-N-{2-[(4-{[3-chloro-4-(1,3-thiazol-4-ylmethoxy)phenyl]amino}quinazolin-5-yl)oxy]ethyl}-2,4-dihydroxybutanamide;

(2S)-N-{2-[(4-{[3-chloro-4-(1,3-thiazol-4-ylmethoxy)phenyl]amino}quinazolin-5-yl)oxy]ethyl}-2,4-dihydroxybutanamide;

(2R)-N-{(1R)-2-[(4-{[3-chloro-4-(1,3-thiazol-4-ylmethoxy)phenyl]amino}quinazolin-5-yl)oxy]-1-methylethyl}-2,4-dihydroxybutanamide;

(2S)-N-{(1R)-2-[(4-{[3-chloro-4-(1,3-thiazol-4-ylmethoxy)phenyl]amino}quinazolin-5-yl)oxy]-1-methylethyl}-2,4-dihydroxybutanamide;

N-methyl-N-{2-[(4-{[3-methyl-4-(pyridin-2-ylmethoxy)phenyl]amino}quinazolin-5-yl)oxy]ethyl}acetamide;

N-methyl-N-{2-[(4-{[3-methyl-4-(1,3-thiazol-4-ylmethoxy)phenyl]amino}quinazolin-5-yl)oxy]ethyl}acetamide;

N-methyl-N-(2-{[4-({3-methyl-4-[(5-methylisoxazol-3-yl)methoxy]phenyl}amino) quinazolin-5-yl]oxy}ethyl)acetamide;

2-hydroxy-N-methyl-N-{2-[(4-{[3-methyl-4-(1,3-thiazol-2-ylmethoxy)phenyl]amino}quinazolin-5-yl)oxy]ethyl}acetamide;

2-hydroxy-N-{2-[(4-{[3-methyl-4-(pyridin-2-ylmethoxy)phenyl]amino}quinazolin-5-yl)oxy]ethyl}acetamide;

2-hydroxy-N-{2-[(4-{[3-methyl-4-(1,3-thiazol-4-ylmethoxy)phenyl]amino}quinazolin-5-yl)oxy]ethyl}acetamide;

N-{2-[(4-{[3-chloro-4-(pyridin-2-ylmethoxy)phenyl]amino}quinazolin-5-yl)oxy]-1,1-dimethylethyl}-2-hydroxyacetamide;

2-hydroxy-N-{(2R)-2-[(4-{[3-methyl-4-(pyridin-2-ylmethoxy)phenyl]amino}quinazolin-5-yl)oxy]propyl}acetamide;

2-hydroxy-N-{(2R)-2-[(4-{[3-methyl-4-(1,3-thiazol-4-ylmethoxy)phenyl]amino}quinazolin-5-yl)oxy]propyl}acetamide;

N-((2R)-2-{[4-({4-[(3-fluorobenzyl)oxy]-3-methylphenyl}amino)quinazolin-5-yl]oxy}propyl)-2-hydroxyacetamide;

2-hydroxy-N-{(2R)-2-[(4-{[3-methyl-4-(1,3-thiazol-2-ylmethoxy)phenyl]amino}quinazolin-5-yl)oxy]propyl}acetamide;

N-{(2R)-2-[(4-{[3-methyl-4-(pyridin-2-ylmethoxy)phenyl]amino}quinazolin-5-yl)oxy]propyl}acetamide;

N-{(2R)-2-[(4-{[3-methyl-4-(1,3-thiazol-4-ylmethoxy)phenyl]amino}quinazolin-5-yl)oxy]propyl}acetamide;

N-((2R)-2-{[4-({4-[(3-fluorobenzyl)oxy]-3-methylphenyl}amino)quinazolin-5-yl]oxy}propyl)acetamide;

N-{(2R)-2-[(4-{[3-methyl-4-(1,3-thiazol-2-ylmethoxy)phenyl]amino}quinazolin-5-yl)oxy]propyl}acetamide;

2-hydroxy-N-methyl-N-{(2R)-2-[(4-{[3-methyl-4-(pyridin-2-ylmethoxy)phenyl]amino}quinazolin-5-yl)oxy]propyl}acetamide;

2-hydroxy-N-methyl-N-{(2R)-2-[(4-{[3-methyl-4-(1,3-thiazol-4-ylmethoxy)phenyl]amino}quinazolin-5-yl)oxy]propyl}acetamide;

2-hydroxy-N-methyl-N-((2R)-2-{[4-({3-methyl-4-[(5-methylisoxazol-3-yl)methoxy]phenyl}amino)quinazolin-5-yl]oxy}propyl)acetamide;

N-methyl-N-{(1R)-1-methyl-2-[(4-{[3-methyl-4-(pyridin-2-ylmethoxy)phenyl]amino}quinazolin-5-yl)oxy]ethyl}acetamide;

N-methyl-N-{(1R)-1-methyl-2-[(4-{[3-methyl-4-(1,3-thiazol-4-ylmethoxy)phenyl]amino}quinazolin-5-yl)oxy]ethyl}acetamide;

N-{(1R)-2-[(4-{[3-chloro-4-(1,3-thiazol-4-ylmethoxy)phenyl]amino}quinazolin-5-yl)oxy]-1-methylethyl}-2-hydroxy-N-methylacetamide;

2-hydroxy-N-methyl-N-{(1R)-1-methyl-2-[(4-{[3-methyl-4-(pyridin-2-ylmethoxy)phenyl]amino}quinazolin-5-yl)oxy]ethyl}acetamide;

2-hydroxy-N-methyl-N-{(1R)-1-methyl-2-[(4-{[3-methyl-4-(1,3-thiazol-4-ylmethoxy)phenyl]amino}quinazolin-5-yl)oxy]ethyl}acetamide;

N-{(2R)-2-[(4-{[3-chloro-4-(pyridin-2-ylmethoxy)phenyl]amino}quinazolin-5-yl)oxy]propyl}-1-hydroxy-N-methylcyclopropanecarboxamide;

(2S)-N-{(2R)-2-[(4-{[3-chloro-4-(pyridin-2-ylmethoxy)phenyl]amino}quinazolin-5-yl)oxy]propyl}-2-hydroxy-N-methylpropanamide;

N-{(2R)-2-[(4-{[3-chloro-4-(pyridin-2-ylmethoxy)phenyl]amino}quinazolin-5-yl)oxy]propyl}-2-hydroxy-N,2-dimethylpropanamide;

(2R)-N-{(2R)-2-[(4-{[3-chloro-4-(pyridin-2-ylmethoxy)phenyl]amino}quinazolin-5-yl)oxy]propyl}-2-hydroxy-N-methylpropanamide;

(2R)-N-{(2R)-2-[(4-{[3-chloro-4-(pyridin-2-ylmethoxy)phenyl]amino}quinazolin-5-yl)oxy]propyl}-2-methoxy-N-methylpropanamide;

methyl-{2-[(4-{[3-chloro-4-(pyridin-2-ylmethoxy)phenyl]amino}quinazolin-5-yl)oxy]ethyl}methylcarbamate;

N-{2-[(4-{[3-chloro-4-(pyridin-2-ylmethoxy)phenyl]amino}quinazolin-5-yl)oxy]ethyl}-N,N'-dimethylurea;

N'-(2-chloroethyl)-N-{2-[(4-{[3-chloro-4-(pyridin-2-ylmethoxy)phenyl]amino}quinazolin-5-yl)oxy]ethyl}-N-methylurea;

N-{(2R)-2-[(4-{[3-chloro-4-(pyridin-2-ylmethoxy)phenyl]amino}quinazolin-5-yl)oxy]propyl}-N'-methylurea;

[((R)-2-{4-[3-chloro-4-(pyridin-2-ylmethoxy)phenylamino]quinazolin-5-yloxy}propylcarbamoyl)methyl]methylcarbamic acid tert-butyl ester;

$N^1$-{(2R)-2-[(4-{[3-chloro-4-(pyridin-2-ylmethoxy)phenyl]amino}quinazolin-5-yl)oxy]propyl}-$N^2$-methylglycinamide; and N-{2-[(4-{[3-chloro-4-(1-methyl-1-pyridin-2-ylethoxy)phenyl]amino}quinazolin-5-yl)oxy]ethyl}-N-methylacetamide;

or a pharmaceutically acceptable salt thereof.

A particular compound of the invention is, for example, one or more quinazoline derivatives of the formula Ib selected from:

N-{2-[(4-{3-chloro-4-(pyridin-2-ylmethoxy)anilino}quinazolin-5-yl)oxy]ethyl}-2-methoxy-N-methylacetamide;

N-{2-[(4-{3-chloro-4-(pyridin-2-ylmethoxy)anilino}quinazolin-5-yl)oxy]ethyl}-2-(dimethylamino)-N-methylacetamide;

N-{(2R)-2-[(4-{3-chloro-4-(pyridin-2-ylmethoxy)anilino}quinazolin-5-yl)oxy]propyl}-2-methoxy-N-methylacetamide);

2-hydroxy-N-methyl-N-{2-[(4-{3-methyl-4-(pyrazin-2-ylmethoxy)anilino}quinazolin-5-yl)oxy]ethyl}acetamide;

2-hydroxy-N-methyl-N-{2-[(4-{3-methyl-4-(1,3-thiazol-4-ylmethoxy)anilino}quinazolin-5-yl)oxy]ethyl}acetamide;

2-hydroxy-N-methyl-N-(2-{[4-(3-methyl-4-[(5-methylisoxazol-3-yl)methoxy]anilino)quinazolin-5-yl]oxy}ethyl)acetamide;

N-{(2R)-2-[(4-{3-chloro-4-(pyridin-2-ylmethoxy)anilino}quinazolin-5-yl)oxy]propyl}-2-methoxyacetamide;

N-(2-{[4-(3-chloro-4-[(6-methylpyridin-2-yl)methoxy]anilino)quinazolin-5-yl]oxy}ethyl)-2-hydroxy-N-methylacetamide;

N-((2R)-2-{[4-(3-chloro-4-[(6-methylpyridin-2-yl)methoxy]anilino)quinazolin-5-yl]oxy}propyl)-2-hydroxy-N-methylacetamide;

N-(2-{[4-(3-chloro-4-[(6-methylpyridin-2-yl)methoxy]anilino)quinazolin-5-yl]oxy}ethyl)-N-methylacetamide;

N-(2-{[4-(3-chloro-4-[(2-fluorobenzyl)oxy]anilino)quinazolin-5-yl]oxy}ethyl)-N-methylacetamide;

N-(2-{[4-(3-chloro-4-[(3-fluorobenzyl)oxy]anilino)quinazolin-5-yl]oxy}ethyl)-N-methylacetamide;

N-{2-[(4-{3-chloro-4-(1,3-thiazol-4-ylmethoxy)anilino}quinazolin-5-yl)oxy]ethyl}-N-methylacetamide;

N-{2-[(4-{3-chloro-4-(pyrazin-2-ylmethoxy)anilino}quinazolin-5-yl)oxy]ethyl}-N-methylacetamide;

N-{(2R)-2-[(4-{3-chloro-4-(pyridin-2-ylmethoxy)anilino}quinazolin-5-yl)oxy]propyl}-2-hydroxyacetamide;

N-{2-[(4-{3-chloro-4-(pyridin-2-ylmethoxy)anilino}quinazolin-5-yl)oxy]ethyl}-N-methylacetamide;

2-hydroxy-N-methyl-N-{2-[(4-{3-methyl-4-(pyridin-2-ylmethoxy)anilino}quinazolin-5-yl)oxy]ethyl}acetamide;

N-{(1R)-2-[(4-{3-chloro-4-(pyridin-2-ylmethoxy)anilino}quinazolin-5-yl)oxy]-1-methylethyl}acetamide;

N-{(1R)-2-[(4-{3-chloro-4-(pyridin-2-ylmethoxy)anilino}quinazolin-5-yl)oxy]-1-methylethyl}-2-hydroxyacetamide;

N-{2-[(4-{3-chloro-4-(pyridin-2-ylmethoxy)anilino}quinazolin-5-yl)oxy]ethyl}-2-hydroxy-N-methylacetamide;

N-(2-{[4-(3-chloro-4-[(3-fluorobenzyl)oxy]anilino)quinazolin-5-yl]oxy}ethyl)-2-hydroxy-N-methylacetamide;

N-{2-[(4-{3-chloro-4-(1,3-thiazol-4-ylmethoxy)anilino}quinazolin-5-yl)oxy]ethyl}-2-hydroxy-N-methylacetamide;

N-{2-[(4-{3-chloro-4-(pyrazin-2-ylmethoxy)anilino}quinazolin-5-yl)oxy]ethyl}-2-hydroxy-N-methylacetamide;

N-{2-[(4-{3-chloro-4-(pyridin-2-ylmethoxy)anilino}quinazolin-5-yl)oxy]ethyl}acetamide;

N-{(2R)-2-[(4-{3-chloro-4-(pyridin-2-ylmethoxy)anilino}quinazolin-5-yl)oxy]propyl}acetamide;

N-{(2R)-2-[(4-{3-chloro-4-(pyridin-2-ylmethoxy)anilino}quinazolin-5-yl)oxy]propyl}-2-hydroxy-N-methylacetamide;

N-{(2R)-2-[(4-{3-chloro-4-(pyrazin-2-ylmethoxy)anilino}quinazolin-5-yl)oxy]propyl}-2-hydroxy-N-methylacetamide;

N-((2R)-2-{[4-(3-chloro-4-[(3-fluorobenzyl)oxy]anilino)quinazolin-5-yl]oxy}propyl)-2-hydroxy-N-methylacetamide;

N-{(2R)-2-[(4-{3-chloro-4-(1,3-thiazol-4-ylmethoxy)anilino}quinazolin-5-yl)oxy]propyl}-2-hydroxy-N-methylacetamide;

N-{(2R)-2-[(4-{3-chloro-4-(pyridin-2-ylmethoxy)anilino}quinazolin-5-yl)oxy]propyl}-N-methylacetamide;

N-{2-[(4-{[3-chloro-4-(pyridin-2-ylmethoxy)phenyl]amino}quinazolin-5-yl)oxy]ethyl}-N-ethylacetamide;

N-{2-[(4-{[3-chloro-4-(pyridin-2-ylmethoxy)phenyl]amino}quinazolin-5-yl)oxy]ethyl}-N-ethyl-2-hydroxyacetamide;

N-{2-[(4-{[3-chloro-4-(pyridin-2-ylmethoxy)phenyl]amino}quinazolin-5-yl)oxy]ethyl}-N-propylacetamide;

N-{2-[(4-{[3-chloro-4-(pyridin-2-ylmethoxy)phenyl]amino}quinazolin-5-yl)oxy]ethyl}-2-hydroxy-N-propylacetamide;

N-{2-[(4-{[3-chloro-4-(pyridin-2-ylmethoxy)phenyl]amino}quinazolin-5-yl)oxy]ethyl}-N-isopropylacetamide;

N-{2-[(4-{[3-chloro-4-(pyridin-2-ylmethoxy)phenyl]amino}quinazolin-5-yl)oxy]ethyl}-2-hydroxy-N-isopropylacetamide;

N-allyl-N-{2-[(4-{[3-chloro-4-(pyridin-2-ylmethoxy)phenyl]amino}quinazolin-5-yl)oxy]ethyl}acetamide;

N-allyl-N-{2-[(4-{[3-chloro-4-(pyridin-2-ylmethoxy)phenyl]amino}quinazolin-5-yl)oxy]ethyl}-2-hydroxyacetamide;

N-{2-[(4-{[3-chloro-4-(pyridin-2-ylmethoxy)phenyl]amino}quinazolin-5-yl)oxy]ethyl}-N-cyclopropylacetamide;

N-{2-[(4-{[3-chloro-4-(pyridin-2-ylmethoxy)phenyl]amino}quinazolin-5-yl)oxy]ethyl}-N-cyclopropyl-2-hydroxyacetamide;

N-{2-[(4-{[3-chloro-4-(pyridin-2-ylmethoxy)phenyl]amino}quinazolin-5-yl)oxy]ethyl}-N-(cyclopropylmethyl)acetamide;

N-{2-[(4-{[3-chloro-4-(pyridin-2-ylmethoxy)phenyl]amino}quinazolin-5-yl)oxy]ethyl}-N-(cyclopropylmethyl)-2-hydroxyacetamide;

N-{2-[(4-{[3-chloro-4-(pyridin-2-ylmethoxy)phenyl]amino}quinazolin-5-yl)oxy]ethyl}-N-cyclobutylacetamide;

N-{2-[(4-{[3-chloro-4-(pyridin-2-ylmethoxy)phenyl]amino}quinazolin-5-yl)oxy]ethyl}-N-cyclobutyl-2-hydroxyacetamide;

N-{2-[(4-{[3-chloro-4-(pyridin-2-ylmethoxy)phenyl]amino}quinazolin-5-yl)oxy]ethyl}-N-(1-methylpiperidin-4-yl)acetamide;

N-{2-[(4-{[3-chloro-4-(pyridin-2-ylmethoxy)phenyl]amino}quinazolin-5-yl)oxy]ethyl}-N-(tetrahydro-2H-pyran-4-yl)acetamide;

N-{2-[(4-{[3-chloro-4-(pyridin-2-ylmethoxy)phenyl]amino}quinazolin-5-yl)oxy]ethyl}-2-hydroxy-N-(tetrahydro-2H-pyran-4-yl)acetamide;

N-{2-[(4-{[3-chloro-4-(pyridin-2-ylmethoxy)phenyl]amino}quinazolin-5-yl)oxy]ethyl}-N-(2-hydroxyethyl)acetamide;

N-{2-[(4-{[3-chloro-4-(pyridin-2-ylmethoxy)phenyl]amino}quinazolin-5-yl)oxy]ethyl}-2-hydroxy-N-(2-hydroxyethyl)acetamide;

N-{2-[(4-{[3-chloro-4-(pyridin-2-ylmethoxy)phenyl]amino}quinazolin-5-yl)oxy]ethyl}-N-(2-methoxyethyl)acetamide;

N-{2-[(4-{[3-chloro-4-(pyridin-2-ylmethoxy)phenyl]amino}quinazolin-5-yl)oxy]ethyl}-2-hydroxy-N-(2-methoxyethyl)acetamide;

N-{2-[(4-{[3-chloro-4-(pyridin-2-ylmethoxy)phenyl]amino}quinazolin-5-yl)oxy]ethyl}-N-prop-2-yn-1-ylacetamide;

N-{2-[(4-{[3-chloro-4-(pyridin-2-ylmethoxy)phenyl]amino}quinazolin-5-yl)oxy]ethyl}-2-hydroxy-N-prop-2-yn-1-ylacetamide;

N-{2-[(4-{[3-chloro-4-(pyridin-2-ylmethoxy)phenyl]amino}quinazolin-5-yl)oxy]ethyl}-2-hydroxy-N-methylpropanamide;

N-{2-[(4-{[3-chloro-4-(pyridin-2-ylmethoxy)phenyl]amino}quinazolin-5-yl)oxy]ethyl}-N-methyl-tetrahydrofuranyl-2-carboxamide;

N-{2-[(4-{[3-chloro-4-(pyridin-2-ylmethoxy)phenyl]amino}quinazolin-5-yl)oxy]ethyl}-N,1-dimethylprolinamide;

N-{2-[(4-{[3-chloro-4-(pyridin-2-ylmethoxy)phenyl]amino}quinazolin-5-yl)oxy]ethyl}-2-hydroxy-N,2-dimethylpropanamide;

N-{2-[(4-{[3-chloro-4-(pyridin-2-ylmethoxy)phenyl]amino}quinazolin-5-yl)oxy]ethyl}-1-hydroxy-N-methylcyclopropanecarboxamide;

$N^1$-{2-[(4-{[3-chloro-4-(pyridin-2-ylmethoxy)phenyl]amino}quinazolin-5-yl)oxy]ethyl}-$N^1$,$N^2$-dimethylglycinamide;

N-{2-[(4-{[3-chloro-4-(pyridin-2-ylmethoxy)phenyl]amino}quinazolin-5-yl)oxy]ethyl}-3-hydroxy-N,2,2-trimethylpropanamide;

N-{2-[(4-{[3-chloro-4-(pyridin-2-ylmethoxy)phenyl]amino}quinazolin-5-yl)oxy]ethyl}-3-hydroxy-N-methylpropanamide;

N-{(2S)-2-[(4-{[3-chloro-4-(pyridin-2-ylmethoxy)phenyl]amino}quinazolin-5-yl)oxy]propyl}acetamide;

N-{(2S)-2-[(4-{[3-chloro-4-(pyridin-2-ylmethoxy)phenyl]amino}quinazolin-5-yl)oxy]propyl}-2-hydroxyacetamide;

$N^1$-{(2S)-2-[(4-{[3-chloro-4-(pyridin-2-ylmethoxy)phenyl]amino}quinazolin-5-yl)oxy]propyl}-$N^2$,$N^2$-dimethylglycinamide;

N-{(2S)-2-[(4-{[3-chloro-4-(pyridin-2-ylmethoxy)phenyl]amino}quinazolin-5-yl)oxy]propyl}-2-methoxyacetamide;

N-{(2S)-2-[(4-{[3-chloro-4-(pyridin-2-ylmethoxy)phenyl]amino}quinazolin-5-yl)oxy]propyl}-2-(methylsulfonyl)acetamide;

N-{2-[(4-{[3-chloro-4-(pyridin-2-ylmethoxy)phenyl]amino}quinazolin-5-yl)oxy]ethyl}-2-hydroxyacetamide;

$N^1$-{2-[(4-{[3-chloro-4-(pyridin-2-ylmethoxy)phenyl]amino}quinazolin-5-yl)oxy]ethyl}-$N^2$,$N^2$-dimethylglycinamide;

N-{2-[(4-{[3-chloro-4-(pyridin-2-ylmethoxy)phenyl]amino}quinazolin-5-yl)oxy]ethyl}-2-methoxyacetamide;

N-{2-[(4-{[3-chloro-4-(pyridin-2-ylmethoxy)phenyl]amino}quinazolin-5-yl)oxy]ethyl}-2-(methylsulfonyl)acetamide;

N-{(2S)-2-[(4-{[3-chloro-4-(pyridin-2-ylmethoxy)phenyl]amino}quinazolin-5-yl)oxy]propyl}-N-methylacetamide;

N-{(2S)-2-[(4-{[3-chloro-4-(pyridin-2-ylmethoxy)phenyl]amino}quinazolin-5-yl)oxy]propyl}-2-hydroxy-N-methylacetamide;

$N^1$-{(2S)-2-[(4-{[3-chloro-4-(pyridin-2-ylmethoxy)phenyl]amino}quinazolin-5-yl)oxy]propyl}-$N^1$,$N^2$,$N^2$-trimethylglycinamide;

N-{(2S)-2-[(4-{[3-chloro-4-(pyridin-2-ylmethoxy)phenyl]amino}quinazolin-5-yl)oxy]propyl}-2-methoxy-N-methylacetamide;

N-{(2S)-2-[(4-{[3-chloro-4-(pyridin-2-ylmethoxy)phenyl]amino}quinazolin-5-yl)oxy]propyl}-N-methyl-2-(methylsulfonyl)acetamide;

N-{(2R)-2-[(4-{[3-chloro-4-(pyrazin-2-ylmethoxy)phenyl]amino}quinazolin-5-yl)oxy]propyl}-N-methylacetamide;

N-{(2R)-2-[(4-{[3-chloro-4-(1,3-thiazol-4-ylmethoxy)phenyl]amino}quinazolin-5-yl)oxy]propyl}-N-methylacetamide;

N-((2R)-2-{[4-({3-chloro-4-[(3-fluorobenzyl)oxy]phenyl}amino)quinazolin-5-yl]oxy}propyl)-N-methylacetamide;

N-((2R)-2-{[4-({3-chloro-4-[(2-fluorobenzyl)oxy]phenyl}amino)quinazolin-5-yl]oxy}propyl)-N-methylacetamide;

N-{(1R)-2-[(4-{[3-chloro-4-(pyridin-2-ylmethoxy)phenyl]amino}quinazolin-5-yl)oxy]-1-methylethyl}-2-hydroxy-N-methylacetamide;

N-{(1R)-2-[(4-{[3-chloro-4-(pyridin-2-ylmethoxy)phenyl]amino}quinazolin-5-yl)oxy]-1-methylethyl}-N-methylacetamide;

N-{(1S)-2-[(4-{[3-chloro-4-(pyridin-2-ylmethoxy)phenyl]amino}quinazolin-5-yl)oxy]-1-methylethyl}-2-hydroxy-N-methylacetamide;

N-{(1S)-2-[(4-{[3-chloro-4-(pyridin-2-ylmethoxy)phenyl]amino}quinazolin-5-yl)oxy]-1-methylethyl}-N-methylacetamide;

N-{(1S)-2-[(4-{[3-chloro-4-(pyridin-2-ylmethoxy)phenyl]amino}quinazolin-5-yl)oxy]-1-methylethyl}-2-methoxy-N-methylacetamide;

N-{(1S)-2-[(4-{[3-chloro-4-(pyridin-2-ylmethoxy)phenyl]amino}quinazolin-5-yl)oxy]-1-methylethyl}-2-hydroxyacetamide;

N-{(1S)-2-[(4-{[3-chloro-4-(pyridin-2-ylmethoxy)phenyl]amino}quinazolin-5-yl)oxy]-1-methylethyl}acetamide;

$N^1$-{(1S)-2-[(4-{[3-chloro-4-(pyridin-2-ylmethoxy)phenyl]amino}quinazolin-5-yl)oxy]-1-methylethyl}-$N^2$,$N^2$-dimethylglycinamide;

$N^1$-{(2R)-2-[(4-{[3-chloro-4-(pyridin-2-ylmethoxy)phenyl]amino}quinazolin-5-yl)oxy]propyl}-$N^2$,$N^2$-dimethylglycinamide;

(2S)-N-{2-[(4-{[3-chloro-4-(pyridin-2-ylmethoxy)phenyl]amino}quinazolin-5-yl)oxy]ethyl}-2,4-dihydroxybutanamide;

(2R)-N-{2-[(4-{[3-chloro-4-(pyridin-2-ylmethoxy)phenyl]amino}quinazolin-5-yl)oxy]ethyl}-2,4-dihydroxybutanamide;

(2R)-N-{(2R)-2-[(4-{[3-chloro-4-(pyridin-2-ylmethoxy)phenyl]amino}quinazolin-5-yl)oxy]propyl}-2,4-dihydroxybutanamide;

(2S)-N-{(2R)-2-[(4-{[3-chloro-4-(pyridin-2-ylmethoxy)phenyl]amino}quinazolin-5-yl)oxy]propyl}-2,4-dihydroxybutanamide;

(2R)-N-{(2S)-2-[(4-{[3-chloro-4-(pyridin-2-ylmethoxy)phenyl]amino}quinazolin-5-yl)oxy]propyl}-2,4-dihydroxybutanamide;

(2S)-N-{(2S)-2-[(4-{[3-chloro-4-(pyridin-2-ylmethoxy)phenyl]amino}quinazolin-5-yl)oxy]propyl}-2,4-dihydroxybutanamide;

(2S)-N-{(1R)-2-[(4-{[3-chloro-4-(pyridin-2-ylmethoxy)phenyl]amino}quinazolin-5-yl)oxy]-1-methylethyl}-2,4-dihydroxybutanamide;

(2R)-N-{(1R)-2-[(4-{[3-chloro-4-(pyridin-2-ylmethoxy)phenyl]amino}quinazolin-5-yl)oxy]-1-methylethyl}-2,4-dihydroxybutanamide;

(2R)-N-{2-[(4-{[3-chloro-4-(1,3-thiazol-4-ylmethoxy)phenyl]amino}quinazolin-5-yl)oxy]ethyl}-2,4-dihydroxybutanamide;

(2S)-N-{2-[(4-{[3-chloro-4-(1,3-thiazol-4-ylmethoxy)phenyl]amino}quinazolin-5-yl)oxy]ethyl}-2,4-dihydroxybutanamide;

(2R)-N-{(1R)-2-[(4-{[3-chloro-4-(1,3-thiazol-4-ylmethoxy)phenyl]amino}quinazolin-5-yl)oxy]-1-methylethyl}-2,4-dihydroxybutanamide;

(2S)-N-{(1R)-2-[(4-{[3-chloro-4-(1,3-thiazol-4-ylmethoxy)phenyl]amino}quinazolin-5-yl)oxy]-1-methylethyl}-2,4-dihydroxybutanamide;

N-methyl-N-{2-[(4-{[3-methyl-4-(pyridin-2-ylmethoxy)phenyl]amino}quinazolin-5-yl)oxy]ethyl}acetamide;

N-methyl-N-{2-[(4-{[3-methyl-4-(1,3-thiazol-4-ylmethoxy)phenyl]amino}quinazolin-5-yl)oxy]ethyl}acetamide;

N-methyl-N-(2-{[4-({3-methyl-4-[(5-methylisoxazol-3-yl)methoxy]phenyl}amino) quinazolin-5-yl]oxy}ethyl)acetamide;

2-hydroxy-N-methyl-N-{2-[(4-{[3-methyl-4-(1,3-thiazol-2-ylmethoxy)phenyl]amino}quinazolin-5-yl)oxy]ethyl}acetamide;

2-hydroxy-N-{2-[(4-{[3-methyl-4-(pyridin-2-ylmethoxy)phenyl]amino}quinazolin-5-yl)oxy]ethyl}acetamide;

2-hydroxy-N-{2-[(4-{[3-methyl-4-(1,3-thiazol-4-ylmethoxy)phenyl]amino}quinazolin-5-yl)oxy]ethyl}acetamide;

N-{2-[(4-{[3-chloro-4-(pyridin-2-ylmethoxy)phenyl]amino}quinazolin-5-yl)oxy]-1,1-dimethylethyl}-2-hydroxyacetamide;

2-hydroxy-N-{(2R)-2-[(4-{[3-methyl-4-(pyridin-2-ylmethoxy)phenyl]amino}quinazolin-5-yl)oxy]propyl}acetamide;

2-hydroxy-N-{(2R)-2-[(4-{[3-methyl-4-(1,3-thiazol-4-ylmethoxy)phenyl]amino}quinazolin-5-yl)oxy]propyl}acetamide;

N-((2R)-2-{[4-({4-[(3-fluorobenzyl)oxy]-3-methylphenyl}amino)quinazolin-5-yl]oxy}propyl)-2-hydroxyacetamide;

2-hydroxy-N-{(2R)-2-[(4-{[3-methyl-4-(1,3-thiazol-2-ylmethoxy)phenyl]amino}quinazolin-5-yl)oxy]propyl}acetamide;

N-{(2R)-2-[(4-{[3-methyl-4-(pyridin-2-ylmethoxy)phenyl]amino}quinazolin-5-yl)oxy]propyl}acetamide;

N-{(2R)-2-[(4-{[3-methyl-4-(1,3-thiazol-4-ylmethoxy)phenyl]amino}quinazolin-5-yl)oxy]propyl}acetamide;

N-((2R)-2-{[4-({4-[(3-fluorobenzyl)oxy]-3-methylphenyl}amino)quinazolin-5-yl]oxy}propyl)acetamide;

N-{(2R)-2-[(4-{[3-methyl-4-(1,3-thiazol-2-ylmethoxy)phenyl]amino}quinazolin-5-yl)oxy]propyl}acetamide;

2-hydroxy-N-methyl-N-{(2R)-2-[(4-{[3-methyl-4-(pyridin-2-ylmethoxy)phenyl]amino}quinazolin-5-yl)oxy]propyl}acetamide;

2-hydroxy-N-methyl-N-{(2R)-2-[(4-{[3-methyl-4-(1,3-thiazol-4-ylmethoxy)phenyl]amino}quinazolin-5-yl)oxy]propyl}acetamide;

2-hydroxy-N-methyl-N-((2R)-2-{[4-({3-methyl-4-[(5-methylisoxazol-3-yl)methoxy]phenyl}amino)quinazolin-5-yl]oxy}propyl)acetamide;

N-methyl-N-{(1R)-1-methyl-2-[(4-{[3-methyl-4-(pyridin-2-ylmethoxy)phenyl]amino}quinazolin-5-yl)oxy]ethyl}acetamide;

N-methyl-N-{(1R)-1-methyl-2-[(4-{[3-methyl-4-(1,3-thiazol-4-ylmethoxy)phenyl]amino}quinazolin-5-yl)oxy]ethyl}acetamide;

N-{(1R)-2-[(4-{[3-chloro-4-(1,3-thiazol-4-ylmethoxy)phenyl]amino}quinazolin-5-yl)oxy]-1-methylethyl}-2-hydroxy-N-methylacetamide;

2-hydroxy-N-methyl-N-{(1R)-1-methyl-2-[(4-{[3-methyl-4-(pyridin-2-ylmethoxy)phenyl]amino}quinazolin-5-yl)oxy]ethyl}acetamide;

2-hydroxy-N-methyl-N-{(1R)-1-methyl-2-[(4-{[3-methyl-4-(1,3-thiazol-4-ylmethoxy)phenyl]amino}quinazolin-5-yl)oxy]ethyl}acetamide;

N-{(2R)-2-[(4-{[3-chloro-4-(pyridin-2-ylmethoxy)phenyl]amino}quinazolin-5-yl)oxy]propyl}-1-hydroxy-N-methylcyclopropanecarboxamide;

(2S)-N-{(2R)-2-[(4-{[3-chloro-4-(pyridin-2-ylmethoxy)phenyl]amino}quinazolin-5-yl)oxy]propyl}-2-hydroxy-N-methylpropanamide;

N-{(2R)-2-[(4-{[3-chloro-4-(pyridin-2-ylmethoxy)phenyl]amino}quinazolin-5-yl)oxy]propyl}-2-hydroxy-N,2-dimethylpropanamide;

(2R)-N-{(2R)-2-[(4-{[3-chloro-4-(pyridin-2-ylmethoxy)phenyl]amino}quinazolin-5-yl)oxy]propyl}-2-hydroxy-N-methylpropanamide;

(2R)-N-{(2R)-2-[(4-{[3-chloro-4-(pyridin-2-ylmethoxy)phenyl]amino}quinazolin-5-yl)oxy]propyl}-2-methoxy-N-methylpropanamide;

methyl-{2-[(4-{[3-chloro-4-(pyridin-2-ylmethoxy)phenyl]amino}quinazolin-5-yl)oxy]ethyl}methylcarbamate;

N-{2-[(4-{[3-chloro-4-(pyridin-2-ylmethoxy)phenyl]amino}quinazolin-5-yl)oxy]ethyl}-N,N'-dimethylurea;

N'-(2-chloroethyl)-N-{2-[(4-{[3-chloro-4-(pyridin-2-ylmethoxy)phenyl]amino}quinazolin-5-yl)oxy]ethyl}-N-methylurea;

N-{(2R)-2-[(4-{[3-chloro-4-(pyridin-2-ylmethoxy)phenyl]amino}quinazolin-5-yl)oxy]propyl}-N'-methylurea;

[((R)-2-{4-[3-chloro-4-(pyridin-2-ylmethoxy)phenylamino]quinazolin-5-yloxy}propylcarbamoyl)methyl]methylcarbamic acid tert-butyl ester; and $N^1$-{(2R)-2-[(4-{[3-chloro-4-(pyridin-2-ylmethoxy)phenyl]amino}quinazolin-5-yl)oxy]propyl}-$N^2$-methylglycinamide;

or a pharmaceutically acceptable salt thereof.

A particular compound of the invention is, for example, one or more quinazoline derivatives of the formula Ic selected from:

2-hydroxy-N-methyl-N-((2R)-2-{[4-({3-methyl-4-[(6-methylpyridin-3-yl)oxy]phenyl}amino)quinazolin-5-yl]oxy}propyl)acetamide;

N-methyl-N-((2R)-2-{[4-({3-methyl-4-[(6-methylpyridin-3-yl)oxy]phenyl}amino)quinazolin-5-yl]oxy}propyl)acetamide;

$N^1,N^2,N^2$-trimethyl-$N^1$-((2R)-2-{[4-({3-methyl-4-[(6-methylpyridin-3-yl)oxy]phenyl}amino)quinazolin-5-yl]oxy}propyl)glycinamide;

N-methyl-N-((2R)-2-{[4-({3-methyl-4-[(6-methylpyridin-3-yl)oxy]phenyl}amino)quinazolin-5-yl]oxy}propyl)-2-pyrrolidin-1-ylacetamide;

N-methyl-N-((2R)-2-{[4-({3-methyl-4-[(6-methylpyridin-3-yl)oxy]phenyl}amino)quinazolin-5-yl]oxy}propyl)-2-morpholin-4-ylacetamide;

N-methyl-N-((2R)-2-{[4-({3-methyl-4-[(6-methylpyridin-3-yl)oxy]phenyl}amino)quinazolin-5-yl]oxy}propyl)-2-(4-methylpiperazin-1-yl)acetamide;

152-hydroxy-N-methyl-N-((2S)-2-{[4-({3-methyl-4-[(6-methylpyridin-3-yl)oxy]phenyl}amino)quinazolin-5-yl]oxy}propyl)acetamide;

N-methyl-N-((2S)-2-{[4-({3-methyl-4-[(6-methylpyridin-3-yl)oxy]phenyl}amino)quinazolin-5-yl]oxy}propyl)acetamide;

N-methyl-N-((2S)-2-{[4-({3-methyl-4-[(6-methylpyridin-3-yl)oxy]phenyl}amino)quinazolin-5-yl]oxy}propyl)-2-pyrrolidin-1-ylacetamide;

(2S)-2,4-dihydroxy-N-((2R)-2-{[4-({3-methyl-4-[(6-methylpyridin-3-yl)oxy]phenyl}amino)quinazolin-5-yl]oxy}propyl)butanamide;

(2S)-4-bromo-2-hydroxy-N-((2R)-2-{[4-({3-methyl-4-[(6-methylpyridin-3-yl)oxy]phenyl}amino)quinazolin-5-yl]oxy}propyl)butanamide;

N-(2-chloroethyl)-N'-((2R)-2-{[4-({3-methyl-4-[(6-methylpyridin-3-yl)oxy]phenyl}amino)quinazolin-5-yl]oxy}propyl)urea;

2-hydroxy-N-methyl-N-((1R)-1-methyl-2-{[4-({3-methyl-4-[(6-methylpyridin-3-yl)oxy]phenyl}amino)quinazolin-5-yl]oxy}ethyl)acetamide;

N-methyl-N-((1R)-1-methyl-2-{[4-({3-methyl-4-[(6-methylpyridin-3-yl)oxy]phenyl}amino)quinazolin-5-yl]oxy}ethyl)acetamide;

2-hydroxy-N-methyl-N-((1S)-1-methyl-2-{[4-({3-methyl-4-[(6-methylpyridin-3-yl)oxy]phenyl}amino)quinazolin-5-yl]oxy}ethyl)acetamide;

N-methyl-N-((1S)-1-methyl-2-{[4-({3-methyl-4-[(6-methylpyridin-3-yl)oxy]phenyl}amino)quinazolin-5-yl]oxy}ethyl)acetamide;

2-hydroxy-N-methyl-N-(2-{[4-({3-methyl-4-[(6-methylpyridin-3-yl)oxy]phenyl}amino)quinazolin-5-yl]oxy}ethyl)acetamide; and N-methyl-N-(2-{[4-({3-methyl-4-[(6-methylpyridin-3-yl)oxy]phenyl}amino)quinazolin-5-yl]oxy}ethyl)acetamide;

or a pharmaceutically acceptable salt thereof.

A quinazoline derivative of the formula I, or a pharmaceutically acceptable salt thereof, may be prepared by any process known to be applicable to the preparation of chemically-related compounds. Suitable processes include, for example, those illustrated in International Patent Applications WO 96/15118, WO 01/94341, WO 03/040108 and WO 03/040109. Such processes, when used to prepare a quinazoline derivative of the formula I are provided as a further feature of the invention and are illustrated by the following representative process variants in which, unless otherwise stated, $R^1$, $R^2$, $R^3$, $R^4$, $R^{4a}$, $R^5$, $R^{5a}$, $R^6$, $X^1$, $Q^1$, A, m, and n have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

Process (a) the coupling, conveniently in the presence of a suitable base, of a quinazoline of the formula II:

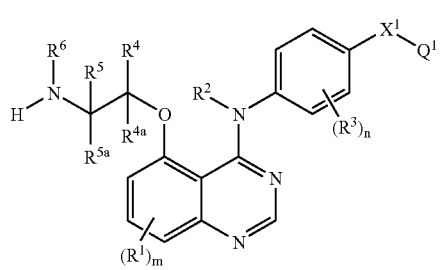

wherein $R^1$, $R^2$, $R^3$, $R^4$, $R^{4a}$, $R^5$, $R^{5a}$, $R^6$, $X^1$, $Q^1$, m, and n have any of the meanings defined hereinbefore except that any functional group is protected if necessary, with a carboxylic acid of the formula III, or a reactive derivative thereof:

   A-COOH   III wherein A has any of the meanings defined hereinbefore except that any functional group is protected if necessary;

or

Process (b) for the preparation of those compounds of the formula I wherein $X^1$ is $OC(R^7)_2$, $SC(R^7)_2$ or $N(R^7)C(R^7)_2$, the reaction, conveniently in the presence of a suitable base, of a quinazoline of the formula IV:

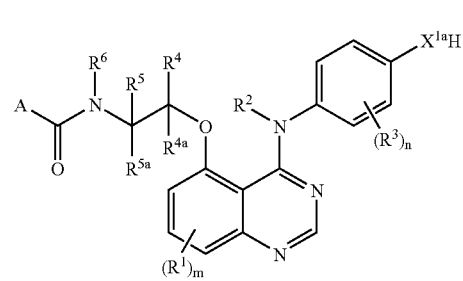

wherein $X^{1a}$ is O, S or $N(R^7)$ and $R^1$, $R^2$, $R^3$, $R^4$, $R^{4a}$, $R^5$, $R^{5a}$, $R^6$, $R^7$, A, m and n have any of the meanings defined hereinbefore except that any functional group is protected if necessary, with a compound of the formula V or a salt thereof:

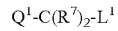   $Q^1-C(R^7)_2-L^1$   V wherein $L^1$ is a suitable displaceable group and $Q^1$ and $R^7$ have any of the meanings defined hereinbefore except that any functional group is protected if necessary;

Process (c) for the preparation of those compounds of the formula I wherein A is $R^{14}$ and $R^{14}$ is $NHR^{17}$ or $Q^3-X^5$— (wherein $R^{17}$ and $Q^3$ have any of the meanings defined hereinbefore and $X^5$ is NH), the coupling of a quinazoline of the formula II as defined above with an isocyanate of the formula IIIa:

   A-NCO   IIIa wherein A is $R^{14}$ as previously defined in this section except that any functional group is protected if necessary;

Process (d) the reaction of a quinazoline of the formula II wherein $R^6$ is hydrogen:

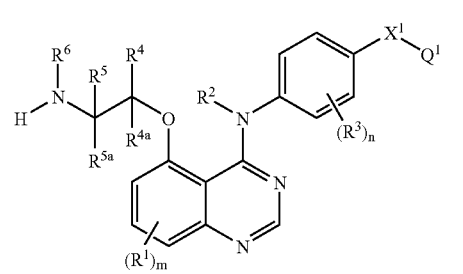

wherein $R^1$, $R^2$, $R^3$, $R^4$, $R^{4a}$, $R^5$, $R^{5a}$, $X^1$, $Q^1$, m, and n have any of the meanings defined hereinbefore except that any functional group is protected if necessary, with α-hydroxy-γ-butyrolactone (for example (S)-(−)-α-hydroxy-γ-butyrolactone or (R)-(+)-α-hydroxy-γ-butyrolactone) wherein any functional group is protected if necessary;

or

Process (e) the coupling of a quinazoline of the formula VI:

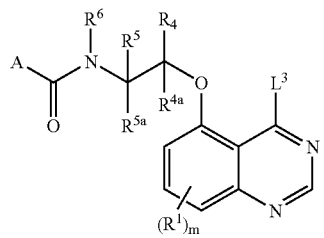

wherein $R^1$, $R^4$, $R^{4a}$, $R^5$, $R^{5a}$, $R^6$, A and m have any of the meanings defined hereinbefore except that any functional group is protected if necessary, with a compound of the formula IIb:

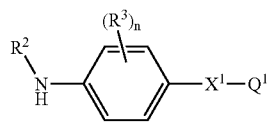

wherein $R^2$, $R^3$, $X^1$, $Q^1$ and n have any of the meanings defined hereinbefore except that any functional group is protected if necessary;

Process (f) for the preparation of those compounds of the formula I wherein $X^1$ is O and $Q^1$ is 2-pyridyl, 4-pyridyl, 2-pyrimidyl, 4-pyrimidyl, 2-pyrazinyl or 3-pyridazinyl, the reaction, conveniently in the presence of a suitable base and a suitable catalyst, of a quinazoline of the formula VII:

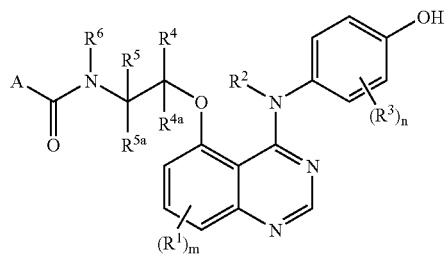

wherein $R^1$, $R^2$, $R^3$, $R^4$, $R^{4a}$, $R^5$, $R^{5a}$, $R^6$, A, m and n have any of the meanings defined hereinbefore except that any functional group is protected if necessary, with 2-bromopyridine, 4-bromopyridine, 2-chloropyrimidine, 4-chloropyrimidine, 2-chloropyrazine or 3-chloropyridazine; or Process (g) for the preparation of those compounds of the formula I wherein A is Z-$(CR^{12}R^{13})_p$—, wherein Z is $NR^{16}R^{17}$, the reaction, conveniently in the presence of a suitable base, of a quinazoline of the formula VIII:

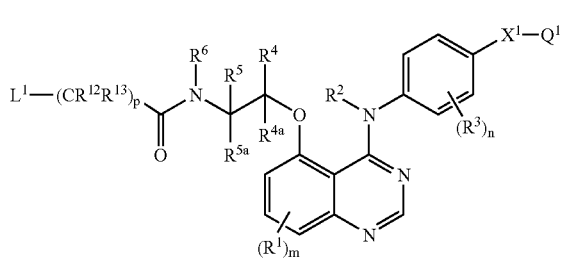

wherein $L^1$ is a suitable displaceable group and $R^1$, $R^2$, $R^3$, $R^4$, $R^{4a}$, $R^5$, $R^{5a}$, $R^6$, $R^{12}$, $R^{13}$, $X^1$, $Q^1$, m, n and p have any of the meanings defined hereinbefore except that any functional group is protected if necessary, with a compound of the formula IXa, or a reactive derivative thereof:

H—$NR^{16}R^{17}$   IXa wherein $R^{16}$ and $R^{17}$ have any of the meanings defined hereinbefore except that any functional group is protected if necessary;

and thereafter, if necessary:
(i) converting a quinazoline derivative of the formula I into another quinazoline derivative of the formula I;
(ii) removing any protecting group that is present by conventional means;
(iii) forming a pharmaceutically acceptable salt.

Specific conditions for the above reactions are as follows:

Process (a)

The coupling reaction is conveniently carried out in the presence of a suitable coupling agent, such as a carbodiimide, or a suitable peptide coupling agent, for example O-(7-azabenzotriazol-1-yl)-N,N,N',N'-tetramethyluronium hexafluoro-phosphate (HATU) or a carbodiimide such as dicyclohexylcarbodiimide, optionally in the presence of a catalyst such as dimethylaminopyridine or 4-pyrrolidinopyridine.

The coupling reaction is conveniently carried out in the presence of a suitable base. A suitable base is, for example, an organic amine base such as, for example, pyridine, 2,6-lutidine, collidine, 4-dimethylaminopyridine, triethylamine, diisopropylethylamine, N-methylmorpholine or diazabicyclo [5.4.0]undec-7-ene, or, for example, an alkali or alkaline earth metal carbonate, for example sodium carbonate, potassium carbonate, cesium carbonate, calcium carbonate.

The reaction is conveniently carried out in the presence of a suitable inert solvent or diluent, for example an ester such as, ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 120° C., conveniently at or near ambient temperature.

By the term "reactive derivative" of the carboxylic acid of the formula III is meant a carboxylic acid derivative that will react with the quinazoline of formula II to give the corresponding amide. A suitable reactive derivative of a carboxylic acid of the formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl azide, for example an azide formed by the reaction of the acid and azide such as diphenylphosphoryl azide; an acyl cyamide, for example a cyamide formed by the reaction of an acid and a cyamide such as diethylphosphoryl cyamide; or an acetoxyacetylchloride. The reaction of such reactive derivatives of carboxylic acid with amines (such as a compound of the formula II) is well known in the art, for example they may be reacted in the presence of a base, such as those described above, and in a suitable solvent, such as those described above. The reaction may conveniently be performed at a temperature as described above.

Preparation of Starting Materials for Process (a)

Compounds of formula III (and reactive derivatives thereof) are commercially available compounds or they are known in the literature, or they can be prepared by standard processes known in the art.

The quinazoline of the formula II may be obtained by conventional procedures. For example, as illustrated in Reaction Scheme 1:

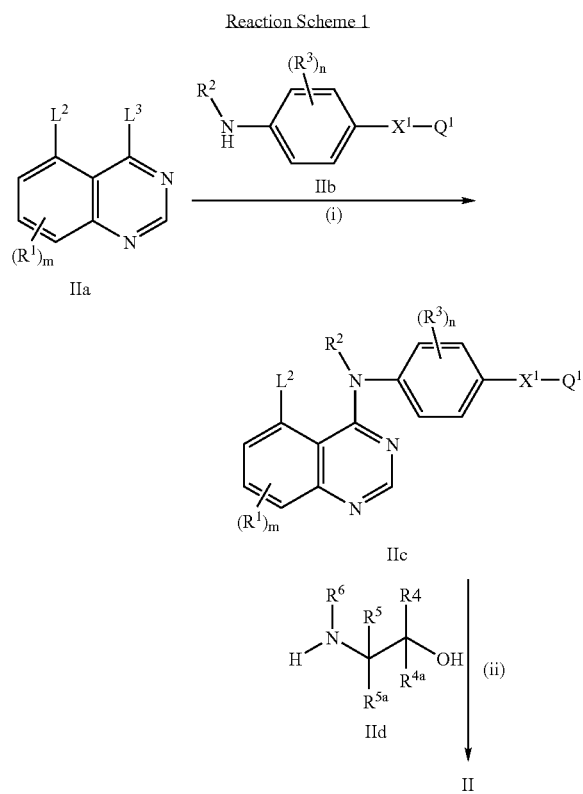

wherein $L^2$ and $L^3$ are suitable displaceable groups, provided that $L^3$ is more labile than $L^2$, and $R^1$, $R^2$, $R^3$, $R^4$, $R^{4a}$, $R^5$, $R^{5a}$, $R^6$, $X^1$, $Q^1$, m, and n have any of the meanings defined hereinbefore except that any functional group is protected if necessary during the reaction set out above, which protecting group(s) are removed if necessary at an appropriate stage in Reaction Scheme 1. For example, instead of using the compound of formula IId in step (ii) of Reaction Scheme 1, the compound IId' (including a protecting group) could be used:

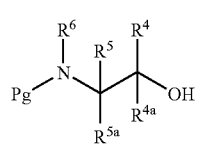

followed by removal of the protecting group, by an appropriate method known to a person skilled in the art.

A suitable displaceable group $L^2$ is for example halogeno or a sulfonyloxy group, for example fluoro, chloro, methylsulfonyloxy or toluene-4-sulfonyloxy group, particularly fluoro. A suitable displaceable group $L^3$ is, for example, halogeno (such as fluoro or chloro) or an alkoxy, aryloxy, mercapto, alkylthio, arylthio, alkylsulfinyl, arylsulfinyl, alkylsulfonyl, arylsulfonyl, alkylsulfonyloxy or arylsulfonyloxy group, for example a chloro, bromo, methoxy, phenoxy, pentafluorophenoxy, methylthio, methanesulfonyl, methanesulfonyloxy or toluene-4-sulfonyloxy group. Preferably $L^2$ and $L^3$ are both halogeno, for example $L^2$ is fluoro and $L^3$ is chloro.

Notes for Reaction Scheme 1

Step (i)

The reaction is conveniently carried out in the presence of an acid. Suitable acids include, for example hydrogen chloride gas (conveniently dissolved in a suitable inert solvent such as diethyl ether or dioxane) or hydrochloric acid.

Alternatively the quinazoline derivative of the formula IIa, wherein $L^3$ is halogen (for example chloro), may be reacted with the compound of the formula IIb in the absence of an acid or a base. In this reaction displacement of the halogeno leaving group $L^3$ results in the formation of the acid $HL^3$ in-situ and the autocatalysis of the reaction.

Alternatively, the reaction of the quinazoline derivative of formula IIa with the compound of formula IIb may be carried out in the presence of a suitable base. A suitable base is, for example, an organic amine base such as, for example, pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate, for example sodium carbonate, potassium carbonate, cesium carbonate, calcium carbonate, or, for example, an alkali metal hydride, for example sodium hydride.

The above reactions are conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulfoxide. The above reactions are conveniently carried out at a temperature in the range, for example, 0 to 250° C., conveniently in the range 40 to 80° C. or, preferably, at or near the reflux temperature of the solvent when used.

Step (ii)

The reaction a quinazoline of the formula IIc and the alcohol of the formula IId is suitably carried out in the presence of a suitable base, for example a strong non-nucleophilic base such as an alkali metal hydride, for example sodium hydride, or an alkali metal amide, for example lithium di-isopropylamide (LDA).

The reaction of the quinazoline of the formula IIc and the alcohol of the formula IId is conveniently carried out in the presence of a suitable inert solvent or diluent, for example a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range of, for example, 10 to 250° C., preferably in the range 40 to 150° C. Conveniently, this reaction may also be performed by heating the reactants in a sealed vessel using a suitable heating apparatus such as a microwave heater.

Conveniently, the reaction a quinazoline of the formula IIc and the alcohol of the formula IId is performed in the presence of a suitable catalyst, for example a crown ether such as 15-crown-5.

Starting Materials for Reaction Scheme 1

The quinazoline of formula IIa may be obtained using conventional methods, for example, when m is 0, $L^2$ is fluoro and $L^3$ is halogeno (for example chloro), 5-fluoro-3,4-dihydroquinazolin-4-one may be reacted with a suitable halogenating agent such as thionyl chloride, phosphoryl chloride or a mixture of carbon tetrachloride and triphenylphosphine. The 5-fluoro-3,4-dihydroquinazoline starting material is commercially available or can be prepared using conventional methods, for example as described in J. Org. Chem., 1952, 17, 164-176.

Compounds of the formula IIb are commercially available compounds or they are known in the literature, or they can be can be prepared by standard processes known in the art. For example, the compound of the formula IIb in which $R^2$ is hydrogen and wherein $X^1$ is O, S, SO, $SO_2$, $N(R^7)$, $OC(R^7)_2$, $SC(R^7)_2$ or $N(R^7)C(R^7)_2$ may be prepared in accordance with Reaction Scheme 2:

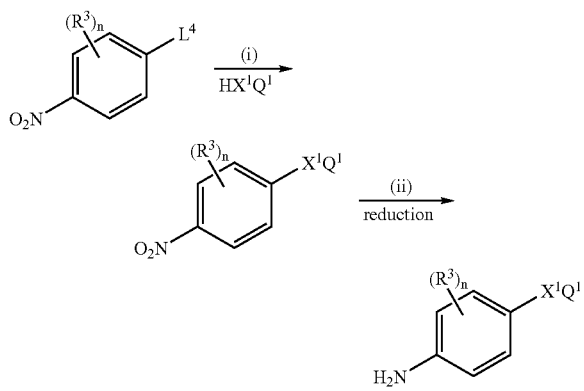

Reaction Scheme 2 wherein $L^4$ is a suitable displaceable group as hereinbefore defined (for example halogeno such as chloro) and $Q^1$, $X^1$, $R^3$ and n are as hereinbefore defined, except any functional group is protected if necessary, and any protecting group that is present in Reaction Scheme 2 is removed if necessary at an appropriate stage of Reaction Scheme 2 by conventional means.

Notes for Reaction Scheme 2

Step (i): The compounds of the formula $HX^1Q^1$ are commercially available, or they are known in the literature, or can be prepared using well known processes in the art. For example compounds of the formula $Q^1CH_2OH$ may be prepared using known methods, for example by reduction of the corresponding ester of the formula $Q^1COOR$, wherein R is, for example (1-6C)alkyl, or benzyl, with a suitable reducing agent, for example sodium borohydride, followed by ester hydrolysis.

The reaction in step (i) is conveniently carried out in the presence of a suitable base and in the presence of a suitable inert diluent or solvent. Suitable reaction conditions, solvents and bases for use in step (i) are analogous to those used in Process (b) described below.

Step (ii): The reduction of the nitro group in step (ii) may be carried out under standard conditions, for example by catalytic hydrogenation over a platinum/carbon, palladium/carbon or nickel catalyst, treatment with a metal such as iron, titanium chloride, tin II chloride or indium, or treatment with another suitable reducing agent such as sodium dithionite.

Compounds of the formula IIb wherein $X^1$ is $OC(R^7)_2$, $SC(R^7)_2$ or $N(R^7)C(R^7)_2$ may, for example, be prepared in accordance with Reaction Scheme 3:

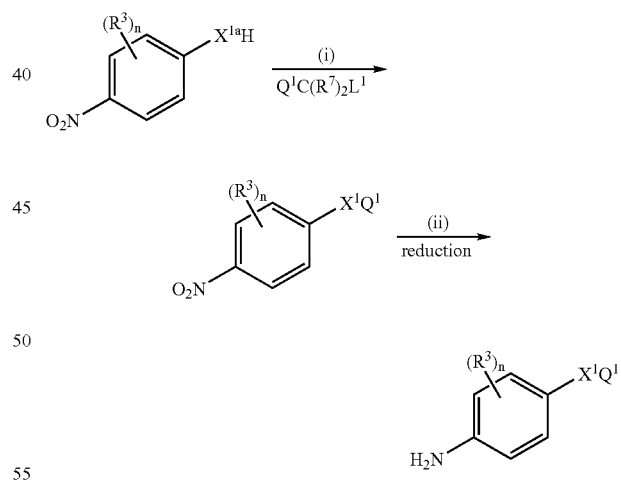

Reaction Scheme 3 wherein $L^1$ is a suitable leaving group as defined hereinafter in relation to Process (b), $X^{1a}$ is as hereinbefore defined in Process (b), and $R^3$, $R^7$, $Q^1$, $X^1$ and n are as hereinbefore defined except any functional group is protected if necessary, and any protecting group that is present in Reaction Scheme 3 is removed if necessary at an appropriate stage of Reaction Scheme 3 by conventional means.

Notes for Reaction Scheme 3

Step (i): Analogous conditions to those used in Process (b)

Step (ii): Analogous conditions to those used in Reaction Scheme 2.

Other suitable methods for preparing compounds of the formula IIb are disclosed in for example WO 03/040108 and as illustrated by the examples herein.

Compounds of the formula IIb wherein $X^1$ is $OC(R^7)_2$ may also be prepared by coupling the appropriate starting nitro phenol in Reaction Scheme 3 ($X^{1a}H$ is OH) with a compound of the formula $Q^1C(R^7)_2OH$, conveniently in the presence of a suitable dehydrating agent. A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 0 to 150° C., preferably at or near ambient temperature.

The alcohols of the formula IId used in Reaction Scheme 1 are commercially available compounds or they are known in the literature, or they can be can be prepared by standard processes known in the art. For example, alcohols of the formula IId may be prepared in accordance with Reaction Scheme 4:

Reaction Scheme 4

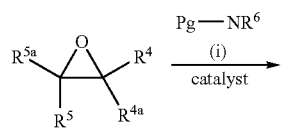

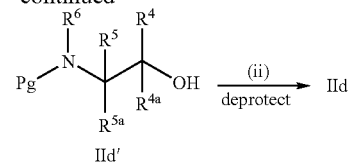

wherein Pg is a suitable amine protecting group such as allyl, and $R^4$, $R^{4a}$, $R^5$ $R^{5a}$ and $R^6$ are as hereinbefore defined.

Notes for Reaction Scheme 4

Step (i): The coupling and ring opening reaction is conveniently carried out in the presence of a suitable metal catalyst such as ytterbium(III) trifluoromethanesulfonate. The reaction is suitably carried out in the presence of an inert solvent or diluent such as dioxane. The reaction is preferably carried out at an elevated temperature, for example from 50 to about 150° C.

Step (ii): The protecting group Pg may be removed using conventional methods, for example when Pg is an allyl group by metal catalysed cleavage. A suitable catalyst is, for example, chlorotris(triphenylphosphine)rhodium (I).

As previously discussed, in embodiments, the alcohol of the formula IId' in Reaction Scheme 4 may be used directly in Process (a) (or in the preparation of the intermediates used in Process (b) described below). In this embodiment the amine protecting group, Pg, may be removed at a convenient stage in the process prior to coupling the acid of the formula III.

The quinazoline of the formula II may alternatively be obtained a conventional procedure, for example as illustrated in Reaction Scheme 1a:

Reaction Scheme 1a

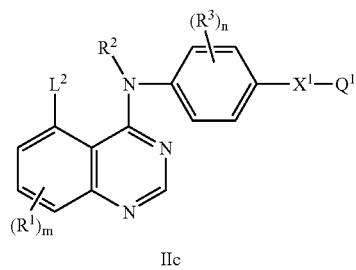

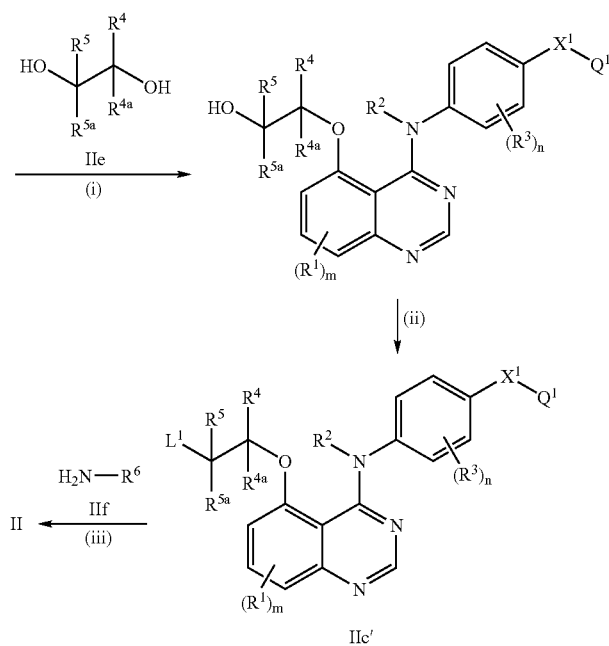

wherein $L^1$ and $L^2$ are suitable displaceable groups and $R^1$, $R^2$, $R^3$, $R^4$, $R^{4a}$, $R^5$, $R^{5a}$, $R^6$, $X^1$, $Q^1$, m and n have any of the meanings defined hereinbefore except that any functional group is protected if necessary during the reaction set out above, which protecting group(s) are removed if necessary at an appropriate stage in Reaction Scheme 1a.

A suitable displaceable group $L^2$ is for example a halogeno or a sulfonyloxy group, for example a fluoro, chloro, methylsulfonyloxy or toluene-4-sulfonyloxy group, particularly fluoro. Preferably $L^2$ is halogeno, for example $L^2$ is fluoro.

A suitable displaceable group $L^1$ in the compound of the formula IIc' is for example a halogeno or a sulfonyloxy group, for example a fluoro, chloro, methylsulfonyloxy or toluene-4-sulfonyloxy group. A particular group $L^1$ is fluoro, chloro or methylsulfonyloxy, particularly chloro.

Notes for Reaction Scheme 1a

Step (i): Analogous conditions to those used in step (ii) of Reaction Scheme 1.

Step (ii): Conducted using a suitable conversion reaction. For example when $L^1$ is chloro, step (ii) is conducted using an appropriate chlorinating agent, for example thionyl chloride.

Step (iii): The reaction of the compound of formula IIc' with the amine of formula IIf may conveniently be carried out in the presence of a suitable base. A suitable base is, for example, an organic amine base such as pyridine, 2,6-lutidine, collidine, 4-dimethylaminopyridine, triethylamine, di-isopropylethylamine, N-methylmorpholine or diazabicyclo[5.4.0]undec-7-ene, or an alkali or alkaline earth metal carbonate such as sodium carbonate, potassium carbonate, cesium carbonate, calcium carbonate, or an alkali metal hydride such as sodium hydride. Alternatively, the reaction may use an excess of the amine of formula IIf in place of the aforementioned suitable base.

If necessary, the reaction may conveniently be carried out in the presence of a suitable catalyst, for example tetrabutylammonium iodide.

The reaction of the compound of the formula IIc' and the amine of the formula IIf is conveniently carried out in the presence of a suitable inert solvent or diluent, for example an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range of, for example, from 25 to 150° C., conveniently at about 100° C.

Starting Materials for Reaction Scheme 1a

Compounds of formula IIc may be prepared using conventional procedures, for example as discussed above in relation to Reaction Scheme 1.

Compounds of formulae IIe and IIf are commercially available compounds or they are known in the literature, or they can be prepared by standard processes known in the art.

Process (b)

A suitable displaceable group $L^1$ in the compound of the formula V is for example a halogeno or a sulfonyloxy group, for example a fluoro, chloro, methylsulfonyloxy or toluene-4-sulfonyloxy group. A particular group $L^1$ is fluoro, chloro or methylsulfonyloxy.

The reaction of the quinazoline of formula IV with the compound of formula V is conveniently carried out in the presence of a suitable base. Suitable bases include, for example, an organic amine base such as, for example, pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate, for example sodium carbonate, potassium carbonate, cesium carbonate, calcium carbonate, or, for example, an alkali metal hydride, for example sodium hydride. A particular base is an alkali or alkaline earth metal carbonate, for example potassium carbonate.

The reaction of the quinazoline of the formula IV and the compound of the formula V is conveniently carried out in the presence of a suitable inert solvent or diluent, for example a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range of, for example, from 25 to 100° C., conveniently at or near ambient temperature.

The reaction of the quinazoline of the formula IV and the compound of the formula V is conveniently carried out in the presence of a suitable catalyst, for example a crown ether such as 18-crown-6.

Preparation of Starting Materials for Process (b)

Compounds of the formula V are commercially available compounds or they are known in the literature, or they can be can be prepared by standard processes known in the art.

The quinazoline of the formula IV may be prepared using conventional methods, for example, when $X^{1a}$ is O, in accordance with Reaction Scheme 5:

Reaction Scheme 5

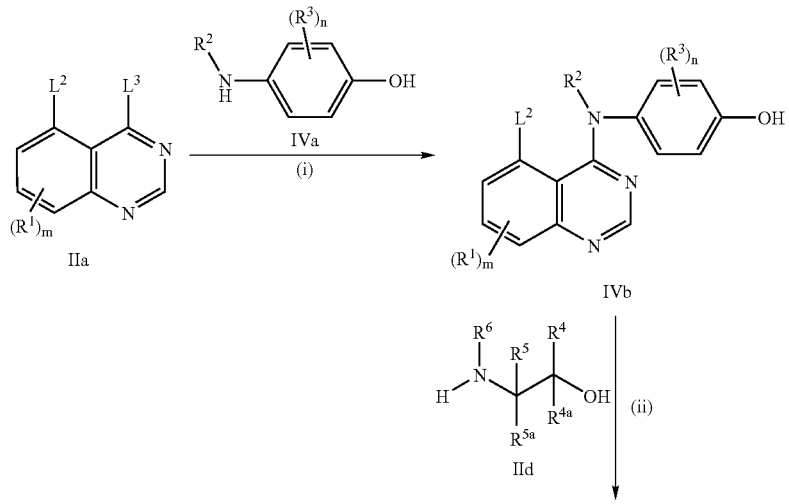

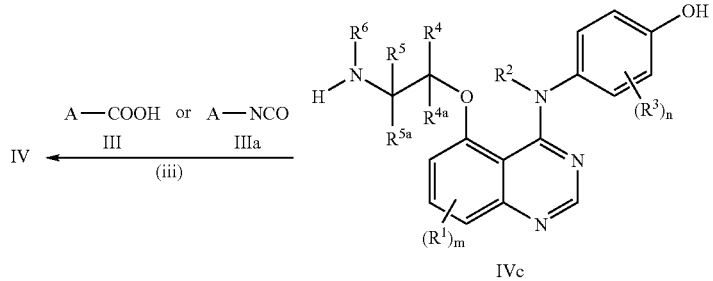

wherein $L^2$ and $L^3$ are suitable displaceable groups, provided that $L^3$ is more labile than $L^2$, as defined above in relation to Reaction Scheme 1, and $R^1$, $R^2$, $R^3$, $R^4$, $R^{4a}$, $R^5$, $R^{5a}$, $R^6$, A, m, and n have any of the meanings defined hereinbefore except that any functional group is protected if necessary during the reaction set out above, which protecting group(s) are removed if necessary at an appropriate stage in Reaction Scheme 5.

Notes for Reaction Scheme 5

Step (i): Analogous conditions to those used in step (i) in Reaction Scheme 1.

Step (ii): Analogous conditions to those used in step (ii) in Reaction Scheme 1.

Step (iii): Analogous conditions to those used in Process (a) or in Process (c). As discussed in relation to Process (a), the compound of formula III may be used as the free acid as depicted in Reaction Scheme 5 or as a reactive derivative of the compound of formula III. Suitable reactive derivatives of the compound of formula III are described in relation to Process (a) above.

Preparation of Starting Materials for Reaction Scheme 5

Compounds of formulae IIa and IId may be obtained by conventional procedures, as discussed above.

Anilines of the formula IVa are commercially available compounds or they are known in the literature, or they can be can be prepared by standard processes known in the art.

Process (c)

The reaction of a compound of the formula II with an isocyanate of the formula IIIa is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 50° C.

Preparation of Starting Materials for Process (c)

The quinazoline of formula II may be obtained by conventional procedures, as discussed above.

The compounds of formula IIIa are commercially available compounds or they are known in the literature, or they can be can be prepared by standard processes known in the art.

Process (d)

The reaction of the compound of formula II and α-hydroxy-γ-butyrolactone is conveniently carried out in the presence of a suitable inert solvent or diluent, for example xylene, toluene or dichlorobenzene (particularly xylene). The reaction is conveniently carried out at a temperature in the range, for example, 100 to 180° C.

Preparation of Starting Materials for Process (d)

The quinazoline of formula II may be obtained by conventional procedures, as discussed above.

The α-hydroxy-γ-butyrolactones are commercially available compounds or they are known in the literature, or they can be can be prepared by standard processes known in the art.

Process (e)

The reaction of the compounds of formula VI and of formula IIb is conveniently carried out using analogous conditions to those described above for Step (i) of Reaction Scheme 1.

Preparation of Starting Materials for Process (e)

The quinazoline of formula VI may be obtained by conventional procedures, as discussed above.

The compounds of formula IIb may be obtained by conventional procedures, as discussed above.

Process (f)

A suitable catalyst for the reaction of a quinazoline of the formula VII and 2-chloropyrimidine, 4-chloropyrimidine, 2-chloropyrazine or 3-chloropyridazine is for example a crown ether such as 18-crown-6.

A suitable catalyst for the reaction of a quinazoline of the formula VII and 2-bromopyridine or 4-bromopyridine is a palladium catalyst, for example a catalyst formed in situ by the reaction of bis(dibenzylideneacetone)palladium and 9,9-dimethyl-4,5-bis(diphenylphosphino)xanthene.

The reaction is conveniently carried out in the presence of a suitable base. A suitable base is, for example, an alkali or alkaline earth metal carbonate, for example sodium carbonate, potassium carbonate, cesium carbonate or calcium carbonate.

The reaction is conveniently performed in a suitable inert solvent or diluent, for example an ether such as tetrahydrofuran or 1,4-dioxane, or a dipolar aprotic solvent such as acetonitrile.

Suitably the reaction is carried out at a temperature of, for example 0 to 180° C., particularly 20° C. to the reflux temperature of the solvent/diluent. Conveniently the reaction may also be carried out by heating the reactants in a sealed vessel using a suitable heating apparatus such as a microwave heater.

Preparation of Starting Materials for Process (f)

The quinazoline of formula VII may be obtained by conventional procedures, as discussed above.

The 2-bromopyridine, 4-bromopyridine, 2-chloropyrimidine, 4-chloropyrimidine, 2-chloropyrazine and 3-chloropyridazine reagents are commercially available compounds or they are known in the literature, or they can be can be prepared by standard processes known in the art.

Process (g)

The reaction of the compound of formula VIII and the amine of formula IXa is conveniently carried out using analogous conditions to those used in step (iii) in Reaction Scheme 1a.

Preparation of Starting Materials for Process (g)

The quinazoline of formula VIII may be obtained by conventional procedures, as discussed above.

The amines of formula IXa are commercially available compounds or they are known in the literature, or they can be can be prepared by standard processes known in the art.

The quinazoline derivative of the formula I may be obtained from the above processes in the form of the free base or alternatively it may be obtained in the form of a salt, such as an acid addition salt. When it is desired to obtain the free base from a salt of the compound of formula I, the salt may be treated with a suitable base, for example, an alkali or alkaline earth metal carbonate or hydroxide, for example sodium carbonate, potassium carbonate, calcium carbonate, sodium hydroxide or potassium hydroxide, or by treatment with ammonia for example using a methanolic ammonia solution such as 7N ammonia in methanol.

The protecting groups used in the processes above may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1 to 4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1 to 20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); lower alkenyl groups (for example allyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); lower alkanoyloxyalkyl groups (for example pivaloyloxymethyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl and allyl, hydrogenation for groups such as benzyl and photolytically for groups such as 2-nitrobenzyloxycarbonyl. For example a tert-butoxycarbonyl protecting group may be removed from an amino group by an acid catalysed hydrolysis using trifluoroacetic acid.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group.

When a pharmaceutically acceptable salt of a quinazoline derivative of the formula I is required, for example an acid-addition salt, it may be obtained by, for example, reaction of said quinazoline derivative with a suitable acid using a conventional procedure.

As mentioned hereinbefore some of the compounds according to the present invention may contain one or more chiral centers and may therefore exist as stereoisomers (for example when $R^4$ is alkyl and $R^{4a}$ is hydrogen). Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free of other stereoisomers, for example containing less than 20%, particularly less than 10% and more particularly less than 5% by weight of other stereoisomers.

In the section above relating to the preparation of the quinazoline derivative of formula I, the expression "inert solvent" refers to a solvent which does not react with the starting materials, reagents, intermediates or products in a manner which adversely affects the yield of the desired product.

Persons skilled in the art will appreciate that, in order to obtain compounds of the invention in an alternative and in some occasions, more convenient manner, the individual process steps mentioned hereinbefore may be performed in a different order, and/or the individual reactions may be performed at a different stage in the overall route (i.e. chemical transformations may be performed upon different intermediates to those associated hereinbefore with a particular reaction).

Certain intermediates used in the processes described above are novel and form a further feature of the present invention. Accordingly there is provided a compound of the formula IV as hereinbefore defined, or a salt thereof. The intermediate may be in the form of a salt of the intermediate. Such salts need not be a pharmaceutically acceptable salt. For example it may be useful to prepare an intermediate in the form of a pharmaceutically non-acceptable salt if, for example, such salts are useful in the manufacture of a compound of formula I.

Biological Assays

The inhibitory activities of compounds were assessed in non-cell based protein tyrosine kinase assays as well as in cell based proliferation assays before their in vivo activity was assessed in Xenograft studies.

a) Protein Tyrosine Kinase phosphorylation Assays

This test measures the ability of a test compound to inhibit the phosphorylation of a tyrosine containing polypeptide substrate by an erb receptor tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM $MgCl_2$, 1 mM ethylene glycol-bis(β-aminoethyl ether) N',N',N',N'-tetraacetic acid (EGTA), plus protease inhibitors and then cleared by centrifugation.

Constitutive kinase activity of these recombinant proteins was determined by their ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 μg of peptide in a 200 μl phosphate buffered saline (PBS) solution and incubated at 4° C. overnight). Plates were washed in 50 mM HEPES pH 7.4 at room temperature to remove any excess unbound synthetic peptide. EGFR or erbB2 activities were assessed by incubation in peptide coated plates for 20 minutes at room temperature in 100 mM HEPES pH 7.4 at room temperature, adenosine trisphosphate (ATP) at Km concentration for the respective enzyme, 10 mM $MnCl_2$, 0.1 mM $Na_3VO_4$, 0.2 mM DL-dithiothreitol (DTT), 0.1% Triton X-100 with test compound in DMSO (final concentration of 2.5%). Reactions were terminated by the removal of the liquid components of the assay followed by washing of the plates with PBS-T (phosphate buffered saline with 0.5% Tween 20).

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (HRP) conjugated sheep anti-mouse secondary antibody (NXA931 from Amersham) for 60 minutes at room temperature. After further washing, HRP activity in each well of the plate was measured colorimetrically using 22'-Azino-di-[3-ethylbenzthiazoline sulfonate (6)]diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of KB cells (human naso-pharangeal carcinoma obtained from the American Type Culture Collection (ATCC)).

KB cells were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.25 \times 10^3$ cells per well of a 96 well plate in DMEM containing 2.5% charcoal stripped serum, 1 mM glutamine and non-essential amino acids at 37° C. in 7.5% $CO_2$ and allowed to settle for 4 hours.

Following adhesion to the plate, the cells are treated with or without EGF (final concentration of 1 ng/ml) and with or without compound at a range of concentrations in dimethylsulfoxide (DMSO) (0.1% final) before incubation for 4 days. Following the incubation period, cell numbers were determined by addition of 50 μl of 3-(4,5-Dimethylthiazol-2-yl)-2,5-diphenyltetrazolium bromide (MTT) (stock 5 mg/ml) for 2 hours. MTT solution was then tipped off, the plate gently tapped dry and the cells dissolved upon the addition of 100 μl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) Cellular EGFR Phosphorylation Assay

This assay measures the ability of a test compound to inhibit the phosphorylation of EGFR in KB cells (human naso-pharangeal carcinoma obtained from the American Type Culture Collection (ATCC).

KB cells were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $2 \times 10^5$ cells per well of a 6 well plate in DMEM containing 2.5% charcoal stripped serum, 2 mM glutamine and non-essential amino acids at 37° C. in 7.5% $CO_2$ and allowed to settle for 72 hours.

Following the 72 hour incubation period, the stripped serum containing media was then replaced with serum-free media (DMEM containing 2 mM glutamine and non-essential amino acids) and incubated at 37° C. in 7.5% $CO_2$ for 72 hours. Following this incubation period, the cells were treated with or without compound at a range of concentrations in dimethylsulfoxide (DMSO) (0.1% final) in serum free DMEM. Following incubation for 1.5 hours at 37° C. in 7.5% $CO_2$, the cells were treated with EGF (final concentration of 1 µg/ml) and incubated at 37° C. in 7.5% $CO_2$ for 3 minutes. The media was then removed and the cells washed twice in ice cold Phosphate Buffered Saline before lysis of the cells with 1 ml of ice cold lysis buffer containing 120 mM $NaCl_2$, 25 mM HEPES, pH 7.6, 5 mM B-Glycerophosphate, 2.5 mM $MgCl_2$, 1 mM EGTA, 0.2 mM EDTA, 1 mM $Na_3VO_4$, 1% Triton X-100, 100 mM NaF, 1 mM DTT, 1 mM PMSF, 10 µg/ml Leupeptin and 10 µg/ml Benzamidine. The lysates were centrifuged in a microfuge at 13000 rpm for 15 minutes and the supernatants taken before analysis by sandwich Elisa.

Nunc Maxisorb F96 Immunoplates were coated with EGFR capture antibody (sc-120, Santa Cruz Biotechnology, Inc.) by incubation at a concentration of 0.16 µg/ml in 100 µl of 50 mM carbonate/bicarbonate buffer, pH 9.6. The plates were incubated at 4° C. overnight with a gentle shaking action. Following overnight incubation, the plates were washed extensively with PBS containing 0.05% Tween before blocking with Superblock (Pierce). 100 µl of lysate was then added to each well and incubated overnight at 4° C. before extensive washing with PBS containing 0.05% Tween.

The immobilised EGFR was then probed with an anti-phosphotyrosine HRP conjugated antibody (4G10, Upstate Biotechnology Inc.) at a dilution of 1 in 800 in PBS containing 0.05% Tween plus 0.5% Bovine Serum Albumen. After further washing, HRP activity in each well of the plate was measured colorimetrically using Tetra Methyl Benzidine (TMB) from Bushranger (Roche Applied Sciences) in phosphate-citrate-perborate buffer containing 10% DMSO as a substrate. This reaction was stopped by the addition of 100 ul of 1M $H_2SO_4$ after 12 minutes and quantified by measurement of the absorbance at 450 nm using a Molecular Devices ThermoMax microplate reader.

Inhibition of EGFR phosphorylation for a given compound was expressed as an $IC_{50}$ value. This was determined by calculation of the concentration of compound that was required to give 50% inhibition of phosphorylation in this assay. The range of phosphorylation was calculated from the positive (vehicle plus EGF) and negative (vehicle minus EGF) control values.

d) Clone 24 Phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% $CO_2$ air incubator at 37° C. Cells were harvested from T75 stock flasks by washing once in PBS (phosphate buffered saline, pH7.4, Gibco No. 10010-015) and harvested using 2 mls of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of $1 \times 10^4$ cells per well (in 10 ul) into clear bottomed 96 well plates (Packard, No. 6005182).

3 days later, Growth Medium was removed from the wells and replaced with 100 ul Assay Medium (phenol red free DMEM, 2 mM glutamine, 1.2 mg/ml G418) either with or without erbB inhibitor compound. Plates were returned to the incubator for 4 hours and then 20 µl of 20% formaldehyde solution in PBS was added to each well and the plate was left at room temperature for 30 minutes. This fixative solution was removed with a multichannel pipette, 100 µl of PBS was added to each well and then removed with a multichannel pipette and then 50 µl PBS was added to each well. Plates were then sealed and stored for up to 2 weeks at 4° C.

Immunostaining was performed at room temperature. Wells were washed once with 200 µl PBS/Tween 20 (made by adding 1 sachet of PBS/Tween dry powder (Sigma, No. P3563) to 1 L of double distilled $H_2O$) using a plate washer then 200 µl Blocking Solution (5% Marvel dried skimmed milk (Nestle) in PBS/Tween 20) was added and incubated for 10 minutes. Blocking Solution was removed using a plate washer and 200 µl of 0.5% Triton X-100/PBS was added to permeabalise the cells. After 10 minutes, the plate washed with 200 µl PBS/Tween 20 and then 200 µl Blocking Solution was added once again and incubated for 15 minutes. Following removal of the Blocking Solution with a plate washer, 30 µl of rabbit polyclonal anti-phospho ErbB2 IgG antibody (epitope phospho-Tyr 1248, SantaCruz, No. SC-12352-R), diluted 1:250 in Blocking Solution, was added to each well and incubated for 2 hours. Then this primary antibody solution was removed from the wells using a plate washer followed by two 200 µl PBS/Tween 20 washes using a plate washer. Then 30 µl of Alexa-Fluor 488 goat anti-rabbit IgG secondary antibody (Molecular Probes, No. A-11008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by two 200 ul PBS/Tween 20 washes using a plate washer. Then 100 µl PBS was added to each plate, incubated for 10 minutes and then removed using a plate washer. Then a further 100 µl PBS was added to each plate and then, without prolonged incubation, removed using a plate washer. Then 50

μl of PBS was added to each well and plates were resealed with black backing tape and stored for up to 2 days at 4° C. before analysis.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an $IC_{50}$ value. This was determined by calculation of the concentration of compound that was required to give 50% inhibition of erbB2 phosphorylation signal.

e) In Vivo BT-474 Xenograft Assay

This assay measures the ability of a test compound to inhibit the growth of a BT-474 tumour cell xenograft (human mammary carcinoma obtained from Dr Baselga, Laboratorio Recerca Oncologica, Paseo Vall D'Hebron 119-129, Barcelona 08035, Spain) in Female Swiss athymic mice (Alderley Park, nu/nu genotype) (Baselga, J. et al. (1998) *Cancer Research*, 58, 2825-2831).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. BT-474 tumour cell xenografts were established in the hind flank of donor mice by subcutaneous injections of $1 \times 10^7$ freshly cultured cells in 100 μl of serum free media with 50% Matrigel per animal. On day 14 post-implant, mice were randomised into groups of 10 prior to the treatment with compound or vehicle control that was administered once daily at 0.1 ml/10 g body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of treatment was calculated by comparison of the mean changes in tumour volume for the control and treated groups, and statistical significance between the two groups was evaluated using a Students t test.

f) hERG-Encoded Potassium Channel Inhibition Assay

This assay determines the ability of a test compound to inhibit the tail current flowing through the human ether-a-go-go-related-gene (hERG)-encoded potassium channel.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin G418 (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at room temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampex, Axon Instruments) was used to set a holding potential (−80 mV) and to deliver a voltage protocol. This protocol was applied every 15 seconds and consisted of a 1 s step to +40 mV followed by a 1 s step to −50 mV. The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
| --- | --- | --- |
| NaCl | — | 137 |
| KCl | 130 | 4 |
| $MgCl_2$ | 1 | 1 |
| $CaCl_2$ | — | 1.8 |
| HEPES | 10 | 10 |
| glucose | — | 10 |
| $Na_2ATP$ | 5 | — |
| EGTA | 5 | — |

| Parameter | Pipette | Bath |
| --- | --- | --- |
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle.

Test compound potency ($IC_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

Although the pharmacological properties of the compounds of the formula I vary with structural change as expected, in general activity possessed by compounds of the formula I, may be demonstrated at the following concentrations or doses in one or more of the above tests (a), (b), (c) and (d):—

Test (a):—$IC_{50}$ in the range, for example, 0.001-5 μM;
Test (b):—$IC_{50}$ in the range, for example, 0.001-5 μM;
Test (c):—$IC_{50}$ in the range, for example, 0.001-5 μM;
Test (c):—$IC_{50}$ in the range, for example, 0.001-5 μM;
Test (d):—activity in the range, for example, 1-200 mg/kg/day;

No physiologically unacceptable toxicity was observed in Test (d) at the effective dose for compounds tested of the present invention. Accordingly no untoward toxicological effects are expected when a compound of formula I, or a pharmaceutically acceptable salt thereof, as defined hereinbefore is administered at the dosage ranges defined hereinafter.

By way of example, Table A illustrates the activity of representative compounds according to the invention. Column 2 of Table A shows $IC_{50}$ data from Test (a) for the inhibition of EGFR tyrosine kinase protein phosphorylation; column 3 shows $IC_{50}$ data from Test (a) for the inhibition of erbB2 tyrosine kinase protein phosphorylation; and column 4 shows $IC_{50}$ data for inhibition of phosphorylation of erbB2 in a MCF7 derived cell line in Test (d) described above:

TABLE A

| Example Number | $IC_{50}$ (μM) Test (a): Inhibition of EGFR tyrosine kinase protein phosphorylation | $IC_{50}$ (μM) Test (a): Inhibition of erbB2 tyrosine kinase protein phosphorylation | $IC_{50}$ (μM) Test (d): Inhibition of erbB2 tyrosine kinase protein phosphorylation |
|---|---|---|---|
| 21 | 0.414 | 0.002 | 0.009 |
| 28 | 0.197 | 0.002 | 0.112 |
| 104 | 1.876 | 0.017 | 0.021 |

According to a further aspect of the invention there is provided a pharmaceutical composition which comprises a quinazoline derivative of the formula I, or a pharmaceutically acceptable thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a quinazoline derivative of the formula I will naturally vary according to the nature and severity of the conditions, the age and sex of the animal or patient and the route of administration, according to well known principles of medicine.

In using a quinazoline derivative of the formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

We have found that the compounds of the present invention possess anti-proliferative properties such as anti-cancer properties that are believed to arise from their erb-B, particularly EGFR and more particularly erbB2 receptor tyrosine kinase inhibitory activity. Furthermore, certain of the compounds according to the present invention possess substantially better potency against the erbB2 receptor tyrosine kinase, than against other tyrosine kinases enzymes, such as EGFR tyrosine kinase. Such compounds possess sufficient potency against the erbB2 receptor tyrosine kinase that they may be used in an amount sufficient to inhibit erbB2 receptor tyrosine kinase whilst demonstrating little, or significantly lower, activity against other tyrosine kinases such as EGFR. Such compounds are likely to be useful for the selective inhibition of erbB2 receptor tyrosine kinase and are likely to be useful for the effective treatment of, for example erbB2 driven tumours. Accordingly, the compounds of the present invention are expected to be useful in the treatment of diseases or medical conditions mediated alone or in part by and erb-B, particularly erbB2 receptor tyrosine kinases, i.e. the compounds may be used to produce a erb-B, particularly an erbB2, receptor tyrosine kinase inhibitory effect in a warm-blooded animal in need of such treatment. Thus the compounds of the present invention provide a method for the treatment of malignant cells characterised by inhibition of the erb-B, particularly erbB2, receptor tyrosine kinase. Particularly the compounds of the invention may be used to produce an anti-proliferative and/or pro-apoptotic and/or anti-invasive effect mediated alone or in part by the inhibition of erb-B, particularly erbB2, receptor tyrosine kinases. Particularly, the compounds of the present invention are expected to be useful in the prevention or treatment of those tumours that are sensitive to inhibition of an erb-B, particularly the erbB2, receptor tyrosine kinase that are involved in the signal transduction steps which drive proliferation and survival of these tumour cells. Accordingly the compounds of the present invention are expected to be useful in the treatment and/or prevention of a number of hyperproliferative disorders by providing an antiproliferative effect. These disorders include, for example psoriasis, benign prostatic hyperplasia (BPH), atherosclerosis and restenosis and, in particular, erb-B, more particularly erb-B2, receptor tyrosine kinase driven tumours. Such benign or malignant tumours may affect any tissue and include non-solid tumours such as leukaemia, multiple myeloma or lymphoma, and also solid tumours, for example bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval tumours.

According to this aspect of the invention there is provided a quinazoline derivative of the formula I, or a pharmaceutically acceptable salt thereof, for use as a medicament.

Thus according to this aspect of the invention there is provided the use of a quinazoline derivative of the formula I, or a pharmaceutically acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative of the formula I, or a pharmaceutically acceptable salt thereof, as hereinbefore defined.

According to a further aspect of the invention there is provided a quinazoline derivative of the formula I, or a pharmaceutically acceptable salt thereof, for use in the production of an anti-proliferative effect in a warm-blooded animal such as man.

According to a further aspect of the invention there is provided the use of a quinazoline derivative of the formula I, or a pharmaceutically acceptable salt thereof, as defined hereinbefore in the manufacture of a medicament for use in the production of an anti-proliferative effect which effect is produced alone or in part by inhibiting erbB2 receptor tyrosine kinase in a warm-blooded animal such as man.

According to a further feature of this aspect of the invention there is provided a method for producing an anti-proliferative effect which effect is produced alone or in part by inhibiting erbB2 receptor tyrosine kinase in a warm-blooded animal, such as man, in need of such treatment which comprises administering to said animal an effective amount of a quinazoline derivative of the formula I, or a pharmaceutically acceptable salt thereof, as hereinbefore defined.

According to a further aspect of the invention there is provided a quinazoline derivative of the formula I, or a pharmaceutically acceptable salt thereof, for use in the production of an anti-proliferative effect which effect is produced alone or in part by inhibiting erbB2 receptor tyrosine kinase in a warm-blooded animal such as man.

According to a further aspect of the present invention there is provided the use of a quinazoline derivative of the formula I, or a pharmaceutically acceptable salt thereof, as defined hereinbefore in the manufacture of a medicament for use in the treatment of a disease or medical condition (for example a cancer as mentioned herein) mediated alone or in part by erb-B, particularly erbB2, receptor tyrosine kinase.

According to a further feature of this aspect of the invention there is provided a method for treating a disease or medical condition (for example a cancer as mentioned herein) mediated alone or in part by erb-B, particularly erbB2, receptor tyrosine kinase in a warm-blooded animal, such as man, in need of such treatment, which comprises administering to said animal an effective amount of a quinazoline derivative of the formula I, or a pharmaceutically acceptable salt thereof, as defined hereinbefore.

According to a further aspect of the invention there is provided a quinazoline derivative of the formula I, or a pharmaceutically acceptable salt thereof, for use in the treatment of a disease or medical condition (for example a cancer as mentioned herein) mediated alone or in part by erb-B, particularly erbB2, receptor tyrosine kinase.

According to a further aspect of the invention there is provided the use of a quinazoline derivative of the formula I, or a pharmaceutically acceptable salt thereof, as defined hereinbefore in the manufacture of a medicament for use in the prevention or treatment of those tumours which are sensitive to inhibition of erbB2 receptor tyrosine kinase that is involved in the signal transduction steps which lead to the proliferation of tumour cells.

According to a further feature of this aspect of the invention there is provided a method for the prevention or treatment of those tumours which are sensitive to inhibition of erbB2 receptor tyrosine kinase, that is involved in the signal transduction steps which lead to the proliferation and/or survival of tumour cells in a warm-blooded animal, such as man, in need of such treatment, which comprises administering to said animal an effective amount of a quinazoline derivative of the formula I, or a pharmaceutically acceptable salt thereof, as defined hereinbefore.

According to a further aspect of the invention there is provided a quinazoline derivative of the formula I, or a pharmaceutically acceptable salt thereof, for use in the prevention or treatment of those tumours which are sensitive to inhibition of the erbB2 receptor tyrosine kinase, that is involved in the signal transduction steps which lead to the proliferation and/or survival of tumour cells. According to a further aspect of the invention there is provided the use of a quinazoline derivative of the formula I, or a pharmaceutically acceptable salt thereof, as defined hereinbefore in the manufacture of a medicament for use in providing a erbB2 receptor tyrosine kinase inhibitory effect.

According to a further feature of this aspect of the invention there is provided a method for providing an erbB2 receptor tyrosine kinase inhibitory effect in a warm-blooded animal, such as man, in need of such treatment, which comprises administering to said animal an effective amount of a quinazoline derivative of the formula I, or a pharmaceutically acceptable salt thereof, as defined hereinbefore.

According to a further aspect of the invention there is provided a quinazoline derivative of the formula I, or a pharmaceutically acceptable salt thereof, for use in providing an erbB2 receptor tyrosine kinase inhibitory effect.

According to a further aspect of the invention there is provided the use of a quinazoline derivative of the formula I, or a pharmaceutically acceptable salt thereof, as defined hereinbefore in the manufacture of a medicament for use in providing a selective erbB2 kinase inhibitory effect.

According to a further feature of this aspect of the invention there is provided a method for providing a selective erbB2 kinase inhibitory effect in a warm-blooded animal, such as man, in need of such treatment, which comprises administering to said animal an effective amount of a quinazoline derivative of the formula I, or a pharmaceutically acceptable salt thereof, as defined hereinbefore.

According to a further aspect of the invention there is provided a quinazoline derivative of the formula I, or a pharmaceutically acceptable salt thereof, for use in providing a selective erbB2 kinase inhibitory effect.

By "a selective erbB2 kinase inhibitory effect" is meant that the quinazoline derivative of Formula I is more potent against erbB2 receptor tyrosine kinase than it is against other kinases. In particular some of the compounds according to the invention are more potent against erbB2 receptor kinase than it is against other tyrosine kinases such as other erb-B receptor tyrosine kinases, particularly EGFR tyrosine kinase. For example a selective erb-B2 kinase inhibitor according to the invention is at least 5 times, preferably at least 10 times, more preferably at least 100 times more potent against erbB2 receptor tyrosine kinase than it is against EGFR tyrosine kinase, as determined from the relative $IC_{50}$ values in suitable assays (for example the by comparing the $IC_{50}$ value from the Clone 24 phospho-erbB2 cell assay (assay d) described above which measure the inhibition of erb-B2 phosphorylation in cells) with the $IC_{50}$ from the KB cellular EGFR phosphorylation assay (assay c) described above which measures the inhibition of EGFR phosphorylation in cells) for a given test compound as described above).

According to a further aspect of the present invention there is provided the use of a quinazoline derivative of the formula I, or a pharmaceutically acceptable salt thereof, as defined hereinbefore in the manufacture of a medicament for use in the treatment of a cancer, for example a cancer selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer.

According to a further feature of this aspect of the invention there is provided a method for treating a cancer, for example a cancer selected from selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer in a warm-blooded animal, such as man, in need of such treatment, which comprises administering to said animal an effective amount of a quinazoline derivative of the formula I, or a pharmaceutically acceptable salt thereof, as defined hereinbefore.

According to a further aspect of the invention there is provided a quinazoline derivative of the formula I, or a pharmaceutically acceptable salt thereof, for use in the treatment of a cancer, for example a cancer selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer.

The anti-proliferative treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:

As mentioned above the size of the dose required for the therapeutic or prophlyactic treatment of a particular disease will necessarily be varied depending upon, amongst other things, the host treated, the route of administration and the severity of the illness being treated.

The anti-proliferative treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, voraole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbB2 antibody trastuzumab [Herceptin™] and the anti-erbB1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the formula I as defined hereinbefore and an additional anti-tumour agent as defined hereinbefore for the conjoint treatment of cancer.

Although the compounds of the formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

The invention will now be illustrated by the following non limiting examples in which, unless stated otherwise:
(i) temperatures are given in degrees Celsius (° C.); operations were carried out at room or ambient temperature, that is, at a temperature in the range of 18-25° C.;
(ii) organic solutions were dried over anhydrous magnesium sulfate; evaporation of solvent was carried out using a rotary evaporator under reduced pressure (600-4000 Pascals; 4.5-30 mmHg) with a bath temperature of up to 80° C.;
(iii) chromatography means flash chromatography on silica gel; thin layer chromatography (TLC) was carried out on silica gel plates;
(iv) in general, the course of reactions was followed by TLC and/or analytical LC-MS, and reaction times are given for illustration only;
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;
(viii) chemical symbols have their usual meanings; SI units and symbols are used;
(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(MH)^+$ which refers to the protonated mass ion; reference to $M^+$ is to the mass ion generated by loss of an electron; and reference to $M-H^+$ is to the mass ion generated by loss of a proton;
(xi) unless stated otherwise compounds containing an asymmetrically substituted carbon and/or sulfur atom have not been resolved;
(xii) where a synthesis is described as being analogous to that described in a previous example the amounts used are the millimolar ratio equivalents to those used in the previous example;
(xiii) all microwave reactions were carried out in a CEM Discover™ microwave synthesis or CEM Marrs microwave synthesisor;
(xiv) preparative high performance liquid chromatography (HPLC) was performed on a Gilson instrument using the following conditions:

| Column: | 21 mm × 10 cm Hichrom RPB |
|---|---|
| Solvent A: | Water + 0.1% trifluoroacetic acid, |
| Solvent B: | Acetonitrile + 0.1% trifluoroacetic acid |
| Flow rate: | 18 ml/min |
| Run time: | 15 minutes with a 10 minute gradient from 5-95% B |
| Wavelength: | 254 nm, bandwidth 10 nm |
| Injection volume | 2.0-4.0 ml; |

(xv) the following abbreviations have been used:
HATU  O-(7-Azabenzotriazol-1-yl)-N,N,N',N'-Tetramethyluronium Hexafluoro-Phosphate; and
THF tetrahydrofuran;
DMF N,N-dimethylformamide;
DMA N,N-dimethylacetamide;
DCM dichloromethane;
DIPEA N,N-diisopropylethylamine;
DMSO dimethylsulfoxide;
IPA Isopropyl alcohol; and
ether diethyl ether.

EXAMPLE 1

N-{2-[(4-{3-Chloro-4-(pyridin-2-ylmethoxy) anilino}quinazolin-5-yl)oxy]ethyl}-N-methylacetamide

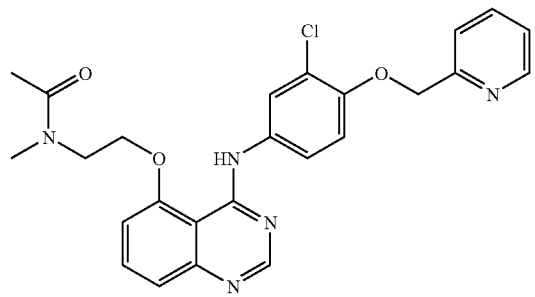

A mixture of HATU (197 mg), diisopropylethylamine (90 µl), acetic acid (22 µl) and N-[3-chloro-4-(pyridin-2-ylmethoxy)phenyl]-5-[2-(methylamino)ethoxy]quinazolin-4-amine (150 mg) in DCM (20 ml) was stirred for 2 hours. The solution washed with water, then brine and concentrated in vacuo. The residue was purified by chromatography using DCM—5% methanol as eluent to give the title compound as a white solid (114 mg, 69%); NMR spectrum (DMSO-d6) 1.95 (s, 3H), 3.00 (s, 3H), 3.89 (t, 2H), 4.48 (m, 2H), 5.29 (s, 2H), 7.18 (d, 1H), 7.24 (d, 1H), 7.35 (m, 2H), 7.59 (m, 2H), 7.72 (dd, 1H), 7.85 (dt, 1H), 7.96 (d, 1H), 8.46 (s, 1H), 8.58 (m, 1H), 9.70 (bs, 1H); Mass spectrum MH+ 478.5.

The N-[3-chloro-4-(pyridin-2-ylmethoxy)phenyl]-5-[2-(methylamino)ethoxy]quinazolin-4-amine used as starting material was prepared as follows:

DMF (0.2 ml) was added to a suspension of 5-fluoro-3,4-dihydro-3H-quinazolin-4-one (1.64 g) in thionyl chloride (10 ml) and the mixture was stirred and heated at 80° C. for 6 hours. Volatile material was removed by evaporation and the residue was azeotroped with toluene (20 ml). The resulting solid was added portion wise to a vigorously stirred mixture of saturated sodium bicarbonate (50 ml), crushed ice (50 g) and DCM (50 ml) such that the temperature was kept below 5° C. The organic phase was separated, dried and concentrated to give 4-chloro-5-fluoroquinazoline (1.82 g, 99%) as a solid which was used without purification; NMR spectrum (CDCl3) 7.35-7.45 (m, 1H), 7.85-7.95 (m, 2H), 9.0 (s, 1H).

4-Chloro-5-fluoroquinazoline (6.75 g) was added to a stirred solution of 3-chloro-4-(2-pyridylmethoxy)aniline (9.27 g, obtained as described in Example 15-21 (note u) of WO 96/15118) in IPA (200 ml), and the solution was stirred and heated at reflux for 8 hours. The solution was allowed to cool to ambient temperature overnight and the precipitated solid was filtered off, washed with acetone and dried. The solid was added to 50% aqueous methanol (400 ml) and the mixture was heated on a steam bath until the entire solid had dissolved. The solution was basified by careful addition of aqueous ammonia (0.880), and the mixture was concentrated to remove methanol. Water (300 ml) was added and the mixture was extracted with DCM (600 ml). The extract washed with water, and brine, and dried. The solvent was removed by evaporation to give a solid, which was re-precipitated from a mixture of ethyl acetate, tetrahydrofuran and isohexane to give N-[3-chloro-4-(pyridin-2-ylmethoxy)phenyl]-5-fluoro-quinazolin-4-amine as a beige solid (6.75 g, 48%); NMR spectrum (DMSO-d6) 5.3 (s, 2H), 7.2-7.3 (d, 1H), 7.35-7.5 (m, 2H), 7.5-7.65 (m, 3H), 7.8-7.95 (m, 3H), 8.55 (s, 1H), 8.55-8.6 (d, 1H), 9.1-9.2 (bs, 1H); Mass spectrum MH+ 381.

Sodium hydride (60% dispersion in mineral oil, 0.63 g) was added to 2-(methylamino)ethanol (0.95 ml), 15-crown-5 (100 µl) and N-[3-chloro-4-(pyridin-2-ylmethoxy)phenyl]-5-fluoroquinazolin-4-amine (1.5 g) in DMA (25 ml) and the reaction heated at 100° C. for 2 hours. The reaction was cooled, quenched with saturated aqueous ammonium chloride solution to pH 7-8. Addition of a small amount of saturated aqueous sodium hydrogen carbonate solution resulted in the formation of a precipitate, which was filtered, washed with water and dried. The solid was purified by chromatography using DCM-5% methanol/7N ammonia as eluent to give N-[3-chloro-4-(pyridin-2-ylmethoxy)phenyl]-5-[2-(methylamino)ethoxy]quinazolin-4-amine as a yellow solid (0.27 g, 45%); NMR spectrum (DMSO-d6) 2.40 (s, 3H), 3.02 (t, 2H), 4.35 (t, 2H), 5.28 (s, 2H), 7.12 (d, 1H), 7.25 (d, 1H), 7.31 (d, 1H), 7.37 (m, 1H), 7.57 (d, 1H), 7.71 (dd, 1H), 7.85 (m, 2H), 8.10 (d, 1H), 8.51 (s, 1H), 8.58 (m, 1H), 10.57 (bs, 1H); Mass spectrum MH+ 436.5.

EXAMPLE 2

Using an analogous procedure to that described in Example 1 the appropriate quinazoline was reacted with the appropriate acid to give the compounds shown in Table I:

TABLE I

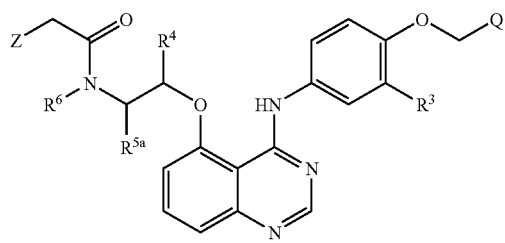

| No. and Note | $Q^1$ | $R^3$ | $R^4$ | $R^{5a}$ | $R^6$ | Z |
|---|---|---|---|---|---|---|
| [1] | 2-pyridyl | Cl | H | H | methyl | methoxy |
| [2] | 2-pyridyl | Cl | H | H | methyl | dimethyl-amino |
| [3] | 2-pyridyl | Cl | (R)-methyl | H | methyl | methoxy |
| [4] | 2-pyridyl | Cl | H | (R)-methyl | H | H |
| [5] | 2-pyridyl | Cl | H | (R)-methyl | H | OH |
| [6] | 2-pyridyl | Cl | H | H | H | H |
| [7] | 2-pyridyl | Cl | (R)-methyl | H | methyl | H |

[1] N-{2-[(4-{3-Chloro-4-(pyridin-2-ylmethoxy)anilino}quinazolin-5-yl)oxy]ethyl}-2-methoxy-N-methylacetamide. Prepared by reacting methoxyacetic acid and N-[3-chloro-4-(pyridin-2-ylmethoxy)phenyl]-5-[2-(methylamino)ethoxy]quinazolin-4-amine (prepared as described in Example 1, preparation of starting materials) in 52% yield; NMR spectrum (DMSO-d6) 3.00 (s, 3H), 3.23 (s, 3H), 3.90 (t, 2H), 4.04 (s, 2H), 4.50 (t, 2H), 5.29 (s, 2H), 7.17 (d, 1H), 7.23 (d, 1H), 7.35 (m, 2H), 7.59 (dd, 1H), 7.72 (dd, 1H), 7.85 (dt, 1H), 7.99 (d, 1H), 8.45 (s, 1H), 8.58 (m, 1H), 9.70 (bs, 1H); Mass spectrum MH+ 508.5.

[2] N-{2-[(4-{3-Chloro-4-(pyridin-2-ylmethoxy)anilino}quinazolin-5-yl)oxy]ethyl}-2-(dimethylamino)-N-methylacetamide. Prepared by reacting N,N-dimethylglycine and N-[3-chloro-4-(pyridin-2-ylmethoxy)phenyl]-5-[2-(methylamino)ethoxy]quinazolin-4-amine (prepared as described in Example 1, preparation of starting materials) in 13% yield; NMR spectrum (DMSO-d6) 2.68 (s, 6H), 3.05 (s, 3H), 3.97 (m, 2H), 4.05 (s, 2H), 4.53 (m, 2H), 5.29 (s, 2H), 7.19 (d, 1H), 7.26 (d, 1H), 7.37 (m, 2H), 7.60 (d, 1H), 7.65 (d, 1H), 7.54 (t, 1H), 7.86 (dt, 1H), 8.02 (d, 1H), 8.50 (s, 1H), 8.58 (m, 1H), 9.70 (bs, 1H); Mass spectrum MH+ 521.6.

[3] N-{(2R)-2-[(4-{3-Chloro-4-(pyridin-2-ylmethoxy)anilino}quinazolin-5-yl)oxy]propyl}-2-methoxy-N-methylacetamide). Prepared by reacting methoxyacetic acid and N-[3-chloro-4-(pyridin-2-ylmethoxy)phenyl]-5-[(1R)-1-methyl-2-(methylamino)ethoxy]quinazolin-4-amine in 31% yield; Mass spectrum MH+ 522.4.

The N-[3-chloro-4-(pyridin-2-ylmethoxy)phenyl]-5-[(1R)-1-methyl-2-(methylamino)ethoxy]quinazolin-4-amine used as starting material was prepared as follows:

(2R)-2-methyloxirane (13.76 g) was added to a suspension of N-methylprop-2-en-1-amine (25 ml) and ytterbium(III) trifluoromethanesulfonate (100 mg) in dioxane (100 ml) and heated to 140° C. for 1 hour under microwave irradiation. The solution was concentrated in vacuo and the residue partitioned between water (100 ml) and ethyl acetate (200 ml). The organic extract was dried and solvent removed in vacuo yielding (2R)-1-[allyl(methyl)amino]propan-2-ol as a yellow oil (8.8 g, 29%); NMR spectrum (CDCl$_3$) 1.20 (d, 3H), 2.33 (s, 3H), 2.27-2.46 (m, 2H), 3.05 (m, 1H), 3.23 (m, 1H), 3.88 (m, 1H), 5.19-5.29 (m, 2H), 5.90 (m, 1H); Mass spectrum M$^+$ 129.

(2R)-1-[allyl(methyl)amino]propan-2-ol was reacted with N-[3-chloro-4-(pyridin-2-ylmethoxy)phenyl]-5-fluoroquinazolin-4-amine using an analogous procedure to that described in Example 1 for the preparation of N-[3-chloro-4-(pyridin-2-ylmethoxy)phenyl]-5-[2-(methylamino)ethoxy]quinazolin-4-amine, to give 5-{(1R)-2-[allyl(methyl)amino]-1-methylethoxy}-N-[3-chloro-4-(pyridin-2-ylmethoxy)phenyl]quinazolin-4-amine in 53% yield; NMR spectrum (DMSO-d6) 1.45 (d, 3H), 2.17 (s, 3H), 2.92-3.07 (m, 2H), 4.93 (m, 1H), 5.00 (d, 1H), 5.10 (d, 1H), 5.30 (s, 2H), 5.64 (m, 1H), 7.20-7.40 (m, 4H), 7.58 (m, 2H), 7.71 (dd, 1H), 7.85 (dd, 1H), 7.98 (m, 1H), 8.47 (s, 1H), 8.58 (d, 1H), 10.32 (bs, 1H).

5-{(1R)-2-[allyl(methyl)amino]-1-methylethoxy}-N-[3-chloro-4-(pyridin-2-ylmethoxy)phenyl]quinazolin-4-amine was heated in acetonitrile/water in the presence of chlorotris(triphenylphosphine)rhodium (I) using an analogous procedure to that described below in Example 4-11 (preparation of starting materials) to give N-[3-chloro-4-(pyridin-2-ylmethoxy)phenyl]-5-[(1R)-1-methyl-2-(methylamino)ethoxy]quinazolin-4-amine in 15% yield; Mass spectrum M$^+$ 450.

[4] N-{(1R)-2-[(4-{3-Chloro-4-(pyridin-2-ylmethoxy)anilino}quinazolin-5-yl)oxy]-1-methylethyl}acetamide. Prepared by reacting 5-{[(2R)-2-aminopropyl]oxy}-N-[3-chloro-4-(pyridin-2-ylmethoxy)phenyl]quinazolin-4-amine and acetic acid in 99% yield; NMR spectrum (DMSO-d6) 1.20 (d, 3H), 1.70 (s, 3H), 4.2-4.3 (m, 2H), 4.4 (m, 1H), 5.35 (s, 2H), 7.3-7.6 (m, 6H), 7.8 (m, 1H), 7.85-8.00 (m, 2H), 8.15 (d, 1H), 8.6 (d, 1H), 8.8 (s, 1H); Mass spectrum MH$^+$ 478.

The 5-{[(2R)-2-aminopropyl]oxy}-N-[3-chloro-4-(pyridin-2-ylmethoxy)phenyl]quinazolin-4-amine used as starting material was prepared by reacting (R)-(–)-2-amino-1-propanol and N-[3-chloro-4-(pyridin-2-ylmethoxy)phenyl]-5-fluoroquinazolin-4-amine using an analogous procedure to that described in Example 1 (for the preparation of N-[3-chloro-4-(pyridin-2-ylmethoxy)phenyl]-5-[2-(methylamino)ethoxy]quinazolin-4-amine) to give 5-{[(2R)-2-aminopropyl]oxy}-N-[3-chloro-4-(pyridin-2-ylmethoxy)phenyl]quinazolin-4-amine in 63% yield; NMR spectrum (DMSO-d6) 1.20 (d, 3H), 3.4 (m, 1H), 4.0 (t, 1H), 4.2 (dd, 1H), 5.3 (s, 2H), 7.1 (d, 1H), 7.2 (d, 1H), 7.3 (m, 2H), 7.6 (d, 1H), 7.7 (m, 2H), 7.9 (m, 1H), 8.25 (d, 1H), 8.5 (s, 1H), 8.6 (d, 1H); Mass spectrum MH$^+$ 436.

[5] N-{(1R)-2-[(4-{3-Chloro-4-(pyridin-2-ylmethoxy)anilino}quinazolin-5-yl)oxy]-1-methylethyl}-2-hydroxyacetamide. Prepared by reacting glycolic acid and 5-{[(2R)-2-aminopropyl]oxy}-N-[3-chloro-4-(pyridin-2-ylmethoxy)phenyl]quinazolin-4-amine in 93% yield; NMR spectrum (DMSO-d6) 1.20 (d, 3H), 3.6-3.8 (m, 2H), 4.3 (m, 2H), 4.5 (m, 1H), 5.35 (s, 2H), 7.25-7.60 (m, 6H), 7.80-7.95 (m, 3H), 8.00 (d, 1H), 8.60 (d, 1H), 8.6 (d, 1H), 8.75 (s, 1H); Mass spectrum MH$^+$ 494.

[6] N-{2-[(4-{3-Chloro-4-(pyridin-2-ylmethoxy)anilino}quinazolin-5-yl)oxy]ethyl}acetamide. Prepared by reacting acetic acid with 5-(2-aminoethoxy)-N-[3-chloro-4-(pyridin-2-ylmethoxy)phenyl]quinazolin-4-amine in 63% yield; NMR spectrum (DMSO-d6) 1.78 (s, 3H), 3.62 (m, 2H), 4.34 (t, 2H), 5.29 (s, 2H), 7.14 (d, 1H), 7.24 (d, 1H), 7.35 (m, 2H), 7.57 (m 2H), 7.72 (t, 1H), 7.87 (t, 1H), 8.01 (d, 1H), 8.25 (bs, 1H), 8.48 (s, 1H), 8.59 (m, 1H) 9.87 (bs, 1H); Mass spectrum MH$^+$ 464.

The 5-(2-aminoethoxy)-N-[3-chloro-4-(pyridin-2-ylmethoxy)phenyl]quinazolin-4-amine used as a starting material was prepared by reacting ethanolamine and N-[3-chloro-4-(pyridin-2-ylmethoxy)phenyl]-5-fluoroquinazolin-4-amine using an analogous procedure to that described in Example 1 for the preparation of N-[3-chloro-4-(pyridin-2-ylmethoxy)phenyl]-5-[2-(methylamino)ethoxy]quinazolin-4-amine, to give 5-(2-aminoethoxy)-N-[3-chloro-4-(pyridin-2-ylmethoxy)phenyl]quinazolin-4-amine in 49% yield; NMR spectrum (DMSO-d6) 3.12 (t, 2H), 3.29 (2H obscured under water), 4.28 (t, 2H), 5.28 (s, 2H), 7.12 (d, 1H), 7.21 (d, 1H), 7.34 (m, 2H), 7.57 (d, 1H), 7.71 (m, 2H), 7.87 (t, 1H), 8.23 (d, 1H), 8.51 (s, 1H), 858 (d, 1H); Mass spectrum MH$^+$ 422.

[7] N-{(2R)-2-[(4-{3-Chloro-4-(pyridin-2-ylmethoxy)anilino}quinazolin-5-yl)oxy]propyl}-N-methylacetamide. Prepared by reacting acetic acid with N-[3-chloro-4-(pyridin-2-ylmethoxy)phenyl]-5-[(1R)-1-methyl-2-(methylamino)ethoxy]quinazolin-4-amine (prepared as described in Example 2-3) to give the title product in 50% yield; NMR spectrum (CDCl$_3$) 1.47 (d, 3H), 2.00 (s, 3H), 3.00 (s, 3H), 3.45 (m, 1H), 3.93 (m, 1H), 5.00 (m, 1H), 5.25 (s, 2H), 6.98 (m, 2H), 7.40 (m, 1H), 7.49 (m, 1H), 7.59 (m, 2H), 7.70 (m, 1H), 7.90 (s, 1H), 8.53 (s, 2H), 9.82 (bs, 1H); Mass spectrum MH$^+$ 492.5.

EXAMPLE 3

2-Hydroxy-N-methyl-N-{2-[(4-{3-methyl-4-(pyridin-2-ylmethoxy)anilino}quinazolin-5-yl)oxy]ethyl}acetamide

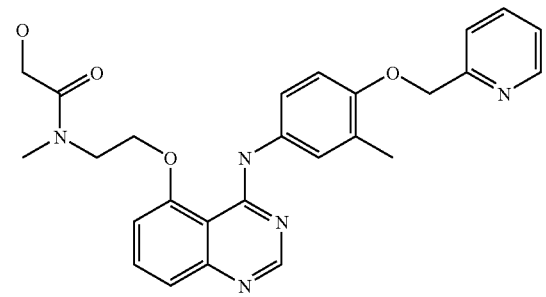

2-Hydroxy-N-[2-({4-[4-hydroxy-3-methylanilino]quinazolin-5-yl}oxy)ethyl]-N-methylacetamide (100 mg), picolyl chloride hydrochloride (60 mg) and potassium carbonate (120 mg) were stirred in DMF (5 ml) to which was added 18-crown-6 (10 mg). The reaction was stirred at room temperature for 2 days. The DMF was removed in vacuo, water (5 ml) was added and then the suspension was extracted with DCM (2×5 ml). The DCM fraction was purified by chromatography using 2.5-5% of 10:1 DCM/methanol containing 0.5% ammonia (0.880) as eluent. The appropriate fractions were evaporated, and the residue was precipitated from DCM/diethyl ether to give the title product as a light yellow solid (28 mg, 23%); NMR spectrum (DMSO-d6, 100° C.) 2.29 (s, 3H), 3.00 (s, 3H), 3.90 (t, 2H), 4.16 (s, 2H), 4.50 (t, 2H), 5.20 (s, 2H), 7.01 (d, 1H), 7.16 (d, 1H), 7.34 (d, 2H), 7.51 (m, 2H), 7.55 (d, 1H), 7.79 (t, 1H), 7.83 (td, 1H), 8.41 (s, 1H), 8.57 (d, 1H), 9.62 (s, 1H); Mass spectrum MH$^+$ 474.

The 2-hydroxy-N-[2-({4-[4-hydroxy-3-methylanilino]quinazolin-5-yl}oxy)ethyl]-N-methylacetamide used as starting material was prepared as follows:

4-Chloro-5-fluoroquinazoline (6.76 g) was dissolved in iso-propanol (200 ml) and 4-amino-2-methylphenol (5.00 g) was added. The mixture was heated under reflux for 2 hours, causing a yellow solid to precipitate. The mixture was cooled to ambient temperature and the solid was collected by filtration. The solid was dissolved in a boiling mixture of methanol (500 ml) and water (100 ml) to give a brown solution. With vigorous stirring, the solution was basified with aqueous ammonia (0.880, 10 ml), causing a light brown solid to precipitate. The mixture was concentrated in vacuo to such a volume that all of the methanol had been removed, leaving the product as a suspension in aqueous solution. The suspension was cooled; the solid was collected by filtration, triturated with ethyl acetate and dried over $P_2O_5$ in a vacuum oven to give 2-methyl-4-[(5-fluoroquinazolin-4-yl)amino]phenol as a light brown solid (8.18 g, 82%); NMR spectrum (DMSO-d6) 3.30 (s, 3H), 6.78 (d, 1H), 7.28 (m, 2H), 7.38 (dd, 1H), 7.57 (d, 1H), 7.78 (m, 1H), 8.43 (s, 1H), 8.88 (d, 1H), 9.22 (s, 1H); Mass spectrum MH+ 270.

A solution of N-methylaminoethanol (0.80 g) in DMA (5 ml) was added dropwise to a suspension of sodium hydride (60% dispersion in mineral oil, 0.43 g) in DMA (20 ml). The reaction was stirred for 30 minutes then 15-crown-5 (50 mg) was added, followed by 2-methyl-4-[(5-fluoroquinazolin-4-yl)amino]phenol (1.00 g). The reaction was heated at 110° C. for 2.5 hours. The reaction was cooled, quenched with saturated ammonium chloride, and concentrated in vacuo. Saturated sodium bicarbonate solution was added causing precipitation of a solid which was collected by filtration, washed with water and precipitated from ethyl acetate to give 2-methyl-4-({5-[2-(methylamino)ethoxy]quinazolin-4-yl}amino)phenol as a grey solid (0.60 g, 50%); NMR spectrum (DMSO-d6) 2.16 (s, 3H), 2.38 (s, 3H), 3.01 (t, 2H), 4.32 (t, 2H), 6.87 (d, 1H), 7.07 (d, 1H), 7.18 (d, 1H), 7.45 (d, 1H), 7.65 (dd, 1H), 7.66 (t, 1H), 8.41 (s, 1H), 10.36 (s, 1H); Mass spectrum M+ 325.

A solution of glycolic acid (100 mg) in DMF (2 ml) was added dropwise to a solution of 2-methyl-4-({5-[2-(methylamino)ethoxy]quinazolin-4-yl}amino)phenol (400 mg) in DMF (4 ml) and the mixture held under sonication for 5 minutes. A solution of HATU (519 mg) in DMF (2 ml) was then added and the solution was stirred at ambient temperature for 16 hours, and then concentrated in vacuo. The residue was treated with water to precipitate a brown solid that was collected by filtration, and washed with water to give 2-hydroxy-N-[2-({4-[4-hydroxy-3-methylanilino]quinazolin-5-yl}oxy)ethyl]-N-methylacetamide as a brown solid (406 mg, 86%); NMR spectrum (DMSO-d6) 2.15 (s, 3H), 2.94 (s, 3H), 3.87 (m, 2H), 4.04 (s, 2H), 4.48 (m, 2H), 6.81 (d, 1H), 7.20 (dd, 1H), 7.25 (d, 1H), 7.35 (m, 2H), 7.92 (t, 1H), 8.64 (s, 1H), 9.46 (s, 1H), 10.49 (s, 1H); Mass spectrum M+ 383.

EXAMPLE 4

Using an analogous procedure to that described in Example 3 the appropriate 4-(4-hydroxyanilino)quinazoline was reacted with the appropriate compound of the formula $Q^1$-$CH_2$-$L^1$ to give the compounds shown in Table 2 below, wherein $Q^1$ is a specified in Table 2 and $L^1$ is chloro or methanesulfonate as specified in the notes for Table 2.

TABLE 2

| No. and Note | $Q^1$ | $R^3$ | $R^4$ | $R^6$ | Z |
|---|---|---|---|---|---|
| [1] | 2-pyrazinyl | methyl | H | methyl | OH |
| [2] | 1,3-thiazol-4-yl | methyl | H | methyl | OH |
| [3] | 5-methylisoxazol-3-yl | methyl | H | methyl | OH |
| [4] | 2-pyridyl | Cl | (R)-methyl | H | methoxy |
| [5] | 2-pyridyl | Cl | H | methyl | OH |
| [6] | 3-fluorophenyl | Cl | H | methyl | OH |
| [7] | 1,3-thiazol-4-yl | Cl | H | methyl | OH |
| [8] | 6-methylpyridin-2-yl | Cl | H | methyl | OH |
| [9] | 2-pyrazinyl | Cl | H | methyl | OH |
| [10] | 2-pyridyl | Cl | (R)-methyl | H | H |
| [11] | 2-pyridyl | Cl | (R)-methyl | methyl | OH |
| [12] | 2-pyrazinyl | Cl | (R)-methyl | methyl | OH |
| [13] | 6-methylpyridin-2-yl | Cl | (R)-methyl | methyl | OH |
| [14] | 3-fluorophenyl | Cl | (R)-methyl | methyl | OH |
| [15] | 1,3-thi azol-4-yl | Cl | (R)-methyl | methyl | OH |
| [16] | 6-methylpyridin-2-yl | Cl | H | methyl | H |
| [17] | 2-fluorophenyl | Cl | H | methyl | H |
| [18] | 3-fluorophenyl | Cl | H | methyl | H |
| [19] | 1,3-thiazol-4-yl | Cl | H | methyl | H |
| [20] | 2-pyrazinyl | Cl | H | methyl | H |
| [21] | 2-pyridyl | Cl | (R)-methyl | H | OH |

[1] 2-Hydroxy-N-methyl-N-{2-[(4-{3-methyl-4-(pyrazin-2-ylmethoxy)anilino}quinazolin-5-yl)oxy]ethyl}acetamide. Prepared by reacting 2-hydroxy-N-[2-({4-[4-hydroxy-3-methylanilino]quinazolin-5-yl}oxy)ethyl]-N-methylacetamide and pyrazin-2-ylmethyl methanesulfonate to give the title product as a pale yellow solid in 34% yield; NMR spectrum (DMSO-d6, 100° C.) 2.26 (s, 3H), 3.00 (s, 3H), 3.92 (t, 2H), 4.16 (s, 2H), 4.51 (t, 2H), 5.26 (s, 2H), 7.05 (d, 1H), 7.16 (d, 1H), 7.35 (d, 1H), 7.52 (m, 2H), 7.69 (t, 1H), 8.40 (s, 1H), 8.60 (d, 1H), 8.64 (d, 1H), 8.81 (s, 1H), 9.63 (s, 1H); Mass spectrum MH+ 475.

The pyrazin-2-ylmethyl methanesulfonate used as starting material was prepared as follows:

Di-iso-propylethylamine (175 μl) and methane sulfonyl chloride (80 μl) were added dropwise to a solution of 2-(hydroxymethyl)-pyrazine (110 mg, prepared as described in *Anales De Quimica* 1979, p 899) in DCM (5 ml) at 0° C. and the reaction allowed to warm to room temperature and stirred for 30 minutes. DCM was removed in vacuo and the residue was used with out further purification.

[2] 2-Hydroxy-N-methyl-N-{2-[(4-{3-methyl-4-(1,3-thiazol-4-ylmethoxy)anilino}quinazolin-5-yl)oxy]ethyl}acetamide. Prepared by reacting 2-hydroxy-N-[2-({4-[4-hydroxy-3-methylanilino]quinazolin-5-yl}oxy)ethyl]-N-methylacetamide and 4-(chloromethyl)-thiazole hydrochloride to give the title product as a white solid in 20% yield; NMR spectrum (DMSO-d6, 100° C.) 2.23 (s, 3H), 3.00 (s, 3H), 3.91 (t, 2H), 4.08 (s, 2H), 4.49 (t, 2H), 5.25 (s, 2H), 7.07 (d, 1H), 7.16 (d, 1H), 7.34 (d, 1H), 7.50 (m, 2H), 7.68 (m, 2H), 8.41 (s, 1H), 9.07 (d, 1H), 9.63 (s, 1H); Mass spectrum MH+ 480.

[3] 2-Hydroxy-N-methyl-N-(2-{[4-(3-methyl-4-[(5-methylisoxazol-3-yl)methoxy]anilino)quinazolin-5-yl]oxy}ethyl)acetamide. Prepared by reacting 2-hydroxy-N-[2-({4-[4-hydroxy-3-methylanilino]quinazolin-5-yl}oxy)ethyl]-N-methylacetamide and 3-(chloromethyl)-5-methylisoxazole to give the title product as a pale grey solid in 30% yield; NMR spectrum (DMSO-d6, 100° C.) 2.22 (s, 3H), 2.41 (s, 3H), 3.00 (s, 3H), 3.92 (t, 2H), 4.05 (s, 2H), 4.48 (t, 2H), 5.15 (s, 2H), 6.28 (s, 1H), 7.05 (d, 1H), 7.16 (d, 1H), 7.34 (d, 1H), 7.48 (m, 2H), 7.68 (t, 1H), 8.42 (s, 1H), 9.62 (s, 1H); Mass spectrum MH+ 478.

[4] N-{(2R)-2-[(4-{3-Chloro-4-(pyridin-2-ylmethoxy)anilino}quinazolin-5-yl)oxy]propyl}-2-methoxyacetamide. Prepared by reacting N-[(2R)-2-({4-[3-chloro-4-hydroxyanilino]quinazolin-5-yl}oxy)propyl]-2-methoxyacetamide and picolyl chloride hydrochloride in 43% yield; NMR spectrum (DMSO-d6) 1.19 (d, 3H), 3.10 (s, 3H), 3.21 (dt, 1H), 3.72 (m, 1H), 3.77 (s, 2H), 4.93 (m, 1H), 5.29 (s, 2H), 7.22 (d, 2H), 7.24 (d, 2H), 7.32 (d, 1H), 7.36 (dd, 1H), 7.58 (m, 2H), 7.71 (t, 1H), 7.86 (td, 1H), 8.15 (d, 1H), 8.19 (t, 1H), 8.47 (s, 1H), 8.59 (d, 1H), 9.97 (s, 1H) Mass spectrum MH+ 508.

The N-[(2R)-2-({4-[3-chloro-4-hydroxyanilino]quinazolin-5-yl}oxy)propyl]-2-methoxyacetamide used as starting material was prepared as follows:

(R)-1-amino-2-propanol was reacted with 2-chloro-4-[(5-fluoroquinazolin-4-yl)amino]phenol (prepared as described in Example 4-4, preparation of starting materials) using an analogous process to that described Example 1 for the preparation of N-[3-chloro-4-(pyridin-2-ylmethoxy)phenyl]-5-[2-(methylamino)ethoxy]quinazolin-4-amine) to give 4-({5-[(1R)-2-amino-1-methylethoxy]quinazolin-4-yl}amino)-2-chlorophenol in 64% yield; NMR spectrum (DMSO-d6) 1.39 (d, 3H), 2.88-3.03 (m, 2H), 3.72-3.85 (m, 1H), 6.95 (d, 1H), 7.15 (d, 1H), 7.29 (d, 1H), 7.45-7.52 (m, 1H), 7.69, (t, 1H), 8.05 (s, 1H), 8.45 (s, 1H) Mass spectrum MH+ 345.

4-({5-[(1R)-2-Amino-1-methylethoxy]quinazolin-4-yl}amino)-2-chlorophenol was reacted with methoxyacetic acid using an analogous process to that described in Example 3 (preparation of starting materials) to give N-[(2R)-2-({4-[3-chloro-4-hydroxyanilino]quinazolin-5-yl}oxy)propyl]-2-methoxyacetamide in 83% yield; NMR spectrum (DMSO-d6) 1.4 (d, 3H), 3.1 (s, 3H), 3.35-3.45 (m, 1H), 3.72-3.85 (m, 3H), 4.95-5.05 (m, 1H), 7.05 (d, 1H), 7.31 (d, 1H), 7.4 (dd, 1H), 7.48 (d, 1H), 7.81 (m, 1H), 7.95 (t, 1H), 8.25 (t, 1H), 8.8 (s, 1H), 10.39 (s, 1H), 10.74 (s, 1H) Mass spectrum MH+ 417.

[5] N-{2-[(4-{3-Chloro-4-(pyridin-2-ylmethoxy)anilino}quinazolin-5-yl)oxy]ethyl}-2-hydroxy-N-methylacetamide. Prepared by reacting picolyl chloride hydrochloride and N-[2-({4-[3-chloro-4-hydroxyanilino]quinazolin-5-yl}oxy)ethyl]-2-hydroxy-N-methylacetamide in 66% yield; NMR spectrum (DMSO-d6) 2.96 (s, 3H), 3.91 (t, 2H), 4.04 (d, 2H), 4.26 (t, 1H), 4.40 (t, 2H), 5.28 (s, 2H), 7.14 (d, 1H), 7.22 (d, 1H), 7.32 (d, 1H), 7.35 (m, 1H), 7.57 (m, 2H), 7.70 (m, 1H), 7.86 (m, 1H), 7.95 (s, 1H), 8.42 (s, 1H), 8.58 (d, 1H), 9.73 (bs, 1H); Mass spectrum MH+ 494.

The N-[2-({4-[(3-chloro-4-hydroxyphenyl)amino]quinazolin-5-yl}oxy)ethyl]-2-hydroxy-N-methylacetamide used as a starting material was prepared as follows:

4-Chloro-5-fluoroquinazoline was reacted with 4-amino-2-chlorophenol using an analogous process to that described in Example 3 for the preparation of 2-methyl-4-[(5-fluoroquinazolin-4-yl)amino]phenol, to give 2-chloro-4-[(5-fluoroquinazolin-4-yl)amino]phenol in 85% yield; NMR spectrum (DMSO-d6) 6.97 (d, 1H), 7.38 (dd, 1H), 7.42 (dd, 1H), 7.59 (d, 1H), 7.73 (d, 1H), 7.81 (dd, 1H), 8.51 (s, 1H), 9.03 (d, 1H), 10.07 (bs, 1H); Mass spectrum MH+ 290.

2-Chloro-4-[(5-fluoroquinazolin-4-yl)amino]phenol was reacted with N-methylaminoethanol using an analogous process to that described in Example 3 for the preparation of 2-methyl-4-({5-[2-(methylamino)ethoxy]quinazolin-4-yl}amino)phenol, to give 2-Chloro-4-({5-[2-(methylamino)ethoxy]quinazolin-4-yl}amino)phenol in 96% yield; NMR spectrum (DMSO-d6) 2.41 (s, 3H), 3.05 (t, 2H), 4.36 (t, 2H), 6.97 (d, 1H), 7.12 (d, 1H), 7.31 (d, 1H), 7.63 (1H, dd), 7.70 (t, 1H), 7.96 (s, 1H), 8.47 (s, 1H) 10.47 (bs, 1H); Mass spectrum MH+ 345.

2-Chloro-4-({5-[2-(methylamino)ethoxy]quinazolin-4-yl}amino)phenol was reacted with glycolic acid using an analogous procedure to that described in Example 3 to give N-[2-({4-[3-Chloro-4-hydroxyanilino]quinazolin-5-yl}oxy)ethyl]-2-hydroxy-N-methylacetamide in 58% yield; NMR spectrum (DMSO-d6) 2.96 (s, 3H), 3.90 (t, 2H), 4.05 (m, 3H), 4.41 (t, 2H), 6.97 (d, 1H), 7.14 (d, 1H), 7.34 (m, 2H), 7.70 (t, 1H), 7.79 (d, 1H), 8.40 (s, 1H), 9.64 (s, 1H), 10.00 (bs, 1H); Mass spectrum MH+ 403.

[6] N-(2-{[4-(3-Chloro-4-[(3-fluorobenzyl)oxy]anilino)quinazolin-5-yl]oxy}ethyl)-2-hydroxy-N-methylacetamide. Prepared by reacting 3-fluorobenzyl chloride and N-[2-({4-[3-chloro-4-hydroxyanilino]quinazolin-5-yl}oxy)ethyl]-2-hydroxy-N-methylacetamide to give the title product in 59% yield; NMR spectrum (DMSO-d6 at 100° C.) 2.91 (s, 3H), 3.83 (t, 2H), 3.99 (bs, 3H), 4.42 (t, 3H), 5.17 (s, 2H), 7.00-7.30 (m, 6H), 7.36 (m, 1H), 7.50 (dd, 1H), 7.63 (t, 1H), 7.89 (d, 1H), 8.38 (s, 1H), 9.62 (bs, 1H); Mass spectrum MH+ 511.

[7] N-{2-[(4-{3-Chloro-4-(1,3-thiazol-4-ylmethoxy)anilino}quinazolin-5-yl)oxy]ethyl}-2-hydroxy-N-methylacetamide. Prepared by reacting 4-(chloromethyl)-1,3-thiazole hydrochloride and N-[2-({4-[3-chloro-4-hydroxyanilino]quinazolin-5-yl}oxy)ethyl]-2-hydroxy-N-methylacetamide to give the title product in 54% yield; NMR spectrum (DMSO-d6 at 100° C.) 2.99 (s, 3H), 3.91 (t, 2H), 4.07 (bs, 3H), 4.50 (t, 2H), 5.34 (s, 2H), 7.17 (d, 1H), 7.30 (d, 1H), 7.36 (d, 1H), 7.59 (dd, 1H), 7.72 (m, 2H), 7.96, (d, 1H), 8.46 (s, 1H), 9.08 (d, 1H), 9.70 (bs, 1H); Mass spectrum MH+ 500.

[8] N-(2-{[4-(3-Chloro-4-[(6-methylpyridin-2-yl)methoxy]anilino)quinazolin-5-yl]oxy}ethyl)-2-hydroxy-N-methylacetamide. A mixture of methanesulfonyl chloride (0.034 ml), triethylamine (0.077 ml) and (6-methylpyridin-2-yl)methanol (44 mg) was stirred in DCM (10 ml) overnight. The solution was concentrated in vacuo and DMF (20 ml) was added, followed by the addition of N-[2-({4-[3-chloro-4-hydroxyanilino]quinazolin-5-yl}oxy)ethyl]-2-hydroxy-N-methylacetamide (125 mg) and potassium carbonate (150 mg) and the mixture stirred for 2 days. The solution was concentrated in vacuo and water (50 ml) was added and the mixture extracted with DCM (60 ml). The extract was dried and concentrated in vacuo and the residue purified by chromatography using DCM—10% methanol (2M ammonia) to give the title compound as a white solid (99 mg, 54%); NMR spectrum (DMSO-d6 at 100° C.) 2.50 (s, 3H obscured by DMSO), 2.99 (s, 3H), 3.92 (t, 2H), 4.06 (bs, 3H), 4.49 (t, 2H), 5.22 (s, 2H), 7.13-7.26 (m, 3H), 7.37 (m, 2H), 7.57 (dd, 1H), 7.72 (m, 2H), 7.98 (d, 1H), 8.46 (s, 1H), 9.70 (bs, 1H); Mass spectrum MH+ 508.

[9] N-{2-[(4-{3-Chloro-4-(pyrazin-2-ylmethoxy)anilino}quinazolin-5-yl)oxy]ethyl}-2-hydroxy-N-methylacetamide. Prepared by reacting pyrazin-2-ylmethyl sulfonate with N-[2-({4-[(3-chloro-4-hydroxyphenyl)amino]quinazolin-5-yl}oxy)ethyl]-2-hydroxy-N-methylacetamide to give the title product in 60% yield; NMR spectrum (DMSO-d6 at 100° C.) 2.99 (s, 3H), 3.91 (t, 2H), 4.07 (bs, 3H), 4.49 (t, 2h), 5.37 (s, 2H), 7.17 (d, 1H), 7.29 (d, 1H), 7.36 (d, 1H), 7.60 (dd, 1H), 7.72 (t, 1H), 7.99 (d, 1H), 8.46 (s, 1H), 8.64 (m, 2H), 8.50 (s, 1H), 9.72 (bs, 1H); Mass spectrum MH+ 495.

[10] N-{(2R)-2-[(4-{3-Chloro-4-(pyridin-2-ylmethoxy)anilino}quinazolin-5-yl)oxy]propyl}acetamide. Prepared by reacting N-[(2R)-2-({4-[3-chloro-4-hydroxyanilino]quinazolin-5-yl}oxy)propyl]acetamide and picolyl chloride hydrochloride in 76% yield; NMR spectrum (DMSO-d6) 1.40 (d, 3H), 1.78 (s, 3H), 3.39 (m, 1H), 3.62 (m, 1H), 4.87 (m, 1H), 5.29 (s, 2H), 7.21-7.40 (m, 4H), 7.57 (m, 2H), 7.71 (t, 1H), 7.87 (m, 1H), 8.12 (d, 1H), 8.22 (t, 1H), 8.49 (s, 1H), 8.58 (d, 1H), 10.00 (bs, 1H); Mass spectrum MH+ 478.

The N-[(2R)-2-({4-[3-chloro-4-hydroxyanilino]quinazolin-5-yl}oxy)propyl]acetamide used as starting material was prepared by reacting 4-({5-[(1R)-2-amino-1-methylethoxy]quinazolin-4-yl}amino)-2-chlorophenol (prepared as described in Example 4-4) with acetic acid using an analogous procedure to that described in Example 3 for the preparation of 2-hydroxy-N-methyl-N-{2-[(4-{3-methyl-4-(pyridin-2-ylmethoxy)anilino}quinazolin-5-yl)oxy]ethyl}acetamide, to give N-[(2R)-2-({4-[3-chloro-4-hydroxyanilino]quinazolin-5-yl}oxy)propyl]acetamide in 28% yield; NMR spectrum (DMSO-d6) 1.40 (d, 3H), 1.78 (s, 1H), 3.40 (m, 1H), 3.62 (m, 1H), 4.87 (m, 1H), 6.99 (d, 1H), 7.23 (d, 1H), 7.31 (d, 1H), 7.41 (dd, 1H), 7.71 (t, 1H), 7.97 (d, 1H), 8.22 (t, 1H), 7.49 (s, 1H), 9.99 (s, 1H), 10.02 (s, 1H); Mass spectrum MH+ 387.

[11] N-{(2R)-2-[(4-{3-Chloro-4-(pyridin-2-ylmethoxy)amino}quinazolin-5-yl)oxy]propyl}-2-hydroxy-N-methylacetamide. Prepared by reacting N-[(2R)-2-({4-[3-chloro-4-hydroxyanilino]quinazolin-5-yl}oxy)propyl]-2-hydroxy-N-methylacetamide and picolyl chloride hydrochloride in 61% yield; NMR spectrum (DMSO-d6 at 100° C.) 1.44 (d, 3H), 2.99 (s, 3H), 3.51 (m, 1H), 4.07 (m, 2H), 4.13 (m, 1H), 5.12 (m, 1H), 5.28 (s, 2H), 7.23 (m, 2H), 7.34 (m, 1H), 7.60 (m, 2H), 7.70 (t, 1H), 7.85 (t, 1H), 8.08 (d, 1H), 8.47 (s, 1H), 8.58 (bd, 1H), 9.87 (bs, 1H); Mass spectrum MH+ 508.

The N-[(2R)-2-({4-[3-chloro-4-hydroxyanilino]quinazolin-5-yl}oxy)propyl]-2-hydroxy-N-methylacetamide used as a starting material was prepared as follows:

2-chloro-4-[(5-fluoroquinazolin-4-yl)amino]phenol (2 g) was added to a stirred solution of (2R)-1-[allyl(methyl)amino]propan-2-ol (2.24 g, prepared as described in Example 2-3) in DMA (100 ml) and sodium hydride (60% dispersion in oil, 692 mg), and the mixture heated to 110° C. for 16 hours. The mixture was concentrated in vacuo then a saturated solution of sodium bicarbonate (200 ml) was added and extracted with DCM (300 ml). The extract washed with brine, dried and concentrated in vacuo and the residue purified by chromatography using DCM—10% methanol/2N ammonia as eluent to give 4-[(5-{(1R)-2-[allyl(methyl)amino]-1-methylethoxy}quinazolin-4-yl)amino]-2-chlorophenol as a yellow solid (1.88 g, 68%); NMR spectrum (DMSO-d6) 1.43 (d, 3H), 2.17 (s, 3H), 2.54 (dd, 1H), 2.97 (m, 3H), 4.94 (m, 1H), 5.00 (dd, 1H), 5.10 (dd, 1H), 5.63 (m, 1H), 6.98 (d, 1H), 7.18 (d, 1H), 7.29 (d, 1H), 7.42 (dd, 1H), 7.69 (t, 1H), 7.84 (d, 1H), 8.44 (s, 1H), 10.01 (bs, 1H), 10.26 (s, 1H); Mass spectrum MH+ 399.

Chlorotris(triphenylphosphine)rhodium(I) (40 mg) was added to a solution of 4-[(5-{(1R)-2-[allyl(methyl)amino]-1-methylethoxy}quinazolin-4-yl)amino]-2-chlorophenol (841 mg) in acetonitrile/water (5:1, 4 ml), and the mixture heated to 130° C. for 10 minutes by microwave irradiation. The cooled mixture was subjected to ion exchange chromatography and product eluted with methanol/2M ammonia yielding 2-chloro-4-({5-[(1R)-1-methyl-2-(methylamino)ethoxy]quinazolin-4-yl}amino)phenol as a brown solid (776 mg, 100%); NMR spectrum (DMSO-d6) 1.40 (d, 3H), 2.33 (s, 3H), 2.87 (m, 2H), 3.29 (1H obscured by water), 4.88 (m, 1H), 6.97 (d, 1H), 7.14 (d, 1H), 7.28 (d, 1H), 7.55 (dd, 1H), 7.68 (t, 1H), 7.95 (d, 1H), 8.45 (s, 1H), 10.51 (bs, 1H); Mass spectrum MH+ 359.

The N-[(2R)-2-({4-[(3-chloro-4-hydroxyphenyl)amino]quinazolin-5-yl}oxy)propyl]-2-hydroxy-N-methylacetamide starting material was prepared by reacting 2-chloro-4-({5-[(1R)-1-methyl-2-(methylamino)ethoxy]quinazolin-4-yl}amino)phenol with and glycolic acid using an analogous procedure to that described in Example 3 for the preparation of 2-hydroxy-N-[2-({4-[4-hydroxy-3-methylanilino]quinazolin-5-yl}oxy)ethyl]-N-methylacetamide, to give N-[(2R)-2-({4-[3-chloro-4-hydroxyanilino]quinazolin-5-yl}oxy)propyl]-2-hydroxy-N-methylacetamide in 57% yield; NMR spectrum (DMSO-d6) 1.39 (d, 3H), 2.91 (m, 1H), 2.97 (s, 3H), 3.39 (dd, 1H), 4.04 (d, 2H), 4.16 (m, 1H), 4.39 (m, 1H), 5.08 (m, 1H), 6.98 (d, 1H), 7.27 (m, 2H), 7.47 (dd, 1H), 7.70 (t, 1H), 7.97 (d, 1H), 8.43 (s, 1H), 9.85 (s, 1H), 9.99 (bs, 1H); Mass spectrum MH+ 417.

[12] N-{(2R)-2-[(4-{3-Chloro-4-(pyrazin-2-ylmethoxy)anilino}quinazolin-5-yl)oxy]propyl}-2-hydroxy-N-methylacetamide. Prepared by reacting pyrazin-2-ylmethyl sulfonate and N-[(2R)-2-({4-[3-chloro-4-hydroxyanilino]quinazolin-5-yl}oxy)propyl]-2-hydroxy-N-methylacetamide to give the title product in 20% yield; NMR spectrum (DMSO-d6) 1.41 (d, 3H), 2.98 (s, 3H), 3.42 (dd, 1H), 4.06 (m, 2H), 4.23 (m, 1H), 4.41 (m, 1H), 5.12 (m, 1H), 5.39 (s, 2H), 7.25-7.38 (m, 3H), 7.72 (m, 2H), 8.15 (d, 1H), 8.48 (s, 1H), 8.68 (d, 2H), 8.87 (s, 1H), 9.96 (s, 1H); Mass spectrum MH+ 509.

[13] N-((2R)-2-{[4-(3-Chloro-4-[(6-methylpyridin-2-yl)methoxy]amino)quinazolin-5-yl]oxy}propyl)-2-hydroxy-N-methylacetamide. Prepared by reacting (6-methylpyridin-2-yl)methanol with N-[(2R)-2-({4-[3-chloro-4-hydroxyanilino]quinazolin-5-yl}oxy)propyl]-2-hydroxy-N-methylacetamide, using an analogous procedure to that described in Example 4-8 (in-situ formation of (6-methylpyridin-2-yl)methyl methanesulfonate), to give the title product in 48% yield; NMR spectrum (DMSO-d6) 1.40 (d, 3H), 2.50 (3H obscured by DMSO), 2.98 (s, 3H), 3.37 (dd, 1H), 4.06 (d, 1H), 4.22 (m, 1H), 4.41 (t, 1H), 5.10 (m, 1H), 5.26 (s, 2H), 7.20-7.30 (m, 3H), 7.33 (d, 1H), 7.37 (d, 1H), 7.67 (dd, 1H), 7.70-7.80 (m, 2H), 8.15 (d, 1H), 8.48 (s, 1H), 9.95 (s, 1H); Mass spectrum MH+ 522.

[14] N-((2R)-2-{[4-(3-Chloro-4-[(3-fluorobenzyl)oxy]anilino)quinazolin-5-yl]oxy}propyl)-2-hydroxy-N-methylacetamide. Prepared by reacting 1-(chloromethyl)-3-fluorobenzene and N-[(2R)-2-({4-[3-chloro-4-hydroxyanilino]quinazolin-5-yl}oxy)propyl]-2-hydroxy-N-methylacetamide to give the title product in 61% yield; NMR spectrum (DMSO-d6) 1.40 (d, 3H), 2.98 (s, 3H), 3.37 (dd, 1H), 4.06 (d, 2H), 4.22 (m, 1H), 4.41 (t, 1H), 5.11 (m, 1H), 5.28 (s, 2H), 7.19 (m, 1H), 7.22-7.38 (m, 5H), 7.47 (m, 1H), 7.68 (dd, 1H), 7.72 (t, 1H), 8.13 (d, 1H), 8.48 (s, 1H), 9.94 (s, 1H); Mass spectrum MH+ 525.

[15] N-{(2R)-2-[(4-{3-Chloro-4-(1,3-thiazol-4-ylmethoxy)anilino}quinazolin-5-yl)oxy]propyl}-2-hydroxy-N-methylacetamide. Prepared by reacting 4-(chloromethyl)-1,3-thiazole hydrochloride and N-[(2R)-2-({4-[3-chloro-4-hydroxyanilino]quinazolin-5-yl}oxy)propyl]-2-hydroxy-N-methylacetamide to give the title product in 61% yield; NMR spectrum (DMSO-d6) 1.41 (d, 3H), 2.98 (s, 3H), 3.38 (dd, 1H), 4.06 (d, 2H), 4.22 (m, 1H), 4.42 (t, 1H), 5.11 (m, 1H), 5.34 (s, 2H), 7.28 (d, 1H), 7.34 (m, 2H), 7.69 (dd, 1H), 7.73 (t, 1H), 7.82 (s, 1H), 8.12 (d, 1H), 8.48 (s, 1H), 9.18 (d, 1H), 9.95 (s, 1H); Mass spectrum MH+ 514.

[16] N-(2-{[4-(3-Chloro-4-[(6-methylpyridin-2-yl)methoxy]anilino)quinazolin-5-yl]oxy}ethyl)-N-methylacetamide. Prepared by reacting (6-methylpyridin-2-yl)methanol and N-[2-({4-[3-chloro-4-hydroxyanilino]quinazolin-5-yl}oxy)ethyl]-N-methylacetamide using the procedure described in Example 4-8 (in-situ formation of (6-methylpyridin-2-yl)methyl methanesulfonate), to give the title product in 67% yield; NMR spectrum (DMSO-d6) 1.94 (s, 3H), 3.06 (s, 3H), 3.27 (s, 3H), 3.84-3.96 (m, 2H), 4.35-4.45 (m, 2H), 5.24 (s, 2H), 7.16 (d, 1H), 7.20-7.27 (m, 2H), 7.32-7.40 (m, 2H), 7.58 (dd, 1H), 7.70-7.79 (m, 2H), 7.92 (d, 1H), 8.45 (s, 1H), 9.74 (s, 1H); Mass spectrum MH+ 492.

The N-[2-({4-[(3-chloro-4-hydroxyanilino]quinazolin-5-yl}oxy)ethyl]-N-methylacetamide used as starting material was prepared as follows:

Acetic acid was reacted with 2-chloro-4-({5-[2-(methylamino)ethoxy]quinazolin-4-yl}amino)phenol (prepared as described in Example 4-5, preparation of starting materials) using an analogous procedure to that described in Example 3 for the preparation of 2-hydroxy-N-[2-({4-[4-hydroxy-3-methylanilino]quinazolin-5-yl}oxy)ethyl]-N-methylacetamide, to give the title product in 56% yield; NMR spectrum (DMSO-d6) 1.96 (s, 3H), 2.48 (s, 3H), 3.84 (m, 2H), 4.36 (t, 2H), 6.96 (d, 1H), 7.14 (d, 1H), 7.32 (m, 2H), 7.70 (m, 2H), 8.40 (s, 1H), 9.62 (bs, 1H), 10.01 (bs, 1H); Mass spectrum MH+ 370.

[17] N-(2-{[4-(3-Chloro-4-[(2-fluorobenzyl)oxy]anilino)quinazolin-5-yl]oxy}ethyl)-N-methylacetamide. Prepared by reacting 2-fluorobenzyl chloride with N-[2-({4-[(3-chloro-4-hydroxyanilino]quinazolin-5-yl}oxy)ethyl]-N-methylacetamide, to give the title product in 71% yield; NMR spectrum (DMSO-d6) 1.94 (s, 3H), 3.05 (s, 3H), 3.89 (t, 2H), 4.40 (t, 2H), 5.27 (s, 2H), 7.17 (d, 1H), 7.22-7.39 (m, 4H), 7.41-7.48 (m, 1H), 7.56-7.65 (m, 2H), 7.73 (dd, 1H), 7.90 (d, 1H), 8.44 (s, 1H), 9.74 (s, 1H); Mass spectrum MH+ 495.

[18] N-(2-{[4-(3-Chloro-4-[(3-fluorobenzyl)oxy]anilino)quinazolin-5-yl]oxy}ethyl)-N-methylacetamide. Prepared by reacting 3-fluorobenzyl chloride and N-[2-({4-[3-chloro-4-hydroxyanilino]quinazolin-5-yl}oxy)ethyl]-N-to give the title product in 80% yield; NMR spectrum (DMSO-d6) 1.94 and 1.97 (each s, together 3H), 2.90 and 3.05 (each s, together 3H), 3.89 and 3.91 (each t, together 2H), 4.40 and 4.55 (each t, together 2H), 5.27 (s, 2H), 7.14-7.27 (m, 3H), 7.29-7.39 (m, 3H), 7.45-7.51 (m, 1H), 7.53-7.60 (m, 1H), 7.73 and 7.76 (each t, together 1H), 7.91 and 8.04 (each d, together 1H), 8.45 and 8.50 (each s, together 1 h), 9.73 and 9.77 (each s, together 1H); Mass spectrum MH+ 495.

[19] N-{2-[(4-{3-Chloro-4-(1,3-thiazol-4-ylmethoxy)anilino}quinazolin-5-yl)oxy]ethyl}-N-methylacetamide. Prepared by reacting 4-(chloromethyl)-1,3-thiazole and N-[2-({4-[3-chloro-4-hydroxyanilino]quinazolin-5-yl}oxy)ethyl]-N-methylacetamide to give the title product in 67% yield; NMR spectrum (DMSO-d6) 1.94 and 1.96 (each s, together 3H), 2.90 and 3.05 (each s, together 3H), 3.89 and 3.92 (each t, together 2H), 4.40 and 4.55 (each t, together 2H), 5.35 (s, 2H), 7.16 and 7.24 (each d, together 1H), 7.34 and 7.37 (each d, together 2H), 7.56 and 7.59 (each dd, together 1H), 7.73 and 7.76 (each t, together 1H), 7.83 (s, 1H), 7.90 and 8.02 (each d, together 1H), 8.44 and 8.50 (each s, together 1H), 9.16 (d, 1H), 9.73 and 9.76 (each s, together 1H); Mass spectrum MH+ 484.

[20] N-{2-[(4-{3-Chloro-4-(pyrazin-2-ylmethoxy)anilino}quinazolin-5-yl)oxy]ethyl}-N-methylacetamide. Prepared by reacting pyrazin-2-ylmethyl methanesulfonate (prepared as described in Example 4-1, preparation of starting materials) and N-[2-({4-[3-chloro-4-hydroxyanilino]quinazolin-5-yl}oxy)ethyl]-N-methylacetamide, to give the title product in 60% yield; NMR spectrum (DMSO-d6) 1.94 and 1.96 (each s, together 3H), 2.90 and 3.05 (each s, together 3H), 3.89 and 3.92 (each t, together 2H), 4.40 and 4.55 (each t, together 2H), 5.40 (s, 2H), 7.16 and 7.24 (each d, together 1H), 7.29-7.39 (m, 2H), 7.58 and 7.60 (each dd, together 1H), 7.73 and 7.76 (each t, together 1H), 7.93 and 8.05 (each d, together 1H), 8.44 and 8.51 (each s, together 1H), 8.68 (d, 1H), 8.69 (d, 1H), 8.87 (s, 1H), 9.74 and 9.77 (each s, together 1H); Mass spectrum MH+ 479.

[21] N-{(2R)-2-[(4-{3-Chloro-4-(pyridin-2-ylmethoxy)anilino}quinazolin-5-yl)oxy]propyl}-2-hydroxyacetamide. Prepared by reacting N-[(2R)-2-({4-[3-chloro-4-hydroxyanilino]quinazolin-5-yl}oxy)propyl]-2-hydroxyacetamide and picolyl chloride hydrochloride to give the title product in 61% yield; NMR spectrum (DMSO-d6) 1.39 (d, 3H), 3.45-3.47 (m, 1H), 3.70-3.83 (m, 3H), 4.86-4.99 (m, 1H), 5.29 (s, 2H), 5.48 (t, 1H), 7.20-7.27 (m, 2H), 7.28-7.39 (m, 2H), 7.54-7.64 (m, 2H), 7.71 (t, 1H), 7.87 (t, 1H), 8.11-8.21 (m, 2H), 8.48 (s, 1H), 8.59 (d, 1H), 9.98 (s, 1H) Mass spectrum MH+ 494.

The N-[(2R)-2-({4-[3-chloro-4-hydroxyanilino]quinazolin-5-yl}oxy)propyl]-2-hydroxyacetamide used as starting material was prepared as follows:

4-({5-[(1R)-2-amino-1-methylethoxy]quinazolin-4-yl}amino)-2-chlorophenol (prepared as described in Example 4-4, preparation of starting materials) was reacted with glycolic acid using an analogous procedure to that used in Example 1 for the preparation of N-{2-[(4-{3-Chloro-4-(pyridin-2-ylmethoxy)anilino}quinazolin-5-yl)oxy]ethyl}-N-methylacetamide, to give the title product in 61% yield; NMR spectrum (DMSO-d6) 1.39 (d, 3H), 3.70-3.80 (m, 3H), 4.90-4.97 (m, 1H), 7.0 (d, 1H), 7.26-7.31 (m, 2H), 7.41 (dd, 1H), 7.75 (t, 1H), 7.92 (d, 1H), 8.16 (t, 1H), 8.53 (s, 1H), 10.09 (s, 1H), 10.15 (s, 1H) Mass spectrum MH+ 403.

EXAMPLE 5

N-{2-[(4-{[3-Chloro-4-(pyridin-2-ylmethoxy)phenyl]amino}quinazolin-5-yl)oxy]ethyl}-N-ethylacetamide

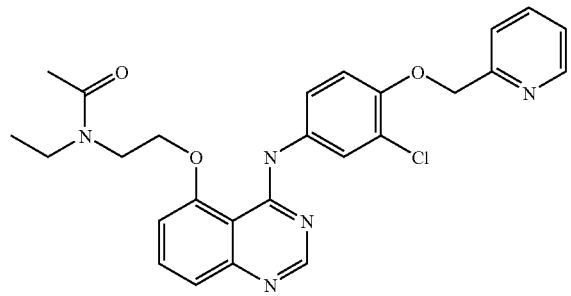

N-[3-Chloro-4-(pyridin-2-ylmethoxy)phenyl]-5-[2-(ethylamino)ethoxy]quinazolin-4-amine (58 mg) in DCM (3 ml) was treated with acetyl chloride (15 mg) and DIPEA (39 mg) and stirred overnight. The solution was purified by chromatography using DCM to 10% 7N ammonia in methanol in DCM to give after trituration with diethyl ether N-{2-[(4-{[3-chloro-4-(pyridin-2-ylmethoxy)phenyl]amino}quinazolin-5-yl)oxy]ethyl}-N-ethylacetamide (39 mg, 61%); NMR spectrum (DMSO-d6) 1.12 (t, 3H), 1.98 (s, 3H), 3.37-3.42 (m, 2H), 3.87 (t, 2H), 4.39 (t, 2H), 5.31 (s, 2H), 7.16 (d, 1H), 7.22-7.28 (m, 1H), 7.33-7.39 (m, 2H), 7.55-7.61

(m, 2H), 7.71-7.75 (m, 1H), 7.87-7.91 (m, 1H), 7.94 (d, 1H), 8.45 (s, 1H), 8.61 (d, 1H), 9.80 (s, 1H); Mass spectrum MH+ 492.

The N-[3-chloro-4-(pyridin-2-ylmethoxy)phenyl]-5-[2-(ethylamino)ethoxy]quinazolin-4-amine used as starting material was prepared as follows:

Ethylene glycol (150 ml) was treated with sodium hydride (60% in oil, 3.15 g) and the exotherm controlled to about 10° C. with an ice-bath. N-[3-Chloro-4-(pyridin-2-ylmethoxy) phenyl]-5-fluoroquinazolin-4-amine (obtained as described in Example 1, preparation of starting materials, 12 g) was added in small portions and the mixture heated at 120° C. for 1 hour. The slurry was cooled, poured into water/saturated ammonium chloride (1.5 litres) and the solid collected and dried to give 2-[(4-{[3-chloro-4-(pyridin-2-ylmethoxy)phenyl]amino}quinazolin-5-yl)oxy]ethanol (12.6 g, 95%); NMR spectrum (DMSO-d6) 3.89-3.98 (m, 2H), 4.33 (t, 2H), 5.27 (s, 2H), 5.37 (t, 1H), 7.13 (d, 1H), 7.23 (d, 1H), 7.31-7.38 (m, 2H), 7.57 (d, 1H), 7.68-7.75 (m, 2H), 7.83-7.90 (m, 1H), 8.26 (d, 1H), 8.54 (s, 1H), 8.58 (d, 1H), 10.41 (s, 11H); Mass spectrum MH+ 422.

To a stirred solution of the 2-[(4-{[3-chloro-4-(pyridin-2-ylmethoxy)phenyl]amino}quinazolin-5-yl)oxy]ethanol (20 g) in DCM (200 ml) and THF (200 ml) was added thionyl chloride (20 ml) at ambient temperature. The solution was then heated under reflux for 2 hours. The solution was cooled and product filtered off to give 5-(2-chloroethoxy)-N-[3-chloro-4-(pyridin-2-ylmethoxy)phenyl]quinazolin-4-amine as its hydrochloride salt (25 g, 98%); NMR spectrum (DMSO-d6) 4.20-4.40 (t, 2H), 4.60-4.80 (t, 2H), 5.40 (s, 2H), 7.20-7.60 (m, 3H), 7.60-7.80 (m, 3H), 7.90-8.10 (m, 3H), 8.60-8.70 (d, 1H), 8.9 (s, 1H), 10.65-10.83 (bs, 1H); Mass spectrum MH+ 441.

5-(2-Chloroethoxy)-N-[3-chloro-4-(pyridin-2-ylmethoxy)phenyl]quinazolin-4-amine (0.400 g) and ethylamine (1.2 g) were heated at 50° C. overnight and then the solution purified by chromatography using DCM to 10% 7N ammonia in methanol in DCM to give N-[3-chloro-4-(pyridin-2-ylmethoxy)phenyl]-5-[2-(ethylamino)ethoxy] quinazolin-4-amine; Mass spectrum MH+ 450.

EXAMPLE 6

N-{2-[(4-{[3-Chloro-4-(pyridin-2-ylmethoxy)phenyl]amino}quinazolin-5-yl)oxy]ethyl}-N-ethyl-2-hydroxyacetamide

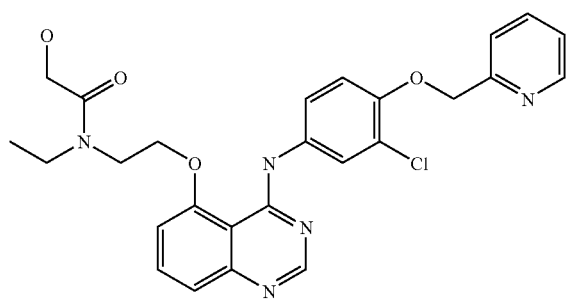

The procedure described in Example 1 was repeated using glycolic acid and N-[3-chloro-4-(pyridin-2-ylmethoxy)phenyl]-5-[2-(ethylamino)ethoxy]quinazolin-4-amine (obtained as described in Example 5, preparation of starting materials) to give the title compound in 70% yield; NMR spectrum (DMSO-d6) 1.10 (t, 3H), 3.29-3.45 (m, 2H), 3.80-3.95 (m, 2H), 4.10 (s, 2H), 4.30-4.55 (m, 2H), 4.42 (t, 1H), 5.30 (s, 2H), 7.18 (d, 1H), 7.22 (d, 1H), 7.30-7.40 (m, 2H), 7.60 (d, 2H), 7.70-7.78 (m, 1H), 7.82-7.92 (m, 1H), 7.95 (s, 1H), 8.43 (s, 1H), 8.60 (d, 1H), 9.80 (s, 1H); Mass spectrum MH+ 508.

EXAMPLE 7

N-{2-[(4-{[3-Chloro-4-(pyridin-2-ylmethoxy)phenyl]amino}quinazolin-5-yl)oxy]ethyl}-N-propylacetamide

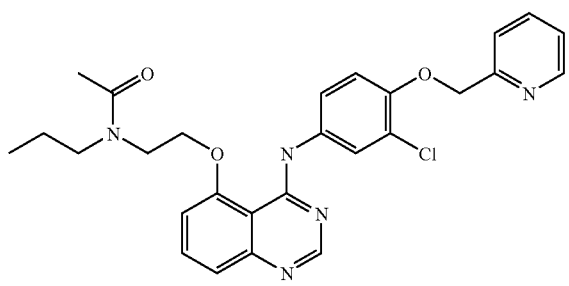

The procedure described in Example 5 was repeated using N-[3-chloro-4-(pyridin-2-ylmethoxy)phenyl]-5-[2-(propylamino)ethoxy]quinazolin-4-amine and acetyl chloride to give the title compound in 70% yield; NMR spectrum (DMSO-d6) 0.82 (t, 3H), 1.53-1.59 (m, 2H), 1.97 (s, 3H), 3.27 (s, 2H), 3.86 (t, 2H), 4.39 (t, 2H), 5.31 (s, 2H), 7.17 (d, 1H), 7.25 (d, 1H), 7.33-7.39 (m, 2H), 7.58-7.60 (m, 2H), 7.71-7.75 (m, 1H), 7.87-7.91 (m, 1H), 7.95 (d, 1H), 8.45 (s, 1H), 8.60 (d, 1H), 9.80 (s, 1H); Mass spectrum MH+ 506.

The N-[3-chloro-4-(pyridin-2-ylmethoxy)phenyl]-5-[2-(propylamino)ethoxy]quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and propylamine; Mass spectrum MH+ 464.

EXAMPLE 8

N-{2-[(4-{[3-Chloro-4-(pyridin-2-ylmethoxy)phenyl]amino}quinazolin-5-yl)oxy]ethyl}-2-hydroxy-N-propylacetamide

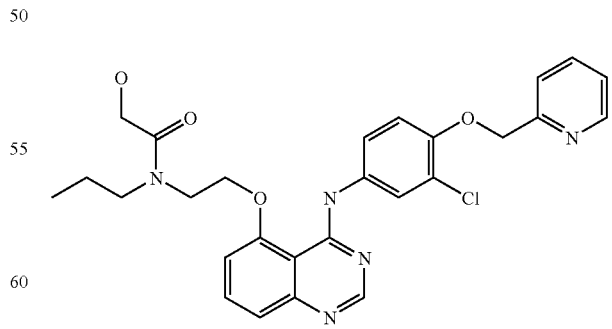

The procedure described in Example 1 was repeated using glycolic acid and N-[3-chloro-4-(pyridin-2-ylmethoxy)phenyl]-5-[2-(propylamino)ethoxy]quinazolin-4-amine (obtained as described in Example 7, preparation of starting materials) to give the title compound in 26% yield; NMR spectrum (DMSO-d6) 0.84 (t, 3H), 1.53-1.65 (m, 2H), 3.26 (t, 2H), 3.95 (t, 2H), 4.14 (d, 2H), 4.38 (t, 1H), 4.47 (t, 2H), 4.53-4.58 (m, 1H), 5.36 (s, 1H), 7.24 (d, 1H), 7.31 (d, 1H), 7.39-7.44 (m, 2H), 7.63-7.67 (m, 2H), 7.76-7.81 (m, 1H), 7.92-7.96 (m, 1H), 8.05 (s, 1H), 8.51 (s, 1H), 8.66 (d, 1H), 9.87 (s, 1H); Mass spectrum MH+ 522.

EXAMPLE 9

N-{2-[(4-{[3-Chloro-4-(pyridin-2-ylmethoxy)phenyl]amino}quinazolin-5-yl)oxy]ethyl}-N-isopropylacetamide

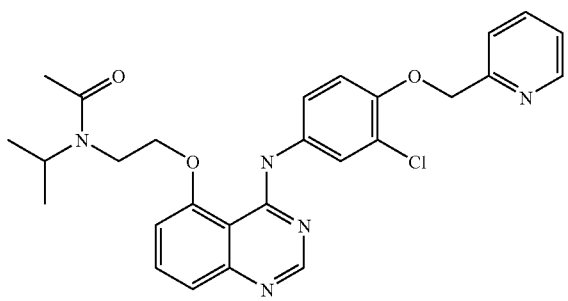

The procedure described in Example 5 was repeated using N-[3-chloro-4-(pyridin-2-ylmethoxy)phenyl]-5-[2-(isopropylamino)ethoxy]quinazolin-4-amine and acetyl chloride to give the title compound in 49% yield; NMR spectrum (DMSO-d6) 1.19 (d, 6H), 2.07 (s, 3H), 3.77 (t, 2H), 4.06-4.14 (m, 1H), 4.34 (t, 2H), 5.31 (s, 2H), 7.21 (d, 1H), 7.27 (d, 1H), 7.32-7.39 (m, 2H), 7.57-7.63 (m, 2H), 7.69-7.75 (m, 1H), 7.86-7.91 (m, 1H), 8.01 (d, 1H), 8.46 (s, 1H), 8.60 (d, 1H), 10.00 (s, 1H); Mass spectrum MH+ 506.

The N-[3-chloro-4-(pyridin-2-ylmethoxy)phenyl]-5-[2-(isopropylamino) ethoxy]quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and isopropylamine; Mass spectrum MH+ 464.

EXAMPLE 10

N-{2-[(4-{[3-Chloro-4-(pyridin-2-ylmethoxy)phenyl]amino}quinazolin-5-yl)oxy]ethyl}-2-hydroxy-N-isopropylacetamide

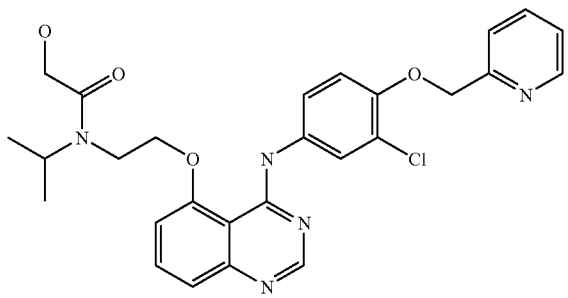

The procedure described in Example 1 was repeated using glycolic acid and N-[3-chloro-4-(pyridin-2-ylmethoxy)phenyl]-5-[2-(isopropylamino)ethoxy]quinazolin-4-amine (obtained as described in Example 9, preparation of starting materials) to give the title compound in 11% yield; NMR spectrum (DMSO-d6) 1.19 (d, 6H), 3.81 (t, 2H), 3.93-4.01 (m, 1H), 4.14-4.18 (m, 2H), 4.35-4.47 (m, 3H), 5.31 (s, 2H), 7.21-7.29 (m, 2H), 7.32-7.40 (m, 2H), 7.56-7.63 (m, 2H), 7.70-7.76 (m, 1H), 7.86-7.91 (m, 1H), 8.04 (s, 1H), 8.47 (s, 1H), 8.60 (d, 1H), 10.02 (s, 1H); Mass spectrum MH+ 522.

EXAMPLE 11

N-Allyl-N-{2-[(4-{[3-chloro-4-(pyridin-2-ylmethoxy)phenyl]amino}quinazolin-5-yl)oxy]ethyl}acetamide

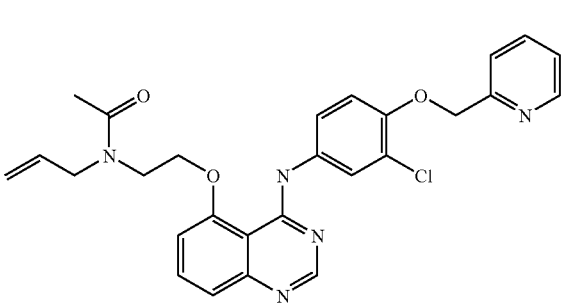

The procedure described in Example 5 was repeated using 5-[2-(allylamino)ethoxy]-N-[3-chloro-4-(pyridin-2-ylmethoxy)phenyl]quinazolin-4-amine and acetyl chloride to give the title compound in 47% yield; NMR spectrum (DMSO-d6) 1.95 (s, 3H), 3.86 (t, 2H), 4.02-4.06 (m, 2H), 4.38 (t, 2H), 5.07-5.18 (m, 2H), 5.31 (s, 2H), 5.82-5.92 (m, 1H), 7.14 (d, 1H), 7.25 (d, 1H), 7.32-7.40 (m, 2H), 7.55-7.61 (m, 2H), 7.70-7.75 (m, 1H), 7.86-7.93 (m, 2H), 8.44 (s, 1H), 8.61 (d, 1H), 9.76 (s, 1H); Mass spectrum MH+ 504.

The 5-[2-(allylamino)ethoxy]-N-[3-chloro-4-(pyridin-2-ylmethoxy)phenyl]quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and allylamine; Mass spectrum MH+ 462.

EXAMPLE 12

N-Allyl-N-{2-[(4-{[3-chloro-4-(pyridin-2-ylmethoxy)phenyl]amino}quinazolin-5-yl)oxy]ethyl}-2-hydroxyacetamide

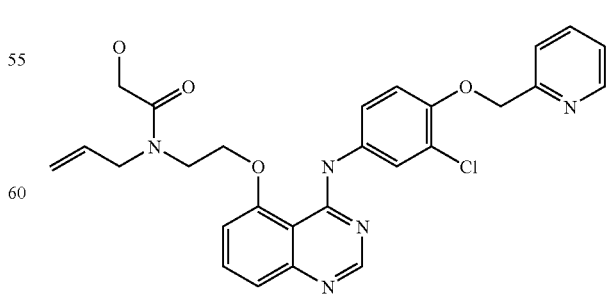

The procedure described in Example 1 was repeated using glycolic acid and 5-[2-(allylamino)ethoxy]-N-[3-chloro-4-

(pyridin-2-ylmethoxy)phenyl]quinazolin-4-amine (obtained as described in Example 11, preparation of starting materials) to give the title compound in 24% yield; NMR spectrum (DMSO-d6) 3.79-4.19 (m, 6H), 4.38-4.63 (m, 3H), 5.06-5.19 (m, 2H), 5.31 (s, 2H), 5.69-5.90 (m, 1H), 7.16 (d, 1H), 7.25 (d, 1H), 7.33-7.39 (m, 2H), 7.56-7.63 (m, 2H), 7.70-7.76 (m, 1H), 7.86-7.91 (m, 1H), 7.98 (s, 1H), 8.45 (s, 1H), 8.61 (d, 1H), 9.80 (s, 1H); Mass spectrum MH+ 520.

EXAMPLE 13

N-{2-[(4-{[3-Chloro-4-(pyridin-2-ylmethoxy)phenyl]amino}quinazolin-5-yl)oxy]ethyl}-N-cyclopropylacetamide

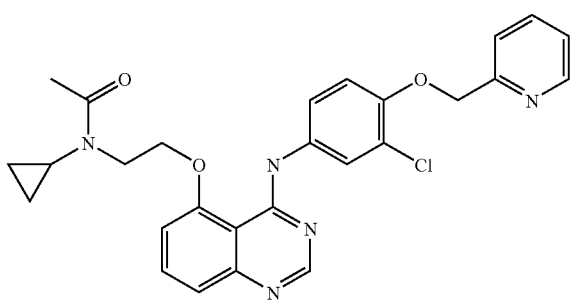

The procedure described in Example 5 was repeated using N-[3-chloro-4-(pyridin-2-ylmethoxy)phenyl]-5-[2-(cyclopropylamino)ethoxy]quinazolin-4-amine and acetyl chloride to give the title compound in 38% yield; NMR spectrum (DMSO-d6) 0.76-0.82 (m, 4H), 2.06 (s, 3H), 2.76-2.83 (m, 1H), 3.87 (t, 2H), 4.42 (t, 2H), 5.31 (s, 2H), 7.19 (d, 1H), 7.26 (d, 1H), 7.32-7.40 (m, 2H), 7.56-7.61 (m, 2H), 7.70-7.75 (m, 1H), 7.86-7.92 (m, 1H), 7.94-7.96 (m, 1H), 8.45 (s, 1H), 8.60 (d, 1H), 9.76 (s, 1H); Mass spectrum MH+ 504.

The N-[3-chloro-4-(pyridin-2-ylmethoxy)phenyl]-5-[2-(cyclopropylamino) ethoxy]quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and cyclopropanamine; Mass spectrum MH+ 462.

EXAMPLE 14

N-{2-[(4-{[3-Chloro-4-(pyridin-2-ylmethoxy)phenyl]amino}quinazolin-5-yl)oxy]ethyl}-N-cyclopropyl-2-hydroxyacetamide

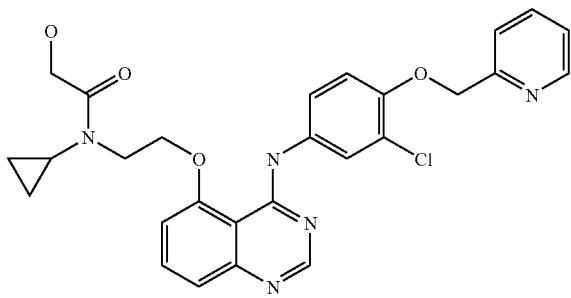

The procedure described in Example 1 was repeated using glycolic acid and N-[3-chloro-4-(pyridin-2-ylmethoxy)phenyl]-5-[2-(cyclopropylamino)ethoxy]quinazolin-4-amine (obtained as described in Example 13, preparation of starting materials) to give the title compound in 19% yield; NMR spectrum (DMSO-d6) 0.73-0.80 (m, 4H), 2.73-2.80 (m, 1H), 3.90 (t, 2H), 4.24 (s, 3H), 4.44 (t, 2H), 5.31 (s, 2H), 7.20 (d, 1H), 7.25 (d, 1H), 7.35 (d, 1H), 7.36-7.40 (m, 1H), 7.57-7.62 (m, 2H), 7.71-7.76 (m, 1H), 7.86-7.92 (m, 1H), 8.01 (d, 1H), 8.46 (s, 1H), 8.61 (d, 1H), 9.80 (s, 1H); Mass spectrum MH+ 520.

EXAMPLE 15

N-{2-[(4-{[3-Chloro-4-(pyridin-2-ylmethoxy)phenyl]amino}quinazolin-5-yl)oxy]ethyl}-N-(cyclopropylmethyl)acetamide

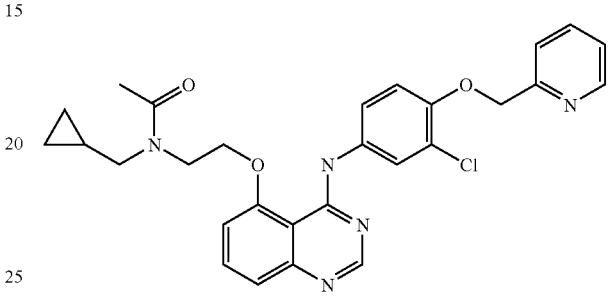

The procedure described in Example 5 was repeated using N-[3-chloro-4-(pyridin-2-ylmethoxy)phenyl]-5-{2-[(cyclopropylmethyl)amino]ethoxy}quinazolin-4-amine and acetyl chloride to give the title compound in 58% yield; NMR spectrum (DMSO-d6) 0.16-0.27 (m, 2H), 0.36-0.52 (m, 2H), 0.97-1.06 (m, 1H), 2.00 (s, 3H), 3.24-3.29 (m, 2H), 3.93-4.02 (m, 2H), 4.33-4.56 (m, 2H), 5.31 (s, 2H), 7.13-7.18 (m, 1H), 7.21-7.29 (m, 1H), 7.31-7.40 (m, 2H), 7.54-7.62 (m, 2H), 7.69-7.79 (m, 1H), 7.86-7.92 (m, 1H), 7.93-7.96 (m, 1H), 8.44 (s, 1H), 8.61 (d, 1H), 9.81 (s, 1H); Mass spectrum MH+ 518.

The N-[3-chloro-4-(pyridin-2-ylmethoxy)phenyl]-5-{2-[(cyclopropylmethyl)amino]ethoxy}quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and (cyclopropylmethyl)amine; Mass spectrum MH+ 476.

EXAMPLE 16

N-{2-[(4-{[3-Chloro-4-(pyridin-2-ylmethoxy)phenyl]amino}quinazolin-5-yl)oxy]ethyl}-N-(cyclopropylmethyl)-2-hydroxyacetamide

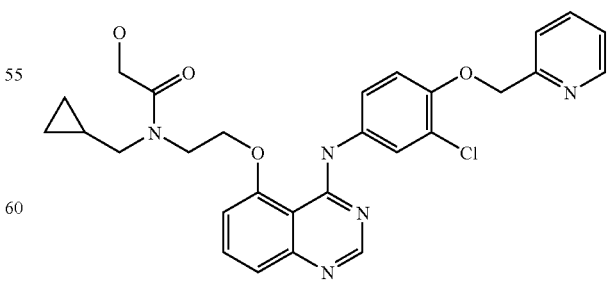

The procedure described in Example 1 was repeated using glycolic acid and N-[3-chloro-4-(pyridin-2-ylmethoxy)phenyl]-5-{2-[(cyclopropylmethyl)amino]ethoxy}quinazolin- 4-amine (obtained as described in Example 15, preparation of starting materials) to give the title compound in 23% yield; NMR spectrum (DMSO-d6)-0.04-0.04 (m, 2H), 0.13-0.29 (m, 2H), 0.74-0.83 (m, 1H), 2.98 (d, 1H), 3.66-3.80 (m, 2H), 3.85-3.93 (m, 2H), 4.12-4.32 (m, 4H), 5.08 (s, 2H), 6.95 (d, 1H), 7.02 (d, 1H), 7.09-7.17 (m, 2H), 7.30-7.40 (m, 2H), 7.47-7.54 (m, 1H), 7.63-7.68 (m, 1H), 7.73-7.82 (m, 1H), 8.21-8.29 (m, 1H), 8.37 (d, 1H), 9.62 (s, 1H); Mass spectrum MH$^+$ 534.

EXAMPLE 17

N-{2-[(4-{[3-Chloro-4-(pyridin-2-ylmethoxy)phenyl]amino}quinazolin-5-yl)oxy]ethyl}-N-cyclobutylacetamide

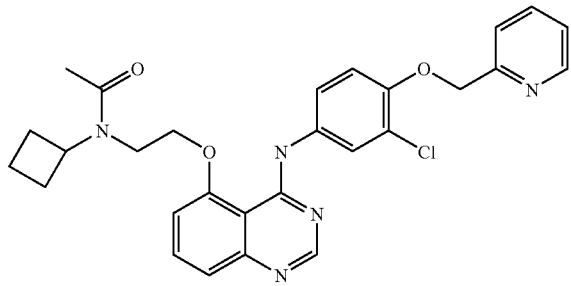

The procedure described in Example 5 was repeated using N-[3-chloro-4-(pyridin-2-ylmethoxy)phenyl]-5-[2-(cyclobutylamino)ethoxy]quinazolin-4-amine and acetyl chloride to give the title compound in 42% yield; NMR spectrum (DMSO-d6) 1.50-1.65 (m, 2H), 2.01 s, 3H), 2.12-2.21 (m, 4H), 3.94 (t, 2H), 4.28-4.38 (m, 3H), 5.31 (s, 2H), 7.19 (d, 1H), 7.26 (d, 1H), 7.32-7.40 (m, 2H), 7.57-7.62 (m, 2H), 7.69-7.76 (m, 1H), 7.86-7.91 (m, 1H), 7.97 (s, 1H), 8.45 (s, 1H), 8.60 (d, 1H), 9.90 (s, 1H); Mass spectrum MH$^+$ 518.

The N-[3-chloro-4-(pyridin-2-ylmethoxy)phenyl]-5-[2-(cyclobutylamino) ethoxy]quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and cyclobutanamine; Mass spectrum MH$^+$ 476.

EXAMPLE 18

N-{2-[(4-{[3-Chloro-4-(pyridin-2-ylmethoxy)phenyl]amino}quinazolin-5-yl)oxy]ethyl}-N-cyclobutyl-2-hydroxyacetamide

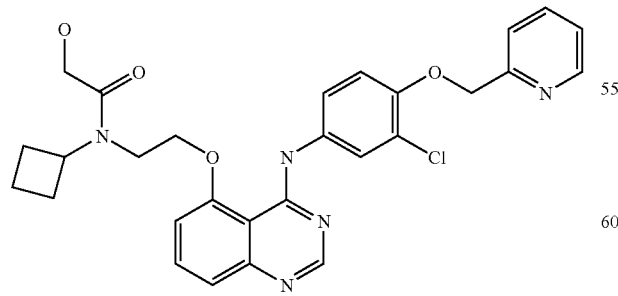

The procedure described in Example 1 was repeated using glycolic acid and N-[3-chloro-4-(pyridin-2-ylmethoxy)phenyl]-5-[2-(cyclobutylamino)ethoxy]quinazolin-4-amine (obtained as described in Example 17, preparation of starting materials) to give the title compound in 22% yield; NMR spectrum (DMSO-d6) 1.49-1.65 (m, 2H), 2.08-2.27 (m, 4H), 3.97 (s, 2H), 4.12 (d, 2H), 4.20-4.29 (m, 1H), 4.32-4.43 (m, 3H), 5.31 (s, 2H), 7.21 (d, 1H), 7.26 (d, 1H), 7.33-7.40 (m, 2H), 7.57-7.63 (m, 2H), 7.71-7.76 (m, 1H), 7.86-7.92 (m, 1H), 8.02 (s, 1H), 8.47 (s, 1H), 8.60 (d, 1H), 9.92 (s, 1H); Mass spectrum MH$^+$ 534.

EXAMPLE 19

N-{2-[(4-{[3-Chloro-4-(pyridin-2-ylmethoxy)phenyl]amino}quinazolin-5-yl)oxy]ethyl}-N-(1-methylpiperidin-4-yl)acetamide

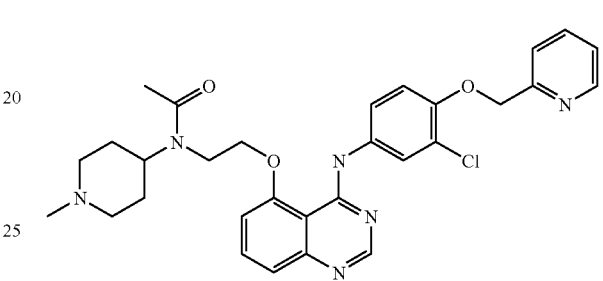

The procedure described in Example 5 was repeated using N-[3-chloro-4-(pyridin-2-ylmethoxy)phenyl]-5-{2-[(1-methylpiperidin-4-yl)amino]ethoxy}quinazolin-4-amine and acetyl chloride to give the title compound in 41% yield; NMR spectrum (DMSO-d6) 1.62-1.90 (m, 4H), 2.09 (s, 3H), 2.15-2.43 (m, 4H), 2.79-3.13 (m, 3H), 3.76-3.83 (m, 2H), 3.86-3.92 (m, 1H), 4.30-4.47 (m, 2H), 5.31 (s, 2H), 7.21 (d, 1H), 7.26 (d, 1H), 7.32-7.40 (m, 2H), 7.57-7.61 (m, 2H), 7.69-7.75 (m, 1H), 7.86-7.92 (m, 1H), 7.98-8.00 (m, 1H), 8.46 (s, 1H), 8.61 (d, 1H), 9.95 (s, 1H); Mass spectrum MH$^+$ 561.

The N-[3-chloro-4-(pyridin-2-ylmethoxy)phenyl]-5-{2-[(1-methylpiperidin-4-yl)amino]ethoxy}quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and 1-methylpiperidin-4-amine; Mass spectrum MH$^+$ 519.

EXAMPLE 20

N-{2-[(4-{[3-Chloro-4-(pyridin-2-ylmethoxy)phenyl]amino}quinazol-5-yl)oxy]ethyl}-N-(tetrahydro-2H-pyran-4-yl)acetamide

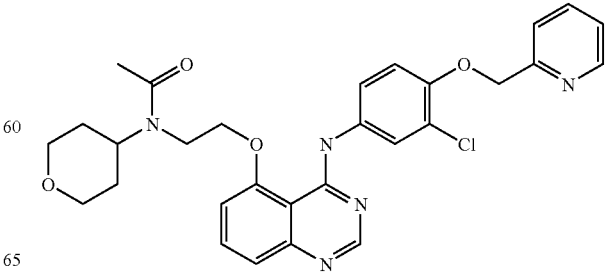

The procedure described in Example 5 was repeated using N-[3-chloro-4-(pyridin-2-ylmethoxy)phenyl]-5-[2-(tetrahydro-2H-pyran-4-ylamino)ethoxy]quinazolin-4-amine and acetyl chloride to give the title compound in 68% yield; NMR spectrum (DMSO-d6) 1.49-1.71 (m, 2H), 1.75-1.98 (m, 2H), 2.11 (s, 3H), 3.36-3.45 (m, 2H), 3.78-3.96 (m, 5H), 4.26-4.46 (m, 2H), 5.31 (s, 2H), 7.22 (d, 1H), 7.26 (d, 1H), 7.33 (d, 1H), 7.35-7.40 (m, 1H), 7.56-7.63 (m, 2H), 7.69-7.75 (m, 1H), 7.86-7.91 (m, 1H), 7.99-8.03 (m, 1H), 8.46 (s, 1H), 8.61 (d, 1H), 9.98 (s, 1H); Mass spectrum MH+ 548.

The N-[3-chloro-4-(pyridin-2-ylmethoxy)phenyl]-5-[2-(tetrahydro-2H-pyran-4-ylamino)ethoxy]quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and tetrahydro-2H-pyran-4-amine; Mass spectrum MH+ 506.

EXAMPLE 21

N-{2-[(4-{[3-Chloro-4-(pyridin-2-ylmethoxy)phenyl]amino}quinazolin-5-yl)oxy]ethyl}-2-hydroxy-N-(tetrahydro-2H-pyran-4-yl)acetamide

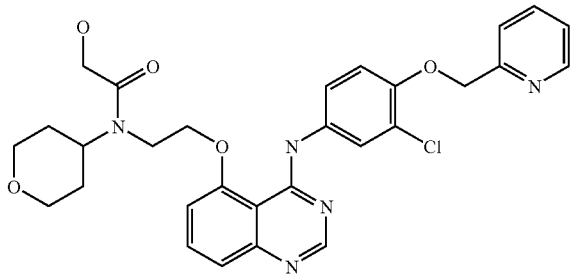

The procedure described in Example 1 was repeated using glycolic acid and N-[3-chloro-4-(pyridin-2-ylmethoxy)phenyl]-5-[2-(tetrahydro-2H-pyran-4-ylamino)ethoxy]quinazolin-4-amine (obtained as described in Example 20, preparation of starting materials) to give the title compound in 12% yield; NMR spectrum (DMSO-d6) 1.53-1.69 (m, 2H), 1.77-2.07 (m, 2H), 3.34-3.42 (m, 2H), 3.73-3.92 (m, 5H), 4.14-4.25 (m, 2H), 4.31-4.54 (m, 3H), 5.31 (s, 2H), 7.21-7.29 (m, 2H), 7.32-7.40 (m, 2H), 7.57-7.63 (m, 2H), 7.70-7.76 (m, 1H), 7.86-7.91 (m, 1H), 8.03 (s, 1H), 8.47 (s, 1H), 8.61 (d, 1H), 9.99 (s, 1H); Mass spectrum MH+ 564.

EXAMPLE 22

N-{2-[(4-{[3-Chloro-4-(pyridin-2-ylmethoxy)phenyl]amino}quinazolin-5-yl)oxy]ethyl}-N-(2-hydroxyethyl)acetamide

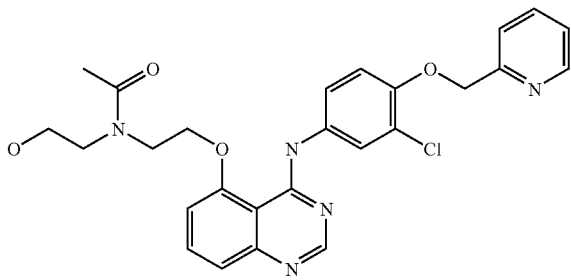

The procedure described in Example 5 was repeated using 2-({2-[(4-{[3-chloro-4-(pyridin-2-ylmethoxy)phenyl]amino}quinazolin-5-yl)oxy]ethyl}amino)ethanol and acetyl chloride to give the title compound in 21% yield; NMR spectrum (DMSO-d6) 2.00 (s, 3H), 3.43 (t, 2H), 3.54-3.59 (m, 2H), 3.88-3.97 (m, 2H), 4.41 (t, 2H), 4.85 (t, 1H), 5.31 (s, 2H), 7.16 (d, 1H), 7.25 (d, 1H), 7.33 (d, 1H), 7.35-7.40 (m, 1H), 7.57-7.62 (m, 2H), 7.70-7.75 (m, 1H), 7.86-7.92 (m, 1H), 7.96 (d, 1H), 8.45 (s, 1H), 8.61 (d, 1H), 9.83 (s, 1H); Mass spectrum MH+ 508.

The 2-({2-[(4-{[3-chloro-4-(pyridin-2-ylmethoxy)phenyl]amino}quinazolin-5-yl)oxy]ethyl}amino)ethanol used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and 2-aminoethanol; Mass spectrum MH+ 466.

EXAMPLE 23

N-{2-[(4-{[3-Chloro-4-(pyridin-2-ylmethoxy)phenyl]amino}quinazolin-5-yl)oxy]ethyl}-2-hydroxy-N-(2-hydroxyethyl)acetamide

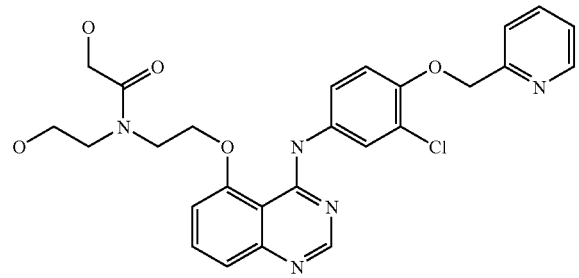

2-({2-[(4-{[3-Chloro-4-(pyridin-2-ylmethoxy)phenyl]amino}quinazolin-5-yl)oxy]ethyl}amino)ethanol (obtained as described in Example 22, preparation of starting materials) (0.208 g) in DCM (10 ml) was treated with 2-chloro-2-oxoethyl acetate (0.091 g) and DIPEA (0.173 g) and stirred for 30 minutes. 7N Ammonia in methanol (20 ml) was added and the solution stirred overnight. The mixture was evaporated and purified by chromatography using DCM to 8% 7N ammonia in methanol in DCM to give the title compound in 30% yield; NMR spectrum (DMSO-d6) 3.37 (t, 2H), 3.56 (t, 2H), 3.95 (t, 2H), 4.11-4.17 (m, 2H), 4.25 (t, 1H), 4.44 (t, 2H), 4.91 (t, 1H), 5.31 (s, 2H), 7.17 (d, 1H), 7.25 (d, 1H), 7.32-7.40 (m, 2H), 7.59 (d, 2H), 7.70-7.76 (m, 1H), 7.86-7.91 (m, 1H), 8.00 (d, 1H), 8.46 (s, 1H), 8.61 (d, 1H), 9.85 (s, 1H); Mass spectrum MH+ 524.

EXAMPLE 24

N-{2-[(4-{[3-Chloro-4-(pyridin-2-ylmethoxy)phenyl]amino}quinazolin-5-yl)oxy]ethyl}-N-(2-methoxyethyl)acetamide

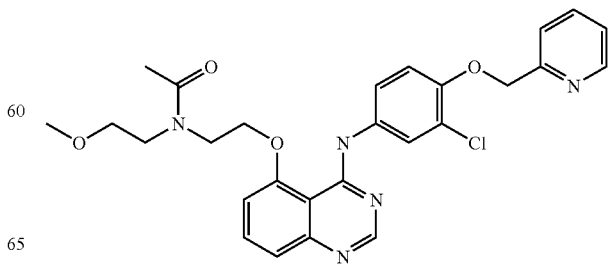

The procedure described in Example 5 was repeated using N-[3-chloro-4-(pyridin-2-ylmethoxy)phenyl]-5-{2-[(2-methoxyethyl)amino]ethoxy}quinazolin-4-amine and acetyl chloride to give the title compound in 30% yield; NMR spectrum (DMSO-d6) 1.99 (s, 3H), 3.24 (s, 3H), 3.46-3.51 (m, 2H), 3.52-3.57 (m, 2H), 3.88-3.98 (m, 2H), 4.37-4.43 (m, 2H), 5.31 (s, 2H), 7.17 (d, 1H), 7.26 (d, 1H), 7.34 (d, 1H), 7.35-7.40 (m, 1H), 7.55-7.63 (m, 2H), 7.71-7.78 (m, 1H), 7.86-7.92 (m, 1H), 7.94 (d, 1H), 8.46 (s, 1H), 8.61 (d, 1H), 9.86 (s, 1H); Mass spectrum MH+ 522.

The N-[3-chloro-4-(pyridin-2-ylmethoxy)phenyl]-5-{2-[(2-methoxyethyl)amino]ethoxy}quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and (2-methoxyethyl)amine; Mass spectrum MH+ 480.

EXAMPLE 25

N-{2-[(4-{[3-Chloro-4-(pyridin-2-ylmethoxy)phenyl]amino}quinazolin-5-yl)oxy]ethyl}-2-hydroxy-N-(2-methoxyethyl)acetamide

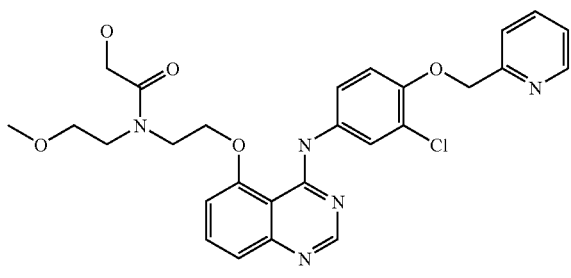

The procedure described in Example 1 was repeated using glycolic acid and N-[3-chloro-4-(pyridin-2-ylmethoxy)phenyl]-5-{2-[(2-methoxyethyl)amino]ethoxy}quinazolin-4-amine (obtained as described in Example 24, preparation of starting materials) to give the title compound in 27% yield; NMR spectrum (DMSO-d6) 3.18 (s, 1H), 3.24 (s, 2H), 3.48 (s, 3H), 3.55-3.60 (m, 1H), 3.86-3.98 (m, 2H), 4.10-4.15 (m, 2H), 4.32 (t, 1H), 4.43 (t, 1H), 4.51-4.57 (m, 1H), 5.31 (s, 2H), 7.17 (d, 1H), 7.25 (d, 1H), 7.33-7.40 (m, 2H), 7.57-7.63 (m, 2H), 7.71-7.76 (m, 1H), 7.86-7.91 (m, 1H), 7.99-8.05 (m, M1H), 8.46 (s, 1H), 8.60 (d, 1H), 9.84 (s, 1H); Mass spectrum MH+ 538.

EXAMPLE 26

N-{2-[(4-{[3-Chloro-4-(pyridin-2-ylmethoxy)phenyl]amino}quinazolin-5-yl)oxy]ethyl}-N-prop-2-yn-1-ylacetamide

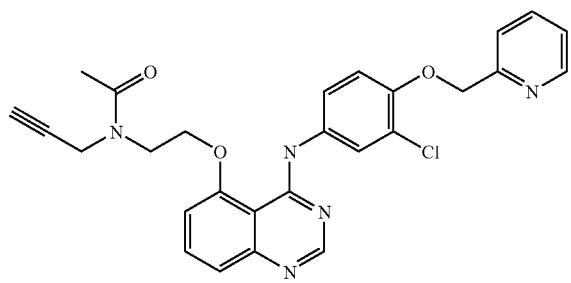

The procedure described in Example 5 was repeated using N-[3-chloro-4-(pyridin-2-ylmethoxy)phenyl]-5-[2-(prop-2-yn-1-ylamino)ethoxy]quinazolin-4-amine and acetyl chloride to give the title compound in 53% yield; NMR spectrum (DMSO-d6) 2.03 (s, 3H), 3.27 (s, 1H), 3.93-4.04 (m, 2H), 4.24-4.32 (m, 2H), 4.43 (t, 1H), 4.56-4.63 (m, 1H), 5.31 (s, 2H), 7.13 (d, 1H), 7.25 (d, 1H), 7.34 (d, 1H), 7.35-7.41 (m, 1H), 7.52-7.63 (m, 2H), 7.70-7.79 (m, 1H), 7.86-7.93 (m, 2H), 8.44 (s, 1H), 8.61 (d, 1H), 9.69 (s, 1H); Mass spectrum MH+ 502.

The N-[3-chloro-4-(pyridin-2-ylmethoxy)phenyl]-5-[2-(prop-2-yn-1-ylamino)ethoxy]quinazolin-4-amine used as starting material was prepared as described in Example 5 (preparation of starting materials) using 5-(2-chloroethoxy)-N-[3-chloro-4-(pyridin-2-ylmethoxy)phenyl]quinazolin-4-amine (obtained as described in Example 5, preparation of starting materials) and prop-2-yn-1-amine; Mass spectrum MH+ 460.

EXAMPLE 27

N-{2-[(4-{[3-Chloro-4-(pyridin-2-ylmethoxy)phenyl]amino}quinazolin-5-yl)oxy]ethyl}-2-hydroxy-N-prop-2-yn-1-ylacetamide

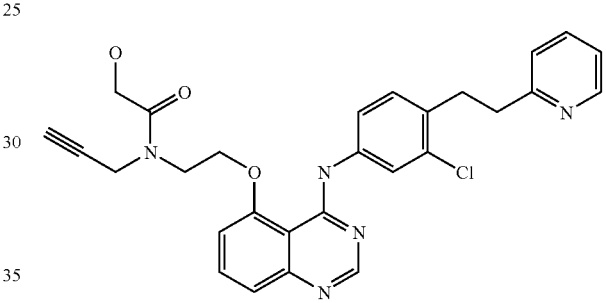

The procedure described in Example 1 was repeated using glycolic acid and N-[3-chloro-4-(pyridin-2-ylmethoxy)phenyl]-5-[2-(prop-2-yn-1-ylamino)ethoxy]quinazolin-4-amine (obtained as described in Example 26, preparation of starting materials) to give the title compound in 26% yield; NMR spectrum (DMSO-d6) 3.98 (s, 2H), 4.16 (s, 2H), 4.28 (s, 2H), 4.47 (s, 1H), 4.55-4.66 (m, 1H), 5.31 (s, 2H), 7.12-7.21 (m, 1H), 7.25 (d, 1H), 7.32-7.40 (m, 2H), 7.59 (d, 2H), 7.70-7.78 (m, 1H), 7.86-7.92 (m, 1H), 7.97-8.06 (m, 1H), 8.43-8.51 (m, 1H), 8.61 (d, 1H), 9.76 (s, 1H); Mass spectrum MH+ 518.

EXAMPLE 28

N-{2-[(4-{[3-Chloro-4-(pyridin-2-ylmethoxy)phenyl]amino}quinazolin-5-yl)oxy]ethyl}-2-hydroxy-N-methylpropanamide

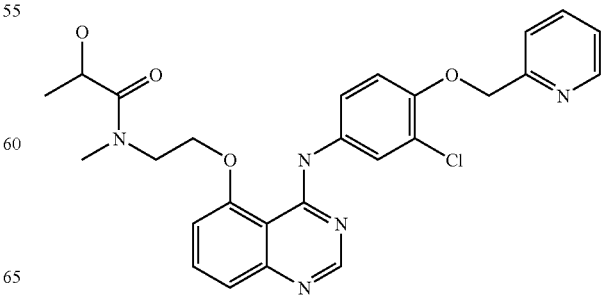

The procedure described in Example 1 was repeated using 2-hydroxypropanoic acid and N-[3-chloro-4-(pyridin-2-ylmethoxy)phenyl]-5-[2-(methylamino)ethoxy]quinazolin-4-amine (obtained as described in Example 1, preparation of starting materials) to give the title compound in 56% yield; NMR spectrum (DMSO-d6) 1.08 (d, 3H), 3.11 (s, 3H), 3.82-4.12 (m, 2H), 4.36-4.47 (m, 3H), 4.52-4.72 (m, 1H), 5.31 (s, 2H), 7.18 (d, 1H), 7.25 (d, 1H), 7.34 (d, 1H), 7.35-7.40 (m, 1H), 7.52-7.62 (m, 2H), 7.70-7.76 (m, 1H), 7.86-7.91 (m, 1H), 7.94-7.97 (m, 1H), 8.44 (s, 1H), 8.61 (d, 1H), 9.75 (s, 1H); Mass spectrum MH+ 508.

EXAMPLE 29

N-{2-[(4-{[3-Chloro-4-(pyridin-2-ylmethoxy)phenyl]amino}quinazolin-5-yl)oxy]ethyl}-N-methyl-tetrahydrofuran-2-carboxamide

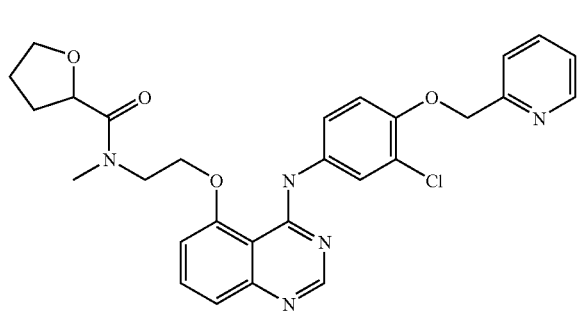

The procedure described in Example 1 was repeated using tetrahydrofuran-2-carboxylic acid and N-[3-chloro-4-(pyridin-2-ylmethoxy)phenyl]-5-[2-(methylamino)ethoxy]quinazolin-4-amine (obtained as described in Example 1, preparation of starting materials) to give the title compound in 89% yield; NMR spectrum (DMSO-d6) 1.64-1.94 (m, 4H), 3.09 (s, 3H), 3.57-3.70 (m, 2H), 3.82-3.97 (m, 2H), 4.42 (t, 2H), 4.60-4.66 (m, 1H), 5.31 (s, 2H), 7.16 (d, 1H), 7.23 (d, 1H), 7.33 (d, 1H), 7.35-7.39 (m, 1H), 7.52-7.57 (m, 1H), 7.59 (d, 1H), 7.70-7.75 (m, 1H), 7.85-7.91 (m, 1H), 7.92 (d, 1H), 8.42 (s, 1H), 8.61 (d, 1H), 9.70 (s, 1H); Mass spectrum MH+ 534.

EXAMPLE 30

N-{2-[(4-{[3-Chloro-4-(pyridin-2-ylmethoxy)phenyl]amino}quinazolin-5-yl)oxy]ethyl}-N,1-dimethylprolinamide

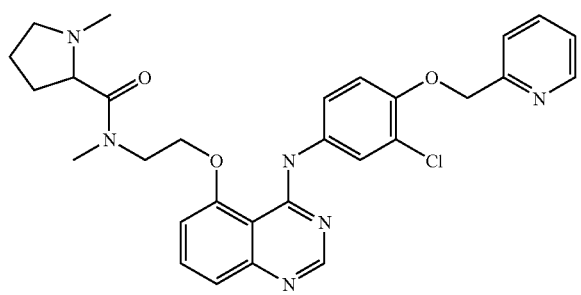

The procedure described in Example 1 was repeated using 1-methylproline and N-[3-chloro-4-(pyridin-2-ylmethoxy)phenyl]-5-[2-(methylamino)ethoxy]quinazolin-4-amine (obtained as described in Example 1, preparation of starting materials) to give the title compound in 38% yield; NMR spectrum (DMSO-d6) 1.55-1.68 (m, 3H), 1.92-2.03 (m, 2H), 2.12 (s, 2H), 3.29 (s, 6H), 3.87-4.03 (m, 2H), 4.40-4.61 (m, 2H), 5.31 (s, 2H), 7.17 (d, 1H), 7.22 (d, 1H), 7.33 (d, 1H), 7.35-7.39 (m, 1H), 7.57-7.63 (m, 2H), 7.69-7.75 (m, 1H), 7.86-7.91 (m, 1H), 8.05 (d, 1H), 8.43 (s, 1H), 8.60 (d, 1H), 9.76 (s, 1H); Mass spectrum MH+ 547.

EXAMPLE 31

N-{2-[(4-{[3-Chloro-4-(pyridin-2-ylmethoxy)phenyl]amino}quinazolin-5-yl)oxy]ethyl}-2-hydroxy-N,2-dimethylpropanamide

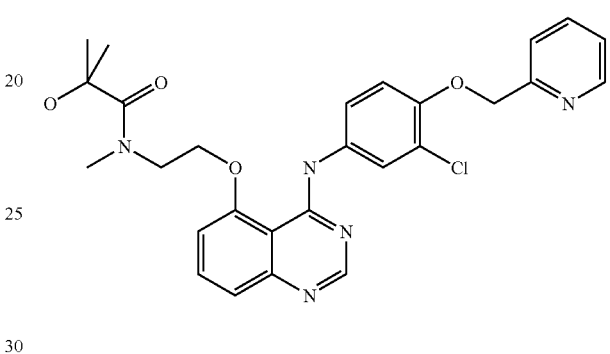

The procedure described in Example 1 was repeated using 2-hydroxy-2-methylpropanoic acid and N-[3-chloro-4-(pyridin-2-ylmethoxy)phenyl]-5-[2-(methylamino)ethoxy]quinazolin-4-amine (obtained as described in Example 1, preparation of starting materials) to give the title compound in 39% yield; NMR spectrum (DMSO-d6) 1.20 (s, 6H), 3.34 (s, 3H), 3.89 (s, 2H), 4.43 (s, 2H), 5.27 (s, 1H), 5.31 (s, 2H), 7.18 (d, 1H), 7.24 (d, 1H), 7.32-7.40 (m, 2H), 7.53-7.57 (m, 1H), 7.58 (d, 1H), 7.70-7.76 (m, 1H), 7.86-7.91 (m, 2H), 8.43 (s, 1H), 8.59-8.61 (m, 1H), 9.75 (s, 1H); Mass spectrum MH+ 522.

EXAMPLE 32

N-{2-[(4-{[3-Chloro-4-(pyridin-2-ylmethoxy)phenyl]amino}quinazolin-5-yl)oxy]ethyl}-1-hydroxy-N-methylcyclopropanecarboxamide

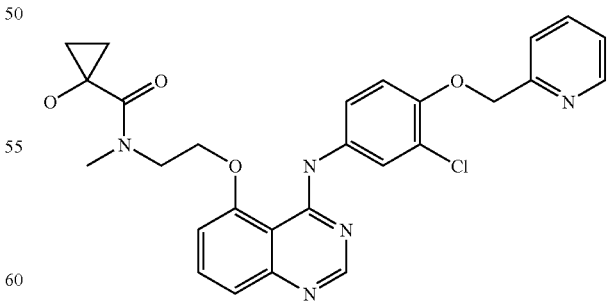

The procedure described in Example 1 was repeated using 1-hydroxycyclopropanecarboxylic acid and N-[3-chloro-4-(pyridin-2-ylmethoxy)phenyl]-5-[2-(methylamino)ethoxy]quinazolin-4-amine (obtained as described in Example 1, preparation of starting materials) to give the title compound in 54% yield; NMR spectrum (DMSO-d6) 0.68-0.80 (m, 4H), 3.30 (s, 3H), 3.84-3.96 (m, 2H), 4.37-4.49 (m, 2H), 5.31 (s, 2H), 6.16-6.23 (m, 1H), 7.14-7.21 (m, 1H), 7.24 (d, 1H), 7.32-7.40 (m, 2H), 7.51-7.56 (m, 1H), 7.59 (d, 1H), 7.71-7.76 (m, 1H), 7.86-7.91 (m, 2H), 8.40-8.47 (m, 1H), 8.61 (d, 1H), 9.68-9.75 (m, 1H); Mass spectrum MH+ 520.

EXAMPLE 33

$N^1$-{2-[(4-{[3-Chloro-4-(pyridin-2-ylmethoxy)phenyl]amino}quinazolin-5-yl)oxy]ethyl}-$N^1$,$N^2$-dimethylglycinamide

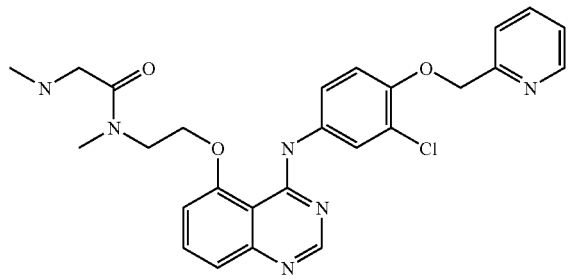

The procedure described in Example 1 was repeated using N-methylglycine and N-[3-chloro-4-(pyridin-2-ylmethoxy)phenyl]-5-[2-(methylamino)ethoxy]quinazolin-4-amine obtained as described in Example 1, preparation of starting materials) to give the title compound in 25% yield; NMR spectrum (DMSO-d6) 3.06 (s, 2H), 3.30 (s, 6H), 3.90 (t, 2H), 4.33-4.42 (m, 3H), 5.31 (s, 2H), 7.16 (d, 1H), 7.24 (d, 1H), 7.34 (d, 1H), 7.35-7.40 (m, 1H), 7.53-7.57 (m, 1H), 7.60 (d, 1H), 7.70-7.75 (m, 1H), 7.86-7.92 (m, 1H), 7.93 (d, 1H), 8.43 (s, 1H), 8.61 (d, 1H), 9.74 (s, 1H); Mass spectrum MH+ 507.

EXAMPLE 34

N-{2-[(4-{[3-Chloro-4-(pyridin-2-ylmethoxy)phenyl]amino}quinazolin-5-yl)oxy]ethyl}-3-hydroxy-N,2,2-trimethylpropanamide

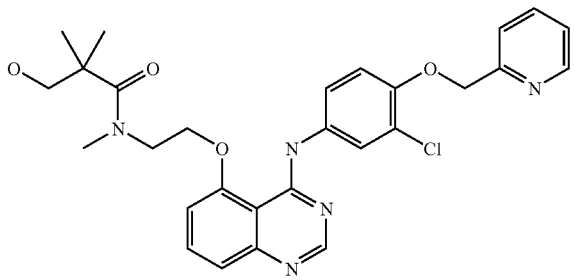

The procedure described in Example 1 was repeated using 3-hydroxy-2,2-dimethylpropanoic acid and N-[3-chloro-4-(pyridin-2-ylmethoxy)phenyl]-5-[2-(methylamino)ethoxy]quinazolin-4-amine (obtained as described in Example 1, preparation of starting materials) to give the title compound in 25% yield; NMR spectrum (DMSO-d6) 1.07 (s, 6H), 3.15 (s, 3H), 3.35 (d, 2H), 3.91 (t, 2H), 4.41-4.48 (m, 3H), 5.30 (s, 2H), 7.18 (d, 1H), 7.24 (d, 1H), 7.34 (d, 1H), 7.35-7.39 (m, 1H), 7.56-7.61 (m, 2H), 7.71-7.76 (m, 1H), 7.86-7.91 (m, 1H), 7.98 (d, 1H), 8.45 (s, 1H), 8.60 (d, 1H), 9.81 (s, 1H); Mass spectrum MH+ 536.

EXAMPLE 35

N-{2-[(4-{[3-Chloro-4-(pyridin-2-ylmethoxy)phenyl]amino}quinazolin-5-yl)oxy]ethyl}-3-hydroxy-N-methylpropanamide (AZ12240261)

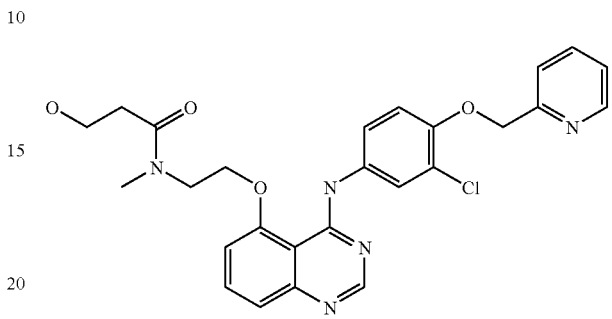

The procedure described in Example 1 was repeated using 3-hydroxypropanoic acid and N-[3-chloro-4-(pyridin-2-ylmethoxy)phenyl]-5-[2-(methylamino)ethoxy]quinazolin-4-amine (obtained as described in Example 1, preparation of starting materials) to give the title compound in 24% yield; NMR spectrum (DMSO-d6) 2.13-2.26 (m, 2H), 2.65-2.79 (m, 2H), 3.30 (s, 3H), 3.87-3.97 (m, 2H), 4.13-4.25 (m, 1H), 4.34-4.61 (m, 2H), 5.31 (s, 2H), 7.15 (d, 1H), 7.25 (d, 1H), 7.32-7.39 (m, 2H), 7.53-7.57 (m, 1H), 7.60 (d, 1H), 7.70-7.76 (m, 1H), 7.86-7.92 (m, 2H), 8.42 (s, 1H), 8.61 (d, 1H), 9.70 (s, 1H); Mass spectrum MH+ 508.

EXAMPLE 36

N-{(2S)-2-[(4-{[3-Chloro-4-(pyridin-2-ylmethoxy)phenyl]amino}quinazolin-5-yl)oxy]propyl}acetamide

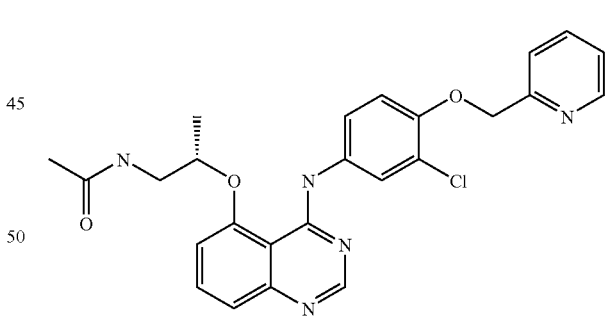

The procedure described in Example 1 was repeated using acetic acid and 5-[(1S)-2-amino-1-methylethoxy]-N-[3-chloro-4-(pyridin-2-ylmethoxy)phenyl]quinazolin-4-amine to give the title compound in 60% yield; NMR spectrum (DMSO-d6) 1.40 (d, 3H), 1.80 (s, 3H), 3.40 (m, 1H), 3.62 (m, 1H), 4.85 (m, 1H), 5.30 (s, 2H), 7.23 (m, 2H), 7.30 (d, 1H), 7.36 (m, 1H), 7.57 (m, 2H), 7.71 (t, 1H), 7.87 (td, 1H), 8.12 (d, 1H), 8.22 (t, 1H), 8.49 (s, 1H), 8.58 (d, 1H), 10.00 (s, 1H); Mass Spectrum MH+ 478.

The 5-[(1S)-2-amino-1-methylethoxy]-N-[3-chloro-4-(pyridin-2-ylmethoxy)phenyl]quinazolin-4-amine used as starting material was prepared as follows:

The procedure described in Example 1 (preparation of starting materials) was repeated using (S)-(+)-1-amino-2-propanol and 5-fluoro-N-[3-chloro-4-(pyridin-2-ylmethoxy)phenyl]quinazolin-4-amine (obtained as described in Example 1, preparation of starting materials) to give 5-[(1S)-2-amino-1-methylethoxy]-N-[3-chloro-4-(pyridin-2-ylmethoxy)phenyl]quinazolin-4-amine in 46% yield; NMR spectrum (DMSO-d6) 1.39 (d, 3H), 2.96 (m, 2H), 4.79 (m, 1H), 5.28 (s, 2H), 7.17 (d, 1H), 7.21 (d, 1H), 7.29 (d, 1H), 7.35 (m, 1H), 7.56 (d, 1H), 7.64 (dd, 1H), 7.70 (t, 1H), 7.86 (dt, 1H), 8.20 (d, 1H), 8.48 (s, 1H), 8.58 (d, 1H), 10.60 (bs, 1H); Mass Spectrum MH+ 435.

EXAMPLE 37

N-{(2S)-2-[(4-{[3-Chloro-4-(pyridin-2-ylmethoxy)phenyl]amino}quinazolin-5-yl)oxy]propyl}-2-hydroxyacetamide

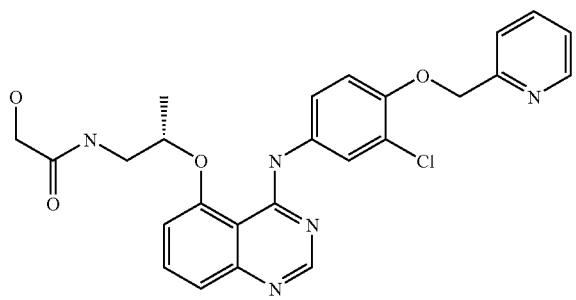

The procedure described in Example 1 was repeated using glycolic acid and 5-[(1S)-2-amino-1-methylethoxy]-N-[3-chloro-4-(pyridin-2-ylmethoxy)phenyl]quinazolin-4-amine (obtained as described in Example 36, preparation of starting materials) to give the title compound in 47% yield; NMR spectrum (DMSO-d6) 1.20 (d, 3H), 3.41 (m, 1H), 3.74 (m, 1H), 3.78 (d, 2H), 4.92 (m, 1H), 5.29 (s, 2H), 5.48 (t, 1H), 7.23 (dd, 2H), 7.31 (d, 1H), 7.35 (m, 1H), 7.58 (m, 2H), 7.70 (t, 1H), 7.87 (td, 1H), 8.13 (d, 1H), 8.17 (t, 1H), 8.47 (s, 1H), 8.58 (d, 1H), 9.98 (s, 1H); Mass Spectrum MH+ 494.

EXAMPLE 38

N$^1$-{(2S)-2-[(4-{[3-Chloro-4-(pyridin-2-ylmethoxy)phenyl]amino}quinazolin-5-yl)oxy]propyl}-N$^2$,N$^2$-dimethylglycinamide

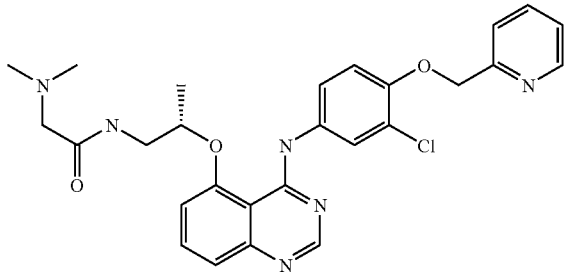

The procedure described in Example 1 was repeated using N,N-dimethylglycine and 5-[(1S)-2-amino-1-methylethoxy]-N-[3-chloro-4-(pyridin-2-ylmethoxy)phenyl] quinazolin-4-amine (obtained as described in Example 36, preparation of starting materials) to give the title compound in 49% yield; NMR spectrum (DMSO-d6) 1.38 (d, 3H), 2.07 (s, 6H), 2.80 (s, 2H), 3.41 (m, 1H), 3.73 (m, 1H), 4.93 (m, 1H), 5.29 (s, 2H), 7.23 (m, 2H), 7.30 (d, 1H), 7.35 (t, 1H), 7.59 (m, 2H), 7.70 (t, 1H), 7.86 (td, 1H), 8.12 (m, 2H), 8.47 (s, 1H), 8.58 (d, 1H), 9.96 (s, 1H); Mass Spectrum MH+ 521.

EXAMPLE 39

N-{(2S)-2-[(4-{[3-Chloro-4-(pyridin-2-ylmethoxy)phenyl]amino}quinazolin-5-yl)oxy]propyl}-2-methoxyacetamide

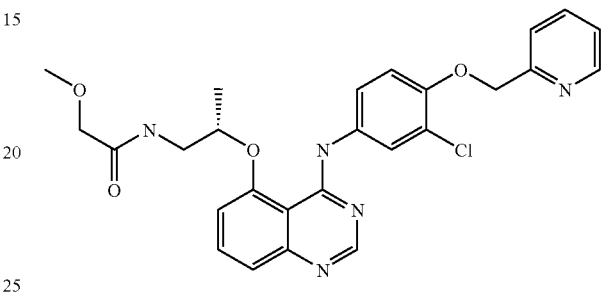

The procedure described in Example 1 was repeated using methoxyacetic acid and 5-[(1S)-2-amino-1-methylethoxy]-N-[3-chloro-4-(pyridin-2-ylmethoxy)phenyl]quinazolin-4-amine (obtained as described in Example 36, preparation of starting materials) to give the title compound in 53% yield; NMR spectrum (DMSO-d6) 1.39 (d, 3H), 3.20 (s, 3H), 3.40 (m, 1H), 3.72 (m, 1H), 3.75 (s, 2H), 4.93 (m, 1H), 5.29 (s, 2H), 7.23 (m, 2H), 7.31 (d, 1H), 7.58 (m, 2H), 7.70 (t, 1H), 7.86 (dt, 1H), 7.95 (s, 1H), 8.12 (d, 1H), 8.19 (t, 1H), 8.47 (s, 1H), 8.58 (m, 1H), 9.97 (s, 1H); Mass Spectrum MH+ 508.

EXAMPLE 40

N-{(2S)-2-[(4-{[3-Chloro-4-(pyridin-2-ylmethoxy)phenyl]amino}quinazolin-5-yl)oxy]propyl}-2-(methylsulfonyl)acetamide

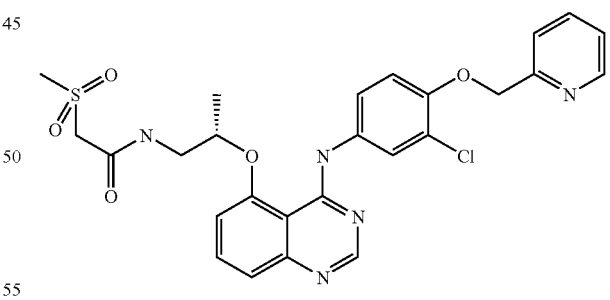

The procedure described in Example 1 was repeated using methanesulfonylacetic acid and 5-[(1S)-2-amino-1-methylethoxy]-N-[3-chloro-4-(pyridin-2-ylmethoxy)phenyl]quinazolin-4-amine (obtained as described in Example 36, preparation of starting materials) to give the title compound in 72% yield; NMR spectrum (DMSO-d6) 1.42 (d, 3H), 3.02 (s, 3H), 3.49 (m, 1H), 3.76 (m, 1H), 4.06 (s, 2H), 4.89 (m, 1H), 5.28 (s, 2H), 7.22 (m, 2H), 7.34 (m, 2H), 7.56 (d, 2H), 7.72 (t, 1H), 7.86 (dt, 1H), 8.15 (d, 1H), 8.48 (s, 1H), 8.58 (d, 1H), 8.71 (t, 1H), 9.93 (s, 1H); Mass Spectrum MH+ 556.

EXAMPLE 41

N-{2-[(4-{[3-Chloro-4-(pyridin-2-ylmethoxy)phenyl]amino}quinazolin-5-yl)oxy]ethyl}-2-hydroxyacetamide

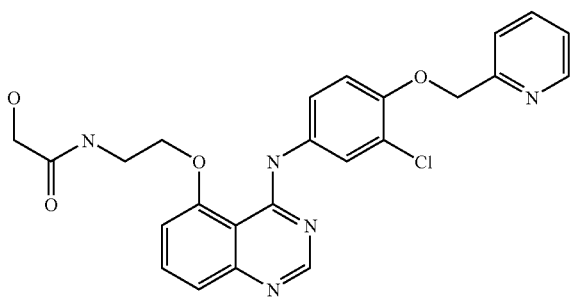

The procedure described in Example 1 was repeated using glycolic acid and 5-(2-aminoethoxy)-N-[3-chloro-4-(pyridin-2-ylmethoxy)phenyl]quinazolin-4-amine (obtained as described in Example 2.6, preparation of starting materials) to give the title compound in 60% yield; NMR spectrum (DMSO-d6) 3.71 (q, 2H), 3.78 (d, 2H), 4.36 (t, 2H), 5.28 (s, 2H), 5.49 (t, 1H), 7.13 (d, 1H), 7.21 (d, 1H), 7.32 (d, 1H), 7.35 (m, 1H), 7.56 (m, 2H), 7.71 (t, 1H), 7.87 (dt, 1H), 7.98 (d, 1H), 8.18 (t, 1H), 8.45 (s, 1H), 8.58 (d, 1H), 9.82 (s, 1H); Mass Spectrum MH+ 480.

EXAMPLE 42

$N^1$-{2-[(4-{[3-Chloro-4-(pyridin-2-ylmethoxy)phenyl]amino}quinazolin-5-yl)oxy]ethyl}-$N^2$,$N^2$-dimethylglycinamide

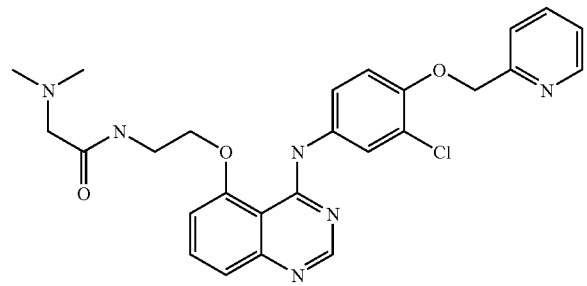

The procedure described in Example 1 was repeated using N,N-dimethylglycine and 5-(2-aminoethoxy)-N-[3-chloro-4-(pyridin-2-ylmethoxy)phenyl]quinazolin-4-amine (obtained as described in Example 2.6, preparation of starting materials) to give the title compound in 31% yield; NMR spectrum (DMSO-d6) 2.08 (s, 6H), 2.79 (s, 2H), 3.68 (q, 2H), 4.36 (t, 2H), 5.29 (s, 2H), 7.13 (d, 1H), 7.21 (d, 1H), 7.34 (m, 2H), 7.55 (m, 2H), 7.70 (t, 1H), 7.86 (dt, 1H), 7.98 (d, 1H), 8.11 (t, 1H), 8.45 (s, 1H), 8.58 (d, 1H), 9.80 (s, 1H); Mass Spectrum MH+ 507.

EXAMPLE 43

N-{2-[(4-{[3-Chloro-4-(pyridin-2-ylmethoxy)phenyl]amino}quinazolin-5-yl)oxy]ethyl}-2-methoxyacetamide

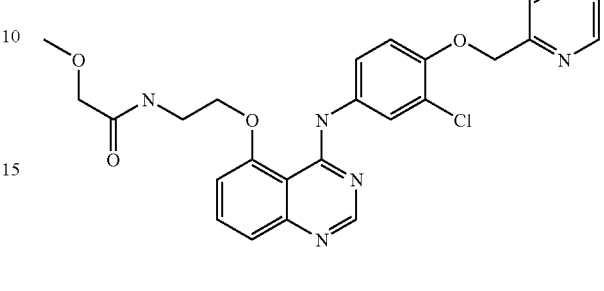

The procedure described in Example 1 was repeated using methoxyacetic acid and 5-(2-aminoethoxy)-N-[3-chloro-4-(pyridin-2-ylmethoxy)phenyl]quinazolin-4-amine (obtained as described in Example 2.6, preparation of starting materials) to give the title compound in 50% yield; NMR spectrum (DMSO-d6) 3.20 (s, 3H), 3.68 (m, 2H), 3.73 (s, 2H), 4.38 (t, 2H), 5.29 (s, 2H), 7.14 (d, 1H), 7.21 (d, 1H), 7.34 (m, 2H), 7.55 (t, 1H), 7.71 (t, 1H), 7.86 (t, 1H), 7.97 (d, 1H), 8.17 (m, 1H), 8.44 (s, 1H), 8.58 (d, 1H), 9.81 (s, 1H); Mass Spectrum MH+ 494.

EXAMPLE 44

N-{2-[(4-{[3-Chloro-4-(pyridin-2-ylmethoxy)phenyl]amino}quinazolin-5-yl)oxy]ethyl}-2-(methylsulfonyl)acetamide

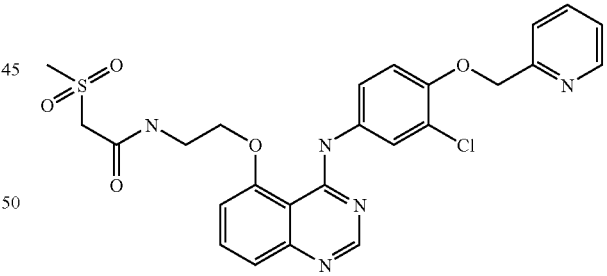

The procedure described in Example 1 was repeated using methanesulfonylacetic acid and 5-(2-aminoethoxy)-N-[3-chloro-4-(pyridin-2-ylmethoxy)phenyl]quinazolin-4-amine (obtained as described in Example 2.6, preparation of starting materials) to give the title compound in 51% yield; NMR spectrum (DMSO-d6) 2.99 (s, 3H), 3.74 (m, 2H), 4.04 (s, 2H), 4.34 (t, 2H), 5.29 (s, 2H), 7.13 (d, 1H), 7.22 (d, 1H), 7.35 (m, 2H), 7.55 (m, 2H), 7.71 (t, 1H), 7.87 (dt, 1H), 8.03 (d, 1H), 8.46 (s, 1H), 8.58 (d, 1H), 8.76 (t, 1H), 9.79 (s, 1H); Mass Spectrum MH+ 542.

EXAMPLE 45

N-{(2S)-2-[(4-{[3-Chloro-4-(pyridin-2-ylmethoxy)phenyl]amino}quinazolin-5-yl)oxy]propyl}-N-methylacetamide

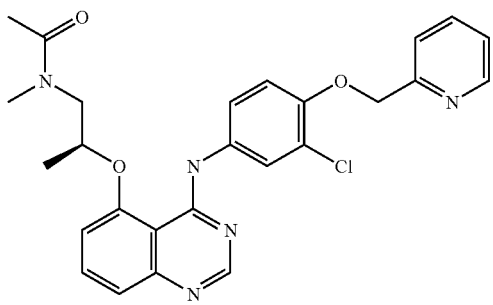

The procedure described in Example 1 was repeated using acetic acid and N-[3-chloro-4-(pyridin-2-ylmethoxy)phenyl]-5-[(1S)-1-methyl-2-(methylamino)ethoxy]quinazolin-4-amine (obtained as described for the R-antipode in Example 2.3, preparation of starting materials, using (2S)-2-methyloxirane) to give the title compound in 51% yield; NMR spectrum (DMSO-d6) 1.36 (d, 3H), 1.94 (s, 3H), 3.03 (s, 3H), 3.32 (1H obscured by H$_2$O), 4.20 (m, 1H), 5.08 (m, 1H), 5.30 (s, 2H), 7.23 (m, 2H), 7.34 (m, 2H), 7.57 (d, 1H), 7.68 (m, 2H), 7.87 (dt, 1H), 8.11 (d, 1H), 8.46 (s, 1H), 8.59 (d, 1H), 9.94 (s, 1H); Mass Spectrum MH$^+$ 492.

EXAMPLE 46

N-{(2S)-2-[(4-{[3-Chloro-4-(pyridin-2-ylmethoxy)phenyl]amino}quinazolin-5-yl)oxy]propyl}-2-hydroxy-N-methylacetamide

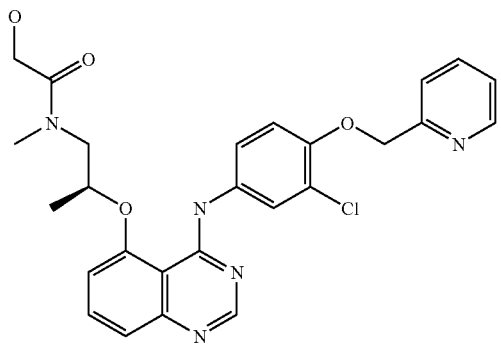

The procedure described in Example 1 was repeated using glycolic acid and N-[3-chloro-4-(pyridin-2-ylmethoxy)phenyl]-5-[(1S)-1-methyl-2-(methylamino) ethoxy]quinazolin-4-amine (obtained as described for the R-antipode in Example 2.3, preparation of starting materials) to give the title compound in 53% yield; NMR spectrum (DMSO-d6) 1.39 (d, 3H), 2.96 (s, 3H), 3.36 (dd, 1H), 4.04 (d, 2H), 4.21 (m, 1H), 4.37 (t, 1H), 5.09 (m, 1H), 5.29 (s, 1H), 7.25 (m, 2H), 7.35 (m, 2H), 7.57 (d, 1H), 7.65 (dd, 1H), 7.70 (t, 1H), 7.87 (dt, 1H), 8.12 (d, 1H), 8.46 (s, 1H), 8.58 (d, 1H), 9.93 (s, 1H); Mass Spectrum MH$^+$ 508.

EXAMPLE 47

N$^1$-{(2S)-2-[(4-{[3-Chloro-4-(pyridin-2-ylmethoxy)phenyl]amino}quinazolin-5-yl)oxy]propyl}-N$^1$,N$^2$,N$^2$-trimethylglycinamide

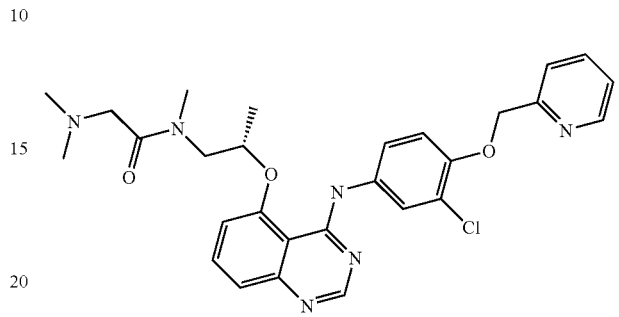

The procedure described in Example 1 was repeated using N,N-dimethylglycine and N-[3-chloro-4-(pyridin-2-ylmethoxy)phenyl]-5-[(1S)-1-methyl-2-(methylamino)ethoxy]quinazolin-4-amine (obtained as described for the R-antipode in Example 2.3, preparation of starting materials) to give the title compound in 27% yield; NMR spectrum (DMSO-d6) 1.37 (d, 3H), 2.06 (s, 6H), 3.08 (s, 3H), 3.23 (dd, 1H), 3.25 (s, 2H), 4.26 (dd, 1H), 5.10 (m, 1H), 5.29 (s, 2H), 7.23 (m, 2H), 7.30 (d, 1H), 7.35 (m, 1H), 7.56 (s, 1H), 7.68 (m, 2H), 7.87 (dt, 1H), 8.13 (d, 1H), 8.44 (s, 1H), 8.58 (d, 1H), 9.90 (s, 1H); Mass Spectrum MH$^+$ 535.

EXAMPLE 48

N-{(2S)-2-[(4-{[3-Chloro-4-(pyridin-2-ylmethoxy)phenyl]amino}quinazolin-5-yl)oxy]propyl}-2-methoxy-N-methylacetamide

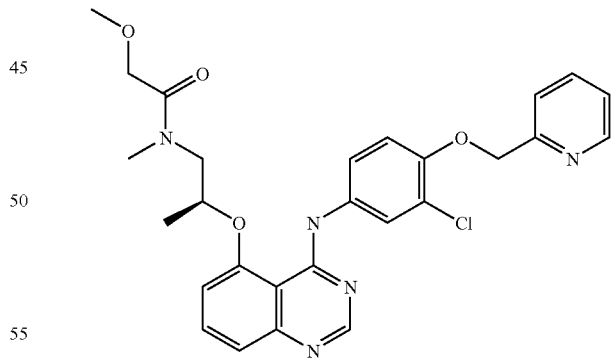

The procedure described in Example 1 was repeated using methoxyacetic acid and N-[3-chloro-4-(pyridin-2-ylmethoxy)phenyl]-5-[(1S)-1-methyl-2-(methylamino)ethoxy]quinazolin-4-amine (obtained as described for the R-antipode in Example 2.3, preparation of starting materials) to give the title compound in 39% yield; NMR spectrum (DMSO-d6) 1.38 (d, 3H), 2.99 (s, 3H), 3.16 (s, 3H), 3.27 (1H obscured by H$_2$O), 4.03 (s, 2H), 4.23 (m, 1H), 5.11 (m, 1H), 5.29 (s, 2H), 7.24 (m, 2H), 7.30 (d, 1H), 7.35 (m, 1H), 7.57 (d, 1H), 7.65, (dd, 1H), 7.71 (t, 1H), 7.86 (dt, 1H), 8.12 (d, 1H), 8.44 (s, 1H), 8.58 (d, 1H), 9.90 (s, 1H); Mass Spectrum MH$^+$ 522.

EXAMPLE 49

N-{(2S)-2-[(4-{[3-Chloro-4-(pyridin-2-ylmethoxy)phenyl]amino}quinazolin-5-yl)oxy]propyl}-N-methyl-2-(methylsulfonyl)acetamide

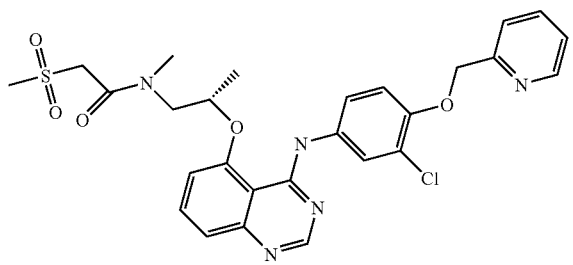

The procedure described in Example 1 was repeated using methanesulfonylacetic acid and N-[3-chloro-4-(pyridin-2-ylmethoxy)phenyl]-5-[(1S)-1-methyl-2-(methylamino)ethoxy]quinazolin-4-amine (obtained as described for the R-antipode in Example 2.3, preparation of starting materials) to give the title compound in 61% yield; NMR spectrum (DMSO-d6) 1.38 (d, 3H), 2.95 (s, 3H), 3.15 (s, 3H), 3.37 (dd, 1H), 4.30 (m, 1H), 4.41 (d, 2H), 5.11 (m, 1H), 5.29 (s, 2H), 7.24 (m, 2H), 7.30 (d, 1H), 7.35 (m, 1H), 7.57 (d, 1H), 7.64 (dd, 1H), 7.70 (t, 1H), 7.86 (dt, 1H), 8.11 (d, 1H), 8.45 (s, 1H), 8.58 (d, 1H), 9.88 (s, 1H); Mass Spectrum MH$^+$ 570.

EXAMPLE 50

N-{(2R)-2-[(4-{[3-Chloro-4-(pyrazin-2-ylmethoxy)phenyl]amino}quinazolin-5-yl)oxy]propyl}-N-methylacetamide

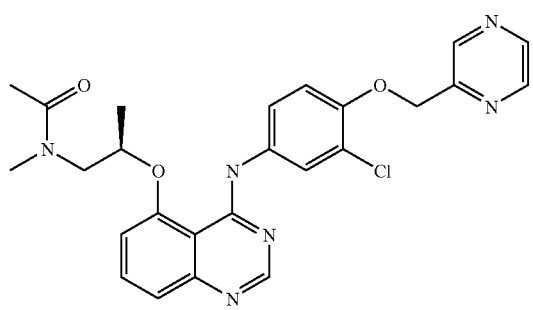

The procedure described in Example 4.1 was repeated using N-[(2R)-2-({4-[(3-chloro-4-hydroxyphenyl)amino]quinazolin-5-yl}oxy)propyl]-N-methylacetamide and pyrazin-2-ylmethyl methanesulfonate to give the title compound in 61% yield; NMR spectrum (DMSO-d6) 1.3 (d, 3H), 1.95 (s, 3H), 3.03 (s, 3H), 3.37 (1H obscured by H$_2$O), 4.21 (dd, 1H), 5.08 (m, 1H), 5.37 (s, 2H), 7.29 (m, 3H), 7.70 (m, 2H), 8.11 (d, 1H), 8.46 (s, 1H), 8.66 (m, 2H), 8.85 (s, 1H), 9.94 (s, 1H); Mass Spectrum MH$^+$ 493.

The N-[(2R)-2-({4-[(3-chloro-4-hydroxyphenyl)amino]quinazolin-5-yl}oxy)propyl]-N-methylacetamide used as starting material was prepared as follows:

The procedure described in Example 3 (preparation of starting materials) was repeated using acetic acid and 2-chloro-4-({5-[(1R)-1-methyl-2-(methylamino)ethoxy]quinazolin-4-yl}amino)phenol (obtained as described in Example 4.11, preparation of starting materials) to give N-[(2R)-2-({4-[(3-chloro-4-hydroxyphenyl)amino]quinazolin-5-yl}oxy)propyl]-N-methylacetamide in 45% yield; NMR spectrum (DMSO-d6) 1.37 (d, 3H), 1.94 (s, 3H), 3.03 (s, 3H), 3.31 (dd, 1H), 4.15 (dd, 1H), 5.06 (m, 1H), 6.97 (d, 1H), 7.23 (d, 1H), 7.29 (d, 1H), 7.46 (dd, 1H), 7.69 (m, 1H), 7.95 (d, 1H), 8.42 (s, 1H), 9.98 (bs, 1H); Mass Spectrum MH$^+$ 401.

EXAMPLE 51

N-{(2R)-2-[(4-{[3-Chloro-4-(1,3-thiazol-4-ylmethoxy)phenyl]amino}quinazolin-5-yl)oxy]propyl}-N-methylacetamide

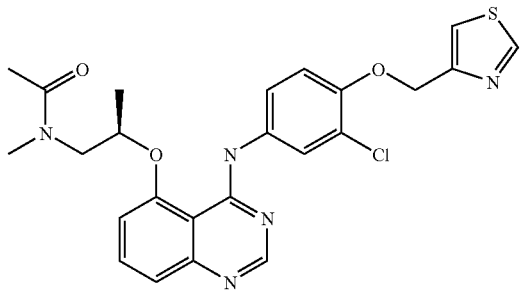

The procedure described in Example 3 was repeated using N-[(2R)-2-({4-[(3-chloro-4-hydroxyphenyl)amino]quinazolin-5-yl}oxy)propyl]-N-methylacetamide (obtained as described for in Example 50, preparation of starting materials) and 4-(chloromethyl)-thiazole hydrochloride to give the title compound in 17% yield; NMR spectrum (DMSO-d6) 1.36 (d, 3H), 1.94 (s, 3H), 3.02 (s, 3H), 3.3O (1H obscured by H$_2$O), 4.21 (dd, 1H), 5.09 (m, 1H), 5.33 (s, 2H), 7.29 (m, 3H), 7.70 (m, 2H), 7.81 (s, 1H), 8.08 (s, 1H), 8.47 (s, 1H), 9.13 (s, 1H), 9.96 (s, 1H); Mass Spectrum MH$^+$ 498.

EXAMPLE 52

N-((2R)-2-{[4-({3-Chloro-4-[(3-fluorobenzyl)oxy]phenyl}amino)quinazolin-5-yl]oxy}propyl)-N-methylacetamide

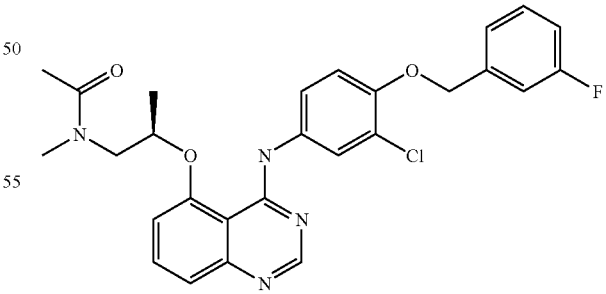

The procedure described in Example 3 was repeated using N-[(2R)-2-({4-[(3-chloro-4-hydroxyphenyl)amino]quinazolin-5-yl}oxy)propyl]-N-methylacetamide (obtained as described for in Example 50, preparation of starting materials) and 3-fluorobenzyl chloride to give the title compound in 87% yield; NMR spectrum (DMSO-d6) 1.36 (d, 3H), 1.93 (s, 3H), 3.04 (s, 3H), 3.27 (1H obscured by H$_2$O), 4.22 (dd, 1H), 5.07 (m, 1H), 5.25 (s, 2H), 7.16 (t, 1H), 7.29 (m, 5H), 7.45 (m, 1H), 7.65 (dd, 1H), 7.71 (t, 1H), 8.09 (d, 1H), 8.46 (s, 1H), 9.93 (s, 1H); Mass Spectrum MH+ 509.

EXAMPLE 53

N-((2R)-2-{[4-({3-Chloro-4-[(2-fluorobenzyl)oxy]phenyl}amino)quinazolin-5-yl]oxy}propyl)-N-methylacetamide

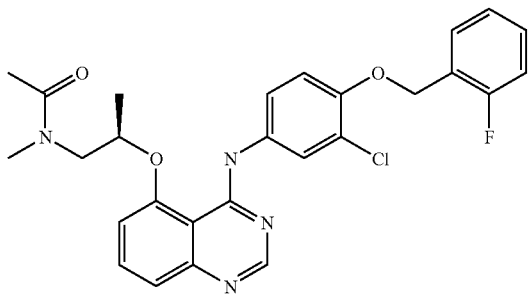

The procedure described in Example 3 was repeated using N-[(2R)-2-({4-[(3-chloro-4-hydroxyphenyl)amino]quinazolin-5-yl}oxy)propyl]-N-methylacetamide (obtained as described for in Example 50, preparation of starting materials) and 2-fluorobenzyl chloride to give the title compound in 72% yield; NMR spectrum (DMSO-d6) 1.37 (d, 3H), 1.94 (s, 3H), 3.04 (s, 3H), 3.30 (1H obscured by H₂O), 4.20 (dd, 1H), 5.07 (m, 1H), 5.25 (s, 2H), 7.27 (m, 5H), 7.43 (m, 1H), 7.59 (t, 1H), 7.67 (dd, 1H), 7.70 (t, 1H), 8.07 (d, 1H), 8.45 (s, 1H), 9.93 (s, 1H); Mass Spectrum MH+ 509.

EXAMPLE 54

N-{(1R)-2-[(4-{[3-Chloro-4-(pyridin-2-ylmethoxy)phenyl]amino}quinazolin-5-yl)oxy]-1-methylethyl}-2-hydroxy-N-methylacetamide

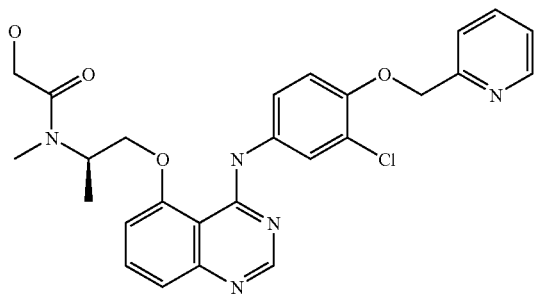

The procedure described in Example 3 was repeated using picolyl chloride hydrochloride and N-[(1R)-2-({4-[(3-chloro-4-hydroxyphenyl)amino]quinazolin-5-yl}oxy)-1-methylethyl]-2-hydroxy-N-methylacetamide to give the title compound in 8% yield; NMR spectrum (DMSO-d6) 1.19 (d, 3H), 2.79 (s, 3H), 3.87-4.26 (m, 3H), 4.38-4.48 (m, 2H), 5.11-5.22 (m, 1H), 5.29 (s, 2H), 7.18-7.25 (m, 2H), 7.32-7.38 (m, 2H), 7.48 (d, 1H), 7.58 (d, 1H), 7.72 (t, 1H), 7.87 (t, 1H), 7.94 (d, 1H), 8.44 (s, 1H), 8.59 (d, 1H), 9.58 (s, 1H); Mass spectrum MH+ 508.3.

The N-[(1R)-2-({4-[(3-chloro-4-hydroxyphenyl)amino]quinazolin-5-yl}oxy)-1-methylethyl]-2-hydroxy-N-methylacetamide used as starting material was prepared as follows:

The procedure described in Example 3 (preparation of starting materials) was repeated using (2R)-2-(methylamino)propan-1-ol (obtained as described in Becker et al., J. Chem. Soc. 1957, 858) and 2-chloro-4-[(5-fluoroquinazolin-4-yl)amino]phenol (obtained as described in Example 4.5, preparation of starting materials) to give 2-chloro-4-[(5-{[(2R)-2-(methylamino)propyl]oxy}quinazolin-4-yl)amino]phenol in >100% yield; NMR spectrum (DMSO-d6) 1.20 (d, 3H), 2.40 (s, 3H), 3.30 (m, 1H), 4.25 (dd, 1H), 4.35 (dd, 1H), 7.00 (d, 1H), 7.10 (d, 1H), 7.30 (d, 1H), 7.60 (dd, 1H), 7.70 (t, 1H), 7.90 (d, 1H), 8.50 (s, 1H); Mass spectrum MH+ 359.1

The procedure described in Example 3 (preparation of starting materials) was repeated using glycolic acid and 2-chloro-4-[(5-{[(2R)-2-(methylamino)propyl]oxy}quinazolin-4-yl)amino]phenol to give N-[(1R)-2-({4-[(3-chloro-4-hydroxyphenyl)amino]quinazolin-5-yl}oxy)-1-methylethyl]-2-hydroxy-N-methylacetamide in 100% yield; Mass spectrum MH+ 416.9.

EXAMPLE 55

N-{(1R)-2-[(4-{[3-Chloro-4-(pyridin-2-ylmethoxy)phenyl]amino}quinazolin-5-yl)oxy]-1-methylethyl}-N-methylacetamide

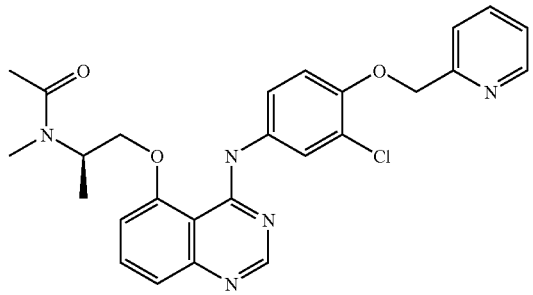

The procedure described in Example 3 was repeated using picolyl chloride hydrochloride and N-[(1R)-2-({4-[(3-chloro-4-hydroxyphenyl)amino]quinazolin-5-yl}oxy)-1-methylethyl]-N-methylacetamide to give the title compound in 7% yield; NMR spectrum (DMSO-d6) 1.18 (d, 3H), 1.83 (s, 3H), 2.84 (s, 3H), 4.19-4.43 (m, 2H), 5.14-5.24 (m, 1H), 5.30 (s, 2H), 7.16-7.27 (m, 2H), 7.32-7.38 (m, 2H), 7.45-7.50 (m, 1H), 7.58 (d, 1H), 7.72 (t, 1H), 7.87 (t, 2H), 8.43 (s, 1H), 8.59 (d, 1H), 9.53 (s, 1H); Mass spectrum MH+ 492.3.

The N-[(1R)-2-({4-[(3-chloro-4-hydroxyphenyl)amino]quinazolin-5-yl}oxy)-1-methylethyl]-N-methylacetamide used as starting material was prepared as follows:

The procedure described in Example 3 (preparation of starting materials) was repeated using acetic acid and 2-chloro-4-[(5-{[(2R)-2-(methylamino)propyl]oxy}quinazolin-4-yl)amino]phenol (obtained as described in Example 54, preparation of starting materials) to give N-[(1R)-2-({4-[(3-chloro-4-hydroxyphenyl)amino]quinazolin-5-yl}oxy)-1-methylethyl]-N-methylacetamide in 100% yield; Mass spectrum MH+ 401.

EXAMPLE 56

N-{(1S)-2-[(4-{[3-Chloro-4-(pyridin-2-ylmethoxy)phenyl]amino}quinazolin-5-yl)oxy]-1-methylethyl}-2-hydroxy-N-methylacetamide

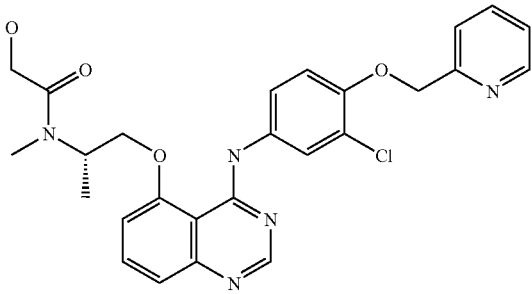

The procedure described in Example 3 was repeated using picolyl chloride hydrochloride and N-[(1S)-2-({4-[(3-chloro-4-hydroxyphenyl)amino]quinazolin-5-yl}oxy)-1-methylethyl]-2-hydroxy-N-methylacetamide to give the title compound in 57% yield; NMR spectrum (DMSO-d6) 1.20 (dd, 3H), 2.80 (d, 3H), 3.10 (m, 1H), 3.80-4.20 (m, 2H), 4.20-4.50 (m, 2H), 5.15 (m, 1H), 5.30 (s, 2H), 7.20 (m, 2H), 7.30 (m, 2H), 7.50 (d, 1H), 7.60 (d, 1H), 7.70 (m, 1H), 7.80-7.95 (m, 2H), 8.40 (d, 1H), 8.60 (d, 1H), 9.60 (s, 1H); Mass spectrum MH+ 508.2.

The N-[(1S)-2-({4-[(3-chloro-4-hydroxyphenyl)amino]quinazolin-5-yl}oxy)-1-methylethyl]-2-hydroxy-N-methylacetamide used as starting material was prepared as follows:

The procedure described in Example 3 (preparation of starting materials) was repeated using (2S)-2-(methylamino)propan-1-ol (obtained as described in Chacchio et al., Tetrahedron, 1995, 51, 5689) and 2-chloro-4-[(5-fluoroquinazolin-4-yl)amino]phenol (obtained as described in Example 4.5, preparation of starting materials) to give 2-chloro-4-[(5-{[(2S)-2-(methylamino)propyl]oxy}quinazolin-4-yl)amino]phenol in >100% yield; NMR spectrum (DMSO-d6) 1.20 (d, 3H), 2.40 (s, 3H), 3.20 (m, 1H), 4.15 (dd, 1H), 4.30 (dd, 1H), 7.00 (d, 1H), 7.10 (d, 1H), 7.30 (d, 1H), 7.60 (dd, 1H), 7.70 (t, 1H), 8.00 (d, 1H), 8.50 (s, 1H); Mass spectrum MH+ 359.4.

The procedure described in Example 3 (preparation of starting materials) was repeated using glycolic acid and 2-chloro-4-[(5-{[(2S)-2-(methylamino)propyl]oxy}quinazolin-4-yl)amino]phenol to give N-[(1S)-2-({4-[(3-chloro-4-hydroxyphenyl)amino]quinazolin-5-yl}oxy)-1-methylethyl]-2-hydroxy-N-methylacetamide in 48% yield; Mass spectrum MH+ 417.3.

EXAMPLE 57

N-{(1S)-2-[(4-{[3-Chloro-4-(pyridin-2-ylmethoxy)phenyl]amino}quinazolin-5-yl)oxy]-1-methylethyl}-N-methylacetamide

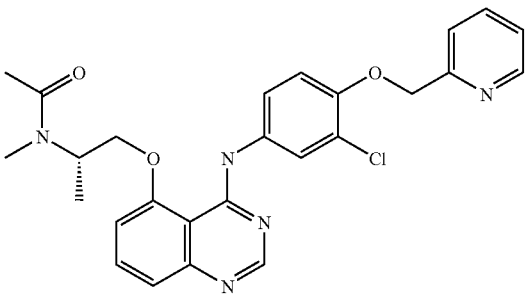

The procedure described in Example 3 was repeated using picolyl chloride hydrochloride and N-[(1S)-2-({4-[(3-chloro-4-hydroxyphenyl)amino]quinazolin-5-yl}oxy)-1-methylethyl]-N-methylacetamide to give the title compound in 34% yield; NMR spectrum (DMSO-d6, 373K) 1.20 (d, 3H), 1.85 (s, 3H), 2.80 (s, 3H), 3.00 (m, 1H), 4.30 (m, 1H), 4.40 (m, 1H), 5.30 (s, 2H), 7.20 (m, 2H), 7.40 (m, 2H), 7.50 (d, 1H), 7.60 (d, 1H), 7.70 (t, 1H), 7.80 (m, 1H), 7.90 (d, 1H), 8.40 (s, 1H), 8.60 (d, 1H), 9.60 (s, 1H); Mass spectrum MH+ 492.2.

The N-[(1S)-2-({4-[(3-chloro-4-hydroxyphenyl)amino]quinazolin-5-yl}oxy)-1-methylethyl]-N-methylacetamide used as starting material was prepared as follows:

The procedure described in Example 3 (preparation of starting materials) was repeated using acetic acid and 2-chloro-4-[(5-{[(2S)-2-(methylamino)propyl]oxy}quinazolin-4-yl)amino]phenol (obtained as described in Example 56, preparation of starting materials) to give N-[(1S)-2-({4-[(3-chloro-4-hydroxyphenyl)amino]quinazolin-5-yl}oxy)-1-methylethyl]-N-methylacetamide in 27% yield; Mass spectrum MH+ 401.3.

EXAMPLE 58

N-{(1S)-2-[(4-{[3-Chloro-4-(pyridin-2-ylmethoxy)phenyl]amino}quinazolin-5-yl)oxy]-1-methylethyl}-2-methoxy-N-methylacetamide

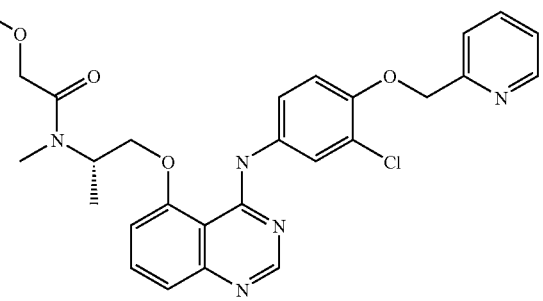

The procedure described in Example 3 was repeated using picolyl chloride hydrochloride and N-[(1S)-2-({4-[(3-chloro-4-hydroxyphenyl)amino]quinazolin-5-yl}oxy)-1-methylethyl]-2-methoxy-N-methylacetamide to give the title compound in 39% yield; NMR spectrum (DMSO-d6, 373K) 1.20 (m, 3H), 2.80 (s, 3H), 3.10 (s, 3H), 3.90 (m, 2H), 4.20 (m, 1H), 4.50 (m, 1H), 5.10 (m, 1H), 5.30 (s, 2H), 7.20 (m, 2H), 7.40 (m, 2H), 7.50 (d, 1H), 7.60 (d, 1H), 7.70 (t, 1H), 7.90 (t, 1H), 7.95 (s, 1H), 8.40 (s, 1H), 8.60 (d, 1H), 9.60 (s, 1H); Mass spectrum F 522.2.

The N-[(1S)-2-({4-[(3-chloro-4-hydroxyphenyl)amino]quinazolin-5-yl}oxy)-1-methylethyl]-2-methoxy-N-methylacetamide used as starting material was obtained as follows:

The procedure described in Example 3 (preparation of starting materials) was repeated using methoxyacetic acid and 2-chloro-4-[(5-{[(2S)-2-(methylamino)propyl]oxy}quinazolin-4-yl)amino]phenol (obtained as described in Example 56, preparation of starting materials) to give N-[(1S)-2-({4-[(3-chloro-4-hydroxyphenyl)amino]quinazolin-5-yl}oxy)-1-methylethyl]-2-methoxy-N-methylacetamide in 49% yield; Mass spectrum MH+ 429.2.

EXAMPLE 59

N-{(1S)-2-[(4-{[3-Chloro-4-(pyridin-2-ylmethoxy)phenyl]amino}quinazolin-5-yl)oxy]-1-methylethyl}-2-hydroxyacetamide

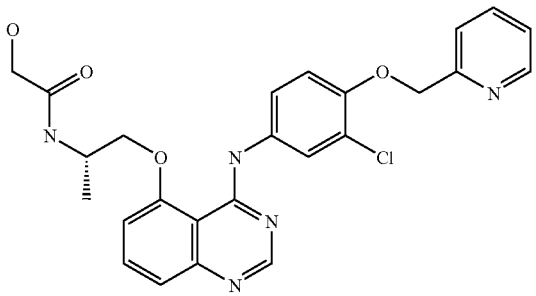

The procedure described in Example 3 was repeated using picolyl chloride hydrochloride and N-[(1S)-2-({4-[(3-chloro-4-hydroxyphenyl)amino]quinazolin-5-yl}oxy)-1-methylethyl]-2-hydroxyacetamide to give the title compound in 57% yield; NMR spectrum (DMSO-d6) 1.23 (d, 3H), 3.64-3.81 (m, 2H), 4.24-4.36 (m, 2H), 4.45-4.59 (m, 1H), 5.29 (s, 2H), 5.45 (t, 1H), 7.13-7.23 (m, 2H), 7.35 (t, 2H), 7.49-7.53 (m, 1H), 7.56-7.59 (m, 1H), 7.72 (t, 1H), 7.87 (t, 1H), 7.99-8.02 (m, 2H), 8.46 (s, 1H), 8.59 (d, 1H), 9.75 (s, 1H); Mass spectrum MH+ 493.95.

The N-[(1S)-2-({4-[(3-chloro-4-hydroxyphenyl)amino]quinazolin-5-yl}oxy)-1-methylethyl]-2-hydroxyacetamide used as starting material was prepared as follows:

The procedure described in Example 3 (preparation of starting materials) was repeated using (2S)-2-aminopropan-1-ol and 2-chloro-4-[(5-fluoroquinazolin-4-yl)amino]phenol (obtained as described in Example 4.5, preparation of starting materials) to give 4-[(5-{[(2S)-2-aminopropyl]oxy}quinazolin-4-yl)amino]-2-chlorophenol in 54% yield; NMR spectrum (DMSO-d6); 1.30 (d, 3H), 3.30 (bs, 2H), 3.80 (m, 1H), 4.40 (m, 2H), 7.00 (d, 1H), 7.20 (d, 1H), 7.30 (d, 1H), 7.50 (dd, 1H), 7.70 (t, 1H), 8.00 (d, 1H), 8.45 (s, 1H); Mass spectrum MH+ 345.1.

The procedure described in Example 3 (preparation of starting materials) was repeated using glycolic acid and 4-[(5-{[(2S)-2-aminopropyl]oxy}quinazolin-4-yl)amino]-2-chlorophenol to give N-[(1S)-2-({4-[(3-chloro-4-hydroxyphenyl)amino]quinazolin-5-yl}oxy)-1-methylethyl]-2-hydroxyacetamide in 73% yield; Mass spectrum MH+ 403.0.

EXAMPLE 60

N-{(1S)-2-[(4-{[3-Chloro-4-(pyridin-2-ylmethoxy)phenyl]amino}quinazolin-5-yl)oxy]-1-methylethyl}acetamide

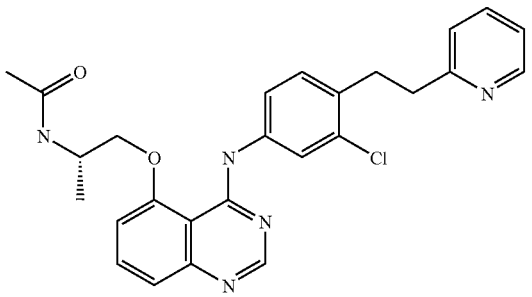

The procedure described in Example 3 was repeated using picolyl chloride hydrochloride and N-[(1S)-2-({4-[(3-chloro-4-hydroxyphenyl)amino]quinazolin-5-yl}oxy)-1-methylethyl]acetamide to give the title compound in 63% yield; NMR spectrum (DMSO-d6) 1.21 (s, 3H), 1.73 (s, 3H), 4.12-4.30 (m, 2H), 4.33-4.43 (m, 1H), 5.29 (s, 2H), 7.15-7.25 (m, 2H), 7.35 (t, 2H), 7.51-7.59 (m, 2H), 7.72 (t, 1H), 7.87 (t, 1H), 7.99 (s, 1H), 8.14 (d, 1H), 8.48 (s, 1H), 8.59 (d, 1H), 9.80 (s, 1H); Mass spectrum MH+ 478.0.

The N-[(1S)-2-({4-[(3-chloro-4-hydroxyphenyl)amino]quinazolin-5-yl}oxy)-1-methylethyl]acetamide used as starting material was prepared as follows:

The procedure described in Example 3 (preparation of starting materials) was repeated using acetic acid and 4-[(5-{[(2S)-2-aminopropyl]oxy}quinazolin-4-yl)amino]-2-chlorophenol (obtained as described in Example 59, preparation of starting materials) to give N-[(1S)-2-({4-[(3-chloro-4-hydroxyphenyl)amino]quinazolin-5-yl}oxy)-1-methylethyl]acetamide in >100% yield; Mass spectrum MH+ 387.0.

EXAMPLE 61

N$^1$-{(1S)-2-[(4-{[3-Chloro-4-(pyridin-2-ylmethoxy)phenyl]amino}quinazolin-5-yl)oxy]-1-methylethyl}-N$^2$,N$^2$-dimethylglycinamide

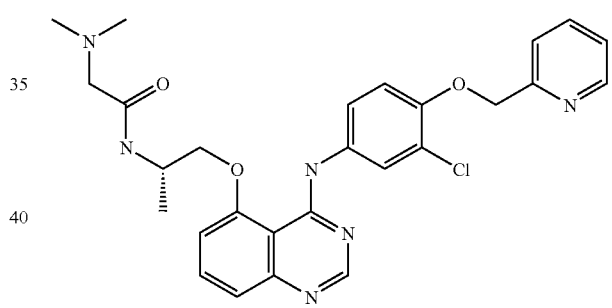

The procedure described in Example 1 was repeated using N,N-dimethylglycine and 5-{[(2S)-2-aminopropyl]oxy}-N-[3-chloro-4-(pyridin-2-ylmethoxy)phenyl]quinazolin-4-amine to give the title compound in 42% yield; NMR spectrum (DMSO-d6) 1.21 (d, 3H), 2.05 (s, 6H), 2.60-2.80 (m, 2H), 4.20-4.40 (m, 2H), 4.40-4.60 (m, 1H), 5.30 (s, 2H), 7.15 (m, 1H), 7.22 (m, 1H), 7.35 (m, 2H), 7.54 (m, 2H), 7.70 (t, 1H), 7.90 (t, 1H), 7.98 (m, 2H), 8.48 (s, 1H), 8.59 (d, 1H), 9.76 (s, 1H); Mass spectrum MH+ 521.4.

The 5-{[(2S)-2-aminopropyl]oxy}-N-[3-chloro-4-(pyridin-2-ylmethoxy)phenyl]quinazolin-4-amine used as starting material was prepared as follows:

The procedure described in Example 2.4 (preparation of starting materials) was repeated using (2S)-2-aminopropan-1-ol and N-[3-chloro-4-(pyridin-2-ylmethoxy)phenyl]-5-fluoroquinazolin-4-amine (obtained as described in Example 1, preparation of starting materials) to give 5-{[(2S)-2-aminopropyl]oxy}-N-[3-chloro-4-(pyridin-2-ylmethoxy)phenyl]quinazolin-4-amine in 51% yield; Mass spectrum MH+ 436.4.

EXAMPLE 62

N[1]-{(2R)-2-[(4-{[3-Chloro-4-(pyridin-2-ylmethoxy)phenyl]amino}quinazolin-5-yl)oxy]propyl}-N[2],N[2]-dimethylglycinamide

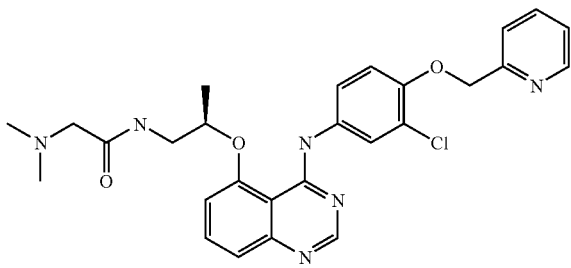

The procedure described in Example 3 was repeated using N[1]-[(2R)-2-({4-[(3-chloro-4-hydroxyphenyl)amino]quinazolin-5-yl}oxy)propyl]-N[2],N[2]-dimethylglycinamide and picolyl chloride hydrochloride to give the title compound in 59% yield; NMR spectrum (CDCl$_3$) 1.47 (d, 3H), 2.11 (s, 6H), 2.88 (s, 2H), 3.50-3.63 (m, 1H), 3.64-3.78 (m, 1H), 4.76-4.90 (m, 1H), 5.23 (s, 2H), 6.92-7.00 (m, 2H), 7.13-7.19 (m, 1H), 7.36-7.49 (m, 2H), 7.52-7.72 (m, 4H), 7.90 (d, 1H), 8.55 (m, 2H), 9.82 (s, 1H); Mass spectrum MH+ 521.0.

The N[1]-[(2R)-2-({4-[(3-chloro-4-hydroxyphenyl)amino]quinazolin-5-yl}oxy)propyl]-N[2],N[2]-dimethylglycinamide amide used as starting material was prepared as follows:

The procedure described in Example 3 (preparation of starting materials) was repeated using 4-({5-[(1R)-2-amino-1-methylethoxy]quinazolin-4-yl}amino)-2-chlorophenol (obtained as described in Example 4.4, preparation of starting materials) and N,N-dimethylglycine to give N[1]-[(2R)-2-({4-[(3-chloro-4-hydroxyphenyl)amino]quinazolin-5-yl}oxy)propyl]-N[2],N[2]-dimethylglycinamide amide in 11% yield; NMR spectrum (CDCl$_3$) 1.46 (d, 3H), 2.09 (s, 6H), 2.84 (d, 2H), 3.52-3.75 (m, 2H), 4.77-4.89 (m, 1H), 6.89-6.99 (m, 2H), 7.27 (dd, 1H), 7.40 (dd, 1H), 7.51-7.61 (m, 2H), 7.80 (d, 1H), 8.52 (s, 1H), 9.76 (s, 1H); Mass spectrum MH+ 430.0.

EXAMPLE 63

(2S)-N-{2-[(4-{[3-Chloro-4-(pyridin-2-ylmethoxy)phenyl]amino}quinazolin-5-yl)oxy]ethyl}-2,4-dihydroxybutanamide

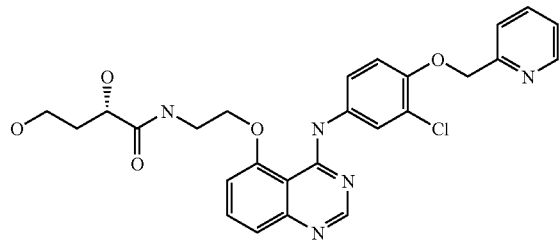

5-(2-aminoethoxy)-N-[3-chloro-4-(pyridin-2-ylmethoxy)phenyl]quinazolin-4-amine (obtained as described in Example 2.6, preparation of starting materials, 0.5 g, 1.19 mmol) was heated to 130° C. in xylene (20 ml) until it had dissolved. (S)-(−)-α-hydroxy-γ-butyrolactone (0.10 ml, 1.31 mmol) was added and the mixture was stirred at 130° C. for 3 hours. More (S)-(−)-α-hydroxy-γ-butyrolactone (0.05 ml, 0.66 mmol) was added and the mixture was heated for a further 2 hours. The resultant precipitate was filtered off while the mixture was hot, washed with diethyl ether (3×10 ml) and dried to give the title compound as a solid (430 mg, 69%); NMR spectrum (DMSO-d6) 1.38-1.55 (m, 1H), 1.69-1.85 (m, 1H), 3.37-3.50 (m, 2H), 3.61-3.77 (m, 2H), 3.89-4.00 (m, 1H), 4.28-4.45 (m, 3H), 5.29 (s, 2H), 5.51 (d, 1H), 7.13 (d, 1H), 7.22 (d, 1H), 7.28-7.41 (m, 2H), 7.49-7.62 (m, 2H), 7.71 (t, 1H), 8.01 (d, 1H), 8.14-8.25 (m, 1H), 8.45 (s, 1H), 8.59 (d, 1H), 9.82 (s, 1H); Mass spectrum MH+ 523.9.

EXAMPLE 64

(2R)-N-{2-[(4-{[3-Chloro-4-(pyridin-2-ylmethoxy)phenyl]amino}quinazolin-5-yl)oxy]ethyl}-2,4-dihydroxybutanamide

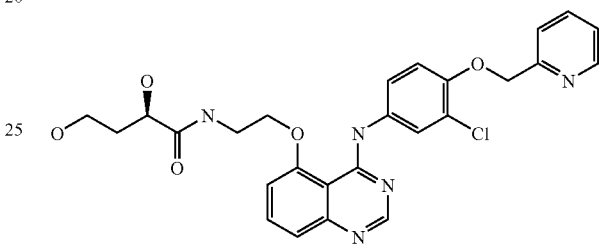

The procedure described in Example 63 was repeated using 5-(2-aminoethoxy)-N-[3-chloro-4-(pyridin-2-ylmethoxy)phenyl]quinazolin-4-amine (obtained as described in Example 2.6, preparation of starting materials) and (R)-(+)-α-hydroxy-γ-butyrolactone to give the title compound in 55% yield; NMR spectrum (DMSO-d6) 1.38-1.55 (m, 1H), 1.69-1.85 (m, 1H), 3.37-3.50 (m, 2H), 3.61-3.77 (m, 2H), 3.89-4.00 (m, 1H), 4.28-4.45 (m, 3H), 5.29 (s, 2H), 5.51 (d, 1H), 7.13 (d, 1H), 7.22 (d, 1H), 7.28-7.41 (m, 2H), 7.49-7.62 (m, 2H), 7.71 (t, 1H), 8.01 (d, 1H), 8.14-8.25 (m, 1H), 8.45 (s, 1H), 8.59 (d, 1H), 9.82 (s, 1H); Mass spectrum MH+ 523.9.

EXAMPLE 65

(2R)-N-{(2R)-2-[(4-{[3-Chloro-4-(pyridin-2-ylmethoxy)phenyl]amino}quinazolin-5-yl)oxy]propyl}-2,4-dihydroxybutanamide

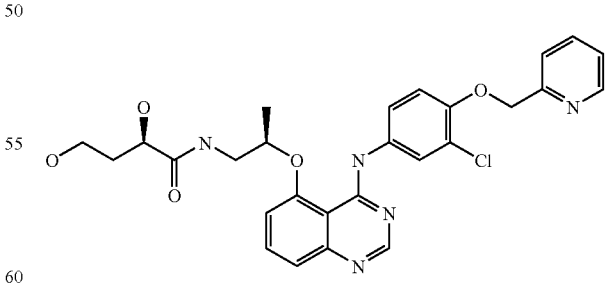

The procedure described in Example 63 was repeated using 5-[(1R)-2-amino-1-methylethoxy]-N-[3-chloro-4-(pyridin-2-ylmethoxy)phenyl]quinazolin-4-amine and (R)-(+)-α-hydroxy-γ-butyrolactone to give the title compound in 54% yield; NMR spectrum (DMSO-d6) 1.39 (d, 3H), 1.43-1.57

(m, 3H), 1.71-1.86 (m, 1H), 3.33-3.53 (m, 3H), 3.65-3.79 (m, 1H), 3.88-4.00 (m, 1H), 4.36 (t, 1H), 4.85-4.96 (m, 1H), 5.29 (s, 2H), 5.45 (d, 1H), 7.24 (d, 2H), 7.28-7.41 (m, 2H), 7.59 (t, 2H), 7.71 (t, 1H), 7.87 (t, 1H), 8.10-8.21 (m, 2H), 8.48 (s, 1H), 8.59 (d, 1H), 9.99 (s, 1H); Mass spectrum MH+ 537.9.

The 5-[(1R)-2-amino-1-methylethoxy]-N-[3-chloro-4-(pyridin-2-ylmethoxy)phenyl]quinazolin-4-amine used as starting material was prepared as follows:

Benzaldehyde (1.46 ml, 14.3 mmol) was added to a solution of 4-({5-[(1R)-2-amino-1-methylethoxy]quinazolin-4-yl}amino)-2-chlorophenol (obtained as described in Example 4.4, preparation of starting materials, 4.5 g, 13.08 mmol) in DMF (50 ml) and the mixture was stirred for 20 minutes. Potassium carbonate (7.23 g, 52.32 mmol), picolyl chloride hydrochloride (2.57 g, 15.70 mmol) and 1,4,7,10,13,16-hexaoxacyclooctadecane (18-crown-6/catalytic amount) were added and the reaction mixture was stirred vigorously for 16 hours. The reaction mixture was concentrated, the residue was stirred in water (250 ml) and the precipitated solid was filtered off. The solid was dissolved in 1M HCl (150 ml) and the solution washed with ethyl acetate (3×50 ml). The aqueous phase was basified with 2M NaOH and the resultant precipitate was filtered off to give 5-[(1R)-2-amino-1-methylethoxy]-N-[3-chloro-4-(pyridin-2-ylmethoxy)phenyl]quinazolin-4-amine (5.69 g, 100%); NMR spectrum (DMSO-d6) 1.39 (d, 3H), 2.88-3.05 (m, 2H), 4.74-4.86 (m, 1H), 5.28 (s, 2H), 7.14-7.25 (m, 2H), 7.30 (d, 1H), 7.33-7.40 (m, 1H), 7.57 (d, 1H), 7.65 (dd, 1H), 7.70 (dt, 1H), 7.87 (dt, 1H), 8.20 (d, 1H), 8.49 (s, 1H), 8.56-8.61 (m, 1H).

EXAMPLE 66

(2S)-N-{(2R)-2-[(4-{[3-Chloro-4-(pyridin-2-ylmethoxy)phenyl]amino}quinazolin-5-yl)oxy]propyl}-2,4-dihydroxybutanamide

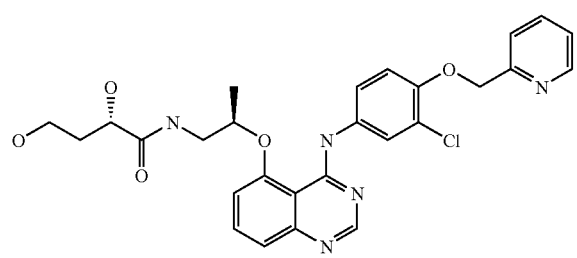

The procedure described in Example 63 was repeated using 5-[(1R)-2-amino-1-methylethoxy]-N-[3-chloro-4-(pyridin-2-ylmethoxy)phenyl]quinazolin-4-amine (obtained as described in Example 65, preparation of starting materials) and (S)-(−)-α-hydroxy-γ-butyrolactone to give the title compound in 78% yield; NMR spectrum (DMSO-d6) 1.31-1.47 (m, 4H), 1.64-1.77 (m, 1H), 3.33-3.50 (m, 3H), 3.71-3.84 (m, 1H), 3.90-4.00 (m, 1H), 4.32 (t, 1H), 4.87-4.98 (m, 1H), 5.29 (s, 2H), 5.48 (d, 1H), 7.18-7.27 (m, 2H), 7.28-7.40 (m, 2H), 7.54-7.64 (m, 2H), 7.87 (dt, 1H), 8.10-8.21 (m, 2H), 8.47 (s, 1H), 8.59 (d, 1H), 9.95 (s, 1H); Mass spectrum MH+ 537.9.

EXAMPLE 67

(2R)-N-{(2S)-2-[(4-{[3-Chloro-4-(pyridin-2-ylmethoxy)phenyl]amino}quinazolin-5-yl)oxy]propyl}-2,4-dihydroxybutanamide

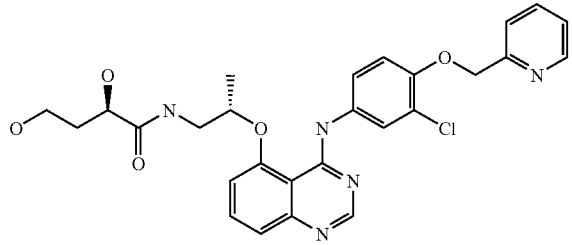

The procedure described in Example 63 was repeated using 5-[(1S)-2-amino-1-methylethoxy]-N-[3-chloro-4-(pyridin-2-ylmethoxy)phenyl]quinazolin-4-amine (obtained as described in Example 36, preparation of starting materials) and (R)-(+)-α-hydroxy-γ-butyrolactone to give the title compound in 62% yield; NMR spectrum (DMSO-d6) 1.31-1.47 (m, 4H), 1.64-1.77 (m, 1H), 3.33-3.50 (m, 3H), 3.71-3.84 (m, 1H), 3.90-4.00 (m, 1H), 4.32 (t, 1H), 4.87-4.98 (m, 1H), 5.29 (s, 2H), 5.48 (d, 1H), 7.18-7.27 (m, 2H), 7.28-7.40 (m, 2H), 7.54-7.64 (m, 2H), 7.87 (dt, 1H), 8.10-8.21 (m, 2H), 8.47 (s, 1H), 8.59 (d, 1H), 9.95 (s, 1H); Mass spectrum MH+ 537.9.

EXAMPLE 68

(2S)-N-{(2S)-2-[(4-{[3-Chloro-4-(pyridin-2-ylmethoxy)phenyl]amino}quinazolin-5-yl)oxy]propyl}-2,4-dihydroxybutanamide

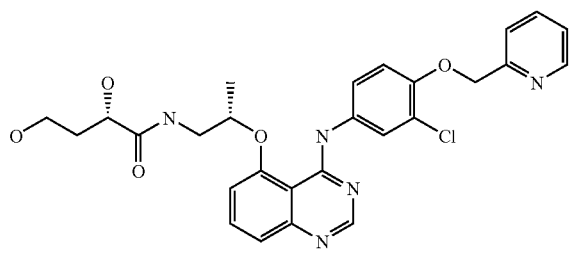

The procedure described in Example 63 was repeated using 5-[(1S)-2-amino-1-methylethoxy]-N-[3-chloro-4-(pyridin-2-ylmethoxy)phenyl]quinazolin-4-amine (obtained as described in Example 36, preparation of starting materials) and (S)-(−)-α-hydroxy-γ-butyrolactone to give the title compound in 60% yield; NMR spectrum (DMSO-d6) 1.39 (d, 3H), 1.43-1.57 (m, 3H), 1.71-1.86 (m, 1H), 3.33-3.53 (m, 3H), 3.65-3.79 (m, 1H), 3.88-4.00 (m, 1H), 4.36 (t, 1H), 4.85-4.96 (m, 1H), 5.29 (s, 2H), 5.45 (d, 1H), 7.24 (d, 2H), 7.28-7.41 (m, 2H), 7.59 (t, 2H), 7.71 (t, 1H), 7.87 (t, 1H), 8.10-8.21 (m, 2H), 8.48 (s, 1H), 8.59 (d, 1H), 9.99 (s, 1H); Mass spectrum MH+ 537.9.

EXAMPLE 69

(2S)-N-{(1R)-2-[(4-{[3-Chloro-4-(pyridin-2-yl-methoxy)phenyl]amino}quinazolin-5-yl)oxy]-1-methylethyl}-2,4-dihydroxybutanamide

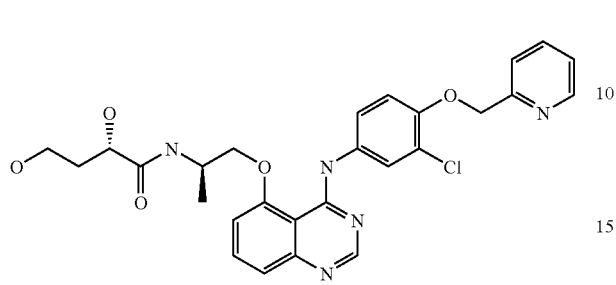

The procedure described in Example 63 was repeated using 5-{[(2R)-2-aminopropyl]oxy}-N-[3-chloro-4-(pyridin-2-ylmethoxy)phenyl]quinazolin-4-amine (obtained as described in Example 2.4, preparation of starting materials) and (S)-(−)-α-hydroxy-γ-butyrolactone to give the title compound in 79% yield; NMR spectrum (DMSO-d6 400 MHz) 1.24 (d, 3H), 1.30-1.41 (m, 1H), 1.63-1.74 (m, 1H), 3.32-3.46 (m, 2H), 3.91-3.98 (m, 1H), 4.24 (dd, 1H), 4.31 (t, 1H), 4.38 (t, 1H), 4.47-4.57 (m, 1H), 5.30 (s, 2H), 5.43 (d, 1H), 7.16 (d, 1H), 7.23 (d, 1H), 7.31-7.41 (m, 2H), 7.56 (dd, 1H), 7.60 (d, 1H), 7.73 (t, 1H), 7.89 (dt, 1H), 7.95 (d, 1H), 8.06 (d, 1H), 8.48 (s, 1H), 8.61 (d, 1H) 9.79 (s, 1H); Mass spectrum MH+ 538.0.

EXAMPLE 70

(2R)-N-{(1R)-2-[(4-{[3-Chloro-4-(pyridin-2-yl-methoxy)phenyl]amino}quinazolin-5-yl)oxy]-1-methylethyl}-2,4-dihydroxybutanamide

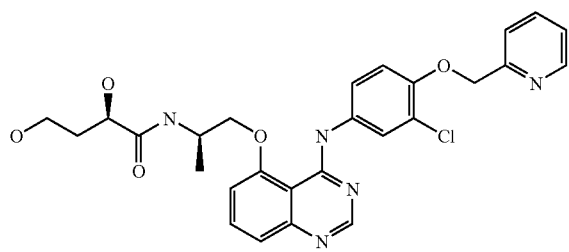

The procedure described in Example 63 was repeated using 5-{[(2R)-2-aminopropyl]oxy}-N-[3-chloro-4-(pyridin-2-ylmethoxy)phenyl]quinazolin-4-amine (obtained as described in Example 2.4, preparation of starting materials) and (R)-(+)-α-hydroxy-γ-butyrolactone to give the title compound in 77% yield; NMR spectrum (DMSO-d6) 1.22 (d, 3H), 1.46-1.60 (m, 1H), 1.72-1.86 (m, 1H), 3.38-3.51 (m, 2H), 3.83-3.93 (m, 1H), 4.20-4.40 (m, 3H), 4.42-4.55 (m, 1H), 5.29 (s, 2H), 5.39 (d, 1H), 7.14 (d, 1H), 7.21 (d, 1H), 7.30-7.40 (m, 2H), 7.47-7.55 (m, 1H), 7.58 (d, 1H), 7.72 (t, 1H), 7.87 (t, 1H), 7.97 (d, 1H), 8.01 (s, 1H), 8.46 (s, 1H), 8.59 (d, 1H), 9.74 (s, 1H); Mass spectrum MH+ 538.0.

EXAMPLE 71

(2R)-N-{2-[(4-{[3-Chloro-4-(1,3-thiazol-4-yl-methoxy)phenyl]amino}quinazolin-5-yl)oxy]ethyl}-2,4-dihydroxybutanamide

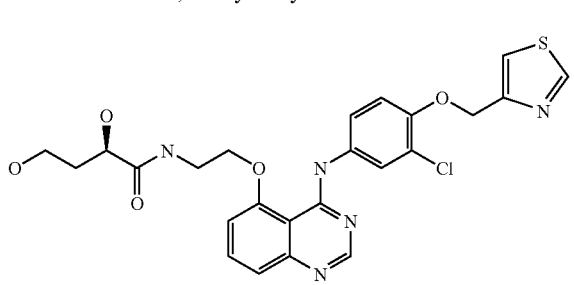

The procedure described in Example 63 was repeated using 5-(2-aminoethoxy)-N-[3-chloro-4-(1,3-thiazol-4-yl-methoxy)phenyl]quinazolin-4-amine and (R)-(+)-α-hydroxy-γ-butyrolactone to give the title compound in 69% yield; NMR spectrum (DMSO-d6 400 MHz) 1.44-1.55 (m, 1H), 1.73-1.85 (m, 1H), 3.41-3.52 (m, 2H), 3.65-3.77 (m, 2H), 3.93-4.02 (m, 1H), 4.31-4.48 (m, 3H), 5.38 (s, 2H), 5.50 (d, 1H), 7.17 (d, 1H), 7.33 (t, 2H), (7.60 (dd, 1H), 7.74 (t, 1H), 7.83 (s, 1H), 8.02 (s, 1H), 8.20 (t, 1H), 8.48 (s, 1H), 9.17 (s, 1H), 9.85 (s, 1H); Mass spectrum MH+ 529.9.

The 5-(2-aminoethoxy)-N-[3-chloro-4-(1,3-thiazol-4-yl-methoxy)phenyl]quinazolin-4-amine used as starting material was prepared as follows:

The procedure described in Example 3 (preparation of starting materials) was repeated using 2-chloro-4-[(5-fluoro-quinazolin-4-yl)amino]phenol (obtained as described in Example 4.5, preparation of starting materials) and ethanolamine to give 4-{[5-(2-aminoethoxy)quinazolin-4-yl]amino}-2-chlorophenol in 84% yield. NMR spectrum (DMSO-d6) 3.12 (t, 2H), 4.27 (t, 2H), 6.96 (d, 1H), 7.11 (d, 1H), 7.31 (d, 1H), 7.53 (dd, 1H), 8.08 (d, 1H), 8.47 (s, 1H); Mass spectrum MH+ 331.0.

The procedure described in Example 65 (preparation of starting materials) was repeated using 4-{[5-(2-aminoethoxy)quinazolin-4-yl]amino}-2-chlorophenol and 4-(chloromethyl)-1,3-thiazole hydrochloride to give 5-(2-aminoethoxy)-N-[3-chloro-4-(1,3-thiazol-4-ylmethoxy)phenyl]quinazolin-4-amine in 91% yield; NMR spectrum (DMSO-d6 400 MHz) 3.02-3.19 (bs, 2H), 4.22-4.36 (m, 2H), 5.33 (s, 2H), 7.14 (d, 1H), 7.27-7.40 (m, 2H), 7.67-7.86 (m, 3H), 8.23 (s, 1H), 8.52 (s, 1H), 9.15 (s, 1H) (3 exchangeables); Mass spectrum MH+ 427.9.

EXAMPLE 72

(2S)-N-{2-[(4-{[3-Chloro-4-(1,3-thiazol-4-yl-methoxy)phenyl]amino}quinazolin-5-yl)oxy]ethyl}-2,4-dihydroxybutanamide

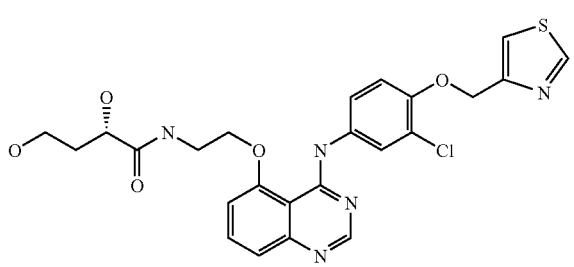

The procedure described in Example 63 was repeated using 5-(2-aminoethoxy)-N-[3-chloro-4-(1,3-thiazol-4-ylmethoxy)phenyl]quinazolin-4-amine (obtained as described in Example 71, preparation of starting materials) and (S)-(−)-α-hydroxy-γ-butyrolactone to give the title compound in 66% yield; NMR spectrum (DMSO-d6 400 MHz) 1.44-1.55 (m, 1H), 1.73-1.85 (m, 1H), 3.41-3.52 (m, 2H), 3.65-3.77 (m, 2H), 3.93-4.02 (m, 1H), 4.31-4.48 (m, 3H), 5.38 (s, 2H), 5.50 (d, 1H), 7.17 (d, 1H), 7.33 (t, 2H), (7.60 (dd, 1H), 7.74 (t, 1H), 7.83 (s, 1H), 8.02 (s, 1H), 8.20 (t, 1H), 8.48 (s, 1H), 9.17 (s, 1H), 9.85 (s, 1H); Mass spectrum MH+ 529.9.

EXAMPLE 73

(2R)-N-{(1R)-2-[(4-{[3-Chloro-4-(1,3-thiazol-4-ylmethoxy)phenyl]amino}quinazolin-5-yl)oxy]-1-methylethyl}-2,4-dihydroxybutanamide

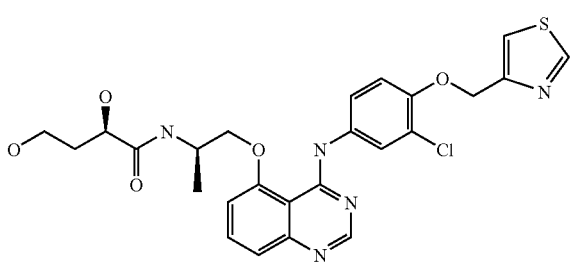

The procedure described in Example 63 was repeated using 5-{[(2R)-2-aminopropyl]oxy}-N-[3-chloro-4-(1,3-thiazol-4-ylmethoxy)phenyl]quinazolin-4-amine and (R)-(+)-α-hydroxy-γ-butyrolactone to give the title compound in 73% yield; NMR spectrum (DMSO-d6) 1.22 (d, 3H), 1.46-1.61 (m, 1H), 1.72-1.87 (m, 1H), 3.40-3.54 (m, 2H), 3.84-3.97 (m, 1H), 4.19-4.41 (m, 3H), 4.42-4.58 (m, 1H), 5.35 (s, 2H), 5.40 (d, 1H), 7.14 (d, 1H), 7.25-7.38 (m, 2H), 7.53 (dd, 1H), 7.72 (t, 1H), 7.80 (d, 1H), 7.92-8.05 (m, 2H), 8.47 (s, 1H), 9.14 (d, 1H), 9.75 (s, 1H); Mass spectrum MH+ 543.9.

The 5-{[(2R)-2-aminopropyl]oxy}-N-[3-chloro-4-(1,3-thiazol-4-ylmethoxy)phenyl]quinazolin-4-amine used as starting material was prepared as follows:

The procedure described in Example 3 (preparation of starting materials) was repeated using 2-chloro-4-[(5-fluoroquinazolin-4-yl)amino]phenol (obtained as described in Example 4.5, preparation of starting materials) and (2R)-2-aminopropan-1-ol to give 4-[(5-{[(2R)-2-aminopropyl]oxy}quinazolin-4-yl)amino]-2-chlorophenol in 100% yield; NMR spectrum (DMSO-d6) 1.16 (d, 3H), 3.29-3.44 (m, 1H), 3.98 (dd, 1H), 4.22 (dd, 1H), 6.96 (d, 1H), 7.09 (d, 1H), 7.30 (d, 1H), 7.58 (dd, 1H), 7.69 (t, 1H), 8.10 (d, 1H), 8.47 (s, 1H) (4 exchangeables); Mass spectrum MH+ 344.9.

The procedure described in Example 65 (preparation of starting materials) was repeated using 4-[(5-{[(2R)-2-aminopropyl]oxy}quinazolin-4-yl)amino]-2-chlorophenol and 4-(chloromethyl)-1,3-thiazole hydrochloride give 5-{[(2R)-2-aminopropyl]oxy}-N-[3-chloro-4-(1,3-thiazol-4-ylmethoxy)phenyl]quinazolin-4-amine in 65% yield; NMR spectrum (DMSO-d6) 1.17 (d, 3H), 3.33-3.45 (m, 1H), 4.00 (dd, 1H)), 4.24 (dd, 1H), 5.32 (s, 2H), 7.11 (d, 1H), 7.30 (d, 1H), 7.33 (d, 1H), 7.67-7.82 (m, 3H), 8.23 (d, 1H), 8.51 (s, 1H), 9.14 (d, 1H); Mass spectrum MH+ 441.9.

EXAMPLE 74

(2S)-N-{(1R)-2-[(4-{[3-Chloro-4-(1,3-thiazol-4-ylmethoxy)phenyl]amino}quinazolin-5-yl)oxy]-1-methylethyl}-2,4-dihydroxybutanamide

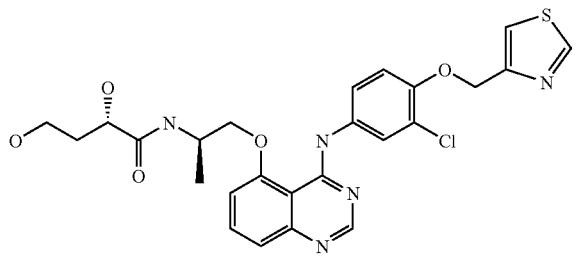

The procedure described in Example 63 was repeated using 5-{[(2R)-2-aminopropyl]oxy}-N-[3-chloro-4-(1,3-thiazol-4-ylmethoxy)phenyl]quinazolin-4-amine (obtained as described in Example 73, preparation of starting materials) and (S)-(−)-α-hydroxy-γ-butyrolactone to give the title compound in 58% yield; NMR spectrum (DMSO-d6) 1.23 (d, 3H), 1.27-1.40 (m, 1H), 1.60-1.62 (m, 1H), 3.33-3.46 (m, 2H), 3.87-3.97 (m, 1H), 4.19-4.41 (m, 3H), 4.42-4.58 (m, 1H), 5.35 (s, 2H), 5.40 (d, 1H), 7.14 (d, 1H), 7.25-7.38 (m, 2H), 7.53 (dd, 1H), 7.72 (t, 1H), 7.80 (d, 1H), 7.92-8.05 (m, 2H), 8.47 (s, 1H), 9.14 (d, 1H), 9.75 (s, 1H); Mass spectrum MH+ 543.9.

EXAMPLE 75

N-Methyl-N-{2-[(4-{[3-methyl-4-(pyridin-2-ylmethoxy)phenyl]amino}quinazolin-5-yl)oxy]ethyl}acetamide

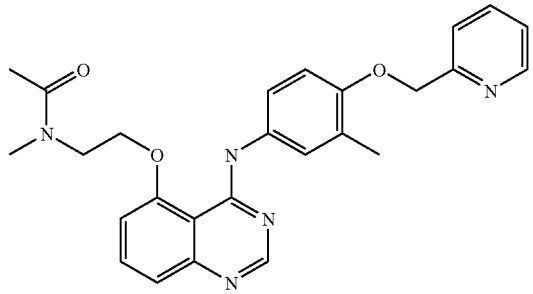

The procedure described in Example 3 was repeated using 2-(chloromethyl)pyridine and N-[2-({4-[(4-hydroxy-3-methylphenyl)amino]quinazolin-5-yl}oxy)ethyl]-N-methylacetamide to give the title compound as a white solid in 11% yield; NMR spectrum (DMSO-d6 373K) 1.94 (s, 3H), 2.28 (s, 3H), 3.00 (s, 3H), 3.88 (t, 2H), 4.46 (m, 2H), 5.20 (s, 2H), 7.01 (d, 1H), 7.16 (d, 1H), 7.34 (m, 2H), 7.51 (m, 2H), 7.55 (d, 1H), 7.68 (t, 1H), 7.83 (td, 1H), 8.41 (s, 1H), 8.58 (d, 1H), 9.63 (s, 1H); Mass spectrum MH+ 458.

The N-[2-({4-[(4-hydroxy-3-methylphenyl)amino]quinazolin-5-yl}oxy)ethyl]-N-methylacetamide used as starting material was prepared as follows:

The procedure described in Example 3 (preparation of starting materials) was repeated using acetic acid and 2-methyl-4-({5-[2-(methylamino)ethoxy]quinazolin-4-yl}amino)

phenol (obtained as described in Example 3, preparation of starting materials) to give N-[2-({4-[(4-hydroxy-3-methylphenyl)amino]quinazolin-5-yl}oxy)ethyl]-N-methylacetamide as a light brown solid in 100% yield; NMR spectrum (DMSO-d6) 1.90 (s, 3H), 2.16 (s, 3H), 3.02 (s, 3H), 3.85 (t, 2H), 4.45 (t, 2H), 6.82 (d, 1H), 7.18 (dd, 1H), 7.25 (d, 1H), 7.34 (m, 2H), 7.92 (t, 1H), 8.65 (s, 1H), 9.45 (s, 1H), 10.52 (s, 1H); Mass spectrum MH+ 367.

EXAMPLE 76

N-Methyl-N-{2-[(4-{[3-methyl-4-(1,3-thiazol-4-ylmethoxy)phenyl]amino}quinazolin-5-yl)oxy]ethyl}acetamide

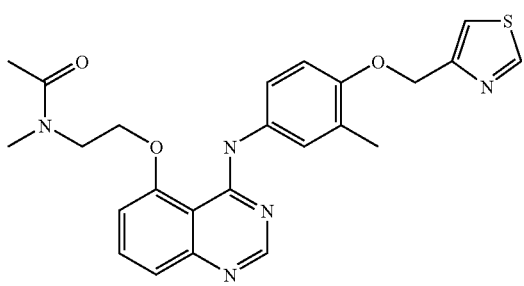

The procedure described in Example 3 was repeated using 4-(chloromethyl)-1,3-thiazole and N-[2-({4-[(4-hydroxy-3-methylphenyl)amino]quinazolin-5-yl}oxy)ethyl]-N-methylacetamide (obtained as described in Example 75, preparation of starting materials) to give the title compound as an off-white solid in 5% yield; NMR spectrum (DMSO-d6 373K) 1.94 (s, 3H), 2.24 (s, 3H), 2.99 (s, 3H), 3.87 (t, 2H), 4.46 (m, 2H), 5.25 (s, 2H), 7.08 (d, 1H), 7.17 (d, 1H), 7.35 (d, 1H), 7.47 (d, 1H), 7.54 (dd, 1H), 7.70 (m, 2H), 8.41 (s, 1H), 9.07 (d, 1H), 9.63 (s, 1H); Mass spectrum MH+ 464.

EXAMPLE 77

N-Methyl-N-(2-{[4-({3-methyl-4-[(5-methylisoxazol-3-yl)methoxy]phenyl}amino) quinazolin-5-yl]oxy}ethyl)acetamide

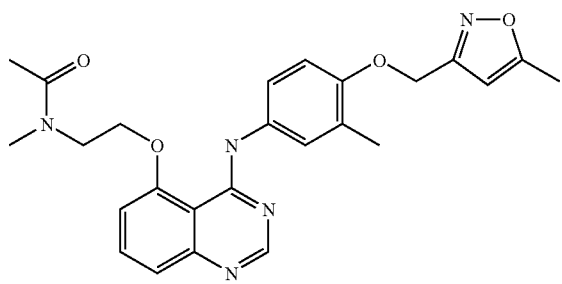

The procedure described in Example 3 was repeated using 3-(chloromethyl)-5-methylisoxazole and N-[2-({4-[(4-hydroxy-3-methylphenyl)amino]quinazolin-5-yl}oxy)ethyl]-N-methylacetamide (obtained as described in Example 75, preparation of starting materials) to give the title compound as a white solid in 14% yield; NMR spectrum (DMSO-d6 373K) 1.95 (s, 3H), 2.23 (s, 3H), 2.43 (s, 3H), 3.57 (s, 3H), 3.88 (t, 2H), 4.47 (m, 2H), 5.15 (s, 2H), 6.29 (s, 1H), 7.05 (d, 1H), 7.15 (d, 1H), 7.34 (d, 1H), 7.48 (d, 1H), 7.54 (dd, 1H), 7.69 (t, 1H), 8.42 (s, 1H), 9.64 (s, 1H); Mass spectrum MH+ 462.

EXAMPLE 78

2-Hydroxy-N-methyl-N-{2-[(4-{[3-methyl-4-(1,3-thiazol-2-ylmethoxy)phenyl]amino}quinazolin-5-yl)oxy]ethyl}acetamide

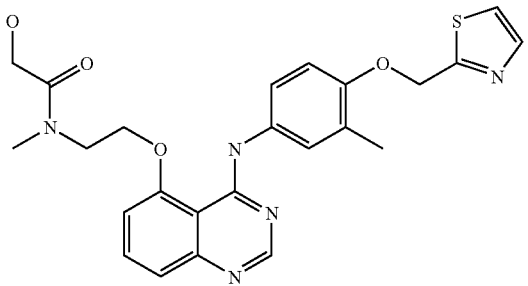

The procedure described in Example 3 was repeated using 2-(chloromethyl)-1,3-thiazole and 2-hydroxy-N-[2-({4-[(4-hydroxy-3-methylphenyl)amino]quinazolin-5-yl}oxy) ethyl]-N-methylacetamide (obtained as described in Example 3, preparation of starting materials) to give the title compound as a white solid in 38% yield; NMR spectrum (DMSO-d6 373K) 2.27 (s, 3H), 2.98 (s, 3H), 3.91 (t, 2H), 4.07 (s, 2H), 4.47 (t, 2H), 5.44 (s, 2H), 7.09 (d, 1H), 7.16 (d, 1H), 7.34 (d, 1H), 7.54 (m, 2H), 7.67 (t, 1H), 7.70 (d, 1H), 7.83 (d, 1H), 8.41 (s, 1H), 9.63 (s, 1H); Mass spectrum MH+ 480.

EXAMPLE 79

2-Hydroxy-N-{2-[(4-{[3-methyl-4-(pyridin-2-ylmethoxy)phenyl]amino}quinazolin-5-yl)oxy]ethyl}acetamide

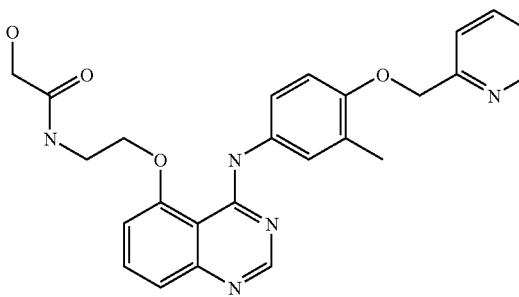

The procedure described in Example 3 was repeated using 2-(chloromethyl)pyridine and 2-hydroxy-N-[2-({4-[(4-hydroxy-3-methylphenyl)amino]quinazolin-5-yl}oxy)ethyl] acetamide to give the title compound as a yellow solid in 27% yield; NMR spectrum (DMSO-d6) 2.27 (s, 3H), 3.71 (q, 2H), 3.77 (d, 2H), 4.38 (t, 2H), 5.20 (s, 2H), 5.49 (t, 1H), 6.98 (d, 1H), 7.14 (d, 1H), 7.31 (d, 1H), 7.35 (dd, 1H), 7.45 (d, 1H), 7.56 (m, 2H), 7.68 (t, 1H), 7.85 (td, 1H), 8.17 (t, 1H), 8.41 (s, 1H), 8.57 (d, 1H), 9.75 (s, 1H); Mass spectrum MH+ 460.

The 2-hydroxy-N-[2-({4-[(4-hydroxy-3-methylphenyl)amino]quinazolin-5-yl}oxy)ethyl]acetamide used as starting material was prepared as follows:

The procedure described in Example 3 (preparation of starting materials) was repeated using ethanolamine and 4-[(5-fluoroquinazolin-4-yl)amino]-2-methylphenol (obtained as described in Example 3, preparation of starting materials) to give 4-{[5-(2-aminoethoxy)quinazolin-4-yl]amino}-2-methylphenol as a grey solid in 23% yield; NMR spectrum (DMSO-d6) 2.14 (s, 3H), 3.09 (d, 2H), 3.28 (s, 2H), 4.25 (t, 2H), 6.77 (d, 1H), 7.08 (d, 1H), 7.28 (d, 1H), 7.46 (dd, 1H), 7.55 (d, 1H), 7.66 (t, 1H), 8.40 (s, 1H), 10.31 (s, 1H); Mass spectrum MH+ 311.

The procedure described in Example 3 (preparation of starting materials) was repeated using glycolic acid and 4-{[5-(2-aminoethoxy)quinazolin-4-yl]amino}-2-methylphenol to give 2-hydroxy-N-[2-({4-[(4-hydroxy-3-methylphenyl)amino]quinazolin-5-yl}oxy)ethyl]acetamide as a light brown solid in 58% yield; NMR spectrum (DMSO-d6) 2.16 (s, 3H), 3.69 (q, 2H), 3.76 (d, 2H), 4.43 (t, 2H), 6.82 (d, 1H), 7.30 (m, 4H), 7.90 (t, 1H), 8.20 (t, 1H), 8.66 (s, 1H), 9.42 (s, 1H), 10.55 (s, 1H); Mass spectrum MH+ 369.

EXAMPLE 80

2-Hydroxy-N-{2-[(4-{[3-methyl-4-(1,3-thiazol-4-ylmethoxy)phenyl]amino}quinazolin-5-yl)oxy]ethyl}acetamide

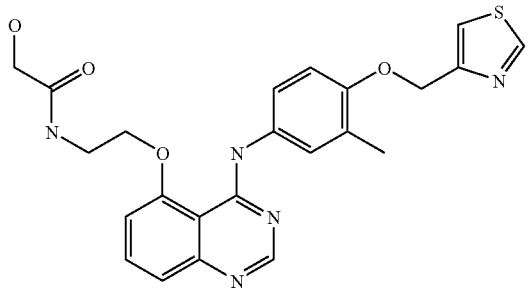

The procedure described in Example 3 was repeated using 4-(chloromethyl)-1,3-thiazole and 2-hydroxy-N-[2-({4-[(4-hydroxy-3-methylphenyl)amino]quinazolin-5-yl}oxy)ethyl]acetamide (obtained as described in Example 79, preparation of starting materials) to give the title compound as a yellow solid in 21% yield; NMR spectrum (DMSO-d6) 2.20 (s, 3H), 3.71 (q, 2H), 3.77 (d, 2H), 4.38 (t, 2H), 5.23 (s, 2H), 5.49 (t, 1H), 7.08 (d, 1H), 7.13 (d, 1H), 7.32 (d, 1H), 7.44 (d, 1H), 7.57 (dd, 1H), 7.69 (t, 1H), 7.77 (d, 1H), 8.17 (t, 1H), 8.42 (s, 1H), 9.14 (d, 1H), 9.77 (s, 1H); Mass spectrum MH+ 466.

EXAMPLE 81

N-{2-[(4-{[3-Chloro-4-(pyridin-2-ylmethoxy)phenyl]amino}quinazolin-5-yl)oxy]-1,1-dimethylethyl}-2-hydroxyacetamide

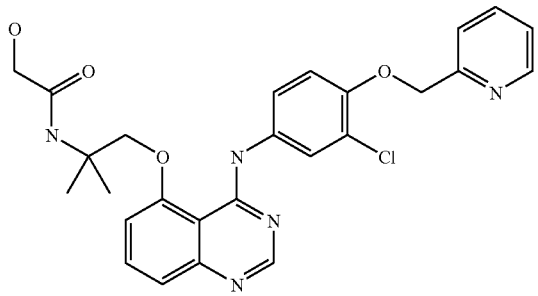

The procedure described in Example 3 was repeated using 2-(chloromethyl)pyridine and 2-hydroxy-N-[2-({4-[(4-hydroxy-3-methylphenyl)amino]quinazolin-5-yl}oxy)-1,1-dimethylethyl]acetamide to give the title compound as a white solid in 16% yield; NMR spectrum (DMSO-d6) 1.46 (s, 6H), 3.72 (d, 2H), 4.42 (s, 2H), 5.27 (s, 2H), 5.34 (t, 1H), 7.16 (d, 1H), 7.24 (d, 1H), 7.37 (m, 2H), 7.50 (m, 2H), 7.58 (d, 1H), 7.73 (t, 1H), 7.87 (td, 1H), 8.06 (d, 1H), 8.50 (s, 1H), 8.59 (d, 1H), 9.83 (s, 1H); Mass spectrum MH+ 508.

The 2-hydroxy-N-[2-({4-[(4-hydroxy-3-methylphenyl)amino]quinazolin-5-yl}oxy)-1,1-dimethylethyl]acetamide used as starting material was prepared as follows:

The procedure described in Example 3 (preparation of starting materials) was repeated using 2-amino-2-methylpropan-1-ol and 4-[(5-fluoroquinazolin-4-yl)amino]-2-methylphenol (obtained as described in Example 3, preparation of starting materials) to give 4-{[5-(2-amino-2-methylpropoxy)quinazolin-4-yl]amino}-2-methylphenol as a white solid in 78% yield; NMR spectrum (DMSO-d6) 1.34 (s, 6H), 4.23 (s, 2H), 6.97 (d, 1H), 7.18 (d, 1H), 7.35 (d, 1H), 7.52 (dd, 1H), 7.73 (t, 1H), 7.96 (d, 1H), 8.46 (s, 1H), 10.50 (s, 1H); Mass spectrum MH+ 360.

The procedure described in Example 3 (preparation of starting materials) was repeated using glycolic acid and 4-{[5-(2-amino-2-methylpropoxy)quinazolin-4-yl]amino}-2-methylphenol to give 2-hydroxy-N-[2-({4-[(4-hydroxy-3-methylphenyl)amino]quinazolin-5-yl}oxy)-1,1-dimethylethyl]acetamide as a light brown solid in 53% yield; NMR spectrum (DMSO-d6) 1.47 (s, 6H), 3.69 (d, 2H), 4.47 (s, 2H), 7.04 (d, 1H), 7.38 (m, 3H), 7.78 (d, 1H), 7.96 (t, 1H), 8.18 (t, 1H), 8.80 (s, 1H), 10.40 (s, 1H), 10.67 (s, 1H); Mass spectrum MH+ 417.

EXAMPLE 82

2-Hydroxy-N-{(2R)-2-[(4-{[3-methyl-4-(pyridin-2-ylmethoxy)phenyl]amino}quinazolin-5-yl)oxy]propyl}acetamide

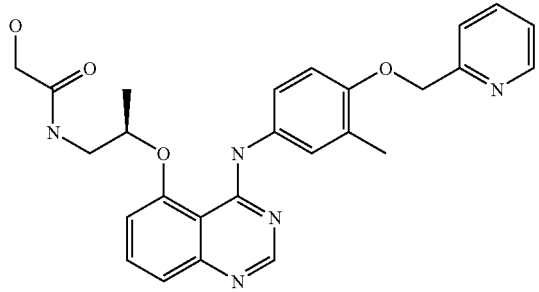

The procedure described in Example 3 was repeated using 2-(chloromethyl)pyridine and 2-hydroxy-N-[(2R)-2-({4-[(4-hydroxy-3-methylphenyl)amino]quinazolin-5-yl}oxy)propyl]acetamide to give the title compound as a white solid in 29% yield; NMR spectrum (DMSO-d6) 1.40 (d, 3H), 2.27 (s, 3H), 3.43 (dt, 1H), 3.72 (dt, 1H), 3.80 (d, 2H), 4.94 (m, 1H), 5.20 (s, 2H), 5.46 (t, 1H), 7.00 (d, 1H), 7.21 (d, 1H), 7.30 (d, 1H), 7.34 (dd, 1H), 7.56 (m, 3H), 7.68 (t, 1H), 7.85 (td, 1H), 8.16 (t, 1H), 8.43 (s, 1H), 8.58 (d, 1H), 9.94 (s, 1H); Mass spectrum MH+ 474.

The 2-hydroxy-N-[(2R)-2-({4-[(4-hydroxy-3-methylphenyl)amino]quinazolin-5-yl}oxy)propyl]acetamide used as starting material was prepared as follows:

The procedure described in Example 3 (preparation of starting materials) was repeated using (R)-(−)-1-amino-propan-2-ol and 4-[(5-fluoroquinazolin-4-yl)amino]-2-methylphenol (obtained as described in Example 3, preparation of starting materials) to give 4-({5-[(1R)-2-amino-1-methylethoxy]quinazolin-4-yl}amino)-2-methylphenol as a brown solid in 65% yield; NMR spectrum (DMSO-d6) 1.39 (d, 3H), 2.16 (s, 3H), 2.96 (m, 2H), 3.30 (s, 2H), 4.96 (m, 1H), 6.77 (d, 1H), 7.14 (d, 1H), 7.25 (d, 1H), 7.44 (dd, 1H), 7.51 (d, 1H), 7.67 (t, 1H), 8.39 (s, 1H), 9.16 (s, 1H), 10.50 (s, 1H); Mass spectrum MH+ 325.

The procedure described in Example 3 (preparation of starting materials) was repeated using glycolic acid and 4-({5-[(1R)-2-amino-1-methylethoxy]quinazolin-4-yl}amino)-2-methylphenol to give 2-hydroxy-N-[(2R)-2-({4-[(4-hydroxy-3-methylphenyl)amino]quinazolin-5-yl}oxy)propyl]acetamide as a dark brown solid in 59% yield; NMR spectrum (DMSO-d6) 1.41 (d, 3H), 2.17 (s, 3H), 3.43 (dt, 1H), 3.75 (dt, 1H), 3.78 (s, 2H), 5.01 (m, 1H), 6.84 (d, 1H), 7.30 (d, 1H), 7.32 (dd, 1H), 7.39 (d, 1H), 7.46 (d, 1H), 7.95 (t, 1H), 8.22 (t, 1H), 8.75 (s, 1H), 9.54 (d, 1H), 10.78 (s, 1H); Mass spectrum MH+ 383.

EXAMPLE 83

2-Hydroxy-N-{(2R)-2-[(4-{[3-methyl-4-(1,3-thiazol-4-ylmethoxy)phenyl]amino}quinazolin-5-yl)oxy]propyl}acetamide

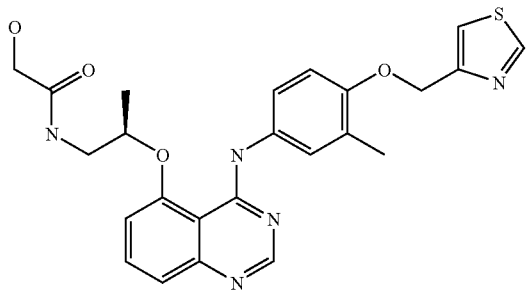

The procedure described in Example 3 was repeated using 4-(chloromethyl)-1,3-thiazole and 2-hydroxy-N-[(2R)-2-({4-[(4-hydroxy-3-methylphenyl)amino]quinazolin-5-yl}oxy)propyl]acetamide (obtained as described in Example 82, preparation of starting materials) to give the title compound as a white solid in 13% yield; NMR spectrum (DMSO-d6) 1.39 (d, 3H), 2.21 (s, 3H), 3.42 (dt, 1H), 3.71 (dt, 1H), 3.79 (d, 2H), 4.95 (m, 1H), 5.24 (s, 2H), 5.48 (t, 1H), 7.09 (d, 1H), 7.23 (d, 1H), 7.29 (d, 1H), 7.54 (d, 1H), 7.62 (dd, 1H), 7.68 (t, 1H), 7.77 (d, 1H), 8.16 (t, 1H), 8.44 (s, 1H), 9.14 (d, 1H), 9.95 (s, 1H); Mass spectrum MH+ 480.

EXAMPLE 84

N-((2R)-2-{[4-({4-[(3-Fluorobenzyl)oxy]-3-methylphenyl}amino)quinazolin-5-yl]oxy}propyl)-2-hydroxyacetamide

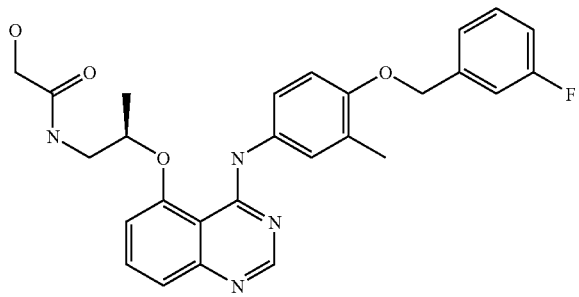

The procedure described in Example 3 was repeated using 1-(chloromethyl)-3-fluorobenzene and 2-hydroxy-N-[(2R)-2-({4-[(4-hydroxy-3-methylphenyl)amino]quinazolin-5-yl}oxy)propyl]acetamide (obtained as described in Example 82, preparation of starting materials) to give the title compound as a light yellow solid in 25% yield; NMR spectrum (DMSO-d6) 1.39 (d, 3H), 2.25 (s, 3H), 3.42 (dt, 1H), 3.72 (dt, 1H), 3.81 (d, 2H), 4.94 (m, 1H), 5.17 (s, 2H), 5.47 (t, 1H), 6.99 (d, 1H), 7.16 (td, 1H), 7.22 (d, 1H), 7.30 (m, 3H), 7.43 (m, 1H), 7.56 (d, 1H), 7.61 (dd, 1H), 7.68 (t, 1H), 8.16 (t, 1H), 8.43 (s, 1H), 9.94 (s, 1H); Mass spectrum MH+ 491.

EXAMPLE 85

2-Hydroxy-N-{(2R)-2-[(4-{[3-methyl-4-(1,3-thiazol-2-ylmethoxy)phenyl]amino}quinazolin-5-yl)oxy]propyl}acetamide

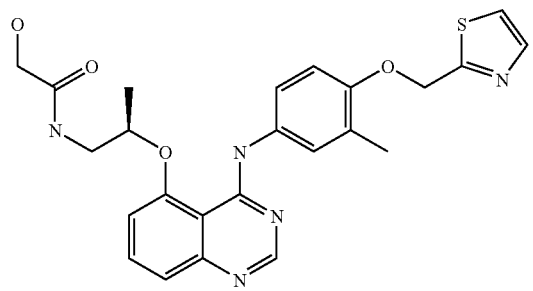

The procedure described in Example 3 was repeated using 2-(chloromethyl)-1,3-thiazole and 2-hydroxy-N-[(2R)-2-({4-[(4-hydroxy-3-methylphenyl)amino]quinazolin-5-yl}oxy)propyl]acetamide (obtained as described in Example 82, preparation of starting materials) to give the title compound as a light brown solid in 31% yield; NMR spectrum (DMSO-d6) 1.39 (d, 3H), 2.25 (s, 3H), 3.42 (dt, 1H), 3.73 (m, 1H), 3.79 (d, 2H), 4.94 (m, 1H), 5.44 (s, 2H), 5.47 (t, 1H), 7.09 (d, 1H), 7.23 (d, 1H), 7.30 (d, 1H), 7.58 (d, 1H), 7.63 (dd, 1H), 7.69 (t, 1H), 7.77 (d, 1H), 7.84 (d, 1H), 8.16 (t, 1H), 8.43 (s, 1H), 9.96 (s, 1H); Mass spectrum MH+ 480.

EXAMPLE 86

N-{(2R)-2-[(4-{[3-Methyl-4-(pyridin-2-ylmethoxy)phenyl]amino}quinazolin-5-yl)oxy]propyl}acetamide

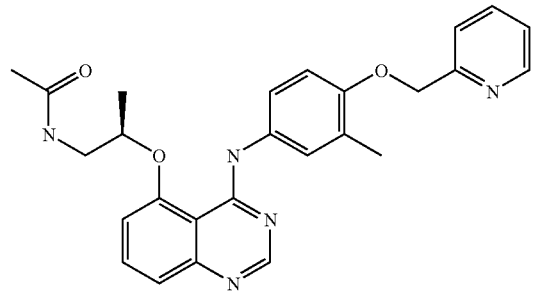

The procedure described in Example 3 was repeated using 2-(chloromethyl)pyridine and N-[(2R)-2-({4-[(4-hydroxy-3-methylphenyl)amino]quinazolin-5-yl}oxy)propyl]acetamide to give the title compound as a white solid in 43% yield; NMR spectrum (DMSO-d6) 1.41 (d, 3H), 1.77 (s, 3H), 2.27 (s, 3H), 3.41 (dt, 1H), 3.58 (dt, 1H), 4.87 (m, 1H), 5.20 (s, 2H), 7.01 (d, 1H), 7.22 (d, 1H), 7.29 (d, 1H), 7.35 (dd, 1H), 7.55

(m, 2H), 7.58 (dd, 1H), 7.69 (t, 1H), 7.85 (td, 1H), 8.23 (t, 1H), 8.45 (s, 1H), 8.58 (d, 1H), 9.97 (s, 1H); Mass spectrum MH+ 458.

The N-[(2R)-2-({4-[(4-hydroxy-3-methylphenyl)amino] quinazolin-5-yl}oxy)propyl]acetamide used as starting material was prepared as follows:

The procedure described in Example 3 (preparation of starting materials) was repeated using acetic acid and 4-({5-[(1R)-2-amino-1-methylethoxy]quinazolin-4-yl}amino)-2-methylphenol (obtained as described in Example 82, preparation of starting materials) to give N-[(2R)-2-({4-[(4-hydroxy-3-methylphenyl)amino]quinazolin-5-yl}oxy) propyl]acetamide as a ginger solid in 90% yield; NMR spectrum (DMSO-d6) 1.41 (d, 3H), 1.76 (s, 3H), 2.17 (s, 3H), 3.41 (dt, 1H), 3.62 (dt, 1H), 4.96 (m, 1H), 6.85 (d, 1H), 7.31 (d, 1H), 7.36 (m, 2H), 7.49 (d, 1H), 7.96 (t, 1H), 8.24 (t, 1H), 8.77 (s, 1H), 9.57 (s, 1H), 10.77 (s, 1H); Mass spectrum MH+ 367.

EXAMPLE 87

N-{(2R)-2-[(4-{[3-Methyl-4-(1,3-thiazol-4-yl-methoxy)phenyl]amino}quinazolin-5-yl)oxy]propyl}acetamide

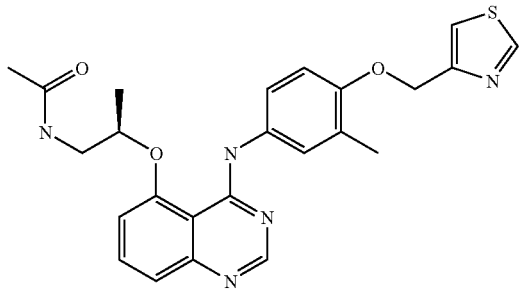

The procedure described in Example 3 was repeated using 4-(chloromethyl)-1,3-thiazole and N-[(2R)-2-({4-[(4-hydroxy-3-methylphenyl)amino]quinazolin-5-yl}oxy)propyl] acetamide (obtained as described in Example 86, preparation of starting materials) to give the title compound as a white solid in 20% yield; NMR spectrum (DMSO-d6) 1.41 (d, 3H), 1.78 (s, 3H), 2.23 (s, 3H), 3.41 (dt, 1H), 3.58 (dt, 1H), 4.87 (m, 1H), 5.25 (s, 2H), 7.11 (d, 1H), 7.21 (d, 1H), 7.29 (d, 1H), 7.53 (d, 1H), 7.63 (dd, 1H), 7.69 (t, 1H), 7.76 (d, 1H), 8.23 (t, 1H), 8.44 (s, 1H), 9.14 (d, 1H), 9.96 (s, 1H); Mass spectrum MH+ 464.

EXAMPLE 88

N-((2R)-2-{[4-({4-[(3-Fluorobenzyl)oxy]-3-methylphenyl}amino)quinazolin-5-yl]oxy}propyl)acetamide

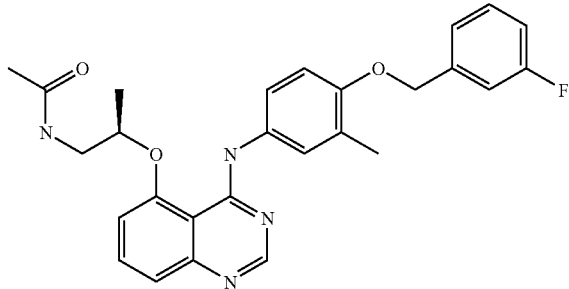

The procedure described in Example 3 was repeated using 1-(chloromethyl)-3-fluorobenzene and N-[(2R)-2-({4-[(4-hydroxy-3-methylphenyl)amino]quinazolin-5-yl}oxy)propyl]acetamide (obtained as described in Example 86, preparation of starting materials) to give the title compound as a white solid in 46% yield; NMR spectrum (DMSO-d6) 1.41 (d, 3H), 1.77 (s, 3H), 2.26 (s, 3H), 3.41 (dt, 1H), 3.58 (dt, 1H), 4.86 (m, 1H), 5.18 (s, 2H), 7.01 (d, 1H), 7.16 (td, 1H), 7.22 (d, 1H), 7.30 (m, 3H), 7.42 (m, 1H), 7.54 (d, 1H), 7.62 (dd, 1H), 7.68 (t, 1H), 8.22 (t, 1H), 8.43 (s, 1H), 9.95 (s, 1H); Mass spectrum MH+ 475.

EXAMPLE 89

N-{(2R)-2-[(4-{[3-Methyl-4-(1,3-thiazol-2-yl-methoxy)phenyl]amino}quinazolin-5-yl)oxy]propyl}acetamide

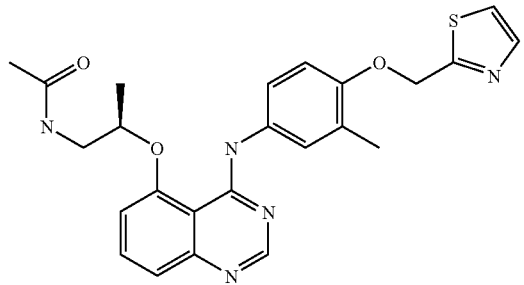

The procedure described in Example 3 was repeated using 2-(chloromethyl)-1,3-thiazole and N-[(2R)-2-({4-[(4-hydroxy-3-methylphenyl)amino]quinazolin-5-yl}oxy)propyl] acetamide (obtained as described in Example 86, preparation of starting materials) to give the title compound as a light brown solid in 25% yield; NMR spectrum (DMSO-d6) 1.41 (d, 3H), 1.77 (s, 3H), 2.25 (s, 3H), 3.42 (dt, 1H), 3.60 (dt, 1H), 4.88 (m, 1H), 5.45 (s, 2H), 7.11 (d, 1H), 7.22 (d, 1H), 7.31 (d, 1H), 7.56 (d, 1H), 7.63 (dd, 1H), 7.68 (t, 1H), 7.76 (d, 1H), 7.83 (d, 1H), 8.23 (t, 1H), 8.43 (s, 1H), 9.97 (s, 1H); Mass spectrum MH+ 464.

EXAMPLE 90

2-Hydroxy-N-methyl-N-{(2R)-2-[(4-{[3-methyl-4-(pyridin-2-ylmethoxy)phenyl]amino}quinazolin-5-yl)oxy]propyl}acetamide

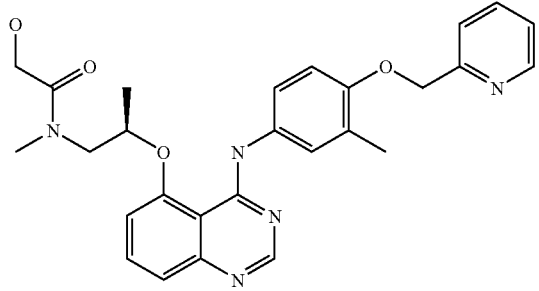

The procedure described in Example 3 was repeated using 2-(chloromethyl)pyridine and 2-hydroxy-N-[(2R)-2-({4-[(4- hydroxy-3-methylphenyl)amino]quinazolin-5-yl}oxy)propyl]-N-methylacetamide to give the title compound as a light yellow solid in 17% yield; NMR spectrum (DMSO-d6 373K) 1.43 (d, 3H), 2.29 (s, 3H), 2.97 (s, 3H), 3.58 (m, 1H), 4.08 (m, 3H), 5.11 (m, 1H), 5.19 (s, 2H), 7.01 (d, 1H), 7.21 (d, 1H), 7.32 (m, 2H), 7.57 (m, 3H), 7.67 (t, 1H), 8.83 (td, 1H), 8.41 (s, 1H), 8.57 (d, 1H), 9.81 (s, 1H); Mass spectrum MH+ 488.

The 2-hydroxy-N-[(2R)-2-({4-[(4-hydroxy-3-methylphenyl)amino]quinazolin-5-yl}oxy)propyl]-N-methylacetamide used as starting material was prepared as follows:

The procedure described in Example 3 (preparation of starting materials) was repeated using (2R)-1-[allyl(methyl)amino]propan-2-ol (obtained as described in Example 2.3, preparation of starting materials) and 4-[(5-fluoroquinazolin-4-yl)amino]-2-methylphenol (obtained as described in Example 3, preparation of starting materials) to give 4-[(5-{(1R)-2-[allyl(methyl)amino]-1-methylethoxy}quinazolin-4-yl)amino]-2-methylphenol as a brown oil in 86% yield; NMR spectrum (DMSO-d6) 1.43 (d, 3H), 2.15 (s, 3H), 2.18 (s, 3H), 2.54 (dd, 1H), 2.88 (dd, 1H), 3.00 (m, 2H), 4.92 (m, 1H), 5.01 (d, 1H), 5.11 (d, 1H), 5.62 (m, 1H), 6.77 (d, 1H), 7.16 (d, 1H), 7.26 (d, 1H), 7.35 (s, 1H), 7.38 (d, 1H), 7.66 (t, 1H), 8.37 (s, 1H), 9.17 (s, 1H), 10.16 (s, 1H); Mass spectrum MH+ 379.

The procedure described in Example 2.3 (preparation of starting materials) was repeated using chlorotris(triphenylphosphine)rhodium (I) and 4-[(5-{(1R)-2-[allyl(methyl)amino]-1-methylethoxy}quinazolin-4-yl)amino]-2-methylphenol to give 2-methyl-4-({5-[(1R)-1-methyl-2-(methylamino)ethoxy]quinazolin-4-yl}amino)-phenol as a brown foam in 56% yield; NMR spectrum (DMSO-d6) 1.41 (d, 3H), 2.15 (s, 3H), 2.33 (s, H), 2.87 (m, 2H), 4.85 (m, 1H), 6.77 (d, 1H), 7.14 (d, 1H), 7.25 (d, 1H), 7.43 (s, 1H), 7.46 (d, 1H), 7.64 (t, 1H), 8.38 (s, 1H), 9.14 (s, 1H), 10.35 (s, 1H); Mass spectrum MH+ 339.

The procedure described in Example 3 (preparation of starting materials) was repeated using glycolic acid and 2-methyl-4-({5-[(1R)-1-methyl-2-(methylamino) ethoxy]quinazolin-4-yl}amino)phenol to give 2-hydroxy-N-[(2R)-2-({4-[(4-hydroxy-3-methylphenyl)amino]quinazolin-5-yl}oxy)propyl]-N-methylacetamide as an orange solid in 81% yield; NMR spectrum (DMSO-d6) 1.38 (d, 3H), 2.15 (s, 3H), 2.96 (s, 3H), 3.35 (dd, 1H), 4.02 (s, 2H), 4.21 (m, 2H), 5.18 (m, 1H), 6.83 (d, 1H), 7.27 (m, 1H), 7.38 (s, 1H), 7.46 (d, 1H), 7.92 (t, 1H), 8.70 (s, 1H), 9.52 (s, 1H), 10.68 (s, 1H); Mass spectrum MH+ 397.

EXAMPLE 91

2-Hydroxy-N-methyl-N-{(2R)-2-[(4-{[3-methyl-4-(1,3-thiazol-4-ylmethoxy)phenyl]amino}quinazolin-5-yl)oxy]propyl}acetamide

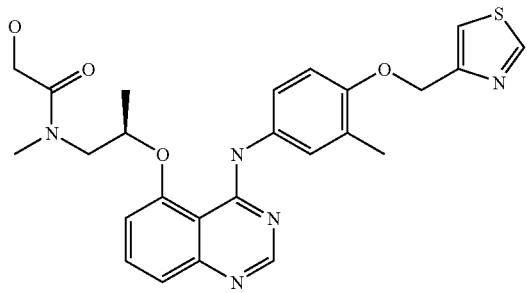

The procedure described in Example 3 was repeated using 4-(chloromethyl)-1,3-thiazole and 2-hydroxy-N-[(2R)-2-({4-[(4-hydroxy-3-methylphenyl)amino]quinazolin-5-yl}oxy)propyl]-N-methylacetamide (obtained as described in Example 90, preparation of starting materials) to give the title compound as a white solid in 41% yield; NMR spectrum (DMSO-d6 373K) 1.43 (d, 3H), 2.24 (s, 3H), 2.97 (s, 3H), 3.57 (m, 1H), 4.07 (m, 3H), 5.13 (m, 1H), 5.25 (s, 2H), 7.09 (d, 1H), 7.11 (d, 1H), 7.34 (d, 1H), 7.57 (m, 2H), 7.69 (m, 2H), 8.42 (s, 1H), 9.07 (d, 1H), 9.82 (s, 1H); Mass spectrum MH+ 494.

EXAMPLE 92

2-Hydroxy-N-methyl-N-((2R)-2-{[4-({3-methyl-4-[(5-methylisoxazol-3-yl)methoxy]phenyl}amino)quinazolin-5-yl]oxy}propyl)acetamide

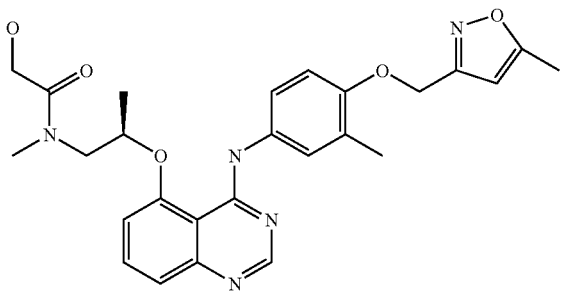

The procedure described in Example 3 was repeated using 3-(chloromethyl)-5-ethylisoxazole and 2-hydroxy-N-[(2R)-2-({4-[(4-hydroxy-3-methylphenyl)amino]quinazolin-5-yl}oxy)propyl]-N-methylacetamide (obtained as described in Example 90, preparation of starting materials) to give the title compound as a white solid in 7% yield; NMR spectrum (DMSO-d6 373K) 1.44 (d, 3H), 2.22 (s, 3H), 2.42 (s, 3H), 2.98 (s, 3H), 3.58 (m, 1H), 4.17 (m, 3H), 5.11 (m, 1H), 5.15 (s, 2H), 6.29 (s, 1H), 7.07 (d, 1H), 7.11 (d, 1H), 7.33 (d, 1H), 7.57 (m, 2H), 7.69 (t, 1H), 8.44 (s, 1H), 9.83 (s, 1H); Mass spectrum MH+ 492.

EXAMPLE 93

N-Methyl-N-{(1R)-1-methyl-2-[(4-{[3-methyl-4-(pyridin-2-ylmethoxy)phenyl]amino}quinazolin-5-yl)oxy]ethyl}acetamide

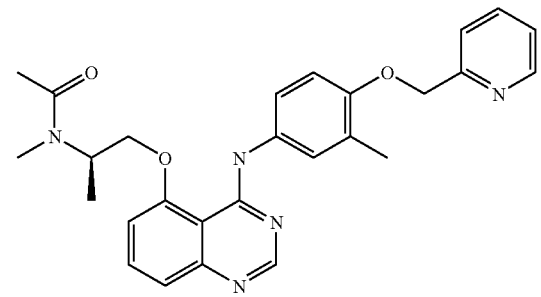

The procedure described in Example 3 was repeated using 2-(chloromethyl)pyridine and N-[(1R)-2-({4-[(4-hydroxy-3- methylphenyl)amino]quinazolin-5-yl}oxy)-1-methylethyl]-N-methylacetamide to give the title compound as a light beige solid in 43% yield; NMR spectrum (DMSO-d6 373K) 1.21 (d, 3H), 1.85 (s, 3H), 2.27 (s, 3H), 2.84 (s, 3H), 4.34 (m, 1H), 4.40 (t, 1H), 5.07 (m, 1H), 5.20 (s, 2H), 7.01 (d, 1H), 7.17 (d, 1H), 7.33 (m, 2H), 7.42 (d, 1H), 7.47 (dd, 1H), 7.55 (d, 1H), 7.67 (t, 1H), 7.82 (td, 1H), 8.41 (s, 1H), 8.57 (d, 1H), 9.50 (s, 1H); Mass spectrum MH+ 472.

The N-[(1R)-2-({4-[(4-hydroxy-3-methylphenyl)amino]quinazolin-5-yl}oxy)-1-methylethyl]-N-methylacetamide used as starting material was prepared as follows:

The procedure described in Example 3 (preparation of starting materials) was repeated using (2R)-2-(methylamino)propan-1-ol (obtained as described in Becker et al., J. Chem. Soc. 1957, 858) and 4-[(5-fluoroquinazolin-4-yl)amino]-2-methylphenol (obtained as described in Example 3, preparation of starting materials) to give 2-methyl-4-[(5-{[(2R)-2-(methylamino)propyl]oxy}quinazolin-4-yl)amino]phenol as a brown solid in 80% yield; NMR spectrum (DMSO-d6) 1.16 (d, 3H), 2.14 (s, 3H), 2.34 (s, 3H), 3.04 (m, 1H), 3.24 (bs, 1H), 4.08 (dd, 1H), 4.25 (dd, 1H), 6.76 (d, 1H), 7.06 (d, 1H), 7.26 (d, 1H), 7.47 (d, 1H), 7.53 (dd, 1H), 7.65 (t, 1H), 8.39 (s, 1H), 9.17 (s, 1H), 10.37 (s, 1H); Mass spectrum MH+ 339.

To a mixture of triethylamine (420 μl) and 2-methyl-4-[(5-{[(2R)-2-(methylamino)propyl]oxy}quinazolin-4-yl)amino]phenol (450 mg) in DCM (5 ml) was added acetyl chloride (190 μl). The reaction was stirred for 30 minutes and then quenched with water and extracted with DCM (×2). The residue was dissolved in 7N MeOH/NH3 and stirred at room temperature for 30 minutes. Solvent was removed in vacuo and water was added. The mixture was extracted with DCM (×2), filtered and then solvent removed to give N-[(1R)-2-({4-[(4-hydroxy-3-methylphenyl)amino]quinazolin-5-yl}oxy)-1-methylethyl]-N-methylacetamide as a pink foam (365 mg, 72%); NMR spectrum (DMSO-d6 373K) 1.41 (d, 3H), 1.86 (s, 3H), 2.17 (s, 3H), 2.83 (s, 3H), 4.36 (m, 2H), 5.04 (m, 1H), 6.77 (d, 1H), 7.16 (d, 1H), 7.29 (m, 3H), 7.67 (t, 1H), 8.38 (s, 1H), 8.78 (s, 1H), 9.43 (s, 1H); Mass spectrum MH+ 381.

EXAMPLE 94

N-Methyl-N-{(1R)-1-methyl-2-[(4-{[3-methyl-4-(1,3-thiazol-4-ylmethoxy)phenyl]amino}quinazolin-5-yl)oxy]ethyl}acetamide

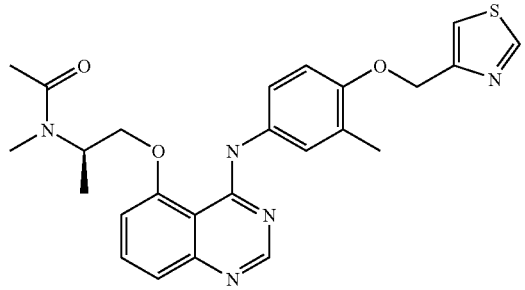

The procedure described in Example 3 was repeated using 4-(chloromethyl)-1,3-thiazole and N-[(1R)-2-({4-[(4-hydroxy-3-methylphenyl)amino]quinazolin-5-yl}oxy)-1-methylethyl]-N-methylacetamide (obtained as described in Example 93, preparation of starting materials) to give the title compound as a white solid in 13% yield; NMR spectrum (DMSO-d6 373K) 1.22 (d, 3H), 1.86 (s, 3H), 2.24 (s, 3H), 2.85 (s, 3H), 4.33 (m, 1H), 4.42 (t, 1H), 5.09 (m, 1H), 5.25 (s, 2H), 7.09 (d, 1H), 7.18 (d, 1H), 7.34 (d, 1H), 7.39 (s, 1H), 7.50 (d, 1H), 7.70 (m, 2H), 8.41 (s, 1H), 9.08 (s, 1H), 9.51 (s, 1H); Mass spectrum MH+ 478.

EXAMPLE 95

N-{(1R)-2-[(4-{[3-Chloro-4-(1,3-thiazol-4-ylmethoxy)phenyl]amino}quinazolin-5-yl)oxy]-1-methylethyl}-2-hydroxy-N-methylacetamide

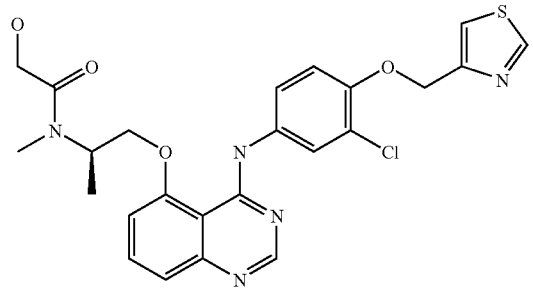

The procedure described in Example 3 was repeated using 4-(chloromethyl)-1,3-thiazole and N-[(1R)-2-({4-[(3-chloro-4-hydroxyphenyl)amino]quinazolin-5-yl}oxy)-1-methylethyl]-2-hydroxy-N-methylacetamide (obtained as described in Example 54, preparation of starting materials) to give the title compound as a white solid in 64% yield; NMR spectrum (DMSO-d6 373K) 1.25 (d, 3H), 2.83 (s, 3H), 3.98 (s, 2H), 4.34 (m, 1H), 4.47 (t, 1H), 4.98 (m, 1H), 5.34 (s, 2H), 7.19 (d, 1H), 7.37 (d, 2H), 7.51 (dd, 1H), 7.70 (t, 1H), 7.74 (d, 1H), 7.93 (d, 1H), 8.46 (s, 1H), 9.08 (s, 1H), 9.57 (s, 1H); Mass spectrum MH+ 514.

EXAMPLE 96

2-Hydroxy-N-methyl-N-{(1R)-1-methyl-2-[(4-{[3-methyl-4-(pyridin-2-ylmethoxy)phenyl]amino}quinazolin-5-yl)oxy]ethyl}acetamide

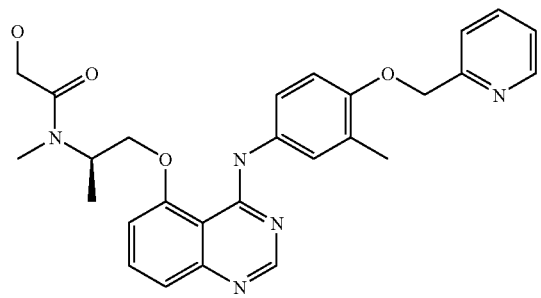

The procedure described in Example 3 was repeated using 2-(chloromethyl)pyridine and 2-hydroxy-N-[(1R)-2-({4-[(4-hydroxy-3-methylphenyl)amino]quinazolin-5-yl}oxy)-1-methylethyl]-N-methylacetamide to give the title compound as a white solid in 15% yield; NMR spectrum (DMSO-d6 373K) 1.25 (d, 3H), 2.28 (s, 3H), 2.83 (s, 3H), 3.96 (s, 2H), 4.35 (m, 1H), 4.46 (t, 1H), 4.97 (m, 1H), 5.19 (s, 2H), 7.01 (d, 1H), 7.18 (d, 2H), 7.33 (m, 2H), 7.44 (m, 1H), 7.56 (d, 1H), 7.68 (t, 1H), 7.83 (td, 1H), 8.40 (s, 1H), 8.58 (d, 1H), 9.48 (s, 1H); Mass spectrum MH+ 488.

The 2-hydroxy-N-[(1R)-2-({4-[(4-hydroxy-3-methylphenyl)amino]quinazolin-5-yl}oxy)-1-methylethyl]-N-methylacetamide used as starting material was prepared as follows:

The procedure described in Example 94 (preparation of starting materials) was repeated using acetoxyacetyl chloride and 2-methyl-4-[(5-{[(2R)-2-(methylamino)propyl]oxy}quinazolin-4-yl)amino]phenol (obtained as described in Example 93, preparation of starting materials) to give 2-hydroxy-N-[(1R)-2-({4-[(4-hydroxy-3-methylphenyl)amino]quinazolin-5-yl}oxy)-1-methylethyl]-N-methylacetamide as an orange foam in 75% yield; NMR spectrum (DMSO-d6 373K) 1.25 (d, 3H), 2.17 (s, 3H), 2.83 (s, 3H), 3.97 (s, 2H), 4.33 (dd, 1H), 4.45 (t, 1H), 4.95 (m, 1H), 6.77 (d, 1H), 7.17 (d, 1H), 7.30 (m, 3H), 7.67 (t, 1H), 8.37 (s, 1H), 8.79 (s, 1H), 9.43 (s, 1H); Mass spectrum MH+ 397.

EXAMPLE 97

2-Hydroxy-N-methyl-N-{(1R)-1-methyl-2-[(4-{[3-methyl-4-(1,3-thiazol-4-ylmethoxy)phenyl]amino}quinazolin-5-yl)oxy]ethyl}acetamide

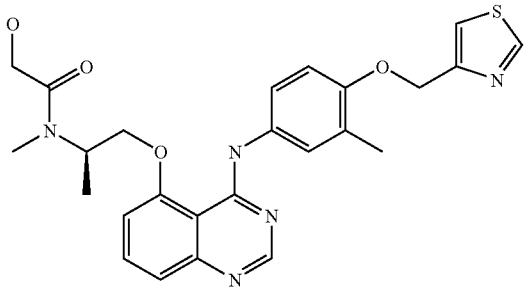

The procedure described in Example 3 was repeated using 4-(chloromethyl)-1,3-thiazole and 2-hydroxy-N-[(1R)-2-({4-[(4-hydroxy-3-methylphenyl)amino]quinazolin-5-yl}oxy)-1-methylethyl]-N-methylacetamide (obtained as described in Example 96, preparation of starting materials) to give the title compound as a foam in 29% yield; NMR spectrum (DMSO-d6 373K) 1.26 (d, 3H), 2.24 (s, 3H), 2.83 (s, 3H), 3.97 (s, 2H), 4.35 (m, 1H), 4.46 (t, 1H), 4.95 (m, 1H), 5.24 (s, 2H), 7.08 (d, 1H), 7.18 (d, 2H), 7.35 (d, 1H), 7.42 (s, 1H), 7.46 (d, 1H), 7.70 (m, 1H), 8.41 (s, 1H), 9.07 (s, 1H), 9.50 (s, 1H); Mass spectrum MH+ 494.

EXAMPLE 98

N-{(2R)-2-[(4-{[3-Chloro-4-(pyridin-2-ylmethoxy)phenyl]amino}quinazolin-5-yl)oxy]propyl}-1-hydroxy-N-methylcyclopropanecarboxamide

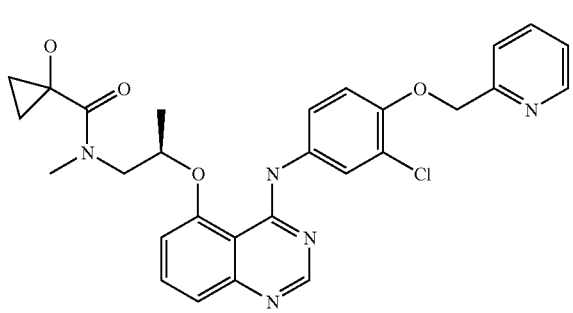

The procedure described in Example 1 was repeated using hydroxy-1-cyclopropane carboxylic acid and N-[3-chloro-4-(pyridin-2-ylmethoxy)phenyl]-5-[(1R)-1-methyl-2-(methylamino)ethoxy]quinazolin-4-amine (obtained as described in Example 2.3, preparation of starting materials) to give the title compound as a foam in 19% yield; NMR spectrum (DMSO-d6) 0.70 (s, 4H), 1.40 (d, 3H), 3.23 (s, 3H), 3.36 (m, 1H), 4.19 (m, 1H), 5.15 (m, 1H), 5.29 (s, 2H), 6.20 (s, 1H), 7.24 (m, 2H), 7.35 (m, 2H), 7.58 (m, 2H), 7.71 (t, 1H), 7.87 (dt, 1H), 8.09 (d, 1H), 8.44 (s, 1H), 8.58 (d, 1H), 9.86 (s, 1H); Mass spectrum MH+ 534.

EXAMPLE 99

(2S)-N-{(2R)-2-[(4-{[3-Chloro-4-(pyridin-2-ylmethoxy)phenyl]amino}quinazolin-5-yl)oxy]propyl}-2-hydroxy-N-methylpropanamide

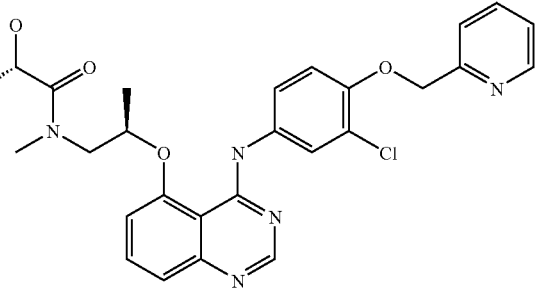

The procedure described in Example 1 was repeated using L-(+)-lactic acid and N-[3-chloro-4-(pyridin-2-ylmethoxy)phenyl]-5-[(1R)-1-methyl-2-(methylamino)ethoxy]quinazolin-4-amine (obtained as described in Example 2.3, preparation of starting materials) to give the title compound as a white solid in 35% yield; NMR spectrum (DMSO-d6 373K) 1.07 (d, 3H), 1.45 (d, 3H), 2.98 (s, 3H), 3.22 (m, 1H), 4.19 (m, 1H), 4.43 (m, 1H), 5.15 (m, 1H), 5.27 (s, 2H), 7.22 (m, 2H), 7.35 (m, 2H), 7.59 (m, 2H), 7.69 (t, 1H), 7.84 (dt, 1H), 8.08 (d, 1H), 8.47 (s, 1H), 8.58 (d, 1H), 9.93 (s, 1H); Mass spectrum MH+ 522.

EXAMPLE 100

N-{(2R)-2-[(4-{[3-Chloro-4-(pyridin-2-ylmethoxy)phenyl]amino}quinazolin-5-yl)oxy]propyl}-2-hydroxy-N,2-dimethylpropanamide

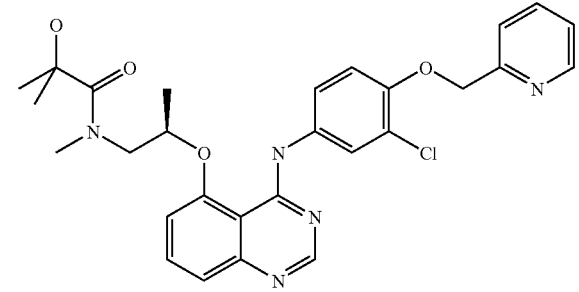

The procedure described in Example 1 was repeated using 2-hydroxy-iso-butyric acid and N-[3-chloro-4-(pyridin-2-ylmethoxy)phenyl]-5-[(1R)-1-methyl-2-(methylamino)ethoxy]quinazolin-4-amine (obtained as described in Example 2.3, preparation of starting materials) to give the title compound as a white solid in 28% yield; NMR spectrum (DMSO-d6 373K) 1.25 (s, 3H), 1.27 (s, 3H), 1.43 (d, 3H), 3.26 (s, 3H), 3.54 (m, 1H), 4.16 (dd, 1H), 5.16 (m, 1H), 5.28 (s, 2H), 7.23 (m, 2H), 7.34 (m, 2H), 7.58 (m, 2H), 7.69 (t, 1H), 7.83 (dt, 1H), 8.07 (d, 1H), 8.46 (s, 1H), 8.58 (d, 1H), 9.88 (s, 1H); Mass spectrum MH+ 536.

EXAMPLE 101

(2R)-N-{(2R)-2-[(4-{[3-Chloro-4-(pyridin-2-yl-methoxy)phenyl]amino}quinazolin-5-yl)oxy]propyl}-2-hydroxy-N-methylpropanamide

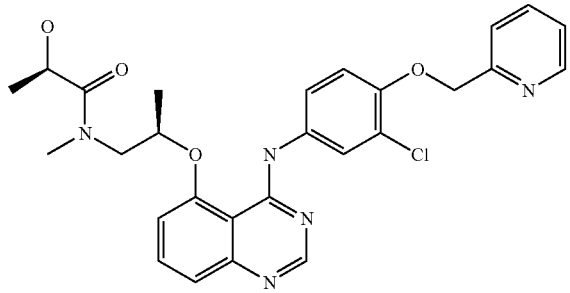

The procedure described in Example 1 was repeated using D-(−)-lactic acid and N-[3-chloro-4-(pyridin-2-ylmethoxy)phenyl]-5-[(1R)-1-methyl-2-(methylamino)ethoxy]quinazolin-4-amine (obtained as described in Example 2.3, preparation of starting materials) to give the title compound as a white solid in 26% yield; NMR spectrum (DMSO-d6 373K) 1.15 (d, 3H), 1.44 (d, 3H), 2.97 (s, 3H), 3.16 (m, 1H), 4.05 (dd, 1H), 4.43 (m, 1H), 5.16 (m, 1H), 5.27 (s, 2H), 7.23 (m, 2H), 7.35 (m, 2H), 7.59 (m, 2H), 7.70 (t, 1H), 7.84 (dt, 1H), 8.09 (d, 1H), 8.47 (s, 1H), 8.59 (d, 1H), 9.90 (s, 1H); Mass spectrum MH+ 522.

EXAMPLE 102

(2R)-N-{(2R)-2-[(4-{[3-Chloro-4-(pyridin-2-yl-methoxy)phenyl]amino}quinazolin-5-yl)oxy]propyl}-2-methoxy-N-methylpropanamide

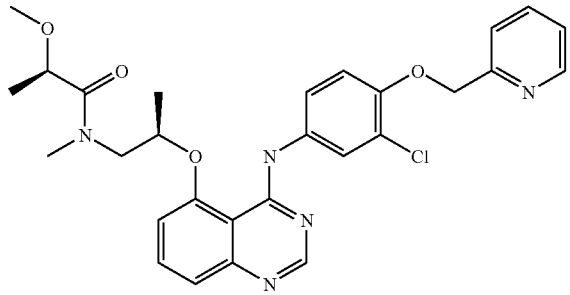

The procedure described in Example 1 was repeated using (R)-(+)-2-methoxypropionic acid and N-[3-chloro-4-(pyridin-2-ylmethoxy)phenyl]-5-[(1R)-1-methyl-2-(methylamino)ethoxy]quinazolin-4-amine (obtained as described in Example 2.3, preparation of starting materials) to give the title compound as a brown gum in 44% yield; NMR spectrum (DMSO-d6 373K) 1.11 (d, 3H), 1.37 (d, 3H), 2.97 (s, 3H), 3.09 (s, 3H), 3.38 (m, 1H), 4.17 (q, 1H), 4.26 (dd, 1H), 5.16 (m, 1H), 5.28 (s, 2H), 7.24 (m, 2H), 7.33 (d, 1H), 7.37 (dd, 1H), 7.56 (d, 1H), 7.64 (dd, 1H), 7.69 (t, 1H), 7.86 (dt, 1H), 8.13 (d, 1H), 8.44 (s, 1H), 8.59 (d, 1H), 9.89 (s, 1H); Mass spectrum MH+ 536.

EXAMPLE 103

2-Hydroxy-N-methyl-N-((2R)-2-{[4-({3-methyl-4-[(6-methylpyridin-3-yl)oxy]phenyl}amino)quinazolin-5-yl]oxy}propyl)acetamide

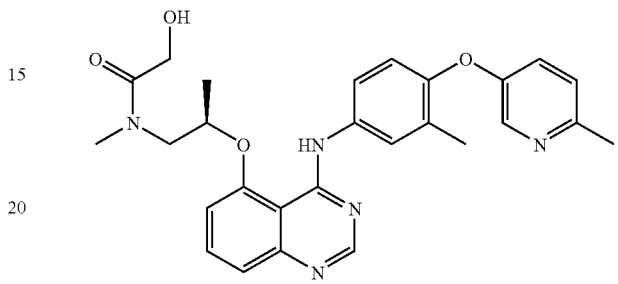

The procedure described in Example 1 was repeated using glycolic acid and 5-[(1R)-1-methyl-2-(methylamino)ethoxy]-N-{3-methyl-4-[(6-methylpyridin-3-yl)oxy]phenyl}quinazolin-4-amine to give the title compound in 86% yield; NMR spectrum (CDCl3) 1.55 (d, 3H), 2.30 (s, 3H), 2.53 (s, 3H), 2.96 (s, 3H), 3.59 (dd, 1H), 4.16-4.07 (m, 3H), 5.08 (m, 1H), 6.92 (d, 1H), 7.02 (d, 1H), 7.09 (d, 1H), 7.14 (d, 1H), 7.50 (m, 2H), 7.65 (m, 2H), 8.28 (s, 1H), 8.61 (s, 1H), 9.87 (s 1H); Mass spectrum: MH+ 488.

The 5-[(1R)-1-methyl-2-(methylamino)ethoxy]-N-{3-methyl-4-[(6-methylpyridin-3-yl)oxy]phenyl}quinazolin-4-amine used as starting material was prepared as follows:

Sodium hydride (25.6 g, 60% dispersion in oil, 0.64 mol) was added portion wise to a solution of 5-hydroxy-2-methylpyridine (70 g, 0.64 mol) in DMA (700 ml) while keeping the temperature below 40° C. At the end of the addition, the mixture was stirred at room temperature for 1 hour and 2-fluoro-5-nitrotoluene (91.3 g, 0.59 mol) in DMA (100 ml) was added slowly. The mixture was stirred at 80° C. for 3 hours and then cooled. The solvents were evaporated under vacuum and the residue was partitioned between ethyl acetate and water. The organic layer washed with water and brine, dried over MgSO4. After evaporation of the solvents, the residue was purified by chromatography on silica gel (eluant: 30% ethyl acetate in petroleum ether) to give 2-methyl-5-(2-methyl-4-nitrophenoxy)pyridine (141 g, 98%) as an oil; NMR spectrum (CDCl3); 2.43 (s, 3H), 2.59 (s, 3H), 6.74 (d, 1H), 7.21 (d, 1H), 7.27 (d, 1H), 8.00 (d, 1H), 8.17 (s, 1H), 8.32 (s, 1H).

A mixture of 2-methyl-5-(2-methyl-4-nitrophenoxy)pyridine (141 g, 0.58 mol) and 10% palladium on charcoal (13 g) in ethyl acetate (200 ml) and ethanol (700 ml) was stirred under an atmosphere of hydrogen (1.2 bar) for 5 hours. After reaction completion, the mixture was purged with nitrogen and the catalyst was filtered off. The filtrate was evaporated to dryness to give 3-methyl-4-[(6-methylpyridin-3-yl)oxy] aniline (120.6 g, 98%) as a white solid; Mass spectrum MH+ 215.

3-Methyl-4-[(6-methylpyridin-3-yl)oxy]aniline (6.42 g, 30 mmol) and 4N hydrogen chloride in dioxane (7.55 ml, 30 mmol) were added to a suspension of 4-chloro-5-fluoroquinazoline (5 g, 27.5 mmol; obtained as described in PCT Int. Appl. WO2001094341, AstraZeneca) in acetonitrile (100 ml). The mixture was stirred at 80° C. for 2 hours. After cooling, the precipitate washed with acetonitrile. This precipitate was partitioned between DCM and 5% aqueous sodium bicarbonate and the pH was adjusted to 8. The organic layer washed with brine and dried over MgSO$_4$. Evaporation of the solvents gave 5-fluoro-N-{3-methyl-4-[(6-methylpyridin-3-yl)oxy]phenyl}quinazolin-4-amine (9.3 g, 94%) as a dark gum which crystallised on standing; NMR spectrum (CDCl$_3$); 2.30 (s, 3H), 2.54 (s, 3H), 6.93 (d, 1H), 7.15-7.08 (m, 2H), 7.22 (m, 1H), 7.56 (d, 1H), 7.63 (s, 1H), 7.71 (m, 2H), 8.27 (s, 1H), 8.37 (d, 1H), 8.71 (s, 1H).

Sodium hydride (960 mg, 60% dispersion in oil, 20 mmol) was added portion wise to an ice-cooled solution of (2R)-1-[allyl(methyl)amino]propan-2-ol (3.87 g, 30 mmol, obtained as described in Example 2.3, preparation of starting materials) and 5-fluoro-N-{3-methyl-4-[(6-methylpyridin-3-yl)oxy]phenyl}quinazolin-4-amine (3.6 g, 10 mmol) in THF (25 ml). The mixture was heated at 65° C. for 24 hours. After cooling, the solvents were evaporated under vacuum. The mixture was diluted with DCM, and washed with water and brine. The organic layer was dried over MgSO$_4$. After evaporation of the solvents, the residue was purified by chromatography on silica gel (eluant: 2 to 4% methanol in DCM) to give 5-{(1R)-2-[allyl(methyl)amino]-1-methylethoxy}-N-{3-methyl-4-[(6-methylpyridin-3-yl)oxy]phenyl}quinazolin-4-amine (2.4 g, 51%) as a brown oil; Mass spectrum: MH$^+$ 470.

A mixture of 5-{(1R)-2-[allyl(methyl)amino]-1-methylethoxy}-N-{3-methyl-4-[(6-methylpyridin-3-yl)oxy]phenyl}quinazolin-4-amine (2.25 g, 4.8 mmol) and chlorotris(triphenylphosphine)rhodium(I) (463 mg, 0.48 ml) in acetonitrile—water (17 ml:3 ml) was heated at reflux for 3 hours. After cooling, the solvents were evaporated under vacuum. The residue was purified by chromatography on silica gel (eluant: 2 to 4% methanol in DCM) to give 5-[(1R)-1-methyl-2-(methylamino)ethoxy]-N-{3-methyl-4-[(6-methylpyridin-3-yl)oxy]phenyl}quinazolin-4-amine (1.70 g, 83%); Mass spectrum: MH$^+$ 430.

EXAMPLE 104

N-Methyl-N-((2R)-2-{[4-({3-methyl-4-[(6-methylpyridin-3-yl)oxy]phenyl}amino)quinazolin-5-yl]oxy}propyl)acetamide

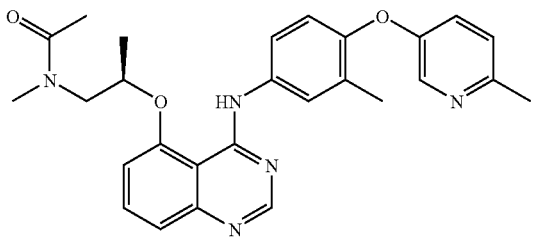

Acetyl chloride (24 µl, 0.33 mmol) was added drop wise to a solution of 5-[(1R)-1-methyl-2-(methylamino)ethoxy]-N-{3-methyl-4-[(6-methylpyridin-3-yl)oxy]phenyl}quinazolin-4-amine (129 mg, 0.30 mmol, obtained as described in Example 103, preparation of starting materials) and DIPEA (105 µl, 0.6 mmol) in DCM (5 ml). The mixture was stirred at room temperature for 2 hours and diluted with DCM. The solution was washed with water and brine, and dried over MgSO$_4$. After evaporation of the solvents, the residue was purified by chromatography on silica gel (eluant: 2 to 4% methanol in DCM) to give the title compound (84 mg, 60%) as a pale solid; NMR spectrum (CDCl$_3$) 1.55 (d, 3H), 2.08 (s, 3H), 2.30 (s, 3H), 2.53 (s, 3H), 3.08 (s, 3H), 3.56 (dd, 1H), 3.93 (dd, 1H), 5.09 (m, 1H), 6.92 (d, 1H), 7.12 (m, 3H), 7.50 (m, 2H), 7.65 (m, 1H), 7.70 (s, 1H), 8.27 (s, 1H), 8.62 (s, 1H); Mass spectrum: MH$^+$ 472.

EXAMPLE 105

N$^1$,N$^2$,N$^2$-Trimethyl-N$^1$-((2R)-2-{[4-({3-methyl-4-[(6-methylpyridin-3-yl)oxy]phenyl}amino)quinazolin-5-yl]oxy}propyl)glycinamide

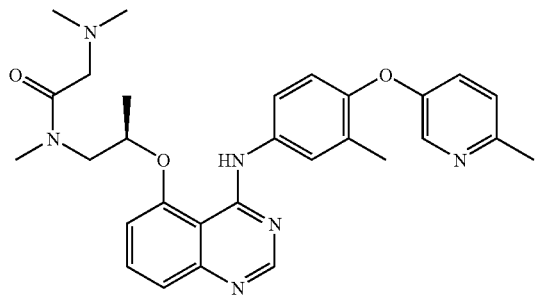

Chloroacetyl chloride (33 µl, 0.42 mmol) was added drop wise to a solution of 5-[(1R)-1-methyl-2-(methylamino)ethoxy]-N-{3-methyl-4-[(6-methylpyridin-3-yl)oxy]phenyl}quinazolin-4-amine (172 mg, 0.40 mmol, obtained as described in Example 103, preparation of starting materials)) and DIPEA (139 µl, 0.8 mmol) in DCM (2 ml). The mixture was stirred at room temperature for 1 hour. THF (5 ml) was added to the solution and dimethylamine was bubbled in the reaction mixture. After 30 minutes, the solvents were evaporated under vacuum. The mixture was diluted with DCM, washed with water and brine, and dried over MgSO$_4$. After evaporation of the solvents, the residue was purified by chromatography on silica gel (eluant: 2 to 4% 7N ammonia-methanol in DCM) to give the title compound (85 mg, 41%) as a pale solid; NMR spectrum (CDCl$_3$) 1.53 (d, 3H), 2.28 (s, 6H), 2.30 (s, 3H), 2.53 (s, 3H), 3.15-3.05 (m, 5H), 3.54 (dd, 1H), 3.95 (dd, 1H), 5.10 (m, 1H), 6.91 (d, 1H), 7.12 (m, 3H), 7.46 (d, 1H), 7.55 (d, 1H), 7.64 (m, 1H), 7.72 (s, 1H), 8.27 (s, 1H), 8.62 (s, 1H); Mass spectrum: MH$^+$ 515.

EXAMPLE 106

N-Methyl-N-((2R)-2-{[4-({3-methyl-4-[(6-methylpyridin-3-yl)oxy]phenyl}amino)quinazolin-5-yl]oxy}propyl)-2-pyrrolidin-1-ylacetamide

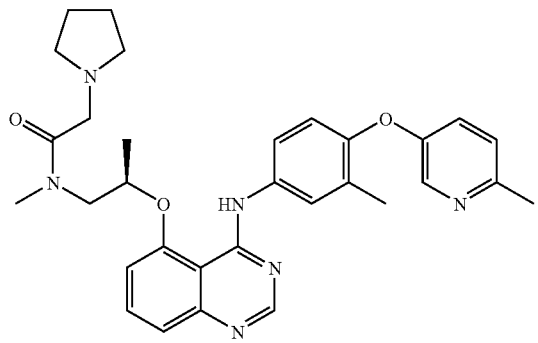

The procedure described in Example 105 was repeated using pyrrolidine (4 equivalents) instead of dimethylamine to give the title compound in 57% yield; NMR spectrum (CDCl$_3$) 1.53 (d, 3H), 1.75 (m, 4H), 2.30 (s, 3H), 2.55 (m, 7H), 3.13 (s, 3H), 3.27 (d, 1H), 3.32 (d, 1H), 3.57 (dd, 1H), 3.92 (dd, 1H), 5.11 (m, 1H), 6.91 (d, 1H), 7.12 (m, 3H), 7.46 (d, 1H), 7.54 (d, 1H), 7.64 (m, 1H), 7.72 (s, 1H), 8.27 (s, 1H), 8.62 (s, 1H); Mass spectrum: MH$^+$ 541.

EXAMPLE 107

N-Methyl-N-((2R)-2-{[4-({3-methyl-4-[(6-methylpyridin-3-yl)oxy]phenyl}amino)quinazolin-5-yl]oxy}propyl)-2-morpholin-4-ylacetamide

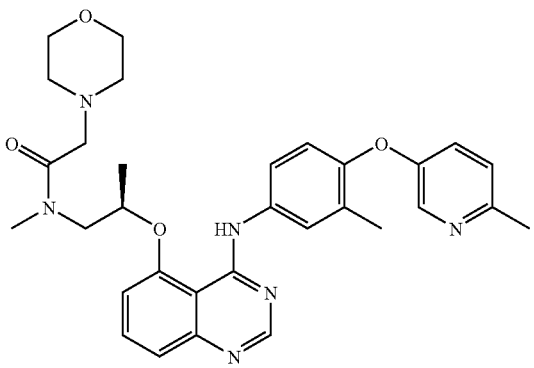

The procedure described in Example 105 was repeated using morpholine (4 equivalents) instead of dimethylamine to give the title compound in 63% yield; NMR spectrum (CDCl$_3$) 1.53 (d, 3H), 2.30 (s, 3H), 2.48 (m, 4H), 2.53 (s, 3H), 3.15 (m, 5H), 3.53 (dd, 1H), 3.65 (m, 4H), 3.97 (dd, 1H), 5.11 (m, 1H), 6.92 (d, 1H), 7.14-7.07 (m, 3H), 7.46 (d, 1H), 7.54 (d, 1H), 7.63 (m, 1H), 7.72 (s, 1H), 8.27 (s, 1H), 8.62 (s, 1H), 9.93 (s, 1H); Mass spectrum: MH$^+$ 557.

EXAMPLE 108

N-Methyl-N-((2R)-2-{[4-({3-methyl-4-[(6-methylpyridin-3-yl)oxy]phenyl}amino)quinazolin-5-yl]oxy}propyl)-2-(4-methylpiperazin-1-yl)acetamide

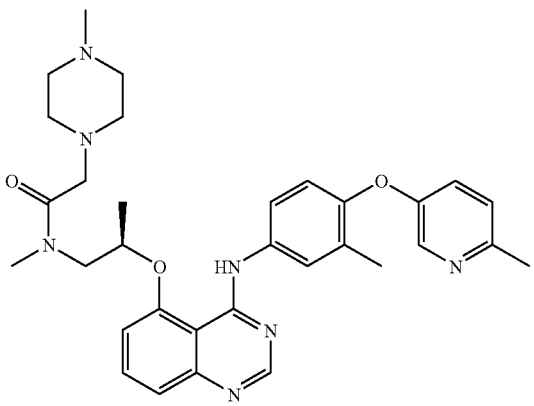

The procedure described in Example 105 was repeated using N-methylpiperazine (4 equivalents) instead of dimethylamine to give the title compound in 68% yield; NMR spectrum (CDCl$_3$) 1.53 (d, 3H), 2.25 (s, 3H), 2.30 (s, 3H), 2.5-2.2 (m, 8H), 2.53 (s, 3H), 3.15 (m, 5H), 3.54 (dd, 1H), 3.94 (dd, 1H), 5.11 (m, 1H), 6.92 (d, 1H), 7.14-7.07 (m, 3H), 7.45 (d, 1H), 7.54 (d, 1H), 7.64 (m, 1H), 7.72 (s, 1H), 8.27 (s, 1H), 8.62 (s, 1H); Mass spectrum: MH$^+$ 570.

EXAMPLE 109

2-Hydroxy-N-methyl-N-((2S)-2-{[4-({3-methyl-4-[(6-methylpyridin-3-yl)oxy]phenyl}amino)quinazolin-5-yl]oxy}propyl)acetamide

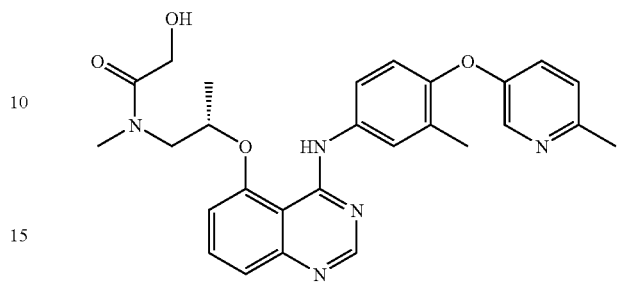

The procedure described in Example 1 was repeated using glycolic acid and 5-[(1S)-1-methyl-2-(methylamino)ethoxy]-N-{3-methyl-4-[(6-methylpyridin-3-yl)oxy]phenyl}quinazolin-4-amine to give the title compound in 46% yield; NMR spectrum (CDCl$_3$) 1.55 (d, 3H), 2.30 (s, 3H), 2.53 (s, 3H), 2.96 (s, 3H), 3.59 (dd, 1H), 4.16-4.07 (m, 3H), 5.08 (m, 1H), 6.92 (d, 1H), 7.02 (d, 1H), 7.09 (d, 1H), 7.14 (d, 1H), 7.50 (m, 2H), 7.65 (m, 2H), 8.28 (s, 1H), 8.61 (s, 1H), 9.87 (s 1H); Mass spectrum: MH$^+$ 488.

The 5-[(1S)-1-methyl-2-(methylamino)ethoxy]-N-{3-methyl-4-[(6-methylpyridin-3-yl)oxy]phenyl}quinazolin-4-amine used as starting material was prepared as follows:

The procedure described in Example 103, preparation of starting materials, was repeated using (2S)-1-[allyl(methyl)amino]propan-2-ol (obtained as described for the R-antipode in Example 2.3, preparation of starting materials) and 5-fluoro-N-{3-methyl-4-[(6-methylpyridin-3-yl)oxy]phenyl}quinazolin-4-amine (obtained as described in Example 103, preparation of starting materials) to give 5-{(1S)-2-[allyl(methyl)amino]-1-methylethoxy}-N-{3-methyl-4-[(6-methylpyridin-3-yl)oxy]phenyl}quinazolin-4-amine in 92% yield as a gum; Mass spectrum: MH$^+$ 470.

The procedure described in Example 103, preparation of starting materials, was repeated using 5-{(1S)-2-[allyl(methyl)amino]-1-methylethoxy}-N-{3-methyl-4-[(6-methylpyridin-3-yl)oxy]phenyl}quinazolin-4-amine to give 5-[(1S)-1-methyl-2-(methylamino)ethoxy]-N-{3-methyl-4-[(6-methylpyridin-3-yl)oxy]phenyl}quinazolin-4-amine in 56% yield; Mass spectrum: MH$^+$ 430.

EXAMPLE 110

N-Methyl-N-((2S)-2-{[4-({3-methyl-4-[(6-methylpyridin-3-yl)oxy]phenyl}amino)quinazolin-5-yl]oxy}propyl)acetamide

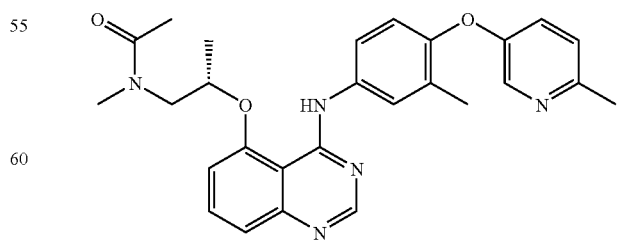

The procedure described in Example 104 was repeated using 5-[(1S)-1-methyl-2-(methylamino)ethoxy]-N-{3-methyl-4-[(6-methylpyridin-3-yl)oxy]phenyl}quinazolin-4-amine (obtained as described in Example 109, preparation of starting materials) and acetic anhydride to give the title compound in 64% yield; NMR spectrum (CDCl$_3$) 1.55 (d, 3H), 2.08 (s, 3H), 2.30 (s, 3H), 2.53 (s, 3H), 3.08 (s, 3H), 3.56 (dd, 1H), 3.93 (dd, 1H), 5.09 (m, 1H), 6.92 (d, 1H), 7.12 (m, 3H), 7.50 (m, 2H), 7.65 (m, 1H), 7.70 (s, 1H), 8.27 (s, 1H), 8.62 (s, 1H); Mass spectrum: MH$^+$ 472.

EXAMPLE 111

N-Methyl-N-((2S)-2-{[4-({3-methyl-4-[(6-methylpyridin-3-yl)oxy]phenyl}amino)quinazolin-5-yl]oxy}propyl)-2-pyrrolidin-1-ylacetamide

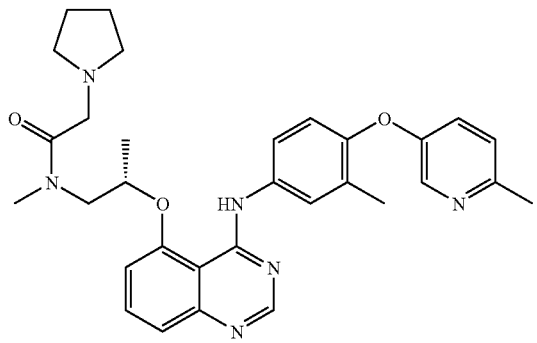

The procedure described in Example 105 was repeated using 5-[(1S)-1-methyl-2-(methylamino)ethoxy]-N-{3-methyl-4-[(6-methylpyridin-3-yl)oxy]phenyl}quinazolin-4-amine (obtained as described in Example 109, preparation of starting materials) and pyrrolidine (4 equivalents) instead of dimethylamine to give the title compound in 51% yield; NMR spectrum (CDCl$_3$) 1.53 (d, 3H), 1.75 (m, 4H), 2.30 (s, 3H), 2.55 (m, 7H), 3.13 (s, 3H), 3.27 (d, 1H), 3.32 (d, 1H), 3.57 (dd, 1H), 3.92 (dd, 1H), 5.11 (m, 1H), 6.91 (d, 1H), 7.12 (m, 3H), 7.46 (d, 1H), 7.54 (d, 1H), 7.64 (m, 1H), 7.72 (s, 1H), 8.27 (s, 1H), 8.62 (s, 1H); Mass spectrum: MH$^+$ 541.

EXAMPLE 112

(2S)-2,4-Dihydroxy-N-((2R)-2-{[4-({3-methyl-4-[(6-methylpyridin-3-yl)oxy]phenyl}amino)quinazolin-5-yl]oxy}propyl)butanamide

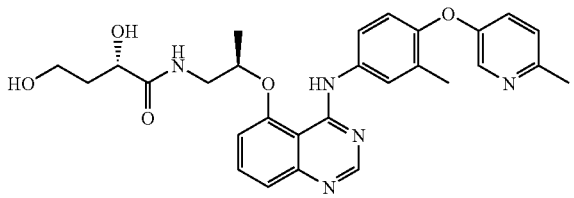

The procedure described in Example 63 was repeated using 5-[(1R)-2-amino-1-methylethoxy]-N-{3-methyl-4-[(6-methylpyridin-3-yl)oxy]phenyl}quinazolin-4-amine and (S)-α-hydroxybutyrolactone to give the title compound in 53% yield as a solid; NMR Spectrum: (CDCl$_3$) 1.55 (d, 3H), 1.79 (m, 1H), 2.05 (m, 1H), 2.26 (s, 3H), 2.49 (s, 3H), 3.90-3.65 (m, 4H), 4.21 (dd, 1H), 4.94 (m, 1H), 6.96 (m, 2H), 7.11 (d, 1H), 7.23 (dd, 1H), 7.39 (d, 1H), 7.43 (m, 1H), 7.60-7.52 (m, 2H), 7.69 (s, 1H), 8.00 (s, 1H), 8.55 (s, 1H); Mass spectrum: MH$^+$ 518.

The 5-[(1R)-2-amino-1-methylethoxy]-N-{3-methyl-4-[(6-methylpyridin-3-yl)oxy]phenyl}quinazolin-4-amine used as starting material was prepared as follows:

The procedure described in Example 103 (preparation of starting materials) was repeated using 5-fluoro-N-{3-methyl-4-[(6-methylpyridin-3-yl)oxy]phenyl}quinazolin-4-amine (obtained as described in Example 103, preparation of starting materials) and (2R)-1-aminopropan-2-ol to give 5-[(1R)-2-amino-1-methylethoxy]-N-{3-methyl-4-[(6-methylpyridin-3-yl)oxy]phenyl}quinazolin-4-amine in 77% yield; Mass spectrum: MH$^+$ 416

EXAMPLE 113

(2S)-4-Bromo-2-hydroxy-N-((2R)-2-{[4-({3-methyl-4-[(6-methylpyridin-3-yl)oxy]phenyl}amino)quinazolin-5-yl]oxy}propyl)butanamide

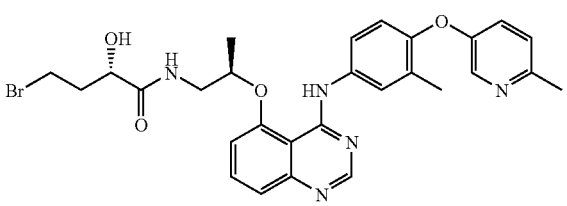

Triphenylphosphine (650 mg, 2.5 mmol) was added portion wise over 30 minutes to a solution of (2S)-2,4-dihydroxy-N-((2R)-2-{[4-({3-methyl-4-[(6-methylpyridin-3-yl)oxy]phenyl}amino)quinazolin-5-yl]oxy}propyl)butanamide (856 mg, 1.65 mmol, obtained as described in Example 112) and carbon tetrabromide (658 mg, 2 mmol) in DCM (10 ml). The mixture was stirred overnight at room temperature. After evaporation of the solvents, the residue was purified by chromatography on silica gel (eluant: 2% to 5% 7N ammonia-methanol in DCM) to give the title compound (712 mg, 74%) as a solid; NMR Spectrum: (CDCl$_3$) 1.53 (d, 3H), 2.07 (m, 1H), 2.28 (s, 3H), 2.38 (m, 1H), 2.52 (s, 3H), 3.51 (t, 2H), 3.80-3.65 (m, 2H), 4.34 (dd, 1H), 4.95 (m, 1H), 6.90 (m, 2H), 7.09 (d, 1H), 7.14 (dd, 1H), 7.28 (m, 1H), 7.50 (m, 3H), 7.63 (s, 1H), 8.23 (s, 1H), 8.44 (s, 1H); Mass spectrum: MH$^+$ 580, 582.

EXAMPLE 114

N-(2-Chloroethyl)-N'-((2R)-2-{[4-({3-methyl-4-[(6-methylpyridin-3-yl)oxy]phenyl}amino)quinazolin-5-yl]oxy}propyl)urea

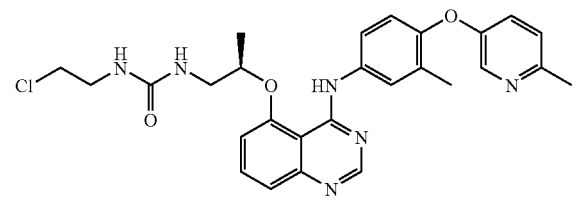

Chloroethylisocyanate (116 μl, 1.36 mmol) was added drop wise to an ice-cooled solution of 5-[(1R)-2-amino-1- methylethoxy]-N-{3-methyl-4-[(6-methylpyridin-3-yl)oxy]phenyl}quinazolin-4-amine (516 mg, 1.24 mmol, obtained as described in Example 112, preparation of starting materials) in DCM (10 ml). The mixture was stirred at 0° C. for 30 minutes and at room temperature for 1 hour. After evaporation of the solvents, the residue was purified by chromatography on silica gel (eluant: 3% to 5% 7N ammonia-methanol in DCM) to give the title compound (584 mg, 74%); NMR Spectrum: (CDCl$_3$) 1.46 (d, 3H), 2.28 (s, 3H), 2.52 (s, 3H), 3.46 (m, 1H), 3.57 (m, 4H), 4.00 (m, 1H), 4.76 (m, 1H), 6.40 (m, 1H), 6.62 (m, 1H), 6.67 (d, 1H), 6.91 (d, 1H), 7.08 (d, 1H), 7.12 (dd, 1H), 7.18 (d, 1H), 7.34 (t, 1H), 7.53 (dd, 1H), 7.67 (s, 1H), 8.27 (s, 1H), 8.34 (s, 1H), 9.82 (s, 1H); Mass spectrum: MH$^+$ 521.

EXAMPLE 115

2-Hydroxy-N-methyl-N-((1R)-1-methyl-2-{[4-({3-methyl-4-[(6-methylpyridin-3-yl)oxy]phenyl}amino)quinazolin-5-yl]oxy}ethyl)acetamide

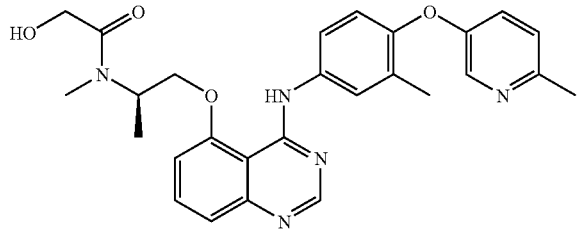

Acetoxyacetyl chloride (70 µl, 0.64 mmol) was added drop wise to an ice-cooled solution of 5-{[(2R)-2-(methylamino)propyl]oxy}-N-{3-methyl-4-[(6-methylpyridin-3-yl)oxy]phenyl}quinazolin-4-amine (250 mg, 0.58 mmol), triethylamine (97 µl, 0.70 mmol) in DCM (7 ml). The mixture was warmed to room temperature and stirred for 2 hours. After evaporation of the solvents under vacuum, the residue was diluted with pyrrolidine (0.50 ml, 6 mmol) and the mixture was stirred at 65° C. for 2 hours. After evaporation of the mixture to dryness, the residue was injected on an HPLC column (C18, 5 microns, 19 mm diameter, 100 mm length) of a preparative HPLC-MS system eluting with a mixture of water (containing 5% methanol and 1% acetic acid) and acetonitrile (gradient). After evaporation of the solvents, the solid was diluted in DCM. The solution washed with aqueous sodium bicarbonate and dried over magnesium sulfate to give the title compound (140 mg, 49%); NMR Spectrum: (CDCl$_3$) 1.34 (d, 3H), 2.30 (s, 3H), 2.53 (s, 3H), 2.79 (s, 3H), 3.12 (m, 1H), 3.95 (dd, 1H), 4.09 (dd, 1H), 4.30-4.15 (m, 2H), 5.40 (m, 1H), 6.91 (m, 2H), 7.09 (d, 1H), 7.17 (dd, 1H), 7.38 (m, 1H), 7.46 (s, 1H), 7.50 (d, 1H), 7.64 (t, 1H), 8.30 (d, 1H), 8.58 (s, 1H), 9.36 (s, 1H); Mass spectrum: MH$^+$ 488.

The 5-{[(2R)-2-(methylamino)propyl]oxy}-N-{3-methyl-4-[(6-methylpyridin-3-yl)oxy]phenyl}quinazolin-4-amine used as starting material was prepared as follows:

The procedure described in Example 103, preparation of starting materials, was repeated using 5-fluoro-N-{3-methyl-4-[(6-methylpyridin-3-yl)oxy]phenyl}quinazolin-4-amine (obtained as described in Example 103, preparation of starting materials) and (2R)-2-(methylamino)propan-1-ol (obtained as described in Becker et al., J. Chem. Soc. 1957, 858) to give 5-{[(2R)-2-(methylamino)propyl]oxy}-N-{3-methyl-4-[(6-methylpyridin-3-yl)oxy]phenyl}quinazolin-4-amine in 75% yield; NMR Spectrum: (CDCl$_3$) 1.30 (d, 3H), 2.28 (s, 3H), 2.52 (s, 3H), 2.53 (s, 3H), 3.20 (m, 1H), 4.09 (m, 1H), 4.21 (m, 1H), 6.89 (m, 2H), 7.14-7.07 (m, 2H), 7.45 (d, 1H), 7.63 (m, 2H), 8.26 (s, 1H), 8.63 (s, 1H), 10.3 (bs, 1H); Mass spectrum: MH$^+$ 430.

EXAMPLE 116

N-Methyl-N-((1R)-1-methyl-2-{[4-({3-methyl-4-[(6-methylpyridin-3-yl)oxy]phenyl}amino)quinazolin-5-yl]oxy}ethyl)acetamide

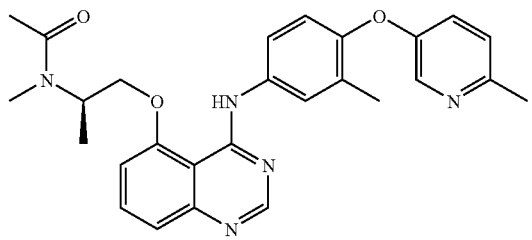

Acetic anhydride (66 µl, 0.70 mmol) was added drop wise to a solution of 5-{[(2R)-2-(methylamino)propyl]oxy}-N-{3-methyl-4-[(6-methylpyridin-3-yl)oxy]phenyl}quinazolin-4-amine (250 mg, 0.58 mmol, obtained as described in Example 115, preparation of starting materials) and potassium carbonate (161 mg, 1.16 mmol) in acetone (10 ml). The mixture was stirred at room temperature for 2 hours. After evaporation of the solvents, the residue was diluted in DCM. The solution washed with aqueous sodium bicarbonate and dried over magnesium sulfate. After evaporation of the solvents, the residue was purified by chromatography on silica gel (eluant: 2 to 5% 7N ammonia-methanol in DCM) to give the title compound (230 mg, 84%); NMR Spectrum: (CDCl$_3$) 1.28 (d, 3H), 1.94 (s, 3H), 2.30 (s, 3H), 2.53 (s, 3H), 2.90 (s, 3H), 4.30-4.10 (m, 2H), 5.38 (m, 1H), 6.92 (m, 2H), 7.08 (d, 1H), 7.14 (dd, 1H), 7.48 (d, 2H), 7.53 (s, 1H), 7.64 (t, 1H), 8.27 (d, 1H), 8.60 (s, 1H), 9.51 (s, 1H); Mass spectrum: MH$^+$ 472.

EXAMPLE 117

2-Hydroxy-N-methyl-N-((1S)-1-methyl-2-{[4-({3-methyl-4-[(6-methylpyridin-3-yl)oxy]phenyl}amino)quinazolin-5-yl]oxy}ethyl)acetamide

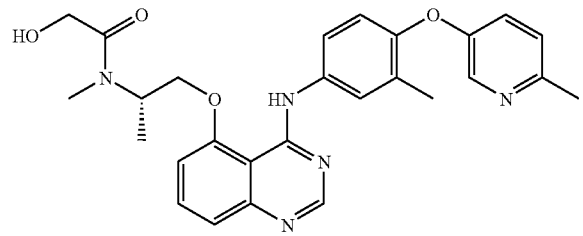

The procedure described in Example 115 was repeated using 5-{[(2S)-2-(methylamino)propyl]oxy}-N-{3-methyl-4-[(6-methylpyridin-3-yl)oxy]phenyl}quinazolin-4-amine to give the title compound in 72% yield; NMR Spectrum: (CDCl$_3$) 1.34 (d, 3H), 2.30 (s, 3H), 2.53 (s, 3H), 2.79 (s, 3H), 3.12 (m, 1H), 3.95 (dd, 1H), 4.09 (dd, 1H), 4.30-4.15 (m, 2H), 5.40 (m, 1H), 6.91 (m, 2H), 7.09 (d, 1H), 7.17 (dd, 1H), 7.38 (m, 1H), 7.46 (s, 1H), 7.50 (d, 1H), 7.64 (t, 1H), 8.30 (d, 1H), 8.58 (s, 1H), 9.36 (s, 1H); Mass spectrum: MH$^+$ 488.

The 5-{[(2S)-2-(methylamino)propyl]oxy}-N-{3-methyl-4-[(6-methylpyridin-3-yl)oxy]phenyl}quinazolin-4-amine used as starting material was prepared as follows:

The procedure described in Example 103, preparation of starting materials, was repeated using 5-fluoro-N-{3-methyl-4-[(6-methylpyridin-3-yl)oxy]phenyl}quinazolin-4-amine (obtained as described in Example 103, preparation of starting materials) and (2S)-2-(methylamino)propan-1-ol (obtained as described in Chacchio et al., Tetrahedron, 1995, 51, 5689) to give 5-{[(2S)-2-(methylamino)propyl]oxy}-N-{3-methyl-4-[(6-methylpyridin-3-yl)oxy]phenyl}quinazolin-4-amine in 71% yield; NMR Spectrum: (CDCl$_3$) 1.30 (d, 3H), 2.28 (s, 3H), 2.52 (s, 3H), 2.53 (s, 3H), 3.20 (m, 1H), 4.09 (m, 1H), 4.21 (m, 1H), 6.89 (m, 2H), 7.14-7.07 (m, 2H), 7.45 (d, 1H), 7.63 (m, 2H), 8.26 (s, 1H), 8.63 (s, 1H); Mass spectrum: MH$^+$ 430.

EXAMPLE 118

N-Methyl-N-((1S)-1-methyl-2-{[4-({3-methyl-4-[(6-methylpyridin-3-yl)oxy]phenyl}amino)quinazolin-5-yl]oxy}ethyl)acetamide

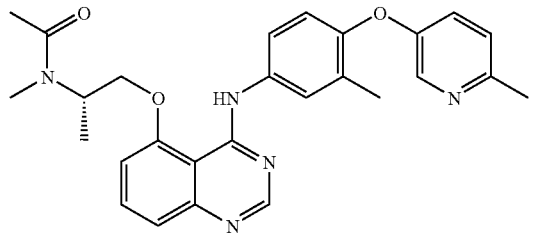

The procedure described in Example 116 was repeated using 5-{[(2S)-2-methylamino)propyl]oxy}-N-{3-methyl-4-[(6-methylpyridin-3-yl)oxy]phenyl}quinazolin-4-mine (obtained as described in Example 117, preparation of starting materials) and acetic anhydride to give the title compound in 88% yield; NMR Spectrum: (CDCl$_3$) 1.28 (d, 3H), 1.94 (s, 3H), 2.30 (s, 3H), 2.53 (s, 3H), 2.90 (s, 3H), 4.30-4.10 (m, 2H), 5.38 (m, 1H), 6.92 (m, 2H), 7.08 (d, 1H), 7.14 (dd, 1H), 7.48 (d, 2H), 7.53 (s, 1H), 7.64 (t, 1H), 8.27 (d, 1H), 8.60 (s, 1H), 9.51 (s, 1H); Mass spectrum: MH$^+$ 472.

EXAMPLE 119

Methyl {2-[(4-{[3-chloro-4-(pyridin-2-ylmethoxy)phenyl]amino}quinazolin-5-yl)oxy]ethyl}methylcarbamate

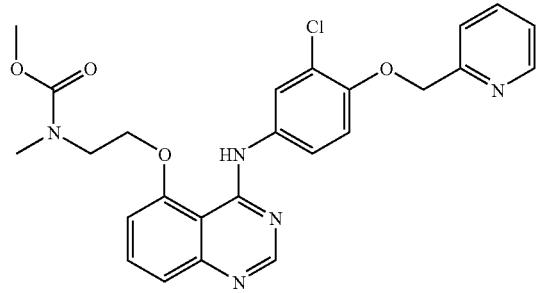

N-[3-chloro-4-(pyridin-2-ylmethoxy)phenyl]-5-[2-(methylamino)ethoxy]quinazolin-4-amine (obtained as described in Example 1, preparation of starting materials, 217 mg) and DIPEA (0.2 ml) were stirred in DCM (20 ml).

Methyl chloroformate (0.043 ml) was added slowly and the resulting solution was stirred for 18 hours. The solution was evaporated and the residue purified by chromatography, eluting with increasing concentrations of methanol in ethyl acetate (5-10%). The appropriate fractions were evaporated to give an oil, which was triturated with acetonitrile to give the title compound as a solid (43 mg, 17%); NMR spectrum (DMSO-d6 @ 373K) 2.88 (s, 3H), 3.30 (s, 3H), 3.75-3.85 (t, 2H), 4.35-4.55 (bs, 2H), 5.30 (s, 2H), 7.10-7.30 (m, 2H), 7.30-7.40 (m, 2H), 7.50-7.60 (m, 2H), 7.70-7.78 (t, 1H), 7.80-7.95 (m, 2H), 8.43 (bs, 1H), 8.75-8.80 (d, 1H), 9.60-9.80 (bs, 1H); Mass spectrum MH$^+$ 494.0.

EXAMPLE 120

N-{2-[(4-{[3-Chloro-4-(pyridin-2-ylmethoxy)phenyl]amino}quinazolin-5-yl)oxy]ethyl}-N,N'-dimethylurea

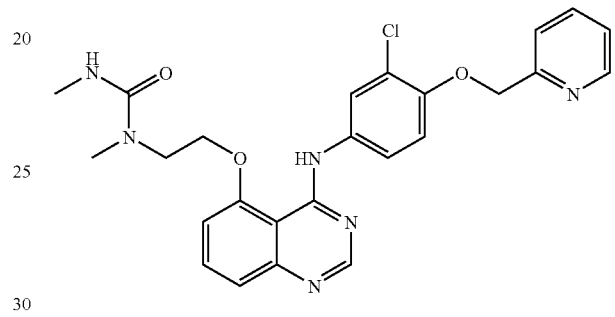

Methyl isocyanate (0.035 ml) was added slowly to a stirred solution of N-[3-chloro-4-(pyridin-2-ylmethoxy)phenyl]-5-[2-(methylamino)ethoxy]quinazolin-4-amine (obtained as described in Example 1, preparation of starting materials, 217 mg) in DCM (10 ml). The resulting solution was stirred for 2 hours and then evaporated. The residue was triturated with acetonitrile and the resulting solid washed with ether to give the title compound as a solid (205 mg, 83%); NMR spectrum (DMSO-d6 @ 373K) 2.85 (s, 3H), 2.95 (s, 3H), 3.75-3.85 (t, 2H), 4.35-4.45 (t, 2H), 5.25 (s, 2H), 5.90-6.00 (bs, 1H), 7.10-7.15 (d, 1H), 7.15-7.25 (d, 1H), 7.30-7.37 (t, 2H), 7.52-7.60 (m, 2H), 7.65-7.73 (t, 1H), 7.80-7.86 (m, 1H), 7.94-7.99 (d, 1H), 8.44 (s, 1,H), 8.55-8.60 (d, 1H), 9.80 (s, 1H); Mass spectrum MH$^+$ 493.4.

EXAMPLE 121

N'-(2-Chloroethyl)-N-{2-[(4-{[3-chloro-4-(pyridin-2-ylmethoxy)phenyl]amino}quinazolin-5-yl)oxy]ethyl}-N-methylurea

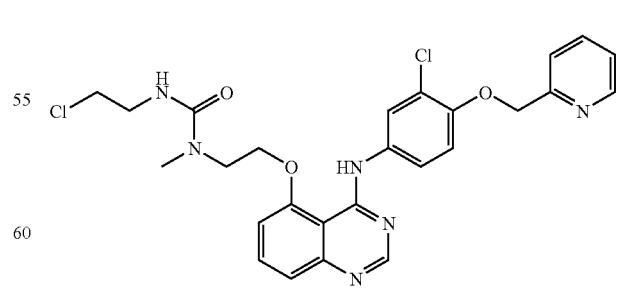

The procedure described in Example 120 was repeated using 2-chloroethyl isocyanate and N-[3-chloro-4-(pyridin-2-ylmethoxy)phenyl]-5-[2-(methylamino)ethoxy]quinazolin-4-amine (obtained as described in Example 1, preparation of starting materials) to give the title compound as a solid in 80% yield; NMR spectrum (DMSO-d6 @ 373K) 2.90 (s, 3H), 3.15-3.25 (q, 2H), 3.43-3.50 (t, 2H), 3.75-3.85 (t, 2H), 4.35-4.45 (t, 2H), 5.25, 6.35 (bs, 1H), 7.08-7.13 (d, 1H), 7.13-7.30 (m, 1H), 7.35-7.40 (m, 2H), 7.50-7.65 (m, 2H), 7.65-7.80 (m, 1H), 7.80-7.90 (t, 1H), 7.95 (d, 1H), 8.50 (s, 1H), 8.55-8.60 (d, 1H), 9.80 (s, 1H); Mass spectrum MH+ 541.3.

EXAMPLE 122

N-{(2R)-2-[(4-{[3-Chloro-4-(pyridin-2-ylmethoxy)phenyl]amino}quinazolin-5-yl)oxy]propyl}-N'-methylurea

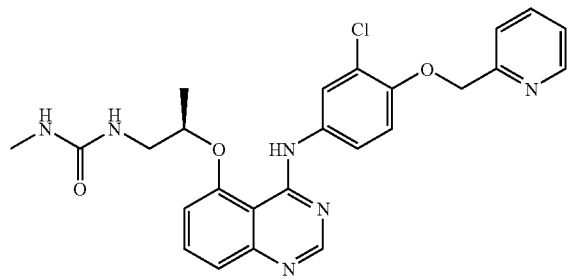

The procedure described in Example 120 was repeated using methyl isocyanate and 5-[(1R)-2-amino-1-methylethoxy]-N-[3-chloro-4-(pyridin-2-ylmethoxy)phenyl]quinazolin-4-amine (obtained as described in Example 65, preparation of starting materials) to give the title compound as a solid in 43% yield; NMR spectrum (DMSO-d6 @ 373K) 1.40-1.45 (d, 3H), 2.50-2.55 (d, 3H), 3.38-3.48 (m, 1H), 3.50-3.60 (m, 1H), 4.83-4.92 (m, 1H), 5.28 (s, 2H), 5.55-5.65 (bs, 1H), 6.00-6.10 (bs, 1H), 7.19-7.24 (dd, 2H), 7.31-7.37 (m, 2H), 7.56-7.62 (m, 2H), 7.66-7.73 (t, 1H), 7.81-7.88 (dt, 1H), 8.06-8.08 (d, 1H), 8.48 (s, 1H), 8.55-8.60 (d, 1H), 9.95-10.05 (bs, 1H); Mass spectrum MH+ 493.4.

EXAMPLE 123

[((R)-2-{4-[3-Chloro-4-(pyridin-2-ylmethoxy)phenylamino]quinazolin-5-yloxy}propylcarbamoyl)methyl]methylcarbamic acid tert-butyl ester

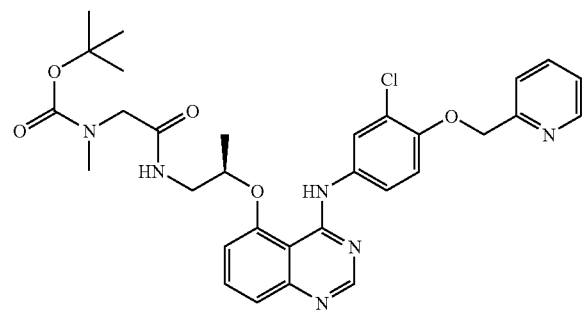

5-[(1R)-2-amino-1-methylethoxy]-N-[3-chloro-4-(pyridin-2-ylmethoxy)phenyl]quinazolin-4-amine (obtained as described in Example 65, preparation of starting materials, 868 mg) was stirred in DCM (40 ml) with DIPEA (1 ml). N-(tert-butoxycarbonyl)sarcosine (400 mg) and HATU (800 mg) were added and mixture was stirred for 18 hours. Volatile material was removed by evaporation and the residue was purified by chromatography, eluting with increasing concentrations of methanol in ethyl acetate (0-10%). Evaporation of the appropriate fractions gave the title compound as a froth (0.50 g); NMR spectrum (DMSO-d6 @ 373k) 1.10 (s, 6H), 1.20 (s, 3H), 1.40-1.42 (d, 3H), 2.72 (s, 3H), 3.40-3.60 (d, 1H, (masked by H$_2$O), 3.60-3.75 (q, 2H), 3.75-3.80 (d, 1H), 4.90-5.00 (bs, 1H), 5.30 (s, 2H), 7.28-7.34 (q, 2H), 7.34-7.40 (m, 1H), 7.42-7.46 (d, 1H), 7.50-7.62 (m, 2H), 7.85-7.91 (dt, 1H), 7.91-7.99 (m, 2H), 8.24-8.34 (bs, 1H), 8.57-8.62 (d, 1H), 8.75 (s, 1H), 10.60-10.70 (bs, 1H); Mass spectrum MH+ 607.

EXAMPLE 124

N$^1$-{(2R)-2-[(4-{[3-Chloro-4-(pyridin-2-ylmethoxy)phenyl]amino}quinazolin-5-yl)oxy]propyl}-N$^2$-methylglycinamide

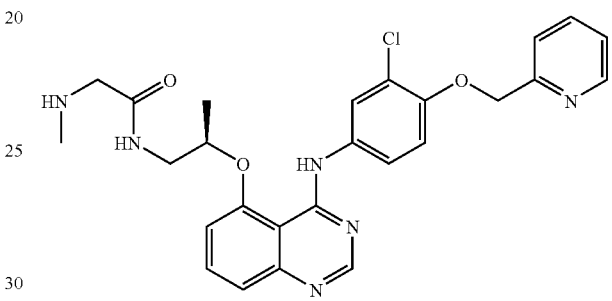

[((R)-2-{4-[3-Chloro-4-(pyridin-2-ylmethoxy)phenylamino]quinazolin-5-yloxy}propylcarbamoyl)methyl]methylcarbamic acid tert-butyl ester (obtained as described in Example 123, 0.50 g) was stirred in trifluoroacetic acid (5 ml) for 20 hours. Volatile material was removed by evaporation and the residue was purified by chromatography, eluting with aqueous ammonia (0.880), methanol, DCM (1:10:90). Evaporation of the appropriate fractions gave the title compound as a solid (60 mg, 15%); (DMSO-d6 @ 373k) 1.47-1.50 (d, 3H), 2.20 (s, 3H), 3.10 (s, 2H), 3.45-3.55 (q, 1H), 3.55-3.65 (q, 1H), 4.85-5.00 (m, 1H), 5.25 (s, 2H), 7.15-7.25 (q, 2H), 7.25-7.30 (m, 2H), 7.55-7.65 (t, 1H), 7.70-7.80 (m, 2H), 8.20 (s, 1H), 8.50 (s, 1H), 8.55-8.60 (d, 1H), 9.85-9.95 (bs, 1H); Mass spectrum MH+ 507.

EXAMPLE 125

2-Hydroxy-N-methyl-N-(2-{[4-({3-methyl-4-[(6-methylpyridin-3-yl)oxy]phenyl}amino)quinazolin-5-yl]oxy}ethyl)acetamide

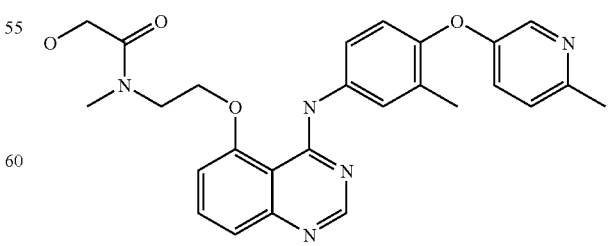

5-[2-(Methylamino)ethoxy]-N-{3-methyl-4-[(6-methylpyridin-3-yl)oxy]phenyl}quinazolin-4-amine (32 mg, 0.077 mmol) and glycolic acid (6 mg, 0.085 mmol) were dissolved in DMA (10 ml). HATU (32 mg, 0.085 mmol) was added, and the mixture was stirred at ambient temperature for 16 hours. The mixture was concentrated in vacuo, and the residue purified by reverse-phase HPLC, eluting with 5 to 50% acetonitrile in $H_2O$ containing 0.2% TFA. The appropriate fraction was evaporated, and the residue dissolved in methanol/DCM (1:1, 25 ml). The mixture was neutralised by stirring overnight with tetraalkylammonium carbonate, polymer bound. The mixture was filtered, and the filtrate was evaporated. Crystallisation from ethyl acetate/iso-hexane gave 2-hydroxy-N-methyl-N-(2-{[4-({3-methyl-4-[(6-methylpyridin-3-yl)oxy]phenyl}amino)quinazolin-5-yl]oxy}ethyl)acetamide as a white crystalline solid (22 mg, 60%); NMR Spectrum (DMSO-d6, 400 MHz, 373K) 2.26 (s, 3H), 2.48 (s, 3H), 3.02 (s, 3H), 3.95 (t, 2H), 4.02-4.11 (m-3H), 4.55 (t, 2H), 6.96 (d, 1H), 7.20 (d, 1H), 7.23 (m, 2H), 7.38 (d, 1H), 7.65 (dd, 1H), 7.70 (d, 1H), 7.73 (dd, 1H), 8.20 (m, 1H), 8.49 (s, 1H), 9.77 (s, 1H); Mass spectrum $MH^+$ 473.9

The 5-[2-(methylamino)ethoxy]-N-{3-methyl-4-[(6-methylpyridin-3-yl)oxy]phenyl}quinazolin-4-amine used as starting material was prepared as follows:

Sodium hydride (60% dispersion in mineral oil, 28 mg, 0.69 mmol) was suspended in DMA (10 ml) and N-methylethanolamine (56 µl, 0.69 mmol) was added under an atmosphere of nitrogen. The mixture was stirred for 20 minutes at ambient temperature, and 5-fluoro-N-{3-methyl-4-[(6-methylpyridin-3-yl)oxy]phenyl}quinazolin-4-amine (obtained as described in Example 103, preparation of starting materials, 100 mg, 0.28 mmol) was added. The mixture was heated under an atmosphere of nitrogen at 110° C. for 1 hour, then at 125° C. for 14 hours. The mixture was cooled to ambient temperature, and acidified with TFA. The mixture was concentrated in vacuo, and the residue purified by reverse-phase HPLC, eluting with 5 to 50% acetonitrile in $H_2O$. The appropriate fractions were evaporated to a volume such that all of the acetonitrile had been removed. The resulting aqueous solution was basified with concentrated aqueous ammonia, and extracted with DCM (4×20 ml). The combined extracts were filtered through a silicone-treated filter paper, and concentrated in vacuo to give 5-[2-(methylamino)ethoxy]-N-{3-methyl-4-[(6-methylpyridin-3-yl)oxy]phenyl}quinazolin-4-amine as a yellow solid (40 mg, 34%); NMR Spectrum ($CDCl_3$, 400 MHz) 2.20 (s, 3H), 2.44 (s, 3H), 2.49 (s, 3H), 3.12 (t, 2H), 4.25 (t, 2H), 6.80 (d, 1H), 6.83 (d, 1H), 7.00 (d, 1H), 7.04 (dd, 1H), 7.39 (d, 1H), 7.55 (dd, 1H), 7.61 (dd, 1H), 7.68 (d, 1H), 8.19 (d, 1H), 8.56 (s, 1H), 10.26 (s, 1H); Mass spectrum $MH^+$ 416.0

EXAMPLE 126

N-Methyl-N-(2-{[4-({3-methyl-4-[(6-methylpyridin-3-yl)oxy]phenyl}amino)quinazolin-5-yl]oxy}ethyl)acetamide

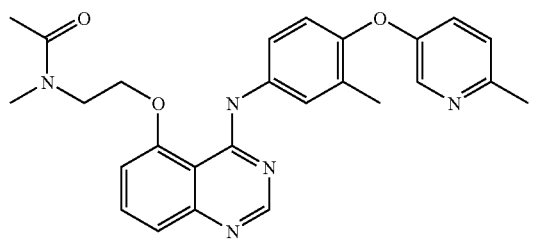

N-{2-[(4-Chloroquinazolin-5-yl)oxy]ethyl}-N-methylacetamide (38 mg, 0.136 mmol) and 3-methyl-4-[(6-methylpyridin-3-yl)oxy]aniline (obtained as described in Example 103, preparation of stating materials, 32 mg, 0.150 mmol) were dissolved in iso-propanol, and the mixture heated to reflux for 1 hour. The mixture was concentrated in vacuo, and the residue purified by chromatography, eluting with 0 to 5.5% (10:1 methanol/conc. $NH_{3(aq)}$) in ethyl acetate. Evaporation of the appropriate fractions gave N-methyl-N-(2-{[4-({3-methyl-4-[(6-methylpyridin-3-yl)oxy]phenyl}amino)quinazolin-5-yl]oxy}ethyl)acetamide as a dry film (24 mg, 39%); NMR Spectrum (DMSO-d6, 400 MHz, 373K) 1.96 (s, 3H), 2.24 (s, 3H), 2.46 (s, 3H), 2.94 (s, 3H), 3.90 (t, 2H), 4.50 (t, 3H), 6.94 (d, 1H), 7.18 (d, 1H), 7.21 (m, 2H), 7.36 (d, 1H), 7.63 (dd, 1H), 7.68 (d, 1H), 7.71 (dd, 1H), 8.17 (dd, 1H), 8.47 (s, 1H), 9.76 (s, 1H); Mass spectrum $MH^+$ 458.4.

The N-{2-[(4-chloroquinazolin-5-yl)oxy]ethyl}-N-methylacetamide used as starting material was prepared as follows:

Sodium hydride (60% dispersion in mineral oil, 732 mg, 18.3 mmol) was suspended in DMA (50 ml) and N-methylethanolamine (734 µl, 9.15 mmol) was added under an atmosphere of nitrogen. The mixture was stirred for 30 minutes at ambient temperature, and 5-fluoroquinazolin-4(3H)-one (1.0 g, 6.10 mmol) was added. The mixture was heated under an atmosphere of nitrogen at 85° C. for 90 minutes. The mixture was cooled to ambient temperature, and the resulting slurry poured into methanol (100 ml). Dowex resin (50WX4-400, 25 g) was added, and the mixture stirred for 1 hour at ambient temperature. The resin was collected by filtration, and washed with methanol (100 ml). The resin was suspended in a solution of ammonia in methanol (2.3 N, 150 ml), and the mixture stirred for 30 minutes. The mixture was filtered and the residue washed with ammonia in methanol (2.3 N, 100 ml). The combined filtrates were concentrated in vacuo, and dried in vacuo (1 mbar, 60° C.) for 16 hours to give 5-[2-(methylamino)ethoxy]quinazolin-4(3H)-one as an off white solid (1.09 g, 82%); NMR Spectrum (DMSO-d6, 400) 2.36 (s, 3H), 2.85 (t, 2H), 5.11 (t, 2H), 6.97 (d, 1H), 7.14 (d, 1H), 7.61 (dd, 1H), 7.97 (s, 1H); Mass spectrum $MH^+$ 220.

5-[2-(Methylamino)ethoxy]quinazolin-4(3H)-one (823 mg, 3.76 mmol) was dissolved in pyridine (25 ml), and the solution cooled to 0° C. Acetic anhydride (1.20 ml, 12.70 mmol) was added drop wise; the solution was warmed to ambient temperature and stirred for 90 minutes. The mixture was concentrated in vacuo, and the residue purified by chromatography, eluting with 4% to 7% (10:1 methanol/conc. $NH_{3(aq)}$) in DCM. Evaporation of the appropriate fractions gave N-methyl-N-{2-[(4-oxo-3,4-dihydroquinazolin-5-yl)oxy]ethyl}acetamide as a white foam (970 mg, 99%); NMR Spectrum (DMSO-d6, 400 MHz, 373K) 2.05 (bs, 3H), 2.92 (s, 3H), 3.71 (bt, 2H), 4.20 (bt, 2H), 7.01 (d, 1H), 7.19 (d, 1H), 7.63 (dd, 1H), 7.89 (s, 1H); Mass spectrum $M+NH_4^+$ 284.0 (ES−) $M-H^+$ 260.0.

N-Methyl-N-{2-[(4-oxo-3,4-dihydroquinazolin-5-yl)oxy]ethyl}acetamide (261 mg, 1.00 mmol) and diiso-propylethylamine (522 µl, 3.00 mmol) were dissolved in DCM (25 ml), and the mixture cooled to 0° C. Phosphorus oxychloride (930 µl, 10 mmol) was added drop wise; the solution was warmed to ambient temperature and stirred for 2 hours. The mixture was cooled to 0° C., and saturated sodium hydrogen carbonate solution (30 ml) was added with vigorous stirring. The stirred mixture was allowed to warm to ambient temperature over 20 minutes. The DCM layer was separated, washed with saturated sodium hydrogen carbonate solution (30 ml), water (30 ml) and brine (30 ml), filtered through a silicone-treated filter paper, and evaporated to give N-{2-[(4-chloroquinazolin-5-yl)oxy]ethyl}-N-methylacetamide as an orange solid (90 mg, 32%); NMR Spectrum (DMSO-d6, 400 MHz, CDCl$_3$) 2.05 (s, 3H), 3.17 (s, 3H), 3.85 (t, 2H), 4.28 (t, 2H), 6.99 (d, 1H), 7.58 (d, 1H), 7.76 (dd, 1H), 8.87 (s, 1H); Mass spectrum 276.4 MH$^+$ (4-OMe derivative—product quenched with MeOH in instrument).

EXAMPLE 127

N-{2-[(4-{[3-Chloro-4-(1-methyl-1-pyridin-2-ylethoxy)phenyl]amino}quinazolin-5-yl)oxy]ethyl}-N-methylacetamide

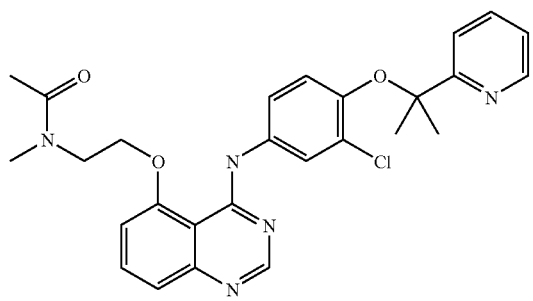

The procedure described in Example 126 was repeated using N-{2-[(4-chloroquinazolin-5-yl)oxy]ethyl}-N-methylacetamide (obtained as described in Example 126, preparation of starting materials, 47 mg, 0.170 mmol) and 3-chloro-4-(1-methyl-1-pyridin-2-ylethoxy)aniline (49 mg, 0.187 mmol) to give the title compound in 31% yield; NMR Spectrum (DMSO-d6, 400 MHz, 373K) 1.75 (s, 6H), 1.92 (s, 3H), 2.94 (s, 3H), 3.88 (t, 2H), 4.47 (t, 2H), 6.62 (d, 1H), 7.16 (d, 1H), 7.31 (ddd, 1H), 7.35 (d, 1H), 7.39 (dd, 1H), 7.70 (dd, 1H), 7.75 (dd, 1H), 7.83 (ddd, 1H), 7.99 (d, 1H), 8.46 (s, 1H), 8.58 (dd, 1H), 9.70 (s, 1H); Mass spectrum MH$^+$ 506.0.

The 3-chloro-4-(1-methyl-1-pyridin-2-ylethoxy)aniline used as starting material was prepared as follows:

Sodium hydride (60% dispersion in mineral oil, 220 mg, 5.50 mmol) was suspended in DMA (30 ml) and 2-pyridin-2-ylpropan-2-ol (obtained as described in Organometallics, 1997, 16, 3303, 754 mg, 5.50 mmol) was added under an atmosphere of nitrogen. The mixture was stirred for 30 minutes at ambient temperature, then cooled to 0° C. 3-Chloro-4-fluoronitrobenzene (878 mg, 5.00 mmol) was added as a solution in DMA (15 ml); the mixture was warmed to room temperature, and was stirred for 2 hours. The mixture was concentrated in vacuo, and the residue partitioned between ethyl acetate (75 ml) and water (75 ml). The aqueous layer was extracted with ethyl acetate (75 ml), and the extractions combined with the organic layer. The combined organics were dried over MgSO$_4$ and concentrated in vacuo. The residue was purified by chromatography, eluting with 0 to 20% ethyl acetate in iso-hexane, giving 2-[1-(2-chloro-4-nitrophenoxy)-1-methylethyl]pyridine as a pale yellow solid (810 mg, 55%); NMR Spectrum (DMSO-d6, 400 MHz, CDCl$_3$) 1.91 (s, 6H), 6.40 (d, 1H), 7.25 (ddd, 1H), 7.50 (d, 1H), 7.70 (ddd, 1H), 7.82 (dd, 1H), 8.30 (d, 1H), 8.65 (d, 1H); Mass spectrum MH$^+$ 293.0, 295.0.

2-[1-(2-Chloro-4-nitrophenoxy)-1-methylethyl]pyridine (800 mg, 2.74 mmol) was dissolved in ethyl acetate (50 ml). The mixture was purged with nitrogen, and platinum on activated carbon (10%, 100 mg) was added. The mixture was hydrogenated for 6 hours using a burette filled with hydrogen. The system was degassed and purged with nitrogen, and the catalyst removed by filtration. The filtrate was concentrated in vacuo, and the residue purified by chromatography, eluting with 20% to 30% ethyl acetate in iso-hexane. The appropriate fractions were evaporated to give 3-chloro-4-(1-methyl-1-pyridin-2-ylethoxy)aniline as a straw-coloured oil (452 mg, 63%); NMR Spectrum (DMSO-d6, 400 MHz, CDCl$_3$) 1.63 (s, 6H), 3.41 (bs, 2H), 6.25 (dd, 1H), 6.35 (d, 1H), 6.65 (d, 1H), 7.11 (ddd, 1H), 7.63 (ddd, 1H), 7.77 (d, 1H), 8.50 (d, 1H).

EXAMPLE 128

Pharmaceutical Compositions

The following illustrates representative pharmaceutical dosage forms of the invention as defined herein (the active ingredient being termed "Compound X") which may be prepared, for therapeutic or prophylactic use in humans:

| (a) | Tablet I | mg/tablet |
|---|---|---|
| | Compound X | 100 |
| | Lactose Ph. Eur | 182.75 |
| | Croscarmellose sodium | 12.0 |
| | Maize starch paste (5% w/v paste) | 2.25 |
| | Magnesium stearate | 3.0 |

| (b) | Injection I | (50 mg/ml) |
|---|---|---|
| | Compound X | 5.0% w/v |
| | 1M Sodium hydroxide solution | 15.0% v/v |
| | 0.1M Hydrochloric acid (to adjust pH to 7.6) | |
| | Polyethylene glycol 400 | 4.5% w/v |
| | Water for injection to 100%. | |

The above compositions may be prepared by conventional procedures well known in the pharmaceutical art. For example, Tablet I may be prepared by blending the components together and compressing the mixture into a tablet.

The invention claimed is:
1. A quinazoline derivative of the formula I:

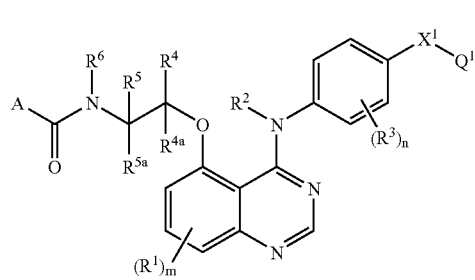

wherein:
m is 0, 1 or 2;
each R$^1$, which may be the same or different, is selected from hydroxy, (1-6C)alkoxy, (3-7C)cycloalkyl-oxy and (3-7C)cycloalkyl-(1-6C)alkoxy,
wherein any CH$_2$ or CH$_3$ group within a R$^1$ substituent optionally bears on each said CH$_2$ or CH$_3$ group one or more halogeno or (1-6C)alkyl substituents, or a substituent selected from hydroxy and (1-6C)alkoxy,
R$^2$ is hydrogen or (1-4C)alkyl;
n is 0, 1, 2, 3 or 4;

each $R^3$, which may be the same or different, is selected from cyano, halogeno, (1-4C)alkyl, trifluoromethyl, (1-4C)alkoxy, (2-4C)alkenyl and (2-4C)alkynyl;

$X^1$ is selected from O, S, SO, $SO_2$, $N(R^7)$, $CON(R^7)$, $CH(OR^7)$, $N(R^7)CO$, $SO_2N(R^7)$, $N(R^7)SO_2$, $OC(R^7)_2$, $C(R^7)_2O$, $SC(R^7)_2$, $C(R^7)_2S$, CO, $C(R^7)_2N(R^7)$ and $N(R^7)C(R^7)_2$, each $R^7$, which may be the same or different, is hydrogen or (1-6C)alkyl;

$Q^1$ is aryl, or heteroaryl,
wherein $Q^1$ optionally bears one or more substituents, which may be the same or different, selected from halogeno, hydroxy, (1-4C)alkyl and (1-4C)alkoxy;

wherein any $CH_2$ or $CH_3$ group within $-X^1-Q^1$ optionally bears on each said $CH_2$ or $CH_3$ group one or more halogeno or (1-6C)alkyl substituents or a substituent selected from hydroxy, cyano, amino, (1-4C)alkoxy, (1-4C)alkylamino and di-[(1-4C)alkylamino];

$R^4$, $R^{4a}$, $R^5$ and $R^{5a}$, which may be the same or different, are selected from hydrogen and (1-6C)alkyl, or $R^4$ and $R^{4a}$ together with the carbon atom to which they are attached form a (3-7C)cycloalkyl ring, or $R^5$ and $R^{5a}$ together with the carbon atom to which they are attached form a (3-7C)cycloalkyl ring, wherein any $CH_2$ or $CH_3$ group within any of $R^4$, $R^{4a}$, $R^5$ and $R^{5a}$ optionally bears on each said $CH_2$ or $CH_3$ group one or more halogeno substituents or a substituent selected from hydroxy, cyano, (1-6C)alkoxy, amino, (2-6C)alkanoyl, (1-6C)alkylamino and di-[(1-6C)alkylamino];

$R^6$ is selected from hydrogen, (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, wherein any heterocyclyl group within an $R^6$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$X^3$—$R^{10}$;

$X^3$ is a direct bond or is selected from O, CO, $SO_2$ and $N(R^{11})$;

$R^{11}$ is hydrogen or (1-4C)alkyl;

$R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, wherein any heterocyclyl group within an $R^6$ substituent optionally bears 1 or 2 oxo or thioxo substituents; and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

A is selected from hydrogen, a group of the formula Z-$(CR^{12}R^{13})_p$— and $R^{14}$;

p is 1, 2, 3, or 4;

each $R^{12}$ and $R^{13}$, which may be the same or different, is selected from hydrogen, (1-6C)alkyl, (2-6C)alkenyl and (2-6C)alkynyl,
or an $R^{12}$ and an $R^{13}$ group attached to the same carbon atom form a (3-7C)cycloalkyl or (3-7C)cycloalkenyl ring, wherein any $CH_2$ or $CH_3$ group within any of $R^{12}$ and $R^{13}$, optionally bears on each said $CH_2$ or $CH_3$ group one or more halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkyl]amino;

Z is selected from hydrogen, $OR^{15}$, $NR^{16}R^{17}$, (1-6C)alkylsulfonyl, (1-6C)alkanesulfonylamino and N-(1-6C)alkyl-(1-6C)alkanesulfonylamino;

each of $R^{15}$, $R^{16}$ and $R^{17}$, which may be the same or different, is selected from hydrogen, (1-6C)alkyl, (2-6C)alkenyl, (2-6C)alkynyl and (1-6C)alkoxycarbonyl, or Z is a group of the formula: $Q^2$-$X^4$—;

$X^4$ is selected from O, $N(R^{18})$, $SO_2$ and $SO_2N(R^{18})$;

$R^{18}$ is hydrogen or (1-6C)alkyl;

$Q^2$ is (3-7C)cycloalkyl, (3-7C)cycloalkenyl or heterocyclyl;

$R^{14}$ is selected from hydrogen, $OR^{19}$ and $NR^{16}R^{17}$;

$R^{19}$ is selected from (1-6C)alkyl, (2-6C)alkenyl and (2-6C)alkynyl, and wherein $R^{16}$ and $R^{17}$ are as defined above, or $R^{14}$ is a group of the formula: $Q^3$-$X^5$—;

$X^5$ is selected from O and $N(R^{20})$;

$R^{20}$ is hydrogen or (1-6C)alkyl;

$Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, or $R^{14}$ is $Q^4$;

$Q^4$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, wherein adjacent carbon atoms in any (2-6C)alkylene chain within a Z or $R^{14}$ substituent are optionally separated by the insertion into the chain of a group selected from O, S, SO, $SO_2$, $N(R^{21})$, CO, —C=C— and —C≡C—;

$R^{21}$ is hydrogen or (1-6C)alkyl, wherein any heterocyclyl group within a Z or $R^{14}$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$;

$X^6$ is a direct bond or is selected from O, CO, $SO_2$ and $N(R^{23})$;

$R^{23}$ is hydrogen or (1-4C)alkyl;

$R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, wherein any heterocyclyl group within a Z or R$^{14}$ substituent optionally bears 1 or 2 oxo or thioxo substituents, and wherein any CH$_2$ or CH$_3$ group within a Z or R$^{14}$ group, other than a CH$_2$ group within a heterocyclyl ring, optionally bears on each said CH$_2$ or CH$_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C) alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

or a pharmaceutically acceptable salt thereof.

2. A quinazoline derivative according to claim 1, wherein:

m is 0, 1 or 2;

each R$^1$, which may be the same or different, is selected from hydroxy, (1-6C)alkoxy, (3-7C)cycloalkyl-oxy and (3-7C)cycloalkyl-(1-6C)alkoxy, wherein any CH$_2$ or CH$_3$ group within a R$^1$ substituent optionally bears on each said CH$_2$ or CH$_3$ group one or more halogeno or (1-6C)alkyl substituents, or a substituent selected from hydroxy and (1-6C)alkoxy, R$^2$ is hydrogen or (1-4C)alkyl;

n is 0, 1, 2, 3 or 4;

each R$^3$, which may be the same or different, is selected from halogeno, (1-4C)alkyl, trifluoromethyl, (1-4C)alkoxy, (2-4C)alkenyl and (2-4C)alkynyl;

X$^1$ is selected from O, S, SO, SO$_2$, N(R$^7$), CH(OR$^7$), CON(R$^7$), N(R$^7$)CO, SO$_2$N(R$^7$), N(R$^7$)SO$_2$, OC(R$^7$)$_2$, C(R$^7$)$_2$O, SC(R$^7$)$_2$, C(R$^7$)$_2$S, CO, C(R$^7$)$_2$N(R$^7$) and N(R$^7$)C(R$^7$)$_2$, each R$^7$, which may be the same or different, is hydrogen or (1-6C)alkyl;

Q$^1$ is aryl, or heteroaryl, wherein Q$^1$ optionally bears one or more substituents, which may be the same or different, selected from halogeno, hydroxy, (1-4C)alkyl and (1-4C)alkoxy, wherein any CH$_2$ or CH$_3$ group within —X$^1$-Q$^1$ optionally bears on each said CH$_2$ or CH$_3$ group one or more halogeno or (1-6C)alkyl substituents or a substituent selected from hydroxy, cyano, amino, (1-4C)alkoxy, (1-4C)alkylamino and di-[(1-4C)alkylamino];

R$^4$, R$^{4a}$, R$^5$ and R$^{5a}$, which may be the same or different, are selected from hydrogen and (1-6 C)alkyl, or R$^4$ and R$^{4a}$ together with the carbon atom to which they are attached form a (3-7C)cycloalkyl ring, or R$^5$ and R$^{5a}$ together with the carbon atom to which they are attached form a (3-7C)cycloalkyl ring, wherein any CH$_2$ or CH$_3$ group within any of R$^4$, R$^{4a}$, R$^5$ and R$^{5a}$ optionally bears on each said CH$_2$ or CH$_3$ group one or more halogeno substituents or a substituent selected from hydroxy, cyano, (1-6C)alkoxy, amino, (2-6C)alkanoyl, (1-6C)alkylamino and di-[(1-6C)alkylamino];

R$^6$ is selected from hydrogen, (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, and wherein any heterocyclyl group within an R$^6$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—X$^3$—R$^{10}$;

X$^3$ is a direct bond or is selected from O, CO, SO$_2$ and N(R$^{11}$),

R$^{11}$ is hydrogen or (1-4C)alkyl, and R$^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, wherein any heterocyclyl group within an R$^6$ substituent optionally bears 1 or 2 oxo or thioxo substituents; and wherein any CH$_2$ or CH$_3$ group within a R$^6$ substituent, other than a CH$_2$ group within a heterocyclyl group, optionally bears on each said CH$_2$ or CH$_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

A is selected from hydrogen, a group of the formula Z-(CR$^{12}$R$^{13}$)$_p$— and R$^{14}$;

p is 1, 2, 3, or 4, each R$^{12}$ and R$^{13}$, which may be the same or different, is selected from hydrogen, (1-6C)alkyl, (2-6C)alkenyl and (2-6C)alkynyl, or an R$^{12}$ and an R$^{13}$ group attached to the same carbon atom form a (3-7C)cycloalkyl or (3-7C)cycloalkenyl ring, wherein any CH$_2$ or CH$_3$ group within any of R$^{12}$ and R$^{13}$, optionally bears on each said CH$_2$ or CH$_3$ group one or more halogeno or (1-6C)alkyl substituents or a substituent selected from hydroxy, cyano, (1-6C)alkyl, (1-6C)alkoxy, amino, (2-6C)alkanoyl, (1-6C)alkylamino and di-[(1-6C)alkyl]amino, Z is selected from hydrogen, OR$^{15}$, NR$^{16}$R$^{17}$, (1-6C)alkylsulfonyl, (1-6C)alkanesulfonylamino and N-(1-6C)alkyl-(1-6C)alkanesulfonylamino, each of R$^{15}$, R$^{16}$ and R$^{17}$, which may be the same or different, is selected from hydrogen, (1-6C)alkyl, (2-6C)alkenyl and (2-6C)alkynyl, or Z is a group of the formula: Q$^2$-X$^4$—;

X$^4$ is selected from O, N(R$^{18}$), SO$_2$ and SO$_2$N(R$^{18}$);

R$^{18}$ is hydrogen or (1-6C)alkyl;

Q$^2$ is (3-7C)cycloalkyl, (3-7C)cycloalkenyl or heterocyclyl;

R$^{14}$ is selected from hydrogen, OR$^{19}$ and NR$^{16}$R$^{17}$;

R$^{19}$ is selected from (1-6C)alkyl, (2-6C)alkenyl and (2-6C)alkynyl, and wherein R$^{16}$ and R$^{17}$ are as defined above, or R$^{14}$ is a group of the formula: Q$^3$-X$^5$—;

X$^5$ is selected from O and N(R$^{20}$), wherein R$^{20}$ is hydrogen or (1-6C)alkyl;

$Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl,
or $R^{14}$ is $Q^4$ wherein $Q^4$ is (3-7C)cycloalkyl, (3-7C)cycloalkenyl or heterocyclyl,
wherein adjacent carbon atoms in any (2-6C)alkylene chain within a Z or $R^{14}$ substituent are optionally separated by the insertion into the chain of a group selected from O, S, SO, $SO_2$, $N(R^{21})$, CO, —C≡C— and —C=C—;
$R^{21}$ is hydrogen or (1-6C)alkyl,
wherein any heterocyclyl group within a Z or $R^{14}$ substituent optionally bears one or more substituents, which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^6$—$R^{22}$;

$X^6$ is a direct bond or is selected from O, CO, $SO_2$ and $N(R^{23})$;
$R^{23}$ is hydrogen or (1-4C)alkyl;
$R^{22}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl,
wherein any heterocyclyl group within a Z or $R^{14}$ substituent optionally bears 1 or 2 oxo or thioxo substituents, and
wherein any $CH_2$ or $CH_3$ group within a Z or $R^{14}$ group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C) alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;
or a pharmaceutically acceptable salt thereof.

3. A quinazoline derivative according to claim 1, wherein $R^4$, $R^{4a}$, $R^5$ and $R^{5a}$, which may be the same or different, are selected from hydrogen and (1-6C)alkyl, and wherein any $CH_2$ or $CH_3$ group within any of $R^4$, $R^{4a}$, $R^5$ and $R^{5a}$ optionally bears on each said $CH_2$ or $CH_3$ group one or more halogeno substituents or a substituent selected from hydroxy, cyano, (1-6C)alkoxy, amino, (2-6C)alkanoyl, (1-6C)alkylamino and di-[(1-6C) alkylamino].

4. A quinazoline derivative according to claim 1, wherein m is 0.

5. A quinazoline derivative according to claim 1, wherein $R^2$ is hydrogen.

6. A quinazoline derivative according to claim 1, wherein n is 0, 1 or 2 and, when present, at least one $R^3$ is in a meta-position (3-position) relative to the nitrogen of the anilino group in formula I.

7. A quinazoline derivative according to claim 1, wherein n is 1 and $R^3$ is selected from halogeno and (1-4C)alkyl.

8. A quinazoline derivative according to claim 7, wherein $R^3$ is chloro.

9. A quinazoline derivative according to claim 7, wherein $R^3$ is methyl.

10. A quinazoline derivative according to claim 1, wherein $X^1$ is selected from O, S, $OC(R^7)_2$, $SC(R^7)_2$, SO, $SO_2$, $N(R^7)$, CO and $N(R^7)C(R^7)_2$ wherein each $R^7$, which may be the same or different, is selected from hydrogen or (1-6C)alkyl.

11. A quinazoline derivative according to claim 1, wherein $X^1$ is selected from O, S and $OC(R^7)_2$ wherein each $R^7$ is, independently, hydrogen or (1-4C)alkyl.

12. A quinazoline derivative according to claim 1, wherein $X^1$ is $OCH_2$.

13. A quinazoline derivative according to claim 1, wherein
$Q^1$ is selected from phenyl and a 5- or 6-membered monocyclic heteroaryl ring, which ring contains 1, 2 or 3 heteroatoms independently selected from oxygen, nitrogen and sulfur, and
wherein $Q^1$ optionally bears one or more substituents, which may be the same or different, selected from halogeno, hydroxy, (1-4C)alkyl (1-4C)alkoxy,
wherein any $CH_2$ or $CH_3$ group within —$X^1$-$Q^1$ optionally bears on each said $CH_2$ or $CH_3$ group one or more halogeno or (1-6C)alkyl substituents or a substituent selected from hydroxy, cyano, amino, (1-4C)alkoxy, (1-4C)alkylamino and di-[(1-4C)alkylamino].

14. A quinazoline derivative according to claim 1, wherein $Q^1$ is selected from phenyl, pyridyl, pyrazinyl, 1,3-thiazolyl, 1H-imidazolyl, 1H-pyrazolyl, 1, 3-oxazolyl and isoxazolyl.

15. A quinazoline derivative according to claim 1,
wherein
$R^6$ is selected from hydrogen, (1-3C)alkyl, (2-3C)alkenyl, (2-3C)alkynyl, (3-5C)cycloalkyl, (3-5C)cycloalkyl-(1-3C)alkyl, heterocyclyl and heterocyclyl-(1-3C)alkyl,
wherein any heterocyclyl group within $R^6$ is a 4, 5, 6 or 7 membered monocyclic saturated or partially saturated heterocyclyl ring containing 1 or 2 heteroatoms selected from oxygen, nitrogen and sulfur, which heterocyclyl group is linked to the group to which it is attached by a ring carbon atom,
wherein any heterocyclyl group within an $R^6$ substituent optionally bears one or more substituents, which may be the same or different, selected from halogeno, trifluoromethyl, cyano, nitro, hydroxy, amino, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^3$—$R^{10}$;

$X^3$ is a direct bond or is selected from O and $N(R^{11})$;
$R^{11}$ is hydrogen or (1-4C)alkyl;
$R^{10}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl,
wherein any heterocyclyl group within an $R^6$ substituent optionally bears 1 or 2 oxo substituents;
and wherein any $CH_2$ or $CH_3$ group within a $R^6$ substituent, other than a $CH_2$ group within a heterocyclyl group, optionally bears on each said $CH_2$ or $CH_3$ group one or more halogeno or (1-6C)alkyl substituents or a substituent selected from hydroxy, amino, (1-6C)alkoxy, (1-6C)alkylamino and di-[(1-6C)alkyl]amino.

16. A quinazoline derivative according to claim 15, wherein $R^6$ is (1-3C)alkyl, and wherein any $CH_2$ or $CH_3$ group within a R⁶ substituent, other than a CH₂ group within a heterocyclyl group, optionally bears on each said CH₂ or CH₃ group one or more halogeno or (1-6C)alkyl substituents or a substituent selected from hydroxy, amino, (1-6C)alkoxy, (1-6C)alkylamino and di-[(1-6C)alkyl]amino.

17. A quinazoline derivative according to claim 1, wherein

A is selected from a group of the formula Z-(CR$^{12}$R$^{13}$)$_p$— and R$^{14}$;

p is 1, 2 or 3;

each R$^{12}$ and R$^{13}$, which may be the same or different, is selected from hydrogen and (1-6C)alkyl, wherein any CH₂ or CH₃ group within any of R$^{12}$ and R$^{13}$ optionally bears on each said CH₂ or CH₃ group one or more halogeno substituents or a substituent selected from hydroxy and (1-6C)alkoxy, Z is selected from hydrogen, OR$^{15}$, NR$^{16}$R$^{17}$ and (1-6C)alkylsulfonyl;

each of R$^{15}$, R$^{16}$ and R$^{17}$, which may be the same or different, is selected from hydrogen, (1-6C)alkyl and (1-6C)alkoxycarbonyl;

R$^{14}$ is selected from OR$^{19}$ and NR$^{16}$R$^{17}$;

R$^{19}$ is selected from (1-6C)alkyl and wherein R$^{16}$ and R$^{17}$ are as defined above, or R$^{14}$ is Q$^4$ Q$^4$ is (3-7C)cycloalkyl, heterocyclyl or heterocyclyl-(1-6C)alkyl, wherein any heterocyclyl group within a Z or R$^{14}$ substituent optionally bears one or more substituents, which may be the same or different, selected from halogeno, hydroxy, (1-6C)alkyl and (1-6C)alkoxy, and wherein any CH₂ or CH₃ group within a Z or R$^{14}$ group, other than a CH₂ group within a heterocyclyl ring, optionally bears on each said CH₂ or CH₃ group one or more halogeno or (1-6C)alkyl substituents or a substituent selected from hydroxy and (1-6C)alkoxy.

18. A quinazoline derivative selected from one or more of the following:

N-{2-[(4-{3-chloro-4-(pyridin-2-ylmethoxy)anilino}quinazolin-5-yl)oxy]ethyl}-2-methoxy-N-methylacetamide;

N-{2-[(4-{3-chloro-4-(pyridin-2-ylmethoxy)anilino}quinazolin-5-yl)oxy]ethyl}-2-(dimethylamino)-N-methylacetamide;

N-{(2R)-2-[(4-{3-chloro-4-(pyridin-2-ylmethoxy)anilino}quinazolin-5-yl)oxy]propyl}-2-methoxy-N-methylacetamide);

2-hydroxy-N-methyl-N-{2-[(4-{3-methyl-4-(pyrazin-2-ylmethoxy)anilino}quinazolin-5-yl)oxy]ethyl}acetamide;

2-hydroxy-N-methyl-N-{2-[(4-{3-methyl-4-(1,3-thiazol-4-ylmethoxy)anilino}quinazolin-5-yl)oxy]ethyl}acetamide;

2-hydroxy-N-methyl-N-(2-{[4-(3-methyl-4-[(5-methylisoxazol-3-yl)methoxy]anilino)quinazolin-5-yl]oxy}ethyl)acetamide;

N-{(2R)-2-[(4-{3-chloro-4-(pyridin-2-ylmethoxy)anilino}quinazolin-5-yl)oxy]propyl}-2-methoxyacetamide;

N-(2-{[4-(3-chloro-4-[(6-methylpyridin-2-yl)methoxy]anilino)quinazolin-5-yl]oxy}ethyl)-2-hydroxy-N-methylacetamide;

N-((2R)-2-{[4-(3-chloro-4-[(6-methylpyridin-2-yl)methoxy]anilino)quinazolin-5-yl]oxy}propyl) -2-hydroxy-N-methylacetamide;

N-(2-{[4-(3-chloro-4-[(6-methylpyridin-2-yl)methoxy]anilino)quinazolin-5-yl]oxy}ethyl)-N-methylacetamide;

N-(2-{[4-(3-chloro-4-[(2-fluorobenzyl)oxy]anilino)quinazolin-5-yl]oxy}ethyl)-N-methylacetamide;

N-(2-{[4-(3-chloro-4-[(3-fluorobenzyl)oxy]anilino)quinazolin-5-yl]oxy}ethyl)-N-methylacetamide;

N-{2-[(4-{3-chloro-4-(1,3-thiazol-4-ylmethoxy)anilino}quinazolin-5-yl)oxy]ethyl}-N-methylacetamide;

N-{2-[(4-{3-chloro-4-(pyrazin-2-ylmethoxy)anilino}quinazolin-5-yl)oxy]ethyl}-N-methylacetamide;

N-{(2R)-2-[(4-{3-chloro-4-(pyridin-2-ylmethoxy)anilino}quinazolin-5-yl)oxy]propyl}-2-hydroxyacetamide;

N-{2-[(4-{3-chloro-4-(pyridin-2-ylmethoxy)anilino}quinazolin-5-yl)oxy]ethyl}-N-methylacetamide;

2-hydroxy-N-methyl-N-{2-[(4-{3-methyl-4-(pyridin-2-ylmethoxy)anilino}quinazolin-5-yl)oxy]ethyl}acetamide;

N-{(1R)-2-[(4-{3-chloro-4-(pyridin-2-ylmethoxy)anilino}quinazolin-5-yl)oxy]-1-methylethyl}acetamide;

N-{(1R)-2-[(4-{3-chloro-4-(pyridin-2-ylmethoxy)anilino}quinazolin-5-yl)oxy]-1-methylethyl}-2-hydroxyacetamide;

N-{2-[(4-{3-chloro-4-(pyridin-2-ylmethoxy)anilino}quinazolin-5-yl)oxy]ethyl}-2-hydroxy-N-methylacetamide;

N-(2-{[4-(3-chloro-4-[(3-fluorobenzyl)oxy]anilino)quinazolin-5-yl]oxy}ethyl)-2-hydroxy-N-methylacetamide;

N-{2-[(4-{3-chloro-4-(1,3-thiazol-4-ylmethoxy)anilino}quinazolin-5-yl)oxy]ethyl}-2-hydroxy-N-methylacetamide;

N-{2-[(4-{3-chloro-4-(pyrazin-2-ylmethoxy)anilino}quinazolin-5-yl)oxy]ethyl}-2-hydroxy-N-methylacetamide;

N-{2-[(4-{3-chloro-4-(pyridin-2-ylmethoxy)anilino}quinazolin-5-yl)oxy]ethyl}acetamide;

N-{(2R)-2-[(4-{3-chloro-4-(pyridin-2-ylmethoxy)anilino}quinazolin-5-yl)oxy]propyl}acetamide;

N-{(2R)-2-[(4-{3-chloro-4-(pyridin-2-ylmethoxy)anilino}quinazolin-5-yl)oxy]propyl}-2-hydroxy-N-methylacetamide;

N-{(2R)-2-[(4-{3-chloro-4-(pyrazin-2-ylmethoxy)anilino}quinazolin-5-yl)oxy]propyl}-2-hydroxy-N-methylacetamide;

N-((2R)-2-{[4-(3-chloro-4-[(3-fluorobenzyl)oxy]anilino)quinazolin-5-yl]oxy}propyl)-2-hydroxy-N-methylacetamide;

N-{(2R)-2-[(4-{3-chloro-4-(1,3-thiazol-4-ylmethoxy)anilino}quinazolin-5-yl)oxy]propyl}-2-hydroxy-N-methylacetamide;

N-{(2R)-2-[(4-{3-chloro-4-(pyridin-2-ylmethoxy)anilino}quinazolin-5-yl)oxy]propyl}-N-methylacetamide;

N-{2-[(4-{[3-chloro-4-(pyridin-2-ylmethoxy)phenyl]amino}quinazolin-5-yl)oxy]ethyl}-N-ethylacetamide;

N-{2-[(4-{[3-chloro-4-(pyridin-2-ylmethoxy)phenyl]amino}quinazolin-5-yl)oxy]ethyl}-N-ethyl-2-hydroxyacetamide;

N-{2-[(4-{[3-chloro-4-(pyridin-2-ylmethoxy)phenyl]amino}quinazolin-5-yl)oxy]ethyl}-N-propylacetamide;

N-{2-[(4-{[3-chloro-4-(pyridin-2-ylmethoxy)phenyl]amino}quinazolin-5-yl)oxy]ethyl}-2-hydroxy-N-propylacetamide;

N-{2-[(4-{[3-chloro-4-(pyridin-2-ylmethoxy)phenyl]amino}quinazolin-5-yl)oxy]ethyl}-N-isopropylacetamide;

N-{2-[(4-{[3-chloro-4-(pyridin-2-ylmethoxy)phenyl]amino}quinazolin-5-yl)oxy]ethyl}-2-hydroxy-N-isopropylacetamide;

N-allyl-N-{2-[(4-{[3-chloro-4-(pyridin-2-ylmethoxy)phenyl]amino}quinazolin-5-yl)oxy]ethyl}acetamide;

N-allyl-N-{2-[(4-{[3-chloro-4-(pyridin-2-ylmethoxy)phenyl]amino}quinazolin-5-yl)oxy]ethyl}-2-hydroxyacetamide;

N-{2-[(4-{[3-chloro-4-(pyridin-2-ylmethoxy)phenyl]amino}quinazolin-5-yl)oxy]ethyl}-N-cyclopropylacetamide;

N-{2-[(4-{[3-chloro-4-(pyridin-2-ylmethoxy)phenyl]amino}quinazolin-5-yl)oxy]ethyl}-N-cyclopropyl-2-hydroxyacetamide;

N-{2-[(4-{[3-chloro-4-(pyridin-2-ylmethoxy)phenyl]amino}quinazolin-5-yl)oxy]ethyl}-N-(cyclopropylmethyl)acetamide;

N-{2-[(4-{[3-chloro-4-(pyridin-2-ylmethoxy)phenyl]amino}quinazolin-5-yl)oxy]ethyl}-N-(cyclopropylmethyl)-2-hydroxyacetamide;

N-{2-[(4-{[3-chloro-4-(pyridin-2-ylmethoxy)phenyl]amino}quinazolin-5-yl)oxy]ethyl}-N-cyclobutylacetamide;

N-{2-[(4-{[3-chloro-4-(pyridin-2-ylmethoxy)phenyl]amino}quinazolin-5-yl)oxy]ethyl}-N-cyclobutyl-2-hydroxyacetamide;

N-{2-[(4-{[3-chloro-4-(pyridin-2-ylmethoxy)phenyl]amino}quinazolin-5-yl)oxy]ethyl}-N-(1-methylpiperidin-4-yl)acetamide;

N-{2-[(4-{[3-chloro-4-(pyridin-2-ylmethoxy)phenyl]amino}quinazolin-5-yl)oxy]ethyl}-N-(tetrahydro-2H-pyran-4-yl)acetamide;

N-{2-[(4-{[3-chloro-4-(pyridin-2-ylmethoxy)phenyl]amino}quinazolin-5-yl)oxy]ethyl}-2-hydroxy-N-(tetrahydro-2H-pyran-4-yl)acetamide;

N-{2-[(4-{[3-chloro-4-(pyridin-2-ylmethoxy)phenyl]amino}quinazolin-5-yl)oxy]ethyl}-N-(2-hydroxyethyl)acetamide;

N-{2-[(4-{[3-chloro-4-(pyridin-2-ylmethoxy)phenyl]amino}quinazolin-5-yl)oxy]ethyl}-2-hydroxy-N-(2-hydroxyethyl)acetamide;

N-{2-[(4-{[3-chloro-4-(pyridin-2-ylmethoxy)phenyl]amino}quinazolin-5-yl)oxy]ethyl}-N-(2-methoxyethyl)acetamide;

N-{2-[(4-{[3-chloro-4-(pyridin-2-ylmethoxy)phenyl]amino}quinazolin-5-yl)oxy]ethyl}-2-hydroxy-N-(2-methoxyethyl)acetamide;

N-{2-[(4-{[3-chloro-4-(pyridin-2-ylmethoxy)phenyl]amino}quinazolin-5-yl)oxy]ethyl}-N-prop-2-yn-1-ylacetamide;

N-{2-[(4-{[3-chloro-4-(pyridin-2-ylmethoxy)phenyl]amino}quinazolin-5-yl)oxy]ethyl}-2-hydroxy-N-prop-2-yn-1-ylacetamide;

N-{2-[(4-{[3-chloro-4-(pyridin-2-ylmethoxy)phenyl]amino}quinazolin-5-yl)oxy]ethyl}-2-hydroxy-N-methylpropanamide;

N-{2-[(4-{[3-chloro-4-(pyridin-2-ylmethoxy)phenyl]amino}quinazolin-5-yl)oxy]ethyl}-N-methyl-tetrahydrofuranyl-2-carboxamide;

N-{2-[(4-{[3-chloro-4-(pyridin-2-ylmethoxy)phenyl]amino}quinazolin-5-yl)oxy]ethyl}-N,1-dimethylprolinamide;

N-{2-[(4-{[3-chloro-4-(pyridin-2-ylmethoxy)phenyl]amino}quinazolin-5-yl)oxy]ethyl}-2-hydroxy-N,2-dimethylpropanamide;

N-{2-[(4-{[3-chloro-4-(pyridin-2-ylmethoxy)phenyl]amino}quinazolin-5-yl)oxy]ethyl}-1-hydroxy-N-methylcyclopropanecarboxamide;

$N^1$-{2-[(4-{[3-chloro-4-(pyridin-2-ylmethoxy)phenyl]amino}quinazolin-5-yl)oxy]ethyl}-$N^1,N^2$-dimethylglycinamide;

N-{2-[(4-{[3-chloro-4-(pyridin-2-ylmethoxy)phenyl]amino}quinazolin-5-yl)oxy]ethyl}-3-hydroxy-N,2,2-trimethylpropanamide;

N-{2-[(4-{[3-chloro-4-(pyridin-2-ylmethoxy)phenyl]amino}quinazolin-5-yl)oxy]ethyl}-3-hydroxy-N-methylpropanamide;

N-{(2S)-2-[(4-{[3-chloro-4-(pyridin-2-ylmethoxy)phenyl]amino}quinazolin-5-yl)oxy]propyl}acetamide;

N-{(2S)-2-[(4-{[3-chloro-4-(pyridin-2-ylmethoxy)phenyl]amino}quinazolin-5-yl)oxy]propyl}-2-hydroxyacetamide;

$N^1$-{(2S)-2-[(4-{[3-chloro-4-(pyridin-2-ylmethoxy)phenyl]amino}quinazolin-5-yl)oxy]propyl}-$N^2,N^2$-dimethylglycinamide;

N-{(2S)-2-[(4-{[3-chloro-4-(pyridin-2-ylmethoxy)phenyl]amino}quinazolin-5-yl)oxy]propyl}-2-methoxyacetamide;

N-{(2S)-2-[(4-{[3-chloro-4-(pyridin-2-ylmethoxy)phenyl]amino}quinazolin-5-yl)oxy]propyl}-2-(methylsulfonyl)acetamide;

N-{2-[(4-{[3-chloro-4-(pyridin-2-ylmethoxy)phenyl]amino}quinazolin-5-yl)oxy]ethyl}-2-hydroxyacetamide;

$N^1$-{2-[(4-{[3-chloro-4-(pyridin-2-ylmethoxy)phenyl]amino}quinazolin-5-yl)oxy]ethyl}-$N^2,N^2$-dimethylglycinamide;

N-{2-[(4-{[3-chloro-4-(pyridin-2-ylmethoxy)phenyl]amino}quinazolin-5-yl)oxy]ethyl}-2-methoxyacetamide;

N-{2-[(4-{[3-chloro-4-(pyridin-2-ylmethoxy)phenyl]amino}quinazolin-5-yl)oxy]ethyl}-2-(methylsulfonyl)acetamide;

N-{(2S)-2-[(4-{[3-chloro-4-(pyridin-2-ylmethoxy)phenyl]amino}quinazolin-5-yl)oxy]propyl}-N-methylacetamide;

N-{(2S)-2-[(4-{[3-chloro-4-(pyridin-2-ylmethoxy)phenyl]amino}quinazolin-5-yl)oxy]propyl}-2-hydroxy-N-methylacetamide;

$N^1$-{(2S)-2-[(4-{[3-chloro-4-(pyridin-2-ylmethoxy)phenyl]amino}quinazolin-5-yl)oxy]propyl}-$N^1,N^2,N^2$-trimethylglycinamide;

N-{(2S)-2-[(4-{[3-chloro-4-(pyridin-2-ylmethoxy)phenyl]amino}quinazolin-5-yl)oxy]propyl}-2-methoxy-N-methylacetamide;

N-{(2S)-2-[(4-{[3-chloro-4-(pyridin-2-ylmethoxy)phenyl]amino}quinazolin-5-yl)oxy]propyl}-N-methyl-2-(methylsulfonyl)acetamide;

N-{(2R)-2-[(4-{[3-chloro-4-(pyrazin-2-ylmethoxy)phenyl]amino}quinazolin-5-yl)oxy]propyl}-N-methylacetamide;

N-{(2R)-2-[(4-{[3-chloro-4-(1,3-thiazol-4-ylmethoxy)phenyl]amino}quinazolin-5-yl)oxy]propyl}-N-methylacetamide;

N-((2R)-2-{[4-({3-chloro-4-[(3-fluorobenzyl)oxy]
phenyl}amino)quinazolin-5-yl]oxy}propyl)-N -methy-
lacetamide;
N-((2R)-2-{[4-({3-chloro-4-[(2-fluorobenzyl)oxy]
phenyl}amino)quinazolin-5-yl]oxy}propyl)-N -methy-
lacetamide;
N-{(1R)-2-[(4-{[3-chloro-4-(pyridin-2-ylmethoxy)phe-
nyl]amino}quinazolin-5-yl)oxy]-1-methylethyl}-2-hy-
droxy-N-methylacetamide;
N-{(1R)-2-[(4-{[3-chloro-4-(pyridin-2-ylmethoxy)phe-
nyl]amino}quinazolin-5-yl)oxy]-1-methylethyl}-N-
methylacetamide;
N-{(1S)-2-[(4-{[3-chloro-4-(pyridin-2-ylmethoxy)phe-
nyl]amino}quinazolin-5-yl)oxy]-1-methylethyl}-2-hy-
droxy-N-methylacetamide;
N-{(1S)-2-[(4-{[3-chloro-4-(pyridin-2-ylmethoxy)phe-
nyl]amino}quinazolin-5-yl)oxy]-1-methylethyl}-N-
methylacetamide;
N-{(1S)-2-[(4-{[3-chloro-4-(pyridin-2-ylmethoxy)phe-
nyl]amino}quinazolin-5-yl)oxy]-1-methylethyl}-2-
methoxy-N-methylacetamide;
N-{(1S)-2-[(4-{[3-chloro-4-(pyridin-2-ylmethoxy)phe-
nyl]amino}quinazolin-5-yl)oxy]-1-methylethyl}-2-hy-
droxyacetamide;
N-{(1S)-2-[(4-{[3-chloro-4-(pyridin-2-ylmethoxy)phe-
nyl]amino}quinazolin-5-yl)oxy]-1-
methylethyl}acetamide;
$N^1$-{(1S)-2-[(4-{[3-chloro-4-(pyridin-2-ylmethoxy)phe-
nyl]amino}quinazolin-5-yl)oxy]-1-methylethyl}-$N^2$,
$N^2$-dimethylglycinamide;
$N^1$-{(2R)-2-[(4-{[3-chloro-4-(pyridin-2-ylmethoxy)phe-
nyl]amino}quinazolin-5-yl)oxy]propyl}-$N^2$,$N^2$-dim-
ethylglycinamide;
(2S)-N-{2-[(4-{[3-chloro-4-(pyridin-2-ylmethoxy)phe-
nyl]amino}quinazolin-5-yl)oxy]ethyl}-2,4-dihydrox-
ybutanamide;
(2R)-N-{2-[(4-{[3-chloro-4-(pyridin-2-ylmethoxy)phe-
nyl]amino}quinazolin-5-yl)oxy]ethyl}-2,4-dihydrox-
ybutanamide;
(2R)-N-{(2R)-2-[(4-{[3-chloro-4-(pyridin-2-ylmethoxy)
phenyl]amino}quinazolin-5-yl)oxy]propyl}-2,4-dihy-
droxybutanamide;
(2S)-N-{(2R)-2-[(4-{[3-chloro-4-(pyridin-2-ylmethoxy)
phenyl]amino}quinazolin-5-yl)oxy]propyl}-2,4-dihy-
droxybutanamide;
(2R)-N-{(2S)-2-[(4-{[3-chloro-4-(pyridin-2-ylmethoxy)
phenyl]amino}quinazolin-5-yl)oxy]propyl}-2,4-dihy-
droxybutanamide;
(2S)-N-{(2S)-2-[(4-{[3-chloro-4-(pyridin-2-ylmethoxy)
phenyl]amino}quinazolin-5-yl)oxy]propyl}-2,4-dihy-
droxybutanamide;
(2S)-N-{(1R)-2-[(4-{[3-chloro-4-(pyridin-2-ylmethoxy)
phenyl]amino}quinazolin-5-yl)oxy]-1-methylethyl}-2,
4-dihydroxybutanamide;
(2R)-N-{(1R)-2-[(4-{[3-chloro-4-(pyridin-2-ylmethoxy)
phenyl]amino}quinazolin-5-yl)oxy]-1-methylethyl}-2,
4-dihydroxybutanamide;
(2R)-N-{2-[(4-{[3-chloro-4-(1,3-thiazol-4-ylmethoxy)
phenyl]amino}quinazolin-5-yl)oxy]ethyl}-2,4-dihy-
droxybutanamide;
(2S)-N-{2-[(4-{[3-chloro-4-(1,3-thiazol-4-ylmethoxy)
phenyl]amino}quinazolin-5-yl)oxy]ethyl}-2,4-dihy-
droxybutanamide;
(2R)-N-{(1R)-2-[(4-{[3-chloro-4-(1,3-thiazol-4-yl-
methoxy)phenyl]amino}quinazolin-5-yl)oxy]-1-meth-
ylethyl}-2,4-dihydroxybutanamide;
(2S)-N-{(1R)-2-[(4-{[3-chloro-4-(1,3-thiazol-4-yl-
methoxy)phenyl]amino}quinazolin-5-yl)oxy]-1-meth-
ylethyl}-2,4-dihydroxybutanamide;
N-methyl-N-{2-[(4-{[3-methyl-4-(pyridin-2-ylmethoxy)
phenyl]amino}quinazolin-5-yl)oxy]ethyl}acetamide;
N-methyl-N-{2-[(4-{[3-methyl-4-(1,3-thiazol-4-yl-
methoxy)phenyl]amino}quinazolin-5-yl)oxy]
ethyl}acetamide;
N-methyl-N-(2-{[4-({3-methyl-4-[(5-methylisoxazol-3-
yl)methoxy]phenyl}amino)quinazolin-5-yl]oxy}ethyl)
acetamide;
2-hydroxy-N-methyl-N-{2-[(4-{[3-methyl-4-(1,3-thia-
zol-2-ylmethoxy)phenyl]amino}quinazolin-5-yl)oxy]
ethyl}acetamide;
2-hydroxy-N-{2-[(4-{[3-methyl-4-(pyridin-2-ylmethoxy)
phenyl]amino}quinazolin-5-yl)oxy]ethyl}acetamide;
2-hydroxy-N-{2-[(4-{[3-methyl-4-(1,3-thiazol-4-yl-
methoxy)phenyl]amino}quinazolin-5-yl)oxy]
ethyl}acetamide;
N-{2-[(4-{[3-chloro-4-(pyridin-2-ylmethoxy)phenyl]
amino}quinazolin-5-yl)oxy]-1,1-dimethylethyl}-2-hy-
droxyacetamide;
2-hydroxy-N-{(2R)-2-[(4-{[3-methyl-4-(pyridin-2-yl-
methoxy)phenyl]amino}quinazolin-5-yl)oxy]
propyl}acetamide;
2-hydroxy-N-{(2R)-2-[(4-{[3-methyl-4-(1,3-thiazol-4-
ylmethoxy)phenyl]amino}quinazolin-5-yl)oxy]
propyl}acetamide;
N-((2R)-2-{[4-({4-[(3-fluorobenzyl)oxy]-3-
methylphenyl}amino)quinazolin-5-yl]oxy}propyl)-2-
hydroxyacetamide;
2-hydroxy-N-{(2R)-2-[(4-{[3-methyl-4-(1,3-thiazol-2-
ylmethoxy)phenyl]amino}quinazolin-5-yl)oxy]
propyl}acetamide;
N-{(2R)-2-[(4-{[3-methyl-4-(pyridin-2-ylmethoxy)phe-
nyl]amino}quinazolin-5-yl)oxy]propyl}acetamide;
N-{(2R)-2-[(4-{[3-methyl-4-(1,3-thiazol-4-ylmethoxy)
phenyl]amino}quinazolin-5-yl)oxy]propyl}acetamide;
N-((2R)-2-{[4-({4-[(3-fluorobenzyl)oxy]-3-
methylphenyl}amino)quinazolin-5-yl]oxy}propyl)ac-
etamide;
N-{(2R)-2-[(4-{[3-methyl-4-(1,3-thiazol-2-ylmethoxy)
phenyl]amino}quinazolin-5-yl)oxy]propyl}acetamide;
2-hydroxy-N-methyl-N-{(2R)-2-[(4-{[3-methyl-4-(pyri-
din-2-ylmethoxy)phenyl]amino}quinazolin-5-yl)oxy]
propyl}acetamide;
2-hydroxy-N-methyl-N-{(2R)-2-[(4-{[3-methyl-4-(1,3-
thiazol-4-ylmethoxy)phenyl]amino}quinazolin-5-yl)
oxy]propyl}acetamide;
2-hydroxy-N-methyl-N-((2R)-2-{[4-({3-methyl-4-[(5-
methylisoxazol-3-yl)methoxy]phenyl}amino)quinazo-
lin-5-yl]oxy}propyl)acetamide;
N-methyl-N-{(1R)-1-methyl-2-[(4-{[3-methyl-4-(pyri-
din-2-ylmethoxy)phenyl]amino}quinazolin-5-yl)oxy]
ethyl}acetamide;
N-methyl-N-{(1R)-1-methyl-2-[(4-{[3-methyl-4-(1,3-
thiazol-4-ylmethoxy)phenyl]amino}quinazolin-5-yl)
oxy]ethyl}acetamide;
N-{(1R)-2-[(4-{[3-chloro-4-(1,3-thiazol-4-ylmethoxy)
phenyl]amino}quinazolin-5-yl)oxy]-1-methylethyl}-2-
hydroxy-N-methylacetamide;
2-hydroxy-N-methyl-N-{(1R)-1-methyl-2-[(4-{[3-me-
thyl-4-(pyridin-2-ylmethoxy)phenyl]
amino}quinazolin-5-yl)oxy]ethyl}acetamide;
2-hydroxy-N-methyl-N-{(1R)-1-methyl-2-[(4-{[3-me-
thyl-4-(1,3-thiazol-4-ylmethoxy)phenyl]
amino}quinazolin-5-yl)oxy]ethyl}acetamide;

N-{(2R)-2-[(4-{[3-chloro-4-(pyridin-2-ylmethoxy)phenyl]amino}quinazolin-5-yl)oxy]propyl}-1-hydroxy-N-methylcyclopropanecarboxamide;

(2S)-N-{(2R)-2-[(4-{[3-chloro-4-(pyridin-2-ylmethoxy)phenyl]amino}quinazolin-5-yl)oxy]propyl}-2-hydroxy-N-methylpropanamide;

N-{(2R)-2-[(4-{[3-chloro-4-(pyridin-2-ylmethoxy)phenyl]amino}quinazolin-5-yl)oxy]propyl}-2-hydroxy-N,2-dimethylpropanamide;

(2R)-N-{(2R)-2-[(4-{[3-chloro-4-(pyridin-2-ylmethoxy)phenyl]amino}quinazolin-5-yl)oxy]propyl}-2-hydroxy-N-methylpropanamide;

(2R)-N-{(2R)-2-[(4-{[3-chloro-4-(pyridin-2-ylmethoxy)phenyl]amino}quinazolin-5-yl)oxy]propyl}-2-methoxy-N-methylpropanamide;

2-hydroxy-N-methyl-N-((2R)-2-{[4-({3-methyl-4-[(6-methylpyridin-3-yl)oxy]phenyl}amino)quinazolin-5-yl]oxy}propyl)acetamide;

N-methyl-N-((2R)-2-{[4-({3-methyl-4-[(6-methylpyridin-3-yl)oxy]phenyl}amino)quinazolin-5-yl]oxy}propyl)acetamide;

$N^1,N^2,N^2$-trimethyl-$N^1$-((2R)-2-{[4-({3-methyl-4-[(6-methylpyridin-3-yl)oxy]phenyl}amino)quinazolin-5-yl]oxy}propyl)glycinamide;

N-methyl-N-((2R)-2-{[4-({3-methyl-4-[(6-methylpyridin-3-yl)oxy]phenyl}amino)quinazolin-5-yl]oxy}propyl)-2-pyrrolidin-1-ylacetamide;

N-methyl-N-((2R)-2-{[4-({3-methyl-4-[(6-methylpyridin-3-yl)oxy]phenyl}amino)quinazolin-5-yl]oxy}propyl)-2-morpholin-4-ylacetamide;

N-methyl-N-((2R)-2-{[4-({3-methyl-4-[(6-methylpyridin-3-yl)oxy]phenyl}amino)quinazolin-5-yl]oxy}propyl)-2-(4-methylpiperazin-1-yl)acetamide;

2-hydroxy-N-methyl-N-((2S)-2-{[4-({3-methyl-4-[(6-methylpyridin-3-yl)oxy]phenyl}amino)quinazolin-5-yl]oxy}propyl)acetamide;

N-methyl-N-((2S)-2-{[4-({3-methyl-4-[(6-methylpyridin-3-yl)oxy]phenyl}amino)quinazolin-5-yl]oxy}propyl)acetamide;

N-methyl-N-((2S)-2-{[4-({3-methyl-4-[(6-methylpyridin-3-yl)oxy]phenyl}amino)quinazolin-5-yl]oxy}propyl)-2-pyrrolidin-1-ylacetamide;

(2S)-2,4-dihydroxy-N-((2R)-2-{[4-({3-methyl-4-[(6-methylpyridin-3-yl)oxy]phenyl}amino)quinazolin-5-yl]oxy}propyl)butanamide;

(2S)-4-bromo-2-hydroxy-N-((2R)-2-{[4-({3-methyl-4-[(6-methylpyridin-3-yl)oxy]phenyl}amino)quinazolin-5-yl]oxy}propyl)butanamide;

N-(2-chloroethyl)-N'-((2R)-2-{[4-({3-methyl-4-[(6-methylpyridin-3-yl)oxy]phenyl}amino)quinazolin-5-yl]oxy}propyl)urea;

2-hydroxy-N-methyl-N-((1R)-1-methyl-2-{[4-({3-methyl-4-[(6-methylpyridin-3-yl)oxy]phenyl}amino)quinazolin-5-yl]oxy}ethyl)acetamide;

N-methyl-N-((1R)-1-methyl-2-{[4-({3-methyl-4-[(6-methylpyridin-3-yl)oxy]phenyl}amino)quinazolin-5-yl]oxy}ethyl)acetamide;

2-hydroxy-N-methyl-N-((1S)-1-methyl-2-{[4-({3-methyl-4-[(6-methylpyridin-3-yl)oxy]phenyl}amino)quinazolin-5-yl]oxy}ethyl)acetamide;

N-methyl-N-((1S)-1-methyl-2-{[4-({3-methyl-4-[(6-methylpyridin-3-yl)oxy]phenyl}amino)quinazolin-5-yl]oxy}ethyl)acetamide;

methyl-{2-[(4-{[3-chloro-4-(pyridin-2-ylmethoxy)phenyl]amino}quinazolin-5-yl)oxy]ethyl}methylcarbamate;

N-{2-[(4-{[3-chloro-4-(pyridin-2-ylmethoxy)phenyl]amino}quinazolin-5-yl)oxy]ethyl}-N,N'-dimethylurea;

N'-(2-chloroethyl)-N-{2-[(4-{[3-chloro-4-(pyridin-2-ylmethoxy)phenyl]amino}quinazolin-5-yl)oxy]ethyl}-N-methylurea;

N-{(2R)-2-[(4-{[3-chloro-4-(pyridin-2-ylmethoxy)phenyl]amino}quinazolin-5-yl)oxy]propyl}-N'-methylurea;

[((R)-2-{4-[3-chloro-4-(pyridin-2-ylmethoxy)phenylamino]quinazolin-5-yloxy}propylcarbamoyl)methyl]methylcarbamic acid tert-butyl ester;

$N^1$-{(2R)-2-[(4-{[3-chloro-4-(pyridin-2-ylmethoxy)phenyl]amino}quinazolin-5-yl)oxy]propyl}-$N^2$-methylglycinamide;

2-hydroxy-N-methyl-N-(2-{[4-({3-methyl-4-[(6-methylpyridin-3-yl)oxy]phenyl}amino)quinazolin-5-yl]oxy}ethyl)acetamide;

N-methyl-N-(2-{[4-({3-methyl-4-[(6-methylpyridin-3-yl)oxy]phenyl}amino)quinazolin-5-yl]oxy}ethyl)acetamide; and N-{2-[(4-{[3-chloro-4-(1-methyl-1-pyridin-2-ylethoxy)phenyl]amino}quinazolin-5-yl)oxy]ethyl}-N-methylacetamide;

or a pharmaceutically acceptable salt thereof.

19. A pharmaceutical composition which comprises a quinazoline derivative of the formula I, or a pharmaceutically acceptable salt thereof, as defined in claim 1 or claim 18 in association with a pharmaceutically-acceptable diluent or carrier.

20. A process for the preparation of a quinazoline derivative of the formula I, or a pharmaceutically acceptable salt thereof, as defined in claim 1 which comprises:

a) the coupling, optionally in the presence of a suitable base, of a quinazoline of the formula II:

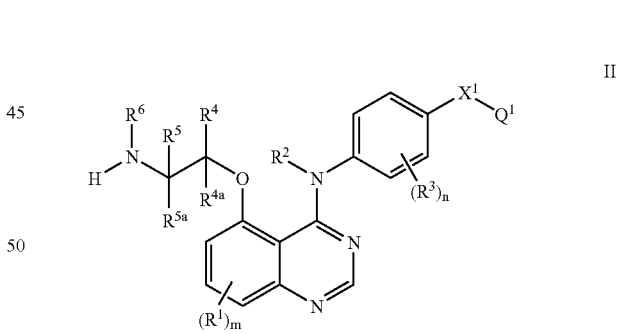

wherein $R^1$, $R^2$, $R^3$, $R^4$, $R^{4a}$, $R^5$, $R^{5a}$, $R^6$, $X^1$, $Q^1$, m, and n have any of the meanings defined in claim 1 except that any functional group is optionally protected, with a carboxylic acid of the formula III, or a reactive derivative thereof:

A-COOH    III wherein A has any of the meanings defined in claim 1 except that any functional group is optionally protected; or (b) for the preparation of those compounds of the formula I wherein $X^1$ is $OC(R^7)_2$, $SC(R^7)_2$ or $N(R^7)C(R^7)_2$, the reaction, conveniently in the presence of a suitable base, of a quinazoline of the formula IV:

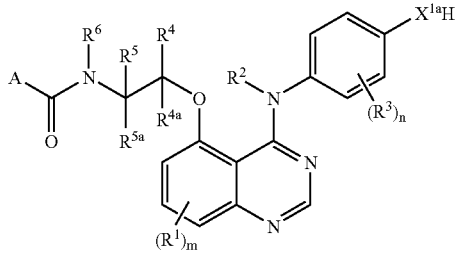

IV wherein $X^{1a}$ is O, S or $N(R^7)$ and $R^1$, $R^2$, $R^3$, $R^4$, $R^{4a}$, $R^5$, $R^{5a}$, $R^6$, $R^7$, A, m, and n have any of the meanings defined in claim 1 except that any functional group is optionally protected, with a compound of the formula V or a salt thereof:

$Q^1\text{-}C(R^7)_2\text{-}L^1$   V wherein $L^1$ is a suitable displaceable group and $Q^1$ and $R^7$ have any of the meanings defined in claim 1 except that any functional group is optionally protected; or (c) for the preparation of those compounds of the formula I wherein A is $R^{14}$ and $R^{14}$ is $NHR^{17}$ or $Q^3\text{-}X^5$— (wherein $R^{17}$ and $Q^3$ are as defined in claim 1 and $X^5$ is NH), the coupling of a quinazoline of the formula II as defined above in (a) with an isocyanate of the formula IIIa:

A-NCO   IIIa wherein A is $R^{14}$ as previously defined in this section except that any functional group is optionally protected; or (d) the reaction of a quinazoline of the formula II wherein $R^6$ is hydrogen:

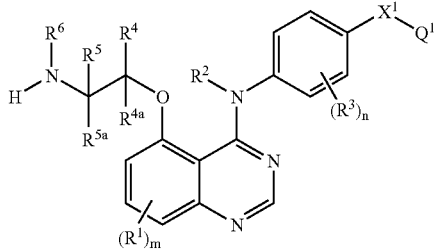

II wherein $R^1$, $R^2$, $R^3$, $R^4$, $R^{4a}$, $R^5$, $R^{5a}$, $X^1$, $Q^1$, m, and n have any of the meanings defined in claim 1 except that any functional group is optionally protected, with α-hydroxy-γ-butyrolactone wherein any functional group is optionally protected; or (e) the coupling of a quinazoline of the formula VI:

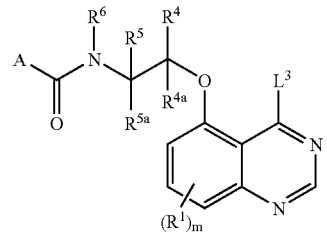

VI wherein $R^1$, $R^4$, $R^{4a}$, $R^5$, $R^{5a}$, $R^6$, A and m have any of the meanings defined in claim 1 except that any functional group is optionally protected, with a compound of the formula IIb:

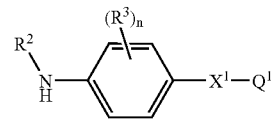

IIb wherein $R^2$, $R^3$, $X^1$, $Q^1$ and n have any of the meanings defined in claim 1 except that any functional group is optionally protected;

(f) for the preparation of those compounds of the formula I wherein $X^1$ is O and $Q^1$ is 2-pyridyl, 4-pyridyl, 2-pyrimidyl, 4-pyrimidyl, 2-pyrazinyl or 3-pyridazinyl, reacting, optionally in the presence of a suitable base and a suitable catalyst, of a quinazoline of the formula VII:

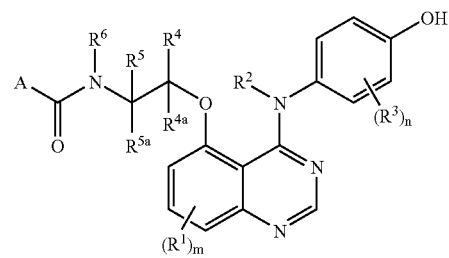

VII wherein $R^1$, $R^2$, $R^3$, $R^4$, $R^{4a}$, $R^5$, $R^{5a}$, $R^6$, A, m and n have any of the meanings defined in claim 1 except that any functional group is optionally protected, with 2-bromopyridine, 4-bromopyridine, 2-chloropyrimidine, 4-chloropyrimidine, 2-chloropyrazine or 3-chloropyridazine; or (g) for the preparation of those compounds of the formula I wherein A is $Z\text{-}(CR^{12}R^{13})_p$—, wherein Z is $NR^{16}R^{17}$, the reaction, conveniently in the presence of a suitable base, of a quinazoline of the formula VIII:

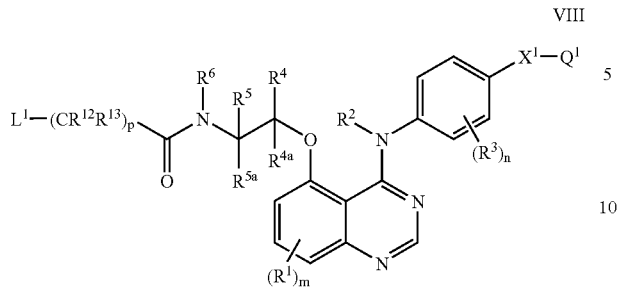

VIII wherein $L^1$ is a suitable displaceable group and $R^1$, $R^2$, $R^3$, $R^4$, $R^{4a}$, $R^5$, $R^{5a}$, $R^6$, $R^{12}$, $R^{13}$, $X^1$, $Q^1$, m, n and p have any of the meanings defined in claim 1 except that any functional group is optionally protected, with a compound of the formula IXa, or a reactive derivative thereof:

$$H\text{—}NR^{16}R^{17} \qquad \text{IXa}$$

wherein $R^{16}$ and $R^{17}$ have any of the meanings defined in claim 1 except that any functional group is optionally protected;

and thereafter, optionally;

(i) removing any protecting group that is present;

(ii) forming a pharmaceutically acceptable salt.

21. A method for treating a breast tumour in a warm-blooded animal in need of such treatment, which comprises administering to the animal an effective amount of a quinazoline derivative of the formula I, or a pharmaceutically acceptable salt thereof, according to claim 1.

* * * * *

UNITED STATES PATENT AND TRADEMARK OFFICE
CERTIFICATE OF CORRECTION

PATENT NO. : 7,625,908 B2
APPLICATION NO. : 10/578663
DATED : December 1, 2009
INVENTOR(S) : Hennequin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 381 days.

Signed and Sealed this

Second Day of November, 2010

David J. Kappos
*Director of the United States Patent and Trademark Office*